(12) United States Patent
Lal et al.

(10) Patent No.: US 7,915,301 B2
(45) Date of Patent: Mar. 29, 2011

(54) INHIBITORS OF CYCLIN DEPENDENT KINASES AND THEIR USE

(75) Inventors: Bansi Lal, Mumbai (IN); Kalpana Joshi, Thane (IN); Sanjeev Kulkarni, Mumbai (IN); Malcolm Mascarenhas, Mumbai (IN); Shrikant Kamble, Mumbai (IN); Maggie Joyce Rathos, Thane (IN); Rajendrakumar Joshi, Mumbai (IN)

(73) Assignee: Piramal Life Science Limited (IN)

( * ) Notice: Subject to any disclaimer, the term of this patent is extended or adjusted under 35 U.S.C. 154(b) by 0 days.

(21) Appl. No.: 11/779,577

(22) Filed: Jul. 18, 2007

(65) Prior Publication Data
US 2008/0108690 A1    May 8, 2008

Related U.S. Application Data

(62) Division of application No. 10/611,539, filed on Jul. 1, 2003, now Pat. No. 7,271,193.

(30) Foreign Application Priority Data

Jul. 8, 2002   (IN) .......................... 616/MUM/2002

(51) Int. Cl.
*A61K 31/4025* (2006.01)
*A61K 31/353* (2006.01)
*C07D 405/04* (2006.01)
*C07D 311/32* (2006.01)

(52) U.S. Cl. ......... 514/422; 514/456; 548/525; 549/399
(58) Field of Classification Search .................. 514/422, 514/456; 548/525; 549/399
See application file for complete search history.

(56) References Cited

U.S. PATENT DOCUMENTS

| 4,900,727 A | 2/1990 | Kattige et al. |
| 5,116,954 A | 5/1992 | Briet et al. |
| 5,284,856 A | 2/1994 | Naik et al. |
| H1427 H | 4/1995 | Briet et al. |
| 5,723,313 A | 3/1998 | Sherr et al. |
| 5,733,920 A | 3/1998 | Mansuri et al. |
| 5,849,733 A | 12/1998 | Kim |
| 6,699,854 B2 | 3/2004 | Wang et al. |
| 7,056,942 B2 * | 6/2006 | Hildesheim et al. .......... 514/411 |

FOREIGN PATENT DOCUMENTS

| WO | WO 01/83469 A1 | 11/2001 |
| WO | WO 2004-004632 | 1/2004 |
| WO | WO 2007-148158 | 12/2007 |

OTHER PUBLICATIONS

Davies et al. "Structure-based design of cyclin-dependent kinase inhibitors" Pharmacology & Therapeutics, 2002, pp. 125-133.*
Toogood, Peter "Cyclin-Dependent Kinase Inhibitors for Treating Cancer" Medicinal Research Reviews, 2001, pp. 487-498.*
PLATINOL-AQ (cisplatin injection) package insert. Revised Apr. 2006.*
Taxol Injection package insert. Revised Jul. 2007.*
Ortega et al., Cyclin D-dependent kinases, INK4 inhibitors and cancer, Biochimica et Biophysica Acta 1602, 2002, pp. 73-87.
Kelland, Expert Opinion on Investigational Drugs, 2000, vol. 9, No. 12, pp. 2903-2911, Ashley Publications Ltd., ISSN: 1354-3784.
Elsayed et al., Selected Novel Anticaner Treatments Targeting Cell Signaling Proteins, The Oncologist, 2001, vol. 6, pp. 517-537.
Parker et al., Blood, Jan. 15, 1998, vol. 91, No. 2, pp. 458-465.
Stadler et al., Jounal of Clinical Oncology, Jan. 2000, vol. 18, No. 2, pp. 371-375.
Patel et al., Journal of Clinical Investigation, Nov. 1998, vol. 102, No. 9, pp. 1674-1681.
Shapiro et al., Clinical Cancer Research, Jun. 2001, vol. 7, pp. 1590-1599.
Senderowicz et al., Journal of National Cancer Institute, Mar. 1, 2000, vol. 92, No. 5, pp. 376-387.
Perez-Roger et al., Current Pharmaceutical Biotechnology, 2000, vol. 1, pp. 107-116, Bentham Science Publishers ltd.

(Continued)

*Primary Examiner* — Joseph R Kosack
(74) *Attorney, Agent, or Firm* — Frommer Lawrence & Haug

(57) ABSTRACT

The present invention relates to novel compounds for the inhibition of cyclin-dependent kinases, and more particularly, to chromenone derivatives of formula (Ia),

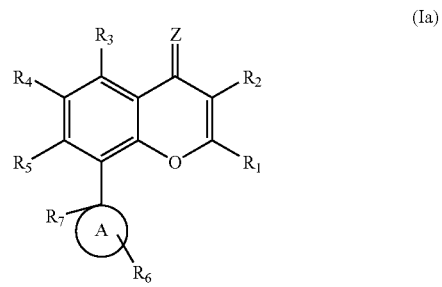

wherein $R_1$, $R_2$, $R_3$, $R_4$, $R_5$, $R_6$, $R_7$ and A have the meanings indicated in the claims. The invention also relates to processes for the preparation of the compounds of formula (Ia), to methods of inhibiting cyclin-dependent kinases and of inhibiting cell proliferation, to the use of the compounds of formula (Ia) in the treatment and prophylaxis of diseases, which can be treated or prevented by the inhibition of cyclin-dependent kinases such as cancer, to the use of the compounds of formula (Ia) in the preparation of medicaments to be applied in such diseases. The invention further relates to compositions containing a compound of formula (Ia) either alone or in combination with another active agent, in admixture or otherwise in association with an inert carrier, in particular pharmaceutical compositions containing a compound of formula (Ia) either alone or in combination with another active agent, together with pharmaceutically acceptable carrier substances and auxiliary substances.

5 Claims, 6 Drawing Sheets

OTHER PUBLICATIONS

Figure 1:
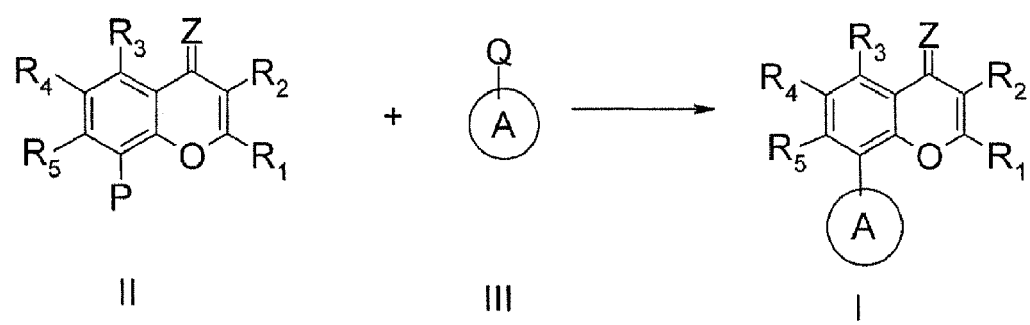

Senderowicz, Oncogene, 2000, vol. 19, pp. 6600-6606, Macmillan Publishers Ltd.
Soni et al.; Journal of the National Cancer Institute (2001), 93(6), 436-446.
Zhang et al.; Cancer Research 57: (1997); 169-175.
Ortega et al; Biochimica et Biophysica Acta 1602 (2002) 73-87.
Wei et al.; Int. J. Cancer: 80, 199-204 (1999); UICC; Wiley-Liss Inc.
Elsayed et al.; The Oncologist, (2001); 6:517-537.
Kohzato et al.; Hepatology Research (2001), 21(1), 27-39 (Abstract only).
Dong Y. et al.; Anticancer Research (2001), 21(1A), 103-108 (Abstract only).
Li JQ et al.; Human Pathology (2001), 32(9), 945-953 (Abstract only).
Naik et al., Tetrahedron, vol. 44., No. 7, (1988) p. 2081-2086, Great Britain, XP002093909.
Ghosh et al., Tetrahedron: Asymmetry, (1998), vol. 9, p. 1-45.
Barnes et al., J. Am. Chem. Soc., 2002, 124 (44), 13097-13105.
Dorland's Pocket Medical Dictionary, publ. W.B. Saunders Co., p. 350 (1989).
The American College Dictionary, publ. Random House, p. 756 (1967).
Senderowicz et al, "Preclinical and Clinical Development of Cyclin-Dependent Kinease Modulators," J. Natl. Cancer Institute, 2000, 376-387.
Naik et al, "An Anti-Inflammatory Cum Immunomodulatory Piperidinylbenzopyranone from *Dyoxylum Binectariferum*: Isolation, Structure and Total Synthesis"; Tetrahedron, 1998, 44(7), 2081-2086.
Pérez-Roger et al, "Inhibition of Cellular Proliferation by Drug Targeting of Cyclin-Dependent Kinases"; Curr. Pharm. Biotechnol, Jul. 1, 2000(1), 107-116.
Losiewocz et al, "Potent Inhibition of CDC2 Kinase Activity by the Flavonoid L86-8275"; Biochemical and Biophysical Research Communications, 1994, 589-595.
J. Org Chem. 1992, 57, 6321-6323.
Larget et al, "Convenient Extension of the Wessely-Moser Rearrangement for the synthesis of Substituted Alkylaminoflavones as Neuroprotective Agents in Vitro"; Bioorganica and Medicinal Chemistry Letters 10 (2000) 835-838.
Tsuritani et al; Organic Letters 2001, vol. 3, No. 17, 2709-2711.
Bang-Chi-Chen et al, "A New Facile Method for the Synthesis of 1-Arylimidazoles-5-Carboxylates", Tetrahedron Letters 41 (2000) 5453-5456.
Falb et al, "A Convenient Synthesis of Chiral Oxazolidin-2-Ones and Thiazolidin-2-Ones and an Improved Preparation of Triphosgene"; Synthetic Communications, 23(20), 2839-2844, 1993.
Hosoi et al, J. Biochem 117, 741-749 (1995).
Ongkeko et al, "Inactivation of CDC2 Increases the Level of Apoptosis Induced by DNA Damage"; Journal of Cell Science 108, 2897-2904, 1995.
Schwartz et al, "Phase I Study of Cyclin-Dependent Kinase Inhibitor Flavopiridol in Comination with Paclitaxel in Patients with Advanced Solid Tumors", 2002.
Tan et al, "Phase I Clinical and Pharmacokinetic Study of Flavopiridol Administered as a Daily 1-Hour Infusion in Patients with Advanced Neoplasms", Journal of Clinical Oncology, vol. 20, No. 19, Oct. 1, 2002, pp. 4074-4082.
Hirama et al, Blood, "Role of the Cyclin-Dependent Kinase Inhibitors in the Development of Cancer", The Journal of the American Society of Hematology, Aug. 1, 1995, Blood, vol. 88, No. 3, Aug. 1, 1995, pp. 841-854.
Edward A. Sausville, "Cyclin-Dependent Kinases: Novel Targets for Cancer Treatment", Developmental Therapeutics Program, pp. 9-21, 1999.
Elsayed et al, "Selected Novel Anticancer Treatments Targeting Cell Signaling Proteins", *The Oncologist*; 2001; 6: pp. 517-537.
Meier et al, "Properties and Potential Applications of Chemical Inhibitors of Cyclin-Dependent Kinases", Pharmacol, Ther., vol. 82, Nos. 2-3, pp. 279-284, 1999.
Sausville et al, "Cyclin-Dependent Kinases: Initial Approaches to Exploit a Novel Therapeutic Target", Pharmacol, Ther. vol. 82, Nos. 2-3, pp. 285-292, 1999.
Parker et al, "Early Induction of Apoptosis in Hematopoieti Cells Lines After Exposure to Flavopiridol", The American Society of Hematology, Blood, vol. 91, No. 2, Jan. 15, 1998; pp. 458-465.
Davies et al., "Structure-Base Design of Cyclin-Dependent Kinase Inhibitors," Pharmacology & Therapeutics, 2002, pp. 125-133.
Toogood, Peter, "Cyclin-Dependent Kinase Inhibitors for Treating Cancer," Medicinal Research Reviews, 2001, pp. 487-498.
Bristol-Myers Squibb Patient Information for Taxol, Mar. 2003.
Schwartz et al., "Phase I Study of the Cyclin-Dependent Kinase Inhibitor Flavopiridol in Comination with Paclitaxel in Patients with Advanced Solid Tumors," Journal of Clinical Oncology, vol. 20, No. 8, pp. 2157-2170; 2002.
Hirama et al., "Role of the Cyclin-Dependent Kinase Inhibitors in the Development of Cancer," Blood, 1995, vol. 86, No. 3, pp. 841-854.
Gross et al., "A Stereocontrolled approach to Substituted piperidones and piperidines; Flavopiridol D-ring analog," Tetrahedron Letters 42, 2001, pp. 1631-1633.

* cited by examiner

INHIBITORS OF CYCLIN DEPENDENT KINASES AND THEIR USE

FIELD OF THE INVENTION

The present invention relates to novel inhibitors of cyclin-dependent kinases (CDKs), to processes for their preparation, their use as active ingredients in pharmaceuticals, in particular for the treatment of proliferative disorders, and to pharmaceutical preparations comprising them.

BACKGROUND OF THE INVENTION

The ability of eukaryotic cells to proliferate in response to a growth signal is tightly controlled by a complex network of ordered biochemical events collectively known as the cell cycle. Mitogenic signals commit cells to entry into a series of regulated steps of the cell cycle. The synthesis of DNA (S phase), and separation of two daughter cells (M phase) are the main features of cell cycle progression. The G1 phase separates the M and S phases and prepares the cell for DNA duplication upon receiving mitogenic signals. The period between the S and M phases is known as the G2 phase during which cells repair errors that occurred during DNA duplication.

Regulators of the cell cycle have gained widespread importance in proliferative diseases. Cyclin-dependent kinases (CDKs) are a family of enzymes which become activated in specific phases of the cell cycle. CDKs consist of a catalytic subunit (the actual cyclin-dependent kinase or CDK) and a regulatory subunit (cyclin). There are at least nine CDKs (CDK1, CDK2, CDK3, CDK4, CDK5, CDK6, CDK7, CDK8, CDK9, etc.) and 15 different types of cyclins (cyclin A, B1, B2, D1, D2, D3, E etc). Each step of the cell cycle is thought to be regulated by such CDK complexes: G1/S transition (CDK2/cyclin A, CDK4/cyclin D1-D3, CDK6/cyclin D3) (Senderwicz A. M. and Sausville E. A., J. Natl. Cancer Inst. 2000, 376-387), S phase (CDK2/cyclin A), G2 phase (CDK1/cyclin A), G2/M transition phase (CDK1/cyclins B).

CDKs are able to phosphorylate many proteins that are involved in cell cycle events, including tumor suppressor proteins, such as the retinoblastoma gene product Rb. The Rb is involved in the G1/S transition of the cell cycle and its phosphorylation by CDKs results in its inactivation (U.S. Pat. No. 5,723,313), which in turn leads to the release of the transcriptional factor E2F and the activation of E2F-responsive genes necessary for progression to the S phase.

A wide variety of diseases are characterized by uncontrolled cell proliferation that results from some fault in the regulatory pathways in the cell cycle [e.g. overexpression of cyclins or deletions of genes encoding CKIs (CDK inhibitory proteins)]. The overexpression of cyclinD1 leads to the deregulation of CDK4-D1 kinase activity and thereby contributes to uncontrolled cell proliferation. With knowledge of the role of CDKs in cell cycle regulation and the discovery that approximately 90% of all neoplasias are associated with CDK hyperactivation leading to the inactivation of the Rb pathway, CDKs are attractive targets for the development of anti-tumor drugs.

The first potent molecule to be developed as an effective CDK inhibitor was a flavone compound, namely flavopiridol [cis-{2-(2-Chloro-phenyl)-5,7-dihydroxy-8-(3-hydroxy-1-methyl-piperidin-4-yl)-chromen-4-one hydrochloride}]. Flavopiridol is known to inhibit different CDKs and it exhibits anti-proliferative activity in vitro against a broad range of human cancer cells. Further research on flavones as a class of compounds offers a potential approach to anti-proliferative therapy. As a result, analogs of flavopiridol have been the subject of other publications. U.S. Pat. No. 5,733,920 describes novel chromone analogs as inhibitors of CDK/Cyclin complexes. U.S. Pat. No. 5,849,733 discloses 2-thio and 2-oxo analogs of flavopiridol as protein kinase inhibitors for the treatment of proliferative diseases. WO 01/83469 discloses 3-hydroxychromen-4-one derivatives as inhibitors of cyclin dependent kinases. U.S. Pat. No. 5,116,954 and US H1427 disclose flavonoid compounds having anticancer and immunomodulatory activity. U.S. Pat. No. 5,284,856 discloses use of benzopyran-4-one derivatives for the control of tumoral diseases. U.S. Pat. No. 4,900,727 discloses benzopyran-4-one derivatives antiinflammatory agents. Anti-inflammatory benzopyran-4-one derivative from Dysoxylum binectariferum is described by R. G. Naik et al in Tetrahedron, 1988, 44 (7), 2081-2086.

The prominent role of CDK/cyclin kinase complexes, in particular CDK4/cyclin D kinase complexes, in the induction of cell proliferation and their deregulation in tumors, makes them ideal targets for developing highly specific anti-proliferative agents.

There is a clear need, however, for CDK inhibitors which can be used as anti-proliferative agents in an efficient or more specific manner. A focused research on CDK inhibitors by the present inventors resulted in the discovery of novel flavone analogs possessing structural features not envisaged in the prior art, as effective inhibitors of CDKs. Moreover, the compounds of the invention inhibit CDKs effectively with greater selectivity than the known CDK inhibitors, which are under clinical trials (Curr. Pharm. Biotechnol. 2000, July (1): 107-116) and also show comparatively low cytotoxicity against various different proliferative cell lines. Therefore, the compounds of the present invention are candidate agents for the treatment of various cell proliferation related disorders.

SUMMARY OF THE INVENTION

The present invention generally relates to compounds of the general formula (Ia), prodrugs, tautomeric forms, stereoisomers, optical isomers, pharmaceutically acceptable salts, pharmaceutically acceptable solvates or polymorphs thereof

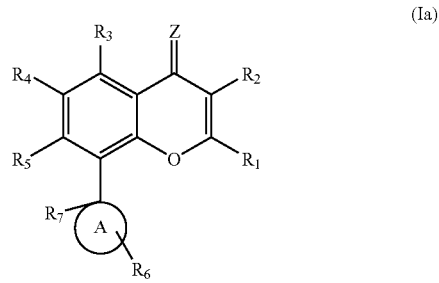

(Ia)

wherein $R_1$ is aryl, heterocycle, $NR_9R_{10}$, $OR_{11}$ or $SR_{11}$;

$R_2$ is hydrogen, alkyl, aryl, heterocycle, $OR_{11}$, halogen, cyano, nitro, $NR_9R_{10}$ or $SR_{11}$;

$R_3$, $R_4$ and $R_5$ are each independently selected from: hydrogen, alkyl, halogen, $OR_{11}$, arylalkoxy, alkylcarbonyloxy, alkoxycarbonyloxy, arylcarbonyloxy, carboxy, cyano, nitro, $NR_9R_{10}$, $SR_{11}$, arylalkylthio, —$SO_2$-alkyl, $SO_2$-aryl, $SO_2NR_9R_{10}$, aryl and heterocycle;

$R_6$ is hydrogen, alkyl, acyl, hydroxyl, $NR_9R_{10}$, alkyloxy, alkyloxycarbonyl, aryloxy,

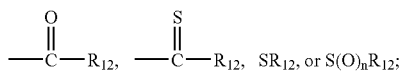

R$_7$ is hydrogen, alkyl, alkylcarbonyl or arylcarbonyl;

R$_8$ is hydrogen, alkyl, aryl, carboxamide, sulfonamide, NR$_9$R$_{10}$ or OR$_{11}$;

R$_9$ and R$_{10}$ are each independently selected from: hydrogen, alkyl, aryl, acyl, heterocycle, alkoxycarbonyl, alkylcarbonyl, arylcarbonyl, heterocyclocarbonyl, carboxamide and sulfonamide; or R$_9$ and R$_{10}$ together with the nitrogen atom to which they are bonded, form a heterocyclic ring, which can have at least one further heteroatom selected from: nitrogen, oxygen, sulfur and phosphorus, and which is saturated, partially unsaturated or aromatic;

R$_{11}$ is hydrogen, alkyl, acyl, aryl or alkoxycarbonyl;

R$_{12}$ is hydrogen, halogen, alkyl, aryl, NR$_9$R$_{10}$, OR$_9$ or heterocycle;

Z is an oxygen atom, a sulfur atom, or NR$_8$; provided that when Z is an oxygen atom, R$_1$ is other than OR$_{11}$ or SR$_{11}$;

n is an integer of 1 or 2;

A is a 5- to 7-membered ring; wherein:

(I) when A is a 5-membered ring it is saturated or unsaturated and represented by any one of the general structures (i) to (v);

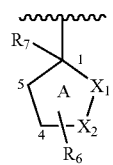

(i)

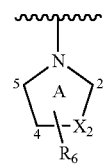

(ii)

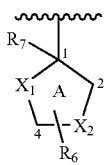

(iii)

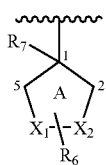

(iv)

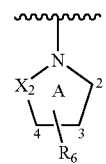

(v)

wherein X$_1$ and X$_2$ are each independently selected from: a methylene group carbon atom and a heteroatom selected from: an oxygen atom, a sulfur atom, S(O)$_p$, a nitrogen atom, provided that at least one of X$_1$ and X$_2$ is a heteroatom, and wherein the nitrogen atom is at least monosubstituted by R$_{13}$, wherein R$_{13}$ is selected from: hydrogen, alkyl, lower alkenyl, aryl, hydroxyl, alkoxy, alkylcarbonyl, cyano, —SO$_2$R$_{10}$ and —CO—(CH$_2$)$_m$—R$_{14}$;

R$_6$ is hydrogen or a substituent as defined above on at least one carbon atom ring member;

R$_{14}$ is hydrogen, alkyl, hydroxyl, NR$_9$R$_{10}$, halogen, —SH, —S-alkyl, —S-aryl, heterocycle or aryl;

R$_7$, R$_9$ and R$_{10}$ are as defined above;

p is an integer of 1 or 2;

m is an integer of 0 to 6;

with the provisos that:

(a) in case of general structures (i) to (iv), when Z is an oxygen atom, X$_2$ is NR$_{13}$, wherein R$_{13}$ is hydrogen, alkyl, C$_1$-C$_4$ alkanoyl or aryl, and X$_1$ is a methylene group carbon atom, then R$_6$ is other than hydrogen or a substituent on the ring member at position 5 selected from: hydroxyl, C$_1$-C$_4$-alkyloxy, C$_1$-C$_4$-alkyloxycarbonyl, aryloxy and NR$_9$R$_{10}$;

(b) in general structure (iv), when Z is an oxygen atom, X$_1$ is NR$_{13}$, wherein R$_{13}$ is hydrogen, alkyl, C$_1$-C$_4$ alkanoyl or aryl and X$_2$ is a methylene group carbon atom, then R$_6$ is other than hydrogen or a substituent on the ring member at position 2 selected from: hydroxyl, C$_1$-C$_4$-alkyloxy, C$_1$-C$_4$-alkyloxycarbonyl, aryloxy and NR$_9$R$_{10}$;

(c) when either X$_1$ or X$_2$ is a heteroatom, or both X$_1$ and X$_2$, are heteroatoms, and A is unsaturated, there is no double bond between ring members at positions 1 and 2 or 1 and 5; or (d) in case of general structure (v), when S(O)$_p$ is at position 5, then R$_6$ is other than hydrogen;

(II) when A is a 6-membered ring, it is a saturated ring of the general structure (vi):

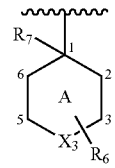

(vi)

wherein X$_3$ is an oxygen atom, a sulfur atom, S(O)$_p$, or a nitrogen atom, wherein the nitrogen atom is at least monosubstituted by R$_{13}$, wherein R$_{13}$ is selected from: hydrogen, alkyl, lower alkenyl, aryl, hydroxyl, alkoxy, alkylcarbonyl, cyano, —SO$_2$R$_{10}$ and —CO—(CH$_2$)$_m$—R$_{14}$; R$_6$ is hydrogen or a substituent as defined above on at least one ring member at any of positions 2, 3, 5 or 6;

with the proviso that when Z is an oxygen atom and X$_3$ is NR$_{13}$ wherein R$_{13}$ is hydrogen, alkyl, C$_1$-C$_4$ alkanoyl or aryl, then R$_6$ is other than hydrogen or a substituent at position 2 or 6 of the 6-membered ring A selected from: hydroxyl, C$_1$-C$_4$-alkyloxy, C$_1$-C$_4$-alkyloxycarbonyl, aryloxy and NR$_9$R$_{10}$;

R$_7$, R$_9$, R$_{10}$, R$_{14}$, p and m are as defined above; and (III) when A is a 7-membered ring, it is a saturated ring of the general structure (vii);

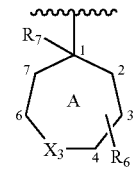

(vii)

wherein $X_3$ is an oxygen atom, a sulfur atom, $S(O)_p$, or a nitrogen atom, wherein the nitrogen atom is at least monosubstituted by $R_{13}$, wherein $R_{13}$ is selected from: hydrogen, alkyl, lower alkenyl, aryl, hydroxyl, alkoxy, alkylcarbonyl, cyano, —$SO_2R_{10}$ and —CO—$(CH_2)_m$—$R_{14}$;

$R_6$ is hydrogen or a substituent as defined above on at least one ring member at any of positions 2, 3, 4, 6 or 7 of A; with the proviso that when Z is an oxygen atom and $X_3$ is $NR_{13}$, wherein $R_{13}$ is hydrogen, alkyl, alkanoyl or aryl, then $R_6$ is other than hydrogen or a substituent at position 7 of the 7-membered ring A selected from: hydroxyl, $C_1$-$C_4$-alkyloxy, $C_1$-$C_4$-alkyloxycarbonyl, aryloxy and $NR_9R_{10}$;

$R_7$, $R_9$, $R_{10}$, $R_{14}$, p and m are as defined above.

The present invention further relates to a sub-group of compounds of formula (Ib), prodrugs, tautomeric forms, stereoisomers, optical isomers, pharmaceutically acceptable salts, pharmaceutically acceptable solvates and polymorphs thereof

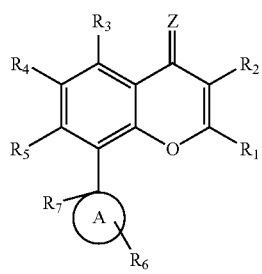

(Ib)

wherein $R_1$ is aryl, heterocycle, $NR_9R_{10}$, $OR_{11}$, or $SR_{11}$;

$R_2$ is hydrogen, alkyl, aryl, heterocycle, $OR_{11}$, halogen, cyano, nitro, $NR_{10}R_{11}$ or $SR_{11}$;

$R_3$, $R_4$ and $R_5$ are each independently selected from: hydrogen, alkyl, halogen, $OR_{11}$, arylalkoxy, alkylcarbonyloxy, alkoxycarbonyloxy, arylcarbonyloxy, carboxy, cyano, nitro, $NR_{10}R_{11}$, $SR_{11}$, arylalkylthio, —$SO_2$-alkyl, $SO_2$-aryl, $SO_2NR_{10}R_{11}$, aryl and heterocycle;

$R_6$ is hydrogen, alkyl, acyl, hydroxyl, $NR_{10}R_{11}$, alkyloxy, alkyloxycarbonyl, aryloxy,

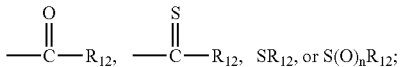

$R_7$ is hydrogen, alkyl, alkylcarbonyl or arylcarbonyl;

$R_8$ is hydrogen, alkyl, aryl, carboxamide, sulfonamide, $NR_{10}R_{11}$ or $OR_{11}$;

$R_{10}$ and $R_{11}$ are each independently selected from: hydrogen, alkyl, aryl, acyl, heterocycle, alkoxycarbonyl, alkylcarbonyl, arylcarbonyl, heterocyclocarbonyl, carboxamide and sulfonamide; or $R_9$ and $R_{10}$, together with the nitrogen atom to which they are bonded, form a 3-, 4-, 5- or 6-membered heterocyclic ring, which can have at least one further heteroatom selected from: nitrogen, oxygen and sulfur, and which is saturated, partially unsaturated or aromatic;

$R_{11}$ is hydrogen, alkyl, acyl, aryl, or alkoxycarbonyl;

$R_{12}$ is hydrogen, halogen, alkyl, aryl, $NR_{10}R_{11}$, $OR_9$ or heterocycle;

Z is an oxygen atom, a sulfur atom, or $NR_8$;

n is an integer of 1 or 2;

A is a saturated 5-membered ring represented by any one of the general structures (i) to (v);

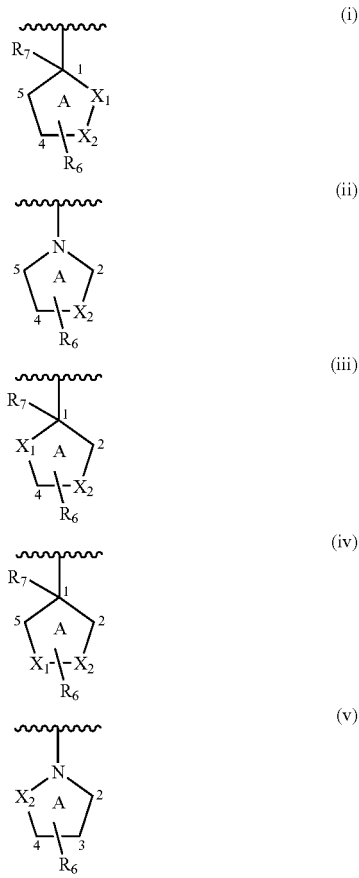

wherein $X_1$ and $X_2$ are each independently selected from: a methylene group and a heteroatom, wherein the heteroatom is selected from: an oxygen atom, a sulfur atom and a nitrogen atom, provided that at least one of $X_1$ and $X_2$ is a heteroatom and wherein the nitrogen atom is at least monosubstituted by $R_{13}$, wherein $R_{13}$ is selected from: hydrogen, alkyl, lower alkenyl, aryl, hydroxyl, alkoxy, alkylcarbonyl, cyano, —$SO_2R_{10}$ and —CO—$(CH_2)_m$—$R_{14}$;

$R_6$ is hydrogen or a substituent as defined above on at least one carbon atom ring member;

$R_7$, $R_9$ and $R_{10}$ are as defined above;

$R_{14}$ is hydrogen, alkyl, hydroxyl, $NR_{10}R_{11}$, halogen, —SH, —S-alkyl, —S-aryl, a heterocycle or aryl; and m is an integer of 0 to 6.

In one embodiment, the present compounds are inhibitors of mammalian CDK/cyclin complexes, as well as inhibitors of insect CDK, plant CDK and of fungal CDK complexes. In another embodiment the present compounds are inhibitors of the kinase activity of CDK/cyclin complexes, e.g. the CDK2/cyclin E and CDK4/cyclin D1 complexes.

As described in more detail below, the present invention further relates to processes for the preparation of compounds of formula (Ia) or (Ib), use of the compounds as active ingredients in pharmaceuticals, and pharmaceutical preparations comprising them. The pharmaceutical preparations can be used to inhibit excessive proliferation of a eukaryotic cell, e.g., a mammalian cell, an insect cell, a plant cell, and/or a fungal cell, and/or prevent dedifferentiation of such cells.

Accordingly, the present compounds can be used in the treatment of proliferative disorders in mammals, especially humans, marked by unwanted proliferation of endogenous tissue.

BRIEF DESCRIPTION OF THE DRAWINGS OF THE INVENTION

FIGS. 1 to 6 represent schemes of preferred processes for the preparation of example compounds of the present invention.

DETAILED DESCRIPTION OF THE INVENTION

The present compounds are inhibitors of CDKs, particularly CDK/cyclin complexes and find use in antiproliferative therapies for diseases characterized by excessive cell growth such as cancers, cardiovascular abnormalities, nephrological disorders, psoriasis, Alzheimer's disease, immunological disorders involving unwanted proliferation of leukocytes, restenosis and other proliferative smooth muscle disorders, viral infections, and mycotic infections.

Listed below are definitions of various terms used to describe the compounds of the present invention. These definitions apply to the terms as they are used throughout the specification (unless they are otherwise limited in specific instances) either individually or as part of a larger group. They should not be interpreted in the literal sense. They are not general definitions and are relevant only for this application.

The terms "flavone", "chromone" and "benzopyranone" or their analogs mean compounds that can be represented by the following basic structure:

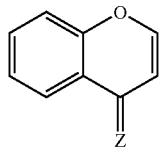

wherein Z may represent an oxygen atom, a sulfur atom or $NR_8$ (where $R_8$ is defined as hereinabove).

As used herein, the term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. Furthermore, unless stated otherwise, the term "alkyl" includes unsubstituted alkyl groups as well as alkyl groups, which are substituted by one or more different substituents. In preferred embodiments, a straight chain or branched chain alkyl has 30 or fewer carbon atoms in its backbone (e.g., $C_1$-$C_{30}$ for straight chain, $C_3$-$C_{30}$ for branched chain), and more preferably 20 or fewer. Likewise, preferred cycloalkyls have from 3-10 carbon atoms in their ring structure, and more preferably have 5, 6 or 7 carbons in the ring structure. Examples of alkyl residues containing from 1 to 20 carbon atoms are: methyl, ethyl, propyl, butyl, pentyl, hexyl, heptyl, octyl, nonyl, decyl, undecyl, dodecyl, tetradecyl, hexadecyl, octadecyl and eicosyl, the n-isomers of all these residues, isopropyl, isobutyl, 1-methylbutyl, isopentyl, neopentyl, 2,2-dimethylbutyl, 2-methylpentyl, 3-methylpentyl, isohexyl, 2,3,4-trimethylhexyl, isodecyl, sec-butyl, or tert-butyl.

Examples of cycloalkyl residues containing 3, 4, 5, 6 or 7 ring carbon atoms are cyclopropyl, cyclobutyl, cyclopentyl, cyclohexyl or cycloheptyl which can also be substituted. The term alkyl as used herein also comprises cycloalkyl-substituted alkyl groups and alkyl-substituted cycloalkyl groups. Examples of cycloalkyl-substituted alkyl groups are: cyclopropylmethyl-, cyclobutylmethyl-, cyclopentylmethyl-, cyclohexylmethyl-, cycloheptylmethyl-, 1-cyclopropylethyl-, 1-cyclobutylethyl-, 1-cyclopentylethyl-, 1-cyclohexylethyl-, 1-cycloheptylethyl-, 2-cyclopropylethyl-, 2-cyclobutylethyl-, 2-cyclopentylethyl-, 2-cyclohexylethyl-, 2-cycloheptylethyl-, 3-cyclopropylpropyl-, 3-cyclobutylpropyl-, 3-cyclopentylpropyl-, 3-cyclohexylpropyl-, 3-cycloheptylpropyl-, etc. in which groups the cycloalkyl group as well as acyclic group can be substituted.

Of course, a cyclic alkyl group has to contain at least three carbon atoms. Thus, a group like ($C_1$-$C_8$)-alkyl is to be understood as comprising, among others, saturated acyclic ($C_1$-$C_8$)-alkyl, ($C_3$-$C_8$)-cycloalkyl, alkyl-cycloalkyl groups or cycloalkyl-alkyl groups like ($C_3$-$C_7$)-cycloalkyl-($C_1$-$C_3$)-alkyl-, wherein the total number of carbon atoms can range from 4 to 8. Similarly, a group like ($C_1$-$C_4$)-alkyl is to be understood as comprising, among others, saturated acyclic ($C_1$-$C_4$)-alkyl, ($C_3$-$C_4$)-cycloalkyl, cyclopropyl-methyl- or methyl-cyclopropyl-.

Unless stated otherwise, the term "alkyl" preferably comprises acyclic saturated hydrocarbon residues which have from 1 to 6 carbon atoms and which can be linear or branched, and cyclic alkyl groups containing from 3 to 8 ring carbon atoms, in particular from 3 to 6 ring carbon atoms. A particular group of saturated acyclic alkyl residues is formed by ($C_1$-$C_4$)-alkyl residues like methyl, ethyl, n-propyl, isopropyl, n-butyl, isobutyl, sec-butyl and tert-butyl.

Unless stated otherwise, and irrespective of any specific substituents bonded to alkyl groups that are indicated in the definition of the compounds of the formula (Ia) or (Ib), alkyl groups can in general be unsubstituted or substituted by one or more, for example 1, 2, 3, 4 or 5 identical or different substituents. Any kind of substituents present in substituted alkyl residues can be present in any desired position provided that the substitution does not lead to an unstable molecule. A substituted alkyl refers to an alkyl residue in which one or more, for example, 1, 2, 3, 4 or 5, hydrogen atoms are replaced with substituents, for example, halogen, hydroxyl, carbonyl, alkoxyl, ester, ether, cyano, amino, amido, imino, sulfhydryl, alkylthio, thioester, sulfonyl, nitro, azido, acyloxy, heterocyclo, aralkyl, or an aryl or heteroaryl group. The carbon backbone of the alkyl group may be interrupted by heteroatoms such as oxygen, sulfur or nitrogen. Examples of substituted acyclic alkyls are hydroxymethyl, hydroxyethyl, 2-hydroxyethyl, aminoethyl or morpholinoethyl. Examples of substituted cycloalkyl groups are cycloalkyl groups which carry as substituent one or more, for example 1, 2, 3, 4 or 5, identical or different acyclic alkyl groups, for example acyclic ($C_1$-$C_4$)-alkyl groups like methyl groups. Examples of substituted cycloalkyl groups are 4-methylcyclohexyl, 4-tert-butylcyclohexyl or 2,3-dimethylcyclopentyl.

It will be understood by those skilled in the art that the moieties substituted on the hydrocarbon chain can themselves be substituted, if appropriate. For example, the substituents of a substituted alkyl may include substituted and unsubstituted forms of amino, imino, amido, sulfonyl (including sulfonate and sulfonamide), as well as ether, alkylthio, carbonyl (including ketones, aldehydes, carboxylates, and esters), —$CF_3$, —CN and the like. Cycloalkyls can be further substituted with alkyl, alkenyl, alkoxyl, alkylthio, aminoalkyls, carbonyl-substituted alkyl, —$CF_3$, cyano (CN), and the like.

The terms "alkoxyl" or "alkoxy" as used herein refers to an alkyl group, as defined above, having an oxygen radical attached thereto. Representative alkoxyl groups include methoxy, ethoxy, propoxy, tert-butoxy and the like.

The term "aralkyl" as used herein refers to an alkyl group, as defined above, substituted with an aryl or heteroaryl group (defined below). Exemplary aralkyl groups include benzyl, —(CH$_2$)-pyridyl, etc.

The terms "alkenyl" and "alkynyl" refer to unsaturated aliphatic groups analogous in length and possible substitution to the alkyls described above, but that contain at least one double or triple bond, respectively, for example 1, 2 or 3 double bonds and/or triple bonds, provided that the double bonds are not located within a cyclic alkyl group in such a manner that an aromatic system results. Examples of alkenyl groups include vinyl, 1-propenyl, 2-propenyl, 2-butenyl, 2-methyl-1-propenyl or 3-methyl-2-butenyl. Examples of alkynyl groups include ethynyl, 2-propynyl, 2-butynyl or 3-butynyl. Alkyl groups can also be unsaturated when they are substituted.

Furthermore, unless otherwise stated, the terms "alkenyl" and "alkynyl" include unsubstituted alkenyl and alkynyl groups as well as alkenyl and alkynyl groups which are substituted by one or more, for example 1, 2, 3, 4 or 5, identical or different groups mentioned above for alkyl, for example, aminoalkenyl, aminoalkynyl, amidoalkenyl, amidoalkynyl, iminoalkenyl, iminoalkynyl, thioalkenyl, thioalkynyl, carbonyl-substituted alkenyl or alkynyl, alkenoxyl or alkynoxyl.

The term "aryl" as used herein refers to monocyclic or polycyclic hydrocarbon groups having up to 14 ring carbon atoms in which at least one carbocyclic ring is present that has a conjugated pi electron system. Examples of $(C_6-C_{14})$-aryl residues are phenyl, naphthyl, biphenyl, fluorenyl or anthracenyl. Examples of $(C_6-C_{10})$-aryl residues are phenyl or naphthyl. Unless stated otherwise, and irrespective of any specific substituents bonded to aryl groups which are indicated in the definition of the compounds of formula (Ia) or (Ib), aryl residues, for example phenyl, naphthyl or fluorenyl, can in general be unsubstituted or substituted by one or more, for example 1, 2, 3, 4 or 5, identical or different substituents. Unless stated otherwise, substituents that can be present in substituted aryl groups are: F, Cl, Br, I, alkyl, alkenyl, alkynyl, $CF_3$, hydroxyl, aryloxy, amino, cyano, nitro, thiol, imine, amide or carbonyl (such as carboxyl, formate, carbamide, an ester, ketone or aldehyde), sulfhydryl, silyl ether, thiocarbonyl (such as thioester, thioacetate or thioformate), sulfonyl, aminoacid ester, or a heterocyclo group which is saturated, partially unsaturated or aromatic aryl residues can be bonded via any desired position, and in substituted aryl residues the substituents can be located in any desired position. For example, in monosubstituted phenyl residues the substituent can be located in the 2-position, the 3-position, the 4-position or the 5-position, with the 2-position being preferred. If the phenyl group carries two substituents, they can be located in 2,3-position, 2,4-position, 2,5-position, 2,6-position, 3,4-position or 3,5-position.

The terms "heterocycle" and "heterocyclo" refer to a saturated, partially unsaturated or aromatic monocyclic or polycyclic heterocyclic ring system containing 3, 4, 5, 6, 7, 8, 9, 10, 11, 12, 13 or 14 ring atoms of which 1, 2, 3 or 4 are identical or different heteroatoms selected from the series consisting of nitrogen, oxygen, sulfur and phosphorus. The heterocyclo group may, for example, have 1 or 2 oxygen atoms and/or 1 or 2 sulfur atoms, 1 to 4 nitrogen atoms and/or 1 or 2 phosphorus atoms in the ring. In monocyclic groups, heterocyclo preferably is a 3-membered, 4-membered, 5-membered, 6-membered or 7-membered ring, particularly preferably a 5-membered or 6-membered ring. Examples of such heterocyclo groups are piperazinyl and piperidinyl. In polycyclic groups, heterocyclo may comprise either fused rings in which two or more carbons are common to two adjoining rings, or bridged rings in which rings are joined through non-adjacent atoms. In polycyclic groups, heterocyclo preferably comprises two fused rings (bicyclic) one of which is a 5-membered or 6-membered heterocyclic ring and the other of which is a 5-membered or 6-membered heterocyclic ring. Exemplary bicyclic and tricyclic heterocyclic groups include benzoxazolyl, quinolyl, isoquinolyl, carbazolyl, indolyl, isoindolyl, phenoxazinyl, benzothiazolyl, benzimidazolyl, benzoxadiazolyl and benzofurazanyl.

The ring heteroatoms can be present in any desired number and in any position with respect to each other provided that the resulting heterocyclic system is known in the art and is stable and suitable as a subgroup in a drug substance. Preferred are heterocyclo groups having 1 or 2 identical or different heteroatoms from the group consisting of: nitrogen, oxygen and sulfur. Examples of such heterocyclo groups are: pyrrolyl, furyl, thiophen-yl, imidazolyl, oxazolyl, isoxazolyl thiazolyl, isothiazolyl triazolyl, pyrazolyl, pyridinyl, pyrazinyl, pyridazinyl, pyrimidinyl, azepinyl, tetrahydrothiophen-yl, tetrahydrofuran-yl, morpholinyl, thiomorpholinyl, tetrahydropyranyl, lactams, pyrrolidinyl, azetidinyl.

The heterocyclo group may be bonded via any ring carbon atom, and in the case of nitrogen heterocycles via any suitable ring nitrogen atom. Thus, for example, a pyrrolyl residue can be 1-pyrrolyl, 2-pyrrolyl or 3-pyrrolyl, a pyrrolidinyl residue can be 1-pyrrolidinyl (=pyrrolidino), 2-pyrrolidinyl or 3-pyrrolidinyl, and imidazolyl can be 1-imidazolyl, 2-imidazolyl, 4-imidazolyl or 5-imidazolyl.

In the group —NR$_9$R$_{10}$, R$_9$ and R$_{10}$ may, together with the nitrogen atom to which they are attached form a heterocyclic ring having one or more heteroatoms. Suitable examples of heterocyclic rings formed by R$_9$ and R$_{10}$, together with the nitrogen to which they are attached, are piperidine, pyrrolidine, morpholine, piperazinyl or imidazole, which can be unsubstituted or substituted as indicated below.

Heterocyclo comprises saturated heterocyclic ring systems which do not contain any double bonds within the rings, as well as mono-unsaturated and poly-unsaturated heterocyclic ring systems which contain one or more, for example 1, 2, 3, 4 or 5, double bonds within the rings provided that the resulting system is stable. Unsaturated rings may be non-aromatic or aromatic. Aromatic heterocyclo groups may also be referred to by the customary term "heteroaryl" for which all the definitions and explanations above and below relating to heterocyclo apply.

Unless stated otherwise, and irrespective of any substituents bonded to heterocyclo groups which are indicated in the definition of the compounds of formula (Ia) or (Ib), the heterocyclo group can be unsubstituted or substituted on ring carbon atoms with one or more, for example 1, 2, 3, 4 or 5 identical or different substituents. Each suitable ring nitrogen atom in a heterocyclo group can independently of each other be unsubstituted, i.e. carry a hydrogen atom, or can be substituted. Examples of substituents for the ring carbon and ring nitrogen atoms are: $(C_1-C_8)$-alkyl, in particular $(C_1-C_4)$-alkyl, alkoxy, halogen, hydroxyl, hydroxy-$(C_1-C_4)$-alkyl such as, for example, hydroxymethyl or 1-hydroxyethyl or 2-hydroxyethyl, alkenyl, alkynyl, $CF_3$, aryloxy, amino, cyano, nitro, thiol, imine, amide or carbonyl (such as carboxyl, formate, carbamide, an ester, ketone or aldehyde), silyl ether, thiocarbonyl (such as thioesters, a thioacetate or a thioformate), sulfonyl, aminoacid ester, heterocyclo, aryl or the like. The substituents can be present at one or more positions provided that a stable molecule results.

The term "heteroatom" as used herein means an atom of any element other than carbon or hydrogen. Preferred heteroatoms are nitrogen, oxygen, sulfur and phosphorous.

Halogen is fluorine, chlorine, bromine or iodine, preferably fluorine, chlorine or bromine.

It will be understood that "substitution" or "substituted with" includes the implicit proviso that such substitution is in accordance with permitted valence of the substituted atom and the substituent, as well as represents a stable compound, which does not readily undergo transformation such as by rearrangement, cyclization, elimination, etc.

It should be noted that any heteroatom with unsatisfied valences is assumed to have the hydrogen atom to satisfy the valences.

"Specific inhibitors" or "specific inhibition" implies the selectivity of the drug for its inhibitory effect towards a particular CDK-cyclin complex.

Certain compounds of the present invention may exist in particular geometric or stereoisomeric forms. Centers of asymmetry that are present in the compounds of formula (Ia) or (Ib) all independently of one another have S configuration or R configuration. The present invention includes all possible enantiomers and diastereomers in pure or substantially pure form and mixtures of two or more stereoisomers, for example mixtures of enantiomers and/or diastereomers, in all ratios. Thus, compounds according to the present invention which can exist as enantiomers can be present in enantiomerically pure form, both as levorotatory and as dextrorotatory antipodes, in the form of racemates and in the form of mixtures of the two enantiomers in all ratios. In the case of a cis/trans isomerism the invention includes both the cis form and the trans form as well as mixtures of these forms in all ratios. The preparation of individual stereoisomers can be carried out, if desired, by separation of a mixture by customary methods. For example, the racemic forms can be resolved by physical methods, such as fractional crystallization or separation by chiral column chromatography. The individual optical isomers can be synthesized in the optically pure form by the use of enzymes or through asymmetric synthesis. A particular enantiomer of a compound of the present invention may be prepared by derivatization with a chiral auxiliary whereby the resulting diastereomeric mixture is separated and the auxiliary group cleaved to provide the pure desired enantiomer. Alternatively, where the compound contains a basic functional group such as an amino or an acidic functional group such as a carboxyl, diastereomeric salts are formed by reacting the compound with an appropriate optically active acid or base, respectively. The diastereomeric salts thus formed are separated by fractional crystallization or chromatographic means well known in the art and the pure enantiomers are subsequently isolated from the diastereomeric salts. The separation of a mixture of stereoisomers can be carried out at the stage of the compounds of formula (Ia) or (Ib) or at the stage of an intermediate during the synthesis. The present invention also includes all tautomeric forms of the compounds of formula (Ia) or (Ib). Additional asymmetric carbon atoms may be present in a substituent such as an alkyl group. All such isomers, as well as mixtures thereof, are intended to be included in this invention.

In case the compounds according to formula (Ia) or (Ib) contain one or more acidic or basic groups, the invention also comprises their corresponding pharmaceutically or toxicologically acceptable salts, in particular their pharmaceutically utilizable salts.

Compounds of formula (Ia) or (Ib) which contain one or more basic groups, i.e. groups which can be protonated, can be present and can be used according to the invention in the form of their addition salts with non-toxic inorganic or organic acids.

Examples of suitable inorganic acids include: boric acid, perchloric acid, hydrochloric acid, hydrobromic acid, sulfuric acid, sulfamic acid, phosphoric acid, nitric acid and other inorganic acids known to the person skilled in the art. Examples of suitable organic acids include: acetic acid, propionic acid, succinic acid, glycolic acid, stearic acid, lactic acid, malic acid, tartaric acid, citric acid, ascorbic acid, pamoic acid, maleic acid, hydroxymaleic acid, phenylacetic acid, glutamic acid, benzoic acid, salicylic acid, sulfanilic acid, 2-acetoxybenzoic acid, fumaric acid, toluenesulfonic acid, methanesulfonic acid, ethane disulfonic acid, oxalic acid, isethionic acid, ketoglutaric acid, benzenesulfonic acid, glycerophosphoric acid and other organic acids known to the person skilled in the art. The compounds of formula (Ia) or (Ib) which contain acidic groups can be used according to the invention, for example, as alkali metal salts like Li, Na, and K salts, as alkaline earth metal salts like Ca, Mg salts, as aluminium salts, as salts of organic bases such as lysine, arginine, guanidine, diethanolamine, choline, tromethamine, or as salts with ammonia. The pharmaceutically acceptable salts of the present invention can be synthesized from the subject compound which contains a basic or acidic moiety by conventional chemical methods. Generally the salts are prepared by contacting the free base or acid with stoichiometric amounts or with an excess of the desired salt-forming inorganic or organic acid or base in a suitable solvent or dispersant or by anion exchange or cation exchange with other salts. Suitable solvents are, for example, ethyl acetate, ether, alcohols, acetone, THF, dioxane or mixtures of these solvents.

The present invention furthermore includes all solvates of compounds of formula (Ia) or (Ib), for example hydrates or adducts with alcohols and also derivatives and prodrugs of the compounds of formula (Ia) or (Ib) which contain physiologically tolerable and cleavable groups, for example esters and amides.

Various polymorphs of compounds of general formula (Ia) or (Ib) forming part of this invention may be prepared by crystallization of compounds of formula (Ia) or (Ib) under different conditions. For example, using different commonly used solvents or their mixtures for crystallization; crystallization at different temperatures; various modes of cooling, ranging from very fast to very slow cooling during crystallizations. Polymorphs may also be obtained by heating or melting the compound followed by gradual or fast cooling. The presence of polymorphs may be determined by IR spectroscopy, solid probe NMR spectroscopy, differential scanning calorimetry, powder X-ray diffraction or such other techniques.

Preferred compounds are those in which one or more of the groups contained therein have the meanings given below, with all the combinations of preferred substituent definitions being a subject of the present invention. With respect to all preferred compounds of formula (Ia) or (Ib) the present invention also includes all stereoisomeric forms and mixtures thereof in all ratios and their pharmaceutically acceptable salts. Further, also all preferred compounds of formula (Ia) or (Ib) are a subject of the present invention in the form of their prodrugs and other derivatives, for example in the form of their esters and amides.

In a first preferred embodiment, the present invention relates to compounds of general formula (Ic), prodrugs, tautomeric forms, stereoisomers, optical isomers, pharmaceutically acceptable salts, pharmaceutically acceptable solvates or polymorphs thereof

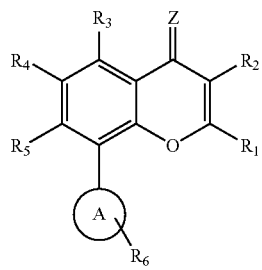

(Ic)

wherein

R₁ is aryl, unsubstituted or substituted by at least one substituent selected from: halogen, $C_1$-$C_4$-alkyl, $C_1$-$C_4$-alkoxy, $C_2$-$C_6$-alkenyl, $C_3$-$C_6$-alkynyl, $C_2$-$C_4$-alkanoyl, nitro, $NR_9R_{10}$, $SR_{11}$, trifluoromethyl, hydroxyl, cyano, carboxy, $C_1$-$C_4$-alkoxycarbonyl and —$C_1$-$C_4$-alkylenehydroxyl; saturated, partially unsaturated or aromatic heterocycle having 1, 2, 3 or 4 identical or different heteroatoms selected from: nitrogen, oxygen, sulfur and phosphorus, wherein the heterocycle is unsubstituted or substituted by at least one substituent selected from: halogen, $C_1$-$C_4$-alkyl, $C_1$-$C_4$-alkoxy, $C_2$-$C_6$-alkenyl, $C_3$-$C_6$-alkynyl, $C_2$-$C_4$-alkanoyl, nitro, $NR_9R_{10}$, $SR_{11}$, trifluoromethyl, hydroxyl, cyano, carboxy, $C_1$-$C_4$-alkoxycarbonyl and —$C_1$-$C_4$-alkylenehydroxyl; $NR_9R_{10}$; $OR_{11}$; or $SR_{11}$;

R₂ is hydrogen; $C_1$-$C_6$-alkyl; aryl, unsubstituted or substituted by at least one substituent selected from: halogen, $C_1$-$C_4$-alkyl, $C_1$-$C_4$-alkoxy, $C_2$-$C_6$-alkenyl, $C_3$-$C_6$-alkynyl, $C_2$-$C_4$-alkanoyl, nitro, $NR_9R_{10}$, $SR_{11}$, trifluoromethyl, hydroxyl, cyano, carboxy, $C_1$-$C_4$-alkoxycarbonyl and —$C_1$-$C_4$-alkylenehydroxyl; saturated, partially unsaturated or aromatic heterocycle having 1, 2, 3 or 4 identical or different heteroatoms selected from: nitrogen, oxygen, sulfur and phosphorus and which is unsubstituted or substituted by at least one substituent selected from: halogen, $C_1$-$C_4$-alkyl, $C_1$-$C_4$-alkoxy, $C_2$-$C_6$-alkenyl, $C_3$-$C_6$-alkynyl, $C_2$-$C_4$-alkanoyl, nitro, $NR_9R_{10}$, $SR_{11}$, trifluoromethyl, hydroxyl, cyano, carboxy, $C_1$-$C_4$-alkoxycarbonyl and —$C_1$-$C_4$-alkylenehydroxyl; $OR_{11}$; halogen; cyano; nitro; $NR_9R_{10}$; or $SR_{11}$;

R₃, R₄ and R₅ are each independently selected from: hydrogen; $C_1$-$C_6$-alkyl; halogen; $OR_{11}$; aryl $C_1$-$C_4$-alkoxy; $C_1$-$C_4$-alkylcarbonyloxy; $C_1$-$C_4$-alkoxycarbonyloxy; arylcarbonyloxy; carboxy; cyano; nitro; $NR_9R_{10}$; $SR_{11}$; aryl-$C_1$-$C_4$-alkylthio; $SO_2$—$C_1$-$C_4$-alkyl; $SO_2$-aryl; $SO_2NR_9R_{10}$; aryl; and saturated, partially unsaturated or aromatic heterocycle having 1, 2, 3 or 4 identical or different heteroatoms selected from: nitrogen, oxygen, sulfur and phosphorus;

R₆ is —$C_1$-$C_4$-alkyleneOR$_{11}$;

R₈ is hydrogen; $C_1$-$C_4$-alkyl; aryl; carboxamide; sulfonamide; $NR_9R_{10}$; or $OR_{11}$;

R₉ and R₁₀ are each independently selected from: hydrogen; $C_1$-$C_6$-alkyl; aryl; $C_1$-$C_4$-alkanoyl; heterocycle, which contains 1, 2, 3 or 4 heteroatoms selected from: nitrogen, oxygen, sulfur and phosphorus; $C_1$-$C_4$-alkoxycarbonyl; $C_1$-$C_4$-alkylcarbonyl; arylcarbonyl; heterocyclocarbonyl, wherein the heterocyclo- contains 1, 2, 3 or 4 heteroatoms selected from: nitrogen, oxygen, sulfur and phosphorus; carboxamide; and sulfonamide; wherein the aryl and heterocycle or heterocyclo- are either unsubstituted or substituted by at least one substituent selected from: halogen, $C_1$-$C_4$-alkyl, $C_1$-$C_4$-alkoxy, $C_2$-$C_6$-alkenyl, $C_3$-$C_6$-alkynyl, $C_2$-$C_4$-alkanoyl, nitro, $NR_9R_{10}$, $SR_{11}$, trifluoromethyl, hydroxyl, cyano, carboxy, $C_1$-$C_4$-alkoxycarbonyl and —$C_1$-$C_4$-alkylenehydroxyl; or R₉ and R₁₀, together with the nitrogen atom to which they are bonded, form a heterocyclic ring which can have at least one further heteroatom selected from: nitrogen, oxygen and sulfur and which is saturated, partially unsaturated or aromatic, the heterocyclic ring being either unsubstituted or substituted by at least one substituent selected from: halogen, $C_1$-$C_4$-alkyl, $C_1$-$C_4$-alkoxy, $C_2$-$C_6$-alkenyl, $C_3$-$C_6$-alkynyl, $C_2$-$C_4$-alkanoyl, nitro, $NR_9$ and $R_{10}$, $SR_{11}$, trifluoromethyl, hydroxyl, cyano, carboxy, —$C_1$-$C_4$-alkoxycarbonyl and —$C_1$-$C_4$-alkylenehydroxyl;

R₁₁ is hydrogen; $C_1$-$C_6$-alkyl; $C_1$-$C_4$-alkanoyl; aryl, unsubstituted or substituted by at least one substituent selected from: halogen, $C_1$-$C_4$-alkyl, $C_1$-$C_4$-alkoxy, $C_2$-$C_6$-alkenyl, $C_3$-$C_6$-alkynyl, $C_2$-$C_4$-alkanoyl, nitro, $NR_9R_{10}$, $SR_{11}$, trifluoromethyl, hydroxyl, cyano, carboxy, $C_1$-$C_4$-alkoxycarbonyl and —$C_1$-$C_4$-alkylenehydroxyl; or $C_1$-$C_4$-alkoxycarbonyl-;

Z is an oxygen atom; a sulfur atom; or $NR_8$;

A is a 5-, 6- or 7-membered ring; wherein:

(I) the 5-membered ring is saturated or unsaturated and represented by any one of the general structures (i) to (v);

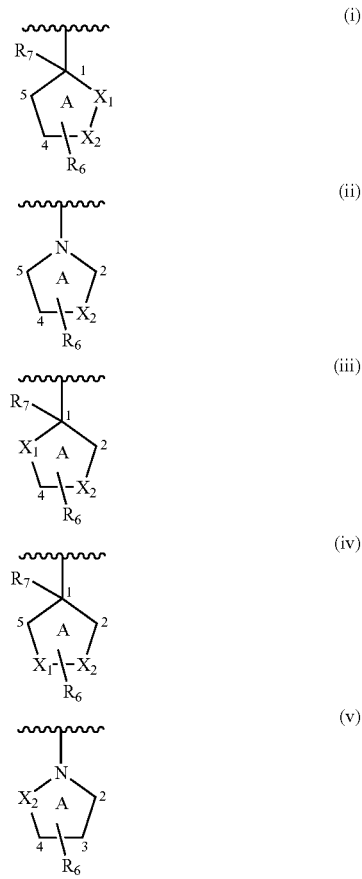

wherein $X_1$ and $X_2$ are each independently selected from: a methylene group and a heteroatom selected from: an oxygen atom, a sulfur atom, $S(O)_p$ and a nitrogen atom, provided that at least one of $X_1$ and $X_2$ is a heteroatom, and wherein the nitrogen atom is at least monosubstituted by $R_{13}$, wherein $R_{13}$ is selected from: hydrogen; $C_1$-$C_6$-alkyl, unsubstituted or substituted by at least one substituent selected from: halogen, hydroxyl, carboxyl, $C_1$-$C_4$-alkoxy, amino, nitro, $C_1$-$C_4$-alkylthio, sulfhydryl and sulfonyl; $C_2$-$C_6$-alkenyl, unsubstituted or substituted by at least one substituent selected from: halogen, hydroxyl, carboxyl, $C_1$-$C_4$-alkoxy, amino, nitro, $C_1$-$C_4$-alkylthio-, sulfhydryl and sulfonyl; aryl, unsubstituted or substituted by at least one substituent selected from: halogen, $C_1$-$C_4$-alkyl, $C_1$-$C_4$-alkoxy, $C_2$-$C_6$-alkenyl, $C_3$-$C_6$-alkynyl, $C_2$-$C_4$-alkanoyl, nitro, $NR_9R_{10}$, $SR_{11}$, trifluoromethyl, hydroxyl, cyano, carboxy, $C_1$-$C_4$-alkoxycarbonyl and —$C_1$-$C_4$-alkylenehydroxyl; hydroxyl; $C_1$-$C_4$-alkoxy; $C_1$-$C_4$-alkylcarbonyl; cyano; —$SO_2R_{10}$; and —CO—$(CH_2)_m$—$R_{14}$;

$R_6$ is a substituent as defined above on at least one carbon atom ring member;

$R_7$ is hydrogen; $C_1$-$C_4$-alkyl; $C_1$-$C_4$-alkylcarbonyl; or arylcarbonyl;

$R_{14}$ is hydrogen; $C_1$-$C_4$-alkyl; hydroxyl; $NR_9R_{10}$; halogen; —SH; —S—$C_1$-$C_4$; —S-aryl; aryl; wherein the aryl is unsubstituted or substituted by at least one substituent selected from: halogen, $C_1$-$C_4$-alkyl, $C_1$-$C_4$-alkoxy, $C_2$-$C_6$-alkenyl, $C_3$-$C_6$-alkynyl, $C_2$-$C_4$-alkanoyl, nitro, $NR_9R_{10}$, $SR_{11}$, trifluoromethyl, hydroxyl, cyano, carboxy, $C_1$-$C_4$-alkoxycarbonyl and —$C_1$-$C_4$-alkylenehydroxyl; a heterocycle containing 1, 2, 3 or 4 heteroatoms selected from: nitrogen, oxygen, sulfur and phosphorus, the heterocycle being unsubstituted or substituted by at least one substituent selected from: halogen, $C_1$-$C_4$-alkyl, $C_1$-$C_4$-alkoxy, $C_2$-$C_6$-alkenyl, $C_3$-$C_6$-alkynyl, $C_2$-$C_4$-alkanoyl, nitro, $NR_9R_{10}$, $SR_{11}$, trifluoromethyl, hydroxyl, cyano, carboxy, $C_1$-$C_4$-alkoxycarbonyl and —$C_1$-$C_4$-alkylenehydroxyl;

p is an integer of 1 or 2; and m is an integer of 0 to 6;

(II) the 6-membered ring is a saturated ring of the general structure (vi):

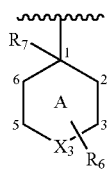

(vi)

wherein $X_3$ is an oxygen atom, a sulfur atom, $S(O)_p$, or a nitrogen atom, wherein the nitrogen atom is at least monosubstituted by $R_{13}$, wherein $R_{13}$ is as defined above;

$R_6$ is a substituent as defined above on at least one ring member at any of positions 2, 3, 5 or 6; $R_7$ is hydrogen; $C_1$-$C_4$-alkyl; $C_1$-$C_4$-alkylcarbonyl; or arylcarbonyl; and (III) the 7-membered ring is a saturated ring of the general structure (vii);

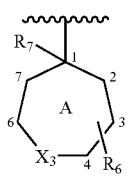

(vii)

wherein $X_3$ is an oxygen atom, a sulfur atom, $S(O)_p$, or a nitrogen atom, wherein the nitrogen atom is at least monosubstituted by $R_{13}$, wherein $R_{13}$ is as defined above;

$R_6$ is a substituent as defined above on at least one ring member at any of positions 2, 3, 4, 6 or 7; and $R_7$ is hydrogen; $C_1$-$C_4$-alkyl; $C_1$-$C_4$-alkylcarbonyl; or arylcarbonyl.

In a second preferred embodiment of the compounds of the formula (Ic) above, the groups $R_1$ to $R_5$, $R_7$, $R_9$ to $R_{11}$, $R_{13}$, $R_{14}$, Z and A, independently from each other, have the preferred meanings given below:

$R_1$ is phenyl, which is unsubstituted or substituted by 1, 2, or 3 identical or different substituents selected from: halogen, $C_1$-$C_4$-alkyl, $C_1$-$C_4$-alkoxy, nitro, $NR_9R_{10}$, $SR_{11}$, trifluoromethyl, hydroxyl, cyano, carboxy, $C_1$-$C_4$-alkoxycarbonyl and —$C_1$-$C_4$-alkylenehydroxyl, or is a heterocycle, which is a saturated, partially unsaturated or aromatic ring containing 5 or 6 ring atoms of which 1, 2 or 3 are identical or different heteroatoms selected from: nitrogen, oxygen, sulfur, and phosphorus, and where the heterocycle is unsubstituted or substituted by 1, 2, or 3 identical or different substituents selected from: halogen, $C_1$-$C_4$-alkyl, $C_1$-$C_4$-alkoxy, nitro, $NR_9R_{10}$, $SR_{11}$, trifluoromethyl, hydroxyl, cyano, carboxy, $C_1$-$C_4$-alkoxycarbonyl and —$C_1$-$C_4$-alkylenehydroxyl;

$R_2$ is hydrogen; $C_1$-$C_6$-alkyl; phenyl, which is unsubstituted or substituted by 1, 2, or 3 identical or different substituents selected from: halogen, $C_1$-$C_4$-alkyl, $C_1$-$C_4$-alkoxy, nitro, $NR_9R_{10}$, $SR_{11}$, trifluoromethyl, hydroxyl, cyano, carboxy, $C_1$-$C_4$-alkoxycarbonyl and —$C_1$-$C_4$-alkylenehydroxyl; $OR_{11}$; halogen; cyano; nitro; $NR_9R_{10}$ or $SR_{11}$;

$R_3$, $R_4$ and $R_5$ are each independently selected from: hydrogen, $C_1$-$C_4$-alkyl, halogen, $OR_{11}$, $C_1$-$C_4$alkylcarbonyloxy, $NR_9R_{10}$, $SO_2NR_9R_{10}$, carboxyl, cyano and nitro;

Z is an oxygen or sulfur atom;

A is a 5- or 6-membered ring; wherein:

in the 5-membered saturated or unsaturated ring represented by any one of the general structures (i) to (v), $X_1$ and $X_2$ are each independently selected from: a methylene group and a heteroatom selected from: oxygen, sulfur, and nitrogen, provided that at least one of $X_1$ and $X_2$ is a heteroatom, and wherein the nitrogen atom is at least monosubstituted by $R_{13}$, wherein $R_{13}$ is selected from: hydrogen; unsubstituted $C_1$-$C_6$-alkyl; or $C_1$-$C_6$-alkyl substituted by halogen, hydroxyl or carboxyl; $C_2$-$C_6$-alkenyl; hydroxyl; $C_1$-$C_6$-alkoxy; $C_1$-$C_4$-alkylcarbonyl; toluenesulfonyl; cyano; $SO_2R_{10}$; —CO—$(CH_2)_m$—$R_{14}$; and phenyl, which is unsubstituted or substituted by at least one substituent selected from: halogen, $C_1$-$C_4$-alkyl, $C_1$-$C_4$-alkoxy, nitro, $NR_9R_{10}$, $SR_{11}$, trifluoromethyl, hydroxyl, cyano, carboxy, $C_1$-$C_4$-alkoxycarbonyl and —$C_1$-$C_4$-alkylenehydroxyl; and $R_7$ is hydrogen;

in the 6-membered saturated ring of the general structure (vi), $X_3$ is an oxygen atom, a sulfur atom, or a nitrogen atom, wherein the nitrogen atom is at least monosubstituted by $R_{13}$, wherein $R_{13}$ is selected from: hydrogen; unsubstituted $C_1$-$C_6$-alkyl; or $C_1$-$C_6$-alkyl substituted by halogen, hydroxyl, or carboxyl; $C_2$-$C_6$-alkenyl; hydroxyl; $C_1$-$C_6$-alkoxy; $C_1$-$C_4$-alkylcarbonyl; toluenesulfonyl; cyano; $SO_2R_{10}$; —CO—$(CH_2)_m$—$R_{14}$; and phenyl, which is unsubstituted or substituted by at least one substituent selected from: halogen, $C_1$-$C_4$-alkyl, $C_1$-$C_4$-alkoxy, nitro, $NR_9R_{10}$, $SR_{11}$, trifluoromethyl, hydroxyl, cyano, carboxy, $C_1$-$C_4$-alkoxycarbonyl and —$C_1$-$C_4$-alkylenehydroxyl; and $R_7$ is hydrogen;

$R_9$ and $R_{10}$ are each independently selected from: hydrogen, $C_1$-$C_4$-alkyl, $C_1$-$C_4$-alkanoyl, $C_1$-$C_4$-alkoxycarbonyl, $C_1$-$C_4$-alkylcarbonyl, carboxamide and sulfonamide, or $R_9$ and $R_{10}$, together with the nitrogen atom to which they are bonded, form a 3-, 4-, 5- or 6-membered heterocyclic ring which can have at least one further heteroatom selected from: nitrogen, oxygen and sulfur, which ring is saturated, partially unsaturated or aromatic, and either unsubstituted or substituted by at least one substituent selected from: halogen, $C_1$-$C_4$-alkyl, $C_1$-$C_4$-alkoxy, $C_2$-$C_6$alkenyl, $C_3$-$C_6$-alkynyl, $C_2$-$C_4$-alkanoyl, nitro, $NR_9R_{10}$, $SR_{11}$, trifluoromethyl, hydroxyl, cyano, carboxy, $C_1$-$C_4$-alkoxycarbonyl and —$C_1$-$C_4$-alkylenehydroxyl;

$R_{11}$, is hydrogen, $C_1$-$C_4$-alkyl, $C_1$-$C_4$-alkanoyl, or $C_1$-$C_4$-alkoxycarbonyl; and $R_{14}$ is hydrogen, $C_1$-$C_4$-alkyl, hydroxyl, —$NR_9R_{10}$, halogen, —SH, or —S—$C_1$-$C_4$-alkyl.

In a third preferred embodiment of compounds of the general formula (Ic), A is a 5-membered saturated or unsaturated ring represented by any one of the general structures (i) to (iv);

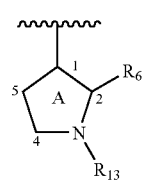

(i)

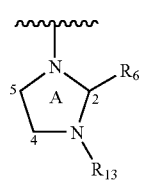

(ii)

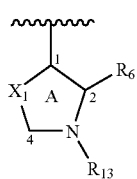

(iii)

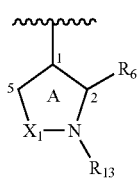

(iv)

wherein $X_1$ is either a methylene group or a heteroatom selected from: oxygen, sulfur, and nitrogen, except that in structures (ii) and (iv) $X_1$ is either a methylene group or a nitrogen atom; and $R_6$ and $R_{13}$ are as defined above; or a 6-membered saturated ring represented by the general structure (vi):

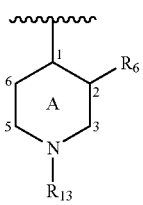

(vi)

wherein $R_6$ and $R_{13}$ are as defined above.

In a fourth embodiment of the compounds of the formula (Ic), $R_1$ is phenyl, which is unsubstituted or substituted by 1, 2, or 3 identical or different substituents selected from: halogen, $C_1$-$C_4$-alkyl, $C_1$-$C_4$-alkoxy, nitro, $NR_9R_{10}$, $SR_{11}$, trifluoromethyl, hydroxyl, cyano, carboxy, $C_1$-$C_4$-alkoxycarbonyl and —$C_1$-$C_4$-alkylenehydroxyl, or is a heterocycle, which is a saturated, partially unsaturated or aromatic ring containing 6 ring atoms of which 1, 2 or 3 are identical or different heteroatoms selected from: nitrogen, oxygen and sulfur, and where the heterocycle is unsubstituted or substituted by 1, 2, or 3 identical or different substituents selected from: halogen, $C_1$-$C_4$-alkyl, $C_1$-$C_4$-alkoxy, nitro, $NR_9R_{10}$, $SR_{11}$, trifluoromethyl, hydroxyl, cyano, carboxy, $C_1$-$C_4$-alkoxycarbonyl and —$C_1$-$C_4$-alkylenehydroxyl;

$R_2$ and $R_4$ are hydrogen; and $R_3$ and $R_5$ are each independently selected from: hydroxyl, $C_1$-$C_4$-alkoxyl and $C_1$-$C_4$-alkylcarbonyloxy.

In a first alternative embodiment, the present invention relates to compounds of general formula (Ig) prodrugs, tautomeric forms, stereoisomers, optical isomers, pharmaceutically acceptable salts, pharmaceutically acceptable solvates or polymorphs thereof

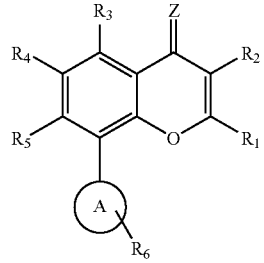

(Ig)

wherein $R_1$ is aryl, unsubstituted or substituted by at least one substituent selected from: halogen, $C_1$-$C_4$-alkyl, $C_1$-$C_4$-alkoxy, $C_2$-$C_6$-alkenyl, $C_3$-$C_6$-alkynyl, $C_2$-$C_4$-alkanoyl, nitro, $NR_9R_{10}$, $SR_{11}$, trifluoromethyl, hydroxyl, cyano, carboxy, —$C_1$-$C_4$-alkoxycarbonyl and —$C_1$-$C_4$-alkylenehydroxyl; saturated, partially unsaturated or aromatic heterocycle having 1, 2, 3 or 4 identical or different heteroatoms selected from: nitrogen, oxygen, sulfur and phosphorus, wherein the heterocycle is unsubstituted or substituted by at least one substituent selected from: halogen, $C_1$-$C_4$-alkyl, $C_1$-$C_4$-alkoxy, $C_2$-$C_6$-alkenyl, $C_3$-$C_6$-alkynyl, $C_2$-$C_4$-alkanoyl, nitro, $NR_9R_{10}$, $SR_{11}$, trifluoromethyl, hydroxyl, cyano, carboxy, $C_1$-$C_4$-alkoxycarbonyl and —$C_1$-$C_4$-alkylenehydroxyl; $NR_9R_{10}$; $OR_{11}$; or $SR_{11}$;

$R_2$ is hydrogen; $C_1$-$C_6$-alkyl; aryl, unsubstituted or substituted by at least one substituent selected from: halogen, $C_1$-$C_4$-alkyl, $C_1$-$C_4$-alkoxy, $C_2$-$C_6$-alkenyl, $C_3$-$C_6$-alkynyl, $C_2$-$C_4$-alkanoyl, nitro, $NR_9R_{10}$, $SR_{11}$, trifluoromethyl, hydroxyl, cyano, carboxy, —$C_1$-$C_4$-alkoxycarbonyl and —$C_1$-$C_4$-alkylenehydroxyl; saturated, partially unsaturated or aromatic heterocycle having 1, 2, 3 or 4 identical or different heteroatoms selected from: nitrogen, oxygen, sulfur and phosphorus, and which is unsubstituted or substituted by at least one substituent selected from: halogen, $C_1$-$C_4$-alkyl, $C_1$-$C_4$-alkoxy, $C_2$-$C_6$-alkenyl, $C_3$-$C_6$-alkynyl, $C_2$-$C_4$-alkanoyl, nitro, $NR_9R_{10}$, $SR_{11}$, trifluoromethyl, hydroxyl, cyano, carboxy, —$C_1$-$C_4$-alkoxycarbonyl and —$C_1$-$C_4$-alkylenehydroxyl; $OR_{11}$; halogen; cyano; nitro; $NR_9R_{10}$; or $SR_{11}$;

$R_3$, $R_4$ and $R_5$ are each independently selected from: hydrogen; $C_1$-$C_6$-alkyl; halogen; $OR_{11}$; aryl $C_1$-$C_4$-alkoxy; $C_1$-$C_4$-alkylcarbonyloxy; $C_1$-$C_4$-alkoxycarbonyloxy; arylcarbonyloxy; carboxy; cyano; nitro; $NR_9R_{10}$; $SR_{11}$, aryl-$C_1$-$C_4$-alkylthio; $SO_2$—$C_1$-$C_4$-alkyl; $SO_2$-aryl; $SO_2NR_9R_{10}$; aryl; and saturated, partially unsaturated or aromatic heterocycle having 1, 2, 3 or 4 identical or different heteroatoms selected from: nitrogen, oxygen, sulfur and phosphorus;

$R_6$ is hydrogen, $C_1$-$C_4$-alkyl, $C_1$-$C_4$-alkanoyl, hydroxyl, $C_1$-$C_4$-alkoxyl, —$C_1$-$C_4$-alkoxycarbonyl, —$C_1$-$C_4$-alkyleneOR$_{11}$, —$C_1$-$C_4$-alkylenehalo, —$C_1$-$C_4$-alkyleneNR$_9$R$_{10}$, —$C_1$-$C_4$-alkyleneC(O)OR$_9$, phenoxy, —NR$_9$R$_{10}$, SR$_{12}$, S(O)$_n$R$_{12}$, —C(O)R$_{12}$ or —C(S)R$_{12}$;

$R_8$ is hydrogen; $C_1$-$C_4$-alkyl, aryl, $C_1$-$C_4$-alkoxycarbonyl, carboxamide, sulfonamide, NR$_9$R$_{10}$ or OR$_{11}$;

$R_9$ and $R_{10}$ are each independently selected from: hydrogen; $C_1$-$C_6$-alkyl; aryl; $C_1$-$C_4$-alkanoyl; heterocycle, which has 1, 2, 3 or 4 heteroatoms selected from: nitrogen, oxygen, sulfur and phosphorus; $C_1$-$C_4$-alkoxycarbonyl; $C_1$-$C_4$-alkylcarbonyl; arylcarbonyl; heterocyclocarbonyl, wherein the heterocyclo- has 1, 2, 3 or 4 heteroatoms selected from: nitrogen, oxygen, sulfur and phosphorus; carboxamide, and sulfonamide; wherein the aryl and heterocycle or heterocyclo- are either unsubstituted or substituted by at least one substituent selected from: halogen, $C_1$-$C_4$-alkyl, $C_1$-$C_4$-alkoxy, $C_2$-$C_6$-alkenyl, $C_3$-$C_6$-alkynyl, $C_2$-$C_4$-alkanoyl, nitro, NR$_9$R$_{10}$, SR$_{11}$, trifluoromethyl, hydroxyl, cyano, carboxy, —$C_1$-$C_4$-alkoxycarbonyl and —$C_1$-$C_4$-alkylenehydroxyl; or $R_9$ and $R_{10}$, together with the nitrogen atom to which they are bonded, form a heterocyclic ring which can have at least one further heteroatom selected from: nitrogen, oxygen and sulfur and which is saturated, partially unsaturated or aromatic, the heterocyclic ring being either unsubstituted or substituted by at least one substituent selected from: halogen, $C_1$-$C_4$-alkyl, $C_1$-$C_4$-alkoxy, $C_2$-$C_6$-alkenyl, $C_3$-$C_6$-alkynyl, $C_2$-$C_4$-alkanoyl, nitro, NR$_9$R$_{10}$, SR$_{11}$, trifluoromethyl, hydroxyl, cyano, carboxy, —$C_1$-$C_4$-alkoxycarbonyl and —$C_1$-$C_4$-alkylenehydroxyl;

$R_{11}$ is hydrogen; $C_1$-$C_6$-alkyl; $C_1$-$C_4$-alkanoyl; aryl, unsubstituted or substituted by at least one substituent selected from: halogen, $C_1$-$C_4$-alkyl, $C_1$-$C_4$-alkoxy, $C_2$-$C_6$-alkenyl, $C_3$-$C_6$-alkynyl, $C_2$-$C_4$-alkanoyl, nitro, NR$_9$R$_{10}$, SR$_{11}$, trifluoromethyl, hydroxyl, cyano, carboxy, —$C_1$-$C_4$-alkoxycarbonyl and —$C_1$-$C_4$-alkylenehydroxyl; or $C_1$-$C_4$-alkoxycarbonyl;

$R_{12}$ is hydrogen; halogen; $C_1$-$C_6$-alkyl; aryl, unsubstituted or substituted by at least one substituent selected from: halogen, $C_1$-$C_4$-alkyl, $C_1$-$C_4$-alkoxy, $C_2$-$C_6$-alkenyl, $C_3$-$C_6$-alkynyl, $C_2$-$C_4$-alkanoyl, nitro, NR$_9$R$_{10}$, SR$_{11}$, trifluoromethyl, hydroxyl, cyano, carboxy, —$C_1$-$C_4$-alkoxycarbonyl and —$C_1$-$C_4$-alkylenehydroxyl; NR$_9$R$_{10}$; OR$_9$; or a heterocycle, unsubstituted or substituted by at least one substituent selected from: halogen, $C_1$-$C_4$-alkyl, $C_1$-$C_4$-alkoxy, $C_2$-$C_6$-alkenyl, $C_3$-$C_6$-alkynyl, $C_2$-$C_4$-alkanoyl, nitro, NR$_9$R$_{10}$, SR$_{11}$, trifluoromethyl, hydroxyl, cyano, carboxy, —$C_1$-$C_4$-alkoxycarbonyl and —$C_1$-$C_4$-alkylenehydroxyl;

Z is an oxygen atom; a sulfur atom; or NR$_8$;

A is a 5-membered saturated or unsaturated ring represented by any one of the general structures (i) to (v);

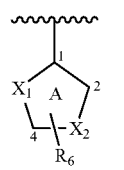

(i)

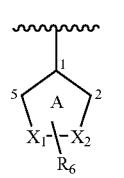

(ii)

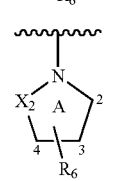

(iii)

(iv)

(v)

wherein $X_1$ and $X_2$ are each independently selected from: a methylene group and a heteroatom selected from: an oxygen atom, a sulfur atom, S(O)$_p$, and a nitrogen atom, provided that at least one of $X_1$ and $X_2$ is a heteroatom, and wherein the nitrogen atom is at least monosubstituted by $R_{13}$, wherein $R_{13}$ is selected from: hydrogen; $C_1$-$C_6$-alkyl, unsubstituted or substituted by at least one substituent selected from: halogen, hydroxyl, carboxyl, $C_1$-$C_4$-alkoxy, amino, nitro, $C_1$-$C_4$-alkylthio, sulfhydryl and sulfonyl; $C_2$-$C_6$-alkenyl, unsubstituted or substituted by at least one substituent selected from: halogen, hydroxyl, carboxyl, $C_1$-$C_4$-alkoxy, amino, nitro, $C_1$-$C_4$-alkylthio-, sulfhydryl and sulfonyl; aryl, unsubstituted or substituted by at least one substituent selected from: halogen, $C_1$-$C_4$-alkyl, $C_1$-$C_4$-alkoxy, $C_2$-$C_6$-alkenyl, $C_3$-$C_6$-alkynyl, $C_2$-$C_4$-alkanoyl, nitro, NR$_9$R$_{10}$, SR$_{11}$, trifluoromethyl, hydroxyl, cyano, carboxy, $C_1$-$C_4$-alkoxycarbonyl and —$C_1$-$C_4$-alkylenehydroxyl; hydroxyl; $C_1$-$C_4$-alkoxy; $C_1$-$C_4$-alkylcarbonyl; cyano; —SO$_2$R$_{10}$; and —CO—(CH$_2$)$_m$—R$_{14}$;

$R_6$ is a substituent as defined above on at least one carbon atom ring member;

$R_{14}$ is hydrogen, $C_1$-$C_4$-alkyl, hydroxyl, NR$_9$R$_{10}$, halogen, —SH, and —S—$C_1$-$C_4$-alkyl;

p is an integer of 1 or 2;

m is an integer of 0 to 6; and n is an integer of 1 or 2.

In a second embodiment of compounds of general formula (Ig), $R_1$ is phenyl, which is unsubstituted or substituted by 1, 2, or 3 identical or different substituents selected from: halogen, $C_1$-$C_4$-alkyl, $C_1$-$C_4$-alkoxy, nitro, NR$_9$R$_{10}$, SR$_{11}$, trifluoromethyl, hydroxyl, cyano, carboxy, $C_1$-$C_4$alkoxycarbonyl and —$C_1$-$C_4$-alkylenehydroxyl, or is a heterocycle, which is a saturated, partially unsaturated or aromatic ring containing 5 or 6 ring atoms of which 1, 2 or 3 are identical or different heteroatoms selected from: nitrogen, oxygen, sulfur and phosphorus, and where the heterocycle is unsubstituted or substituted by 1, 2, or 3 identical or different substituents selected from: halogen, $C_1$-$C_4$-alkyl, $C_1$-$C_4$-alkoxy, nitro, NR$_9$R$_{10}$, SR$_{11}$ trifluoromethyl, hydroxyl, cyano, carboxy, $C_1$-$C_4$-alkoxycarbonyl and —$C_1$-$C_4$-alkylenehydroxyl;

$R_2$ is hydrogen; $C_1$-$C_6$-alkyl; phenyl, unsubstituted or substituted by at least one substituent selected from: halogen, $C_1$-$C_4$-alkyl, $C_1$-$C_4$-alkoxy, nitro, NR$_9$R$_{10}$, SR$_{11}$, trifluoromethyl, hydroxyl, cyano, carboxy, —$C_1$-$C_4$-alkoxycarbonyl and —$C_1$-$C_4$-alkylenehydroxyl; $OR_{11}$; halogen; cyano; nitro; $NR_9R_{10}$ or $SR_{11}$;

$R_3$, $R_4$ and $R_5$ are each independently selected from: hydrogen, $C_1$-$C_4$alkyl, halogen, $OR_{11}$, $C_1$-$C_4$-alkylcarbonyloxy, $NR_9R_{10}$, $SO_2NR_9R_{10}$, carboxyl, cyano and nitro;

A is a 5-membered saturated ring represented by any one of the general structures (i) to (v);

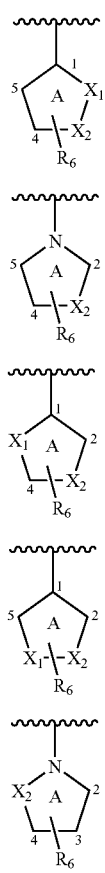

(i)

(ii)

(iii)

(iv)

(v)

wherein $X_1$ and $X_2$ are each independently selected from: a methylene group and a heteroatom selected from: oxygen, sulfur, and nitrogen, provided that at least one of $X_1$ and $X_2$ is a heteroatom, and wherein the nitrogen atom is at least monosubstituted by $R_{13}$, wherein $R_{13}$ is selected from: hydrogen; unsubstituted $C_1$-$C_6$-alkyl; or $C_1$-$C_6$-alkyl substituted by halogen, hydroxyl, or carboxyl; $C_2$-$C_6$-alkenyl; hydroxyl; $C_1$-$C_6$-alkoxy; $C_1$-$C_4$-alkylcarbonyl; toluenesulfonyl; cyano; $SO_2R_{10}$; —CO—$(CH_2)_m$—$R_{14}$; and phenyl, which is unsubstituted or substituted by 1, 2, or 3 identical or different substituents selected from: halogen, $C_1$-$C_4$-alkyl, $C_1$-$C_4$-alkoxy, nitro, $NR_9R_{10}$, $SR_{11}$, trifluoromethyl, hydroxyl, cyano, carboxy, $C_1$-$C_4$-alkoxycarbonyl and —$C_1$-$C_4$-alkylenehydroxyl;

$R_9$ and $R_{10}$ are each independently selected from: hydrogen, $C_1$-$C_4$alkyl, $C_1$-$C_4$-alkanoyl, $C_1$-$C_4$-alkoxycarbonyl, $C_1$-$C_4$-alkylcarbonyl, carboxamide and sulfonamide; or $R_9$ and $R_{10}$, together with the nitrogen atom to which they are bonded, form a 3-, 4-, 5- or 6-membered heterocyclic ring which can have at least one further heteroatom selected from: nitrogen, oxygen and sulfur, which ring is saturated, partially unsaturated or aromatic and either unsubstituted or substituted by at least one substituent selected from: halogen, $C_1$-$C_4$-alkyl, $C_1$-$C_4$-alkoxy, $C_2$-$C_6$-alkenyl, $C_3$-$C_6$-alkynyl, $C_2$-$C_4$-alkanoyl, nitro, $NR_9R_{10}$, $SR_{11}$, trifluoromethyl, hydroxyl, cyano, carboxy, —$C_1$-$C_4$-alkoxycarbonyl and —$C_1$-$C_4$-alkylenehydroxyl;

$R_{11}$, is hydrogen, $C_1$-$C_4$-alkyl, $C_1$-$C_4$-alkanoyl or $C_1$-$C_4$-alkoxycarbonyl;

$R_{12}$ is hydrogen, halogen, $C_1$-$C_4$-alkyl, —$NR_9R_{10}$, or $OR_9$;

$R_{14}$ is hydrogen $C_1$-$C_4$-alkyl, hydroxyl, —$NR_9R_{10}$, halogen, —SH, or —S—$C_1$-$C_4$-alkyl; and Z is an oxygen atom or a sulfur atom.

In a third embodiment of compounds of formula (Ig), $R_1$ can be phenyl, which is unsubstituted or substituted by 1, 2, or 3 identical or different substituents selected from: halogen, $C_1$-$C_4$-alkyl, $C_1$-$C_4$-alkoxy, nitro, $NR_9R_{10}$, $SR_{11}$, trifluoromethyl, hydroxyl, cyano, carboxy, —$C_1$-$C_4$-alkoxycarbonyl and —$C_1$-$C_4$-alkylenehydroxyl; or can be a heterocycle, which is a saturated, partially unsaturated or aromatic ring containing 6 ring atoms of which 1, 2 or 3 are identical or different heteroatoms selected from: nitrogen, oxygen and sulfur, and where the heterocycle is unsubstituted or substituted by 1, 2, or 3 identical or different substituents selected from: halogen, $C_1$-$C_4$-alkyl, $C_1$-$C_4$-alkoxy, nitro, $NR_9R_{10}$, $SR_{11}$, trifluoromethyl, hydroxyl, cyano, carboxy, $C_1$-$C_4$-alkoxycarbonyl and —$C_1$-$C_4$-alkylenehydroxyl;

$R_2$ and $R_4$ can be hydrogen; and $R_3$ and $R_5$ can be each independently selected from: hydroxyl, $C_1$-$C_4$-alkoxyl and $C_1$-$C_4$-alkylcarbonyloxy.

In a fourth embodiment of compounds of the formula (Ig), A can be represented by any one of the general structures (i) to (iv):

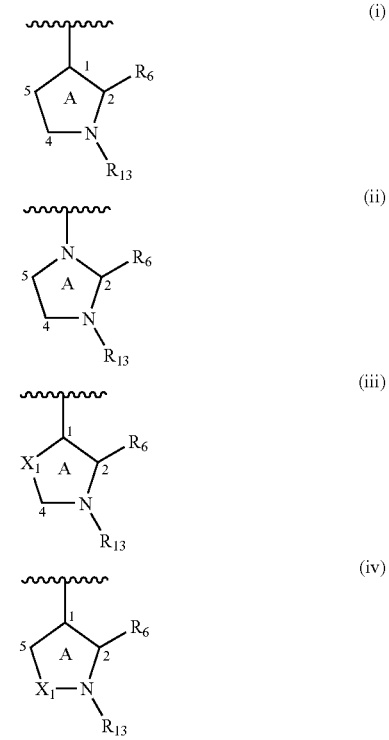

(i)

(ii)

(iii)

(iv)

wherein $X_1$ is either a methylene group or a heteroatom selected from: oxygen, sulfur, and nitrogen, except that in structures (ii) and (iv) $X_1$ is either a methylene group or a nitrogen atom, and wherein $R_{13}$ is selected from: hydrogen;

unsubstituted $C_1$-$C_6$-alkyl; or $C_1$-$C_6$-alkyl substituted by halogen, hydroxyl, or carboxyl; $C_2$-$C_6$-alkenyl; hydroxyl; $C_1$-$C_6$-alkoxy; $C_1$-$C_4$-alkylcarbonyl; toluenesulfonyl; cyano; $SO_2R_{10}$; —CO—$(CH_2)_m$—$R_{14}$; and phenyl, which is unsubstituted or substituted by 1, 2, or 3 identical or different substituents selected from: halogen, $C_1$-$C_4$-alkyl, $C_1$-$C_4$-alkoxy, nitro, $NR_9R_{10}$, $SR_{11}$, trifluoromethyl, hydroxyl, cyano, carboxy, $C_1$-$C_4$-alkoxycarbonyl and —$C_1$-$C_4$-alkylenehydroxyl.

In a further embodiment, the present invention relates to compounds of the general formula (Ic) or (Ig), wherein $R_1$ is phenyl or pyridinyl, substituted by 1, 2 or 3 identical or different substituents selected from: halogen and nitro, $R_2$ and $R_4$ are hydrogen, $R_3$ and $R_5$ are hydroxyl, A is a saturated 5-membered ring represented by any one of the general structures (i) to (v), wherein $X_1$, $X_2$, $R_6$ and $R_{13}$ are as defined. More particularly, $X_1$ is carbon, $X_2$ is nitrogen, $R_6$ is —$C_1$-$C_4$-alkylenehydroxyl, $R_{13}$ is $C_1$-$C_4$-alkyl and Z is an oxygen atom.

In alternative compounds of the formula (Ia) or (Ib), the substituents $R_1$ to $R_7$, A and Z and the groups aryl and heterocyclo or heterocycle, independently from each other, have the following meanings. Hence, one or more of the substituents $R_1$ to $R_7$ and A and Z can have the preferred or particularly preferred meanings given below.

$R_1$ can be selected from: aryl and heterocyclo, each of which can be unsubstituted, mono- or polysubstituted by halogen, $C_1$-$C_4$-alkyl, $C_1$-$C_4$-alkoxy, hydroxyl, carboxyl, COO-alkyl, $CONH_2$, CONHOH, CONH-alkyl, CON-(alkyl)$_2$, nitro, trifluoromethyl, amino, $C_1$-$C_4$-alkylamino, di-$C_1$-$C_4$alkylamino, or phenyl. In one embodiment, the heterocyclo can be an unsaturated 5 or 6-membered ring containing 1 or 2 nitrogen atoms, unsubstituted or mono- or polysubstituted as indicated above. In another embodiment, $R_1$ can be selected from: unsubstituted phenyl; phenyl mono- or polysubstituted by halogen, $C_1$-$C_4$-alkyl, $C_1$-$C_4$-alkoxy, hydroxyl, carboxyl, COO-alkyl, $CONH_2$, CONH-alkyl, CON(alkyl)$_2$, nitro, trifluoromethyl, amino, $C_1$-$C_4$-alkylamino, di-$C_1$-$C_4$-alkylamino or phenyl; and pyridyl mono- or polysubstituted by the substituents indicated above for phenyl. In yet another embodiment, $R_1$ can be selected from: phenyl, chlorophenyl, dichlorophenyl, chlorofluorophenyl, dichlorofluorophenyl, chlorohydroxylphenyl, chlorocarboxyphenyl, chloronitrophenyl, aminochlorophenyl, N-hydroxycarboxychlorophenyl, cyanochlorophenyl, bromophenyl, dibromophenyl, bromofluorophenyl, bromohydroxylphenyl, bromocarboxyphenyl, bromonitrophenyl, aminobromophenyl, N-hydroxycarboxybromophenyl, bromocyanophenyl fluorophenyl, difluorophenyl, fluorohydroxylphenyl, pyridyl, chloropyridyl, dichloropyridyl, chlorofluoropyridyl, chlorohydroxylpyridyl, bromopyridyl, dibromopyridyl, bromofluoropyridyl, bromohydroxylpyridyl, fluoropyridyl, difluoropyridyl, fluorohydroxylpyridyl, and bis-trifluoromethylphenyl.

$R_2$ can be selected from: hydrogen, $C_1$-$C_6$-alkyl, $C_1$-$C_6$-alkoxyl, hydroxyl, nitro, amino and a halogen.

$R_3$, $R_4$ and $R_5$ can be selected from: hydrogen, $C_1$-$C_4$-alkyl, unsubstituted or substituted by: halogen, hydroxyl, or carboxyl; $C_1$-$C_4$-alkoxyl; hydroxyl; carboxyl; nitro; amino; and —O-acyl. In one embodiment, $R_3$ and $R_5$ are hydroxyl or $C_1$-$C_4$-alkylcarbonyloxy, and $R_4$ is hydrogen.

$R_6$ can be selected from: hydrogen; hydroxyl; unsubstituted $C_1$-$C_6$-alkyl; $C_1$-$C_6$—alkyl substituted by halogen, hydroxyl or carboxy; $C_1$-$C_6$-alkoxyl; $C_1$-$C_6$-alkoxycarbonyl; aryloxy; amino; $C_1$-$C_6$-alkylamino; di $C_1$-$C_6$-alkylamino; and —$C_1$-$C_4$-alkylene-O—$C_1$-$C_4$-alkyl. $R_6$ can be —$C_1$-$C_4$-alkylene-OH, and is preferably —$CH_2OH$.

$R_7$ can be hydrogen atom.

Z can be an oxygen atom.

In formula (Ia) or (Ic), A can be a saturated or unsaturated 5-membered ring or a saturated 6-membered ring containing at least one heteroatom selected from: nitrogen, oxygen and sulfur, the ring being unsubstituted or at least monosubstituted by $R_6$. The unsaturated 5-membered ring can have one or two double bonds in its ring structure. In formula (Ia), (Ib), (Ic) or (Ig), A can in particular be a saturated 5-membered ring containing 1 or 2 nitrogen atoms, and in formula (Ia) or (Ic) a saturated 6-membered ring containing 1 nitrogen atom, wherein in both cases the ring is unsubstituted or at least monosubstituted by $R_6$.

When A is a 5-membered ring of general structures (i) to (v) and both $X_1$ and $X_2$ independently represent a heteroatom selected from nitrogen, oxygen and sulfur, the following conditions apply:

(a) A can be unsaturated as valence and stability may permit, (b) $X_1$ can only be the heteroatom nitrogen in the general structures (ii) and (v) and $X_2$ can be any one of the heteroatoms indicated above, (c) $R_6$ can be attached to the carbon ring member at position 4 or 5 when A is of general structure (i), (d) $R_6$ can be attached to the carbon ring member at position 2, 4 or 5 when A is of general structure (ii), (e) $R_6$ can be attached to the carbon ring member at position 2 or 4 when A is of general structure (iii), (f) $R_6$ can be attached to the carbon ring member at position 2 or 5 when A is of general structure (iv), and (g) $R_6$ can be attached to the carbon ring member at position 2, 3 or 4 when A is of general structure (v).

In another embodiment, compounds of formula (Ia), (Ib) or (Ig) are compounds in which A is a saturated 5-membered ring, $X_2$ is $NR_{13}$, where $R_{13}$ is hydrogen, $C_1$-$C_6$-alkyl or acyl, $X_1$ is a methylene group, $R_6$ is selected from: hydrogen, unsubstituted $C_1$-$C_6$-alkyl, $C_1$-$C_6$-alkyl substituted by halogen, hydroxyl or carboxyl, and $R_7$ is hydrogen.

In yet another embodiment, compounds of formula (Ia) are compounds in which A is a 6-membered ring, $X_3$ is $NR_{13}$, where $R_{13}$ is hydrogen, $C_1$-$C_6$-alkyl or acyl, $R_6$ is selected from: hydrogen, unsubstituted $C_1$-$C_6$-alkyl, $C_1$-$C_6$-alkyl substituted by halogen, hydroxyl or carboxyl, and $R_7$ is hydrogen.

In a further embodiment, compounds of formula (Ia) are compounds in which A is a 7-membered ring, $X_3$ is $NR_{13}$, where $R_{13}$ is hydrogen, $C_1$-$C_6$-alkyl or acyl, $R_6$ is selected from: hydrogen, unsubstituted $C_1$-$C_6$-alkyl, $C_1$-$C_6$-alkyl substituted by halogen, hydroxyl or carboxyl, and $R_7$ is hydrogen.

$R_6$ can be —$C_1$-$C_6$-alkylene-OH.

$R_{13}$ can be —$CH_3$.

In yet a further embodiment, compounds of formula (Ia) or (Ib) are compounds in which $R_2$ is hydrogen, halogen, nitro, cyano, $NR_9R_{10}$, wherein $R_9$ and $R_{10}$ are as defined above, or $OR_{11}$, wherein $R_{11}$ is hydrogen or alkyl; $R_3$ and $R_5$ are each independently selected from: hydrogen and $OR_{11}$, wherein $R_{11}$ is hydrogen, alkyl, acyl or aryl; $R_4$ is hydrogen; Z is an oxygen atom, a sulfur atom, or $NR_8$, wherein $R_8$ is hydrogen, alkyl, aryl, carboxamide, $NR_9R_{10}$ or $OR_{11}$, wherein $R_{11}$ and $R_{10}$ are each independently selected from: hydrogen, alkyl, acyl, heterocycle, alkoxycarbonyl, carboxamide and sulfonamide, and $R_{11}$ is selected from: hydrogen, alkyl and acyl.

In a still further embodiment, compounds of formula (Ia) or (Ib) are compounds in which $R_1$ is aryl, or a heterocycle; $R_2$ is hydrogen; at least one of $R_3$ and $R_5$ is $OR_{11}$, wherein $R_{11}$ is hydrogen or alkyl; $R_4$ is hydrogen; $R_6$ is hydroxymethyl, alkoxymethyl or alkylcarbonyloxymethyl; $R_7$ is hydrogen; and Z is an oxygen atom.

Examples of preferred compounds according to the present invention are listed below:

(+/−)-trans-2-(2-Chloro-phenyl)-8-(2-hydroxymethyl-1-methyl-pyrrolidin-3-yl)-5,7-dimethoxy-chromen-4-one;

(+)-trans-2-(2-Chloro-phenyl)-8-(2-hydroxymethyl-1-methyl-pyrrolidin-3-yl)-5,7-dimethoxy-chromen-4-one;

(+)-trans-2-(2-Chloro-phenyl)-5,7-dihydroxy-8-(2-hydroxymethyl-1-methyl-pyrrolidin-3-yl)-chromen-4-one;

(−)-trans-2-(2-Chloro-phenyl)-8-(2-hydroxymethyl-1-methyl-pyrrolidin-3-yl)-5,7-dimethoxy-chromen-4-one;

(−)-trans-2-(2-Chloro-phenyl)-5,7-dihydroxy-8-(2-hydroxymethyl-1-methyl-pyrrolidin-3-yl)-chromen-4-one;

(+)-trans-2-(2-Bromo-phenyl)-8-(2-hydroxymethyl-1-methyl-pyrrolidin-3-yl)-5,7-dimethoxy-chromen-4-one;

(+)-trans-2-(2-Bromo-phenyl)-5,7-dihydroxy-8-(2-hydroxymethyl-1-methyl-pyrrolidin-3-yl)-chromen-4-one;

(+)-trans-2-(4-Bromo-phenyl)-8-(2-hydroxymethyl-1-methyl-pyrrolidin-3-yl)-5,7-dimethoxy-chromen-4-one;

(+)-trans-2-(4-Bromo-phenyl)-5-hydroxy-8-(2-hydroxymethyl-1-methyl-pyrrolidin-3-yl)-7-methoxy-chromen-4-one;

(+)-trans-2-(4-Bromo-phenyl)-5,7-dihydroxy-8-(2-hydroxymethyl-1-methyl-pyrrolidin-3-yl)-chromen-4-one;

(+)-trans-2-(3-Chloro-phenyl)-8-(2-hydroxymethyl-1-methyl-pyrrolidin-3-yl)-5,7-dimethoxy-chromen-4-one;

(+)-trans-2-(3-Chloro-phenyl)-5-hydroxy-8-(2-hydroxymethyl-1-methyl-pyrrolidin-3-yl)-7-methoxy-chromen-4-one;

(+)-trans-2-(3-Chloro-phenyl)-5,7-dihydroxy-8-(2-hydroxymethyl-1-methyl-pyrrolidin-3-yl)-chromen-4-one;

(+)-trans-8-(2-hydroxymethyl-1-methyl-pyrrolidin-3-yl)-2-(2-iodo-phenyl)-5,7-dimethoxy-chromen-4-one;

(+)-trans-5,7-Dihydroxy-8-(2-hydroxymethyl-1-methyl-pyrrolidin-3-yl)-2-(2-iodo-phenyl)-chromen-4-one;

(+)-trans-2-(2-Fluoro-phenyl)-8-(2-hydroxymethyl-1-methyl-pyrrolidin-3-yl)-5,7-dimethoxy-chromen-4-one;

(+)-trans-2-(2-Fluoro-phenyl)-5,7-dihydroxy-8-(2-hydroxymethyl-1-methyl-pyrrolidin-3-yl)-chromen-4-one;

(+)-trans-2-(3-Fluoro-phenyl)-5,7-dimethoxy-8-(2-hydroxymethyl-1-methyl-pyrrolidin-3-yl)-chromen-4-one;

(+)-trans-2-(3-Fluoro-phenyl)-5,7-dihydroxy-8-(2-hydroxymethyl-1-methyl-pyrrolidin-3-yl)-chromen-4-one;

(+)-trans-2-(2,6-Difluoro-phenyl)-8-(2-hydroxymethyl-1-methyl-pyrrolidin-3-yl)-5,7-dimethoxy-chromen-4-one;

(+)-trans-2-(2,6-Difluoro-phenyl)-5,7-dihydroxy-8-(2-hydroxymethyl-1-methyl-pyrrolidin-3-yl)-chromen-4-one;

(+/−)-trans-4-[8-(2-hydroxymethyl-1-methyl-pyrrolidin-3-yl)-5,7-dimethoxy-4-oxo-4H-chromen-2-yl]-benzonitrile;

(+/−)-trans-4-[5,7-Dihydroxy-8-(2-hydroxymethyl-1-methyl-pyrrolidin-3-yl)-4-oxo-4H-chromen-2-yl]-benzonitrile;

(+)-trans-4-{8-[2-hydroxymethyl-1-methyl-pyrrolidin-3-yl]-5,7-dimethoxy-4-oxo-4H-chromen-2-yl}-benzonitrile;

(+)-trans-4-{5,7-Dihydroxy-8-[2-hydroxymethyl-1-methyl-pyrrolidin-3-yl-4-oxo-4H-chromen-2-yl}-benzonitrile;

(+/−)-trans-8-(2-hydroxymethyl-1-methyl-pyrrolidin-3-yl)-5,7-dimethoxy-2-(4-trifluoromethyl-phenyl)-chromen-4-one;

(+/−)-trans-5,7-Dihydroxy-8-(2-hydroxymethyl-1-methyl-pyrrolidin-3-yl)-2-(4-trifluoromethyl-phenyl)-chromen-4-one;

(+)-trans-8-(2-hydroxymethyl-1-methyl-pyrrolidin-3-yl)-5,7-dimethoxy-2-(4-trifluoromethyl-phenyl)-chromen-4-one;

(+)-trans-5,7-Dihydroxy-8-(2-hydroxymethyl-1-methyl-pyrrolidin-3-yl)-2-(4-trifluoromethyl-phenyl)-chromen-4-one;

(−)-trans-8-(2-hydroxymethyl-1-methyl-pyrrolidin-3-yl)-5,7-dimethoxy-2-(4-trifluoromethyl-phenyl)-chromen-4-one;

(−)-trans-5,7-Dihydroxy-8-(2-hydroxymethyl-1-methyl-pyrrolidin-3-yl)-2-(4-trifluoromethyl-phenyl)-chromen-4-one;

(+)-trans-8-(2-hydroxymethyl-1-methyl-pyrrolidin-3-yl)-5,7-dimethoxy-2-phenyl-chromen-4-one;

(+)-trans-5,7-Dihydroxy-8-(2-hydroxymethyl-1-methyl-pyrrolidin-3-yl)-2-phenyl-chromen-4-one;

(+)-trans-8-(2-hydroxymethyl-1-methyl-pyrrolidin-3-yl)-5,7-dimethoxy-2-thiophen-2-yl-chromen-4-one;

(+)-trans-5,7-Dihydroxy-8-[2-hydroxymethyl-1-methyl-pyrrolidin-3-yl]-2-thiophen-2-yl-chromen-4-one;

(+)-trans-4-[5,7-Dihydroxy-8-(2-hydroxymethyl-1-methyl-pyrrolidine-3-yl)-4-oxo-4H-chromen-2-yl]-3-methyl-benzonitrile;

(+)-trans-4-[8-(2-hydroxymethyl-1-methyl-pyrrolidine-3-yl)-5,7-dimethoxy-4-oxo-4H-chromen-2-yl]-3-methyl-benzonitrile;

(+/−)-trans-2-[2-Bromo-5-methoxy-phenyl)-8-(2-hydroxymethyl-1-methyl-pyrrolidin-3-yl]-5,7-dimethoxy-chromen-4-one;

(+/−)-trans-2-(2-Bromo-5-methoxy-phenyl)-5,7-dihydroxy-8-(2-hydroxymethyl-1-methyl-pyrrolidin-3-yl)-chromen-4-one;

(+)-trans-2-[2-Bromo-5-methoxy-phenyl)-8-(2-hydroxymethyl-1-methyl-pyrrolidin-3-yl]-5,7-dimethoxy-chromen-4-one;

(+)-trans-2-(2-Bromo-5-methoxy-phenyl)-5,7-dihydroxy-8-(2-hydroxymethyl-1-methyl-pyrrolidin-3-yl)-chromen-4-one;

(+/−)-trans-2-(2-Bromo-5-hydroxy-phenyl)-5,7-dihydroxy-8-(2-hydroxymethyl-1-methyl-pyrrolidin-3-yl)-chromen-4-one;

(+)-trans-2-(2-Bromo-5-hydroxy-phenyl)-5,7-dihydroxy-8-(2-hydroxymethyl-1-methyl-pyrrolidin-3-yl)-chromen-4-one;

(+/−)-trans-2-[(3,5-Bis-trifluoromethyl)-phenyl]-8-[2-hydroxymethyl-1-methyl-pyrrolidin-3-yl]-5,7-dimethoxy-chromen-4-one;

(+/−)-trans-2-[(3,5-Bis-trifluoromethyl)-phenyl]-5,7-dihydroxy-8-[2-hydroxymethyl-1-methyl-pyrrolidin-3-yl]-chromen-4-one;

(+)-trans-2-(2-Chloro-5-methyl-phenyl)-8-(2-hydroxymethyl-1-methyl-pyrrolidin-3-yl)-5,7-dimethoxy-chromen-4-one;

(+)-trans-2-(2-Chloro-5-methyl-phenyl)-5,7-dihydroxy-8-(2-hydroxymethyl-1-methyl-pyrrolidin-3-yl)-chromen-4-one;

(+)-trans-2-[2-Bromo-5-nitro-phenyl]-8-[-2-hydroxymethyl-1-methyl-pyrrolidin-3-yl]-5,7-dimethoxy-chromen-4-one;

(+)-trans-2-[2-Bromo-5-nitro-phenyl]-8-[2-hydroxymethyl-1-methyl-pyrrolidin-3-yl]-5,7-dihydroxy-chromen-4-one;

(+/−)-trans-2-(-2-Chloro-pyridin-3-yl)-8-(2-hydroxymethyl-1-methyl-pyrrolidin-3-yl)-5,7-dimethoxy-chromen-4-one;

(+/−)-trans-2-(-2-Chloro-pyridin-3-yl)-5,7-dihydroxy-8-(2-hydroxymethyl-1-methyl-pyrrolidin-3-yl)-chromen-4-one;

(+/−)-trans-2-[2-Bromo-5-nitrophenyl-8-[2-hydroxymethyl-1-methyl-pyrrolidin-3-yl]-5,7-dihydroxy-chromen-4-one;

(+)-trans-2-(-2-Chloro-pyridin-3-yl)-5,7-dihydroxy-8-(2-hydroxymethyl-1-methyl-pyrrolidin-3-yl-chromen-4-one;

(+/−)-trans-8-(2-hydroxymethyl-1-methyl-pyrrolidin-3-yl)-5,7-dimethoxy-2-(4-nitrophenyl)-4H-chromen-4-one;

(+/−)-trans-5,7-Dihydroxy-8-(2-hydroxymethyl-1-methyl-pyrrolidine-3-yl)-2-(4-nitrophenyl)-chromen-4-one;

(+/−)-trans-2-(4-Aminophenyl)-5,7-dihydroxy-8-(2-hydroxymethyl-1-methyl-pyrrolidin-3-yl)-chromen-4-one;

(+/−)-trans-8-(2-hydroxymethyl-1-methyl-pyrrolidin-3-yl)-5,7-dimethoxy-2-(2-methoxy-phenyl)-chromen-4-one;

(+/−)-trans-5,7-Dihydroxy-8-(2-hydroxymethyl-1-methyl-pyrrolidin-3-yl)-2-(2-hydroxy-phenyl)-chromen-4-one;

(+)-trans-3-Chloro-4-[8-(2-hydroxymethyl-1-methyl-pyrrolidin-3-yl)-5,7-dimethoxy-4-oxo-4H-chromen-2-yl]-benzonitrile;

(+)-trans-3-Chloro-4-[5,7-dihydroxy-8-(2-hydroxymethyl-1-methyl-pyrrolidin-3-yl)-4-oxo-4H-chromen-2-yl]-benzonitrile;

(+)-trans-2-(4-Bromo-2-chloro-phenyl)-8-(2-hydroxymethyl-1-methyl-pyrrolidin-3-yl)-5,7-dimethoxy-chromen-4-one;

(+)-trans-2-(4-Bromo-2-chloro-phenyl)-5,7-dihydroxy-8-(2-hydroxymethyl-1-methyl-pyrrolidin-3-yl)-chromen-4-one;

(+/−)-trans-2-(2-Chloro-5-dimethylamino-phenyl)-8-(2-hydroxymethyl-1-methyl-pyrrolidin-3-yl)-5,7-dimethoxy-chromen-4-one;

(+/−)-trans-2-(2-Chloro-5-methylamino-phenyl)-5,7-dihydroxy-8-(-2-hydroxy methyl-1-methyl-pyrrolidin-3-yl)-chromen-4-one;

(+/−)-trans-2-(2-Chloro-4-methoxy-phenyl)-8-(2-hydroxymethyl-1-methyl-pyrrolidin-3-yl)-5,7-dimethoxy-chromen-4-one;

(+/−)-trans-2-(2-Chloro-4-hydroxy-phenyl)-5,7-dihydroxy-8-[2-hydroxymethyl-1-methyl-pyrrolidin-3-yl]chromen-4-one;

(+/−)-trans-2-(2-Chloro-5-fluoro-phenyl)-8-(2-hydroxymethyl-1-methyl-pyrrolidin-3-yl)-5,7-dimethoxy-chromen-4-one;

(+/−)-trans-2-(2-Chloro-5-fluoro-phenyl)-5,7-dihydroxy-8-(2-hydroxymethyl-1-methyl-pyrrolidin-3-yl)-chromen-4-one;

(+/−)-trans-2-(2-Chloro-5-methoxy-phenyl)-8-(2-hydroxymethyl-1-methyl-pyrrolidin-3-yl)-5,7-dimethoxy-chromen-4-one;

(+/−)-trans-2-(2-Chloro-5-hydroxy-phenyl)-5,7-dihydroxy-8-(2-hydroxymethyl-1-methyl-pyrrolidin-3-yl)-chromen-4-one;

(+/−)-trans-2-(2-Chloro-5-methoxy-phenyl)-5,7-dihydroxy-8-(2-hydroxymethyl-1-methyl-pyrrolidin-3-yl)-chromen-4-one;

(+/−)-trans-8-(2-Azidomethyl-1-methyl-pyrrolidin-3-yl)-2-(2-chloro-phenyl)-5,7-dimethoxy-chromen-4-one;

(+/−)-trans-8-(2-Aminomethyl-1-methyl-pyrrolidin-3-yl)-2-(2-chloro-phenyl)-5,7-dimethoxy-chromen-4-one;

(+/−)-trans-8-(2-Aminomethyl-1-methyl-pyrrolidin-3-yl)-2-(2-chloro-phenyl)-5,7-dihydroxy-chromen-4-one;

(+/−)-trans-3-{2-(2-Chloro-phenyl)-5,7-dimethoxy-4-oxo-4H-chromen-8-yl]-1-methyl-pyrrolidin-2-yl}-acetonitrile;

(+/−)-trans-{3-[2-(2-Chloro-phenyl)-5,7-dihydroxy-4-oxo-4H-chromen-8-yl]-1-methyl-pyrrolidin-2-yl}-acetonitrile;

(+/−)-trans-2-(2-Chloro-phenyl)-8-(2-imidazol-1-ylmethyl-1-methyl-pyrrolidin-3-yl)-5,7-dimethoxy-chromen-4-one;

(+/−)-trans-2-(2-Chloro-phenyl)-5,7-dihydroxy-8-(2-imidazol-1-ylmethyl-1-methyl-pyrrolidin-3-yl)-chromen-4-one;

(+/−)-trans-2-[2-Chloro-phenyl-8-(2-mercaptomethyl-1-methyl-pyrrolidin-3-yl)]-5,7-dimethoxy-chromen-4-one;

(+/−)-trans-2-(2-Chloro-phenyl)-5,7-dihydroxy-8-(2-mercaptomethyl-1-methyl-pyrrolidin-3-yl)-chromen-4-one;

(+/−)-trans-2-(2-Chlorophenyl)-8-[3-hydroxy-1-(4-methoxyphenyl)piperidin-4-yl]-5,7-dimethoxy-chromen-4-one;

(+/−)-trans-Acetic acid 3-[2-(2-chloro-phenyl)-5,7-dimethoxy-4-oxo-4H-chromen-8-yl]-1-(4-methoxy-phenyl)-pyrrolidin-2-ylmethyl ester;

(+/−)-trans-2-(2-Chloro-phenyl)-8-[2-hydroxymethyl-1-(4-methoxy-phenyl)-pyrrolidin-3-yl]-5,7-dimethoxy-chromen-4-one;

(+/−)-trans-2-(2-Chloro-phenyl)-5,7-dihydroxy-8-[2-hydroxymethyl-1-(4-methoxy-phenyl)-pyrrolidin-3-yl]-chromen-4-one;

(+/−)-trans-Acetic acid-3-[2-(2-chloro-phenyl)-5,7-dimethoxy-4-oxo-4H-chromen-8-yl]-1-propyl-pyrrolidin-2-ylmethyl ester;

(+/−)-trans-2-(2-Chloro-phenyl)-8-[2-hydroxymethyl-1-propyl-pyrrolidin-3-yl]-5,7-dimethoxy-chromen-4-one;

(+/−)-trans-2-(2-Chloro-phenyl)-5,7-dihydroxy-8-(2-hydroxymethyl-1-propyl-pyrrolidin-3-yl)-chromen-4-one;

(+/−)-trans-2-(2-Chloro-4-nitro-phenyl-5,7-dihydroxy-8-(2-hydroxymethyl-1-methyl-pyrrolidin-3-yl)-chromen-4-one;

(+/−)-trans-2-(2-Bromo-4-nitro-phenyl-5,7-dihydroxy-8-(2-hydroxymethyl-1-methyl-pyrrolidin-3-yl)-chromen-4-one;

(+/−)-trans-3-Chloro-4-[5,7-dihydroxy-8-(2-hydroxymethyl-1-methyl-pyrrolidin-3-yl)-4-oxo-4H-chromen-2-yl]-benzoic acid;

(+/−)-trans-3-Bromo-4-[5,7-dihydroxy-8-(2-hydroxymethyl-1-methyl-pyrrolidin-3-yl)-4-oxo-4H-chromen-2-yl]-benzoic acid;

(+/−)-trans-2-(2-Chloro-4-fluoro-phenyl)-5,7-dihydroxy-8-(2-hydroxymethyl-1-methyl-pyrrolidin-3-yl)-chromen-4-one;

(+/−)-trans-2-(4-Amino-2-chloro-phenyl)-5,7-dihydroxy-8-(2-hydroxymethyl-1-methyl-pyrrolidin-3-yl)-chromen-4-one;

(+/−)-trans-2-(2-Bromo-4-fluoro-phenyl)-5,7-dihydroxy-8-(2-hydroxymethyl-1-methyl-pyrrolidin-3-yl)-chromen-4-one;

(+/−)-trans-2-(4-Amino-2-bromo-phenyl)-5,7-dihydroxy-8-(2-hydroxymethyl-1-methyl-pyrrolidin-3-yl)-chromen-4-one;

(+/−)-trans-4-Chloro-3-[5,7-dihydroxy-8-(2-hydroxymethyl-1-methyl-pyrrolidin-3-yl)-4-oxo-4H-chromen-2-yl]-benzoic acid;

(+/−)-trans-4-Bromo-3-[5,7-dihydroxy-8-(2-hydroxymethyl-1-methyl-pyrrolidin-3-yl)-4-oxo-4H-chromen-2-yl]-benzoic acid;

(+/−)-trans-4-Bromo-3-[5,7-dihydroxy-8-(2-hydroxymethyl-1-methyl-pyrrolidin-3-yl)-4-oxo-4H-chromen-2-yl]-N-hydroxy-benzamide;

(+/−)-trans-4-Chloro-3-[5,7-dihydroxy-8-(2-hydroxymethyl-1-methyl-pyrrolidin-3-yl)-4-oxo-4H-chromen-2-yl]-N-hydroxy-benzamide;

(+/−)-trans-3-Chloro-4-[5,7-dihydroxy-8-(2-hydroxymethyl-1-methyl-pyrrolidin-3-yl)-4-oxo-4H-chromen-2-yl]-N-hydroxy-benzamide;

(+/−)-trans-3-Bromo-4-[5,7-dihydroxy-8-(2-hydroxymethyl-1-methyl-pyrrolidin-3-yl)-4-oxo-4H-chromen-2-yl]-N-hydroxy-benzamide;

(+/−)-trans-2-(2,4-Difluoro-phenyl)-5,7-dihydroxy-8-(2-hydroxymethyl-1-methyl-pyrrolidin-3-yl)-chromen-4-one;
(+)-trans-2-(2-Chloro-3-fluoro-phenyl)-8-(2-hydroxymethyl-1-methyl-pyrrolidin-3-yl)-5,7-dimethoxy-chromen-4-one;
(+)-trans-2-(2-Chloro-3-fluoro-phenyl)-5,7-dihydroxy-8-(2-hydroxymethyl-1-methyl-pyrrolidin-3-yl)-chromen-4-one;
(+)-trans-2-(2-Bromo-3-fluoro-phenyl)-8-(2-hydroxymethyl-1-methyl-pyrrolidin-3-yl)-5,7-dimethoxy-chromen-4-one;
(+)-trans-2-(2-Bromo-3-fluoro-phenyl)-5,7-dihydroxy-8-(2-hydroxymethyl-1-methyl-pyrrolidin-3-yl)-chromen-4-one;
(+)-trans-2-(2-Bromo-5-fluoro-phenyl)-8-(2-hydroxymethyl-1-methyl-pyrrolidin-3-yl)-5,7-dimethoxy-chromen-4-one;
(+)-trans-2-(2-Bromo-5-fluoro-phenyl)-5,7-dihydroxy-8-(2-hydroxymethyl-1-methyl-pyrrolidin-3-yl)-chromen-4-one;
(+)-trans-2-(2-Chloro-5-iodo-phenyl)-8-(2-hydroxymethyl-1-methyl-pyrrolidin-3-yl)-5,7-dimethoxy-chromen-4-one;
(+)-trans-2-(2-Chloro-5-iodo-phenyl)-5,7-dihydroxy-8-(2-hydroxymethyl-1-methyl-pyrrolidin-3-yl)-chromen-4-one;
(+)-trans-2-(2-Bromo-5-chloro-phenyl)-8-(2-hydroxymethyl-1-methyl-pyrrolidin-3-yl)-5,7-dimethoxy-chromen-4-one;
(+)-trans-2-(2-Bromo-5-chloro-phenyl)-5,7-dihydroxy-8-(2-hydroxymethyl-1-methyl-pyrrolidin-3-yl)-chromen-4-one;
(+/−)-trans-2-(2-Chloro-phenyl)-5,7-dihydroxy-8-(2-hydroxymethyl-1-methyl-1-oxy-pyrrolidin-3-yl)-chromen-4-one;
(+)-trans-2-(2-Bromo-4-nitro-phenyl)-8-(2-hydroxymethyl-1-methylpyrrolidin-3-yl)-5,7-dimethoxy-chromen-4-one;
(+)-trans-2-(2-Bromo-4-nitro-phenyl)-5,7-dihydroxy-8-(2-hydroxymethyl-1-methyl-pyrrolidin-3-yl)-chromen-4-one;
(+)-trans-2-(4-Amino-2-bromo-phenyl)-8-(2-hydroxymethyl-1-methyl-pyrrolidin-3-yl)-5,7-dimethoxy-chromen-4-one;
(+)-trans-2-(4-Amino-2-bromo-phenyl)-5,7-dihydroxy-8-(2-hydroxymethyl-1-methyl-pyrrolidin-3-yl)-chromen-4-one;
(+)-trans-2-(2-Bromo-4-methoxy-phenyl)-8-(2-hydroxymethyl-1-methyl-pyrrolidin-3-yl)-5,7-dimethoxy-chromen-4-one;
(+)-trans-2-(2-Bromo-4-methoxy-phenyl)-5,7-dihydroxy-8-(2-hydroxymethyl-1-methyl-pyrrolidin-3-yl)-chromen-4-one;
(+)-trans-2-(2-Bromo-4-hydroxy-phenyl)-5,7-dihydroxy-8-(2-hydroxymethyl-1-methyl-pyrrolidin-3-yl)-chromen-4-one;
(+)-trans-Acetic acid 8-(2-acetoxymethyl-1-methyl-pyrrolidin-3-yl)-5-hydroxy-2-(4-nitro-phenyl)-4-oxo-4H-chromen-7-yl ester;
(+)-trans-2-(2,4-Dichloro-5-fluoro-phenyl)-8-(2-hydroxymethyl-1-methyl-pyrrolidin-3-yl)-5,7-dimethoxy-chromen-4-one; and
(+)-trans-2-(2,4-Dichloro-5-fluoro-phenyl-5,7-dihydroxy-8-(2-hydroxymethyl-1-methyl-pyrrolidin-3-yl)-chromen-4-one;
including pharmaceutically acceptable salts of the above listed compounds.

The present invention also relates to processes for the preparation of compounds of formula (Ia), (Ib), (Ic) or (Ig) or pharmaceutically acceptable salts thereof. One such process comprises reacting a benzopyranone of formula (II)

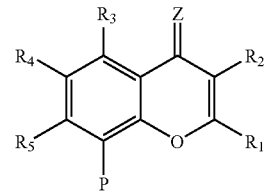

wherein $R_1$, $R_2$, $R_3$, $R_4$, $R_5$ and Z have the meaning defined above and P is a functional group, with a compound of formula (III),

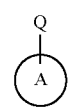

wherein A is substituted by $R_6$ and $R_7$, and A, $R_6$ and $R_7$ have the meaning defined above, except that A is other than a 5-membered ring of the general structure (ii) and (v) above, wherein $X_1$ is a nitrogen atom; Q is a functional group bound to a saturated or unsaturated carbon atom in the A ring, P and Q being capable of forming a carbon-carbon coupling between the respective carbon atoms to which they are attached, and i) where Q is bound to an unsaturated carbon atom, carrying out the reaction in the presence of a metal catalyst, an organic or inorganic base and an organic or inorganic solvent, and followed by treatment with a reducing agent to reduce any double bond between members at positions 1 and 2 or 1 and 5 of 5-membered ring A, between members at positions 1 and 6 or 1 and 2 of 6-membered ring A and between members at positions 1 and 2 or 1 and 7 of 7-membered ring A to a single bond, and ii) where Q is bound to a saturated carbon atom, carrying out the reaction in the presence of a suitable ligand or catalyst and a leaving group, and, if appropriate, converting the resultant compound of formula (Ia), (Ib), (Ic) or (Ig) into a pharmaceutically acceptable salt.

In another process for the preparation of compounds of formula (Ia), (Ib), (Ic) or (Ig) or pharmaceutically acceptable salts thereof, a benzopyranone of formula (II):

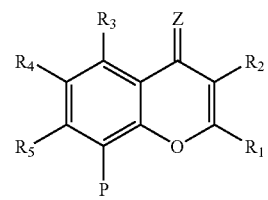

wherein $R_1$, $R_2$, $R_3$, $R_4$, $R_5$ and Z have the meaning defined above and P is a functional group, is reacted with a compound of formula (IIIA),

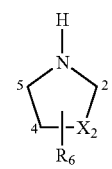

wherein $X_2$ and $R_6$ have the meaning defined above, in the presence of a metal catalyst, an organic or inorganic base and an organic or inorganic solvent, to form a nitrogen-carbon coupling between the carbon of the compound of formula (II) to which P is attached and the nitrogen of the compound of formula (IIIA), and, if appropriate, converting the resultant compound of formula (Ia), (Ib), (Ic) or (Ig) into a pharmaceutically acceptable salt.

Alternatively, a compound of formula (Ia), (Ib), (Ic) or (Ig) or a pharmaceutically acceptable salt thereof can be prepared by reacting a compound of formula (XA):

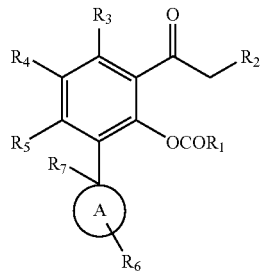

XA or a compound of formula (XIIA):

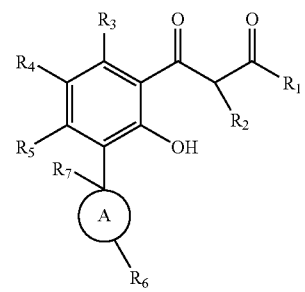

XII A wherein in each case $R_1$, $R_2$, $R_3$, $R_4$, $R_5$, $R_6$, $R_7$ and A are as defined above, with an inorganic base, subsequently adding an acid to the reaction mixture capable of effecting cyclization, and then adding an inorganic base and, if appropriate, converting the resultant compound of formula (Ia), (Ib), (Ic) or (Ig) into a pharmaceutically acceptable salt.

Compound of formula (XIIA) is obtained from compound of formula (XIA)

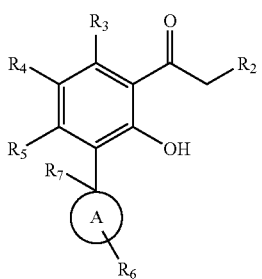

XIA by treatment with an appropriate carboxylic acid ester such as $R_1COOMe$, $R_1COOEt$ etc. or with an acid chloride like $R_1COX$ wherein X is a halogen or with an activated ester such as an anhydride in the presence of a base such as NaH in a solvent such as DMF, THF or 1,4-dioxane.

In the process, A can be selected from:

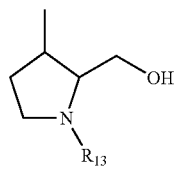

(a)

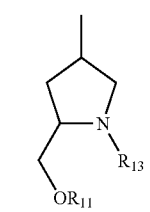

(b)

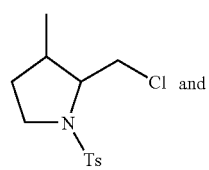

(c)

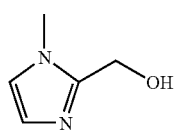

(d)

$R_{11}$ can be hydrogen and/or $R_{13}$ can be methyl.

A process for preparation of a compound of formula (XIIIA) or a pharmaceutically acceptable salt thereof

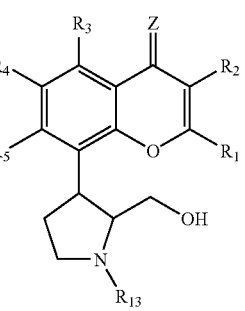

XIIIA wherein $R_1$, $R_2$, $R_3$, $R_4$, $R_5$, $R_{13}$ and Z are as defined above, comprises reacting a compound of formula (VIIA)

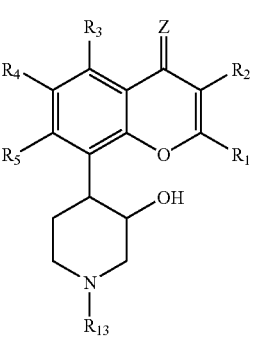

VII A wherein $R_1$, $R_2$, $R_3$, $R_4$, $R_5$, $R_{13}$ and Z are as defined above, with a reagent suitable to effect replacement of the —OH group on the piperidino ring by a good leaving group, in the presence of an organic or inorganic base, followed by adding a suitable organic base in the presence of a suitable organic solvent to effect contraction of the piperidino ring and, if appropriate, converting the resultant compound of formula (XIII) into a pharmaceutically acceptable salt.

A process for the preparation of a compound of formula (XXXIA) or a pharmaceutically acceptable salt thereof

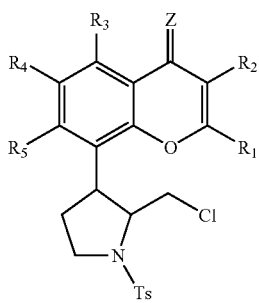

XXXIA wherein $R_1$, $R_2$, $R_3$, $R_4$, $R_5$ and Z are as defined above, comprises reacting a benzopyranone of formula (XXXA):

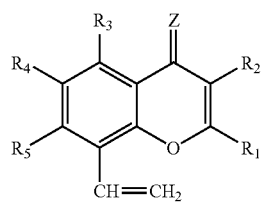

XXXA wherein $R_1$, $R_2$, $R_3$, $R_4$, $R_5$ and Z are as defined above, with N-allyl N-chlorotosylamide in the presence of an alkylborane and, if appropriate, converting the resultant compound of formula (XXXIA) into a pharmaceutically acceptable salt.

A process for the preparation of a compound of formula (XXXVII):

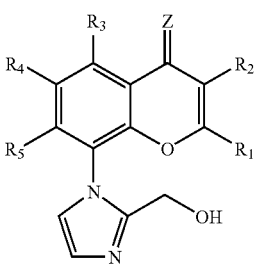

XXXVII wherein $R_1$, $R_2$, $R_3$, $R_4$, $R_5$ and Z are as defined, comprises reacting a compound of formula (XXXVI):

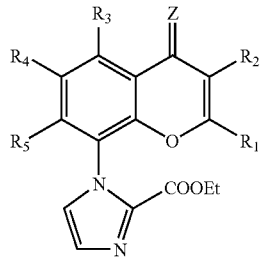

XXXVII wherein $R_1$, $R_2$, $R_3$, $R_4$, $R_5$ and Z are as defined above, with a suitable reducing agent capable of converting the ester group —C(O)OEt on the imidazolyl ring into the group —CH$_2$OH and, if appropriate, converting the resultant compound of formula (XXXVII) into a pharmaceutically acceptable salt. The compound of formula (XXXVI) above is prepared by reacting a compound of formula (XXXV):

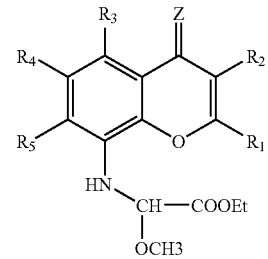

XXXV wherein $R_1$, $R_2$, $R_3$, $R_4$, $R_5$ and Z are as defined, with an isocyanide in the presence of an inorganic base in an organic solvent.

The present invention also relates to a process for the resolution of a compound of general formula (VIIIA) or a pharmaceutically acceptable salt thereof:

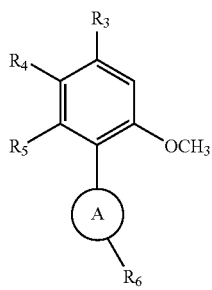

VIII A wherein $R_3$, $R_4$, $R_5$, $R_6$, and A are as defined, which process comprises reacting the racemic compound of formula (VIIIA) with a chiral auxiliary in the presence of a solvent, crystallising out the required diastereomeric salt and subsequently treating with base to obtain the desired enantiomer of the compound of formula (VIII A).

Compounds of general formula (Ia), (Ib), (Ic) or (Ig) and intermediates thereof may be prepared by any of the general schemes outlined below and illustrated in FIGS. 1-6. Unless otherwise specified, the groups A, Z, $R_1$, $R_2$, $R_3$, $R_4$, $R_5$, $R_{11}$, and $R_{13}$ are as defined in respect of general formula (Ia), (Ib), (Ic) or (Ig) above.

Scheme 1 (FIG. 1)

The compounds of the present invention are formed in scheme 1 by a metal catalyzed C—C bond coupling reaction well known in the art. In the compound of formula (II), P is a functional group, for example, Li, a halogen such as Cl, Br or I, a triflate or p-fluorobenzenesulfonate. In the compounds of formulae (I) and (III), A may be an optionally substituted 5-, 6- or 7-membered ring as defined above. In the case of the 5-membered rings of general structures (i), (iii) and (iv), the 6-membered ring of general structure (vi), and the 7-membered ring of general structure (vii), Q is attached to an unsaturated bond at position $C_1$ of ring A and is a halogen or a functionality suitable for coupling with the compound of formula (II) using organometallic catalysts. If Q is triflate then P is selected from Cl, Br or I and vice-versa. Organometallic catalysts such as palladium complexes, for example, $Pd(OAc)_2$, $PdCl_2(PhCN)_2$ and $Pd(Ph_3P)_4$ may be used for coupling. Coupling is carried out in presence of bases like sodium carbonate, potassium carbonate, piperidine and pyrrolidine, using solvents such as DMF. The double bond at position $C_1$ may be reduced after cross coupling, using standard methods like hydroboration or catalytic hydrogenation using catalysts such as palladium or platinum.

Where Q is attached to carbon −1 bearing a single bond, the coupling of P and Q may be effected using an appropriate organostannane (wherein Q may represent the stannate part) and ligand/catalyst such as 1,3-bis(diphenylphosphino)propane, palladium diacetate, lithium chloride and diphenylmethylphosphine and a leaving group such as aryl p-fluorobenzenesulfonate. (Ref Badone, Cecchi et al, Journal of Organic Chemistry, 1992, Vol 57, 6321-6323).

Where A is a 5-membered ring having the general structure (ii) or (v), wherein $X_1$ is N, the 5-membered heterocycle may be coupled directly with the compound of formula (II) using a suitable catalyst such as $Pd(OAc)_2$, $PdCl_2(PhCN)_2$, $Pd(Ph_3P)_4$ and CuI. Coupling is carried out in presence of bases like sodium carbonate, potassium carbonate, piperidine and pyrrolidine using solvents such as DMF.

Figure 2:
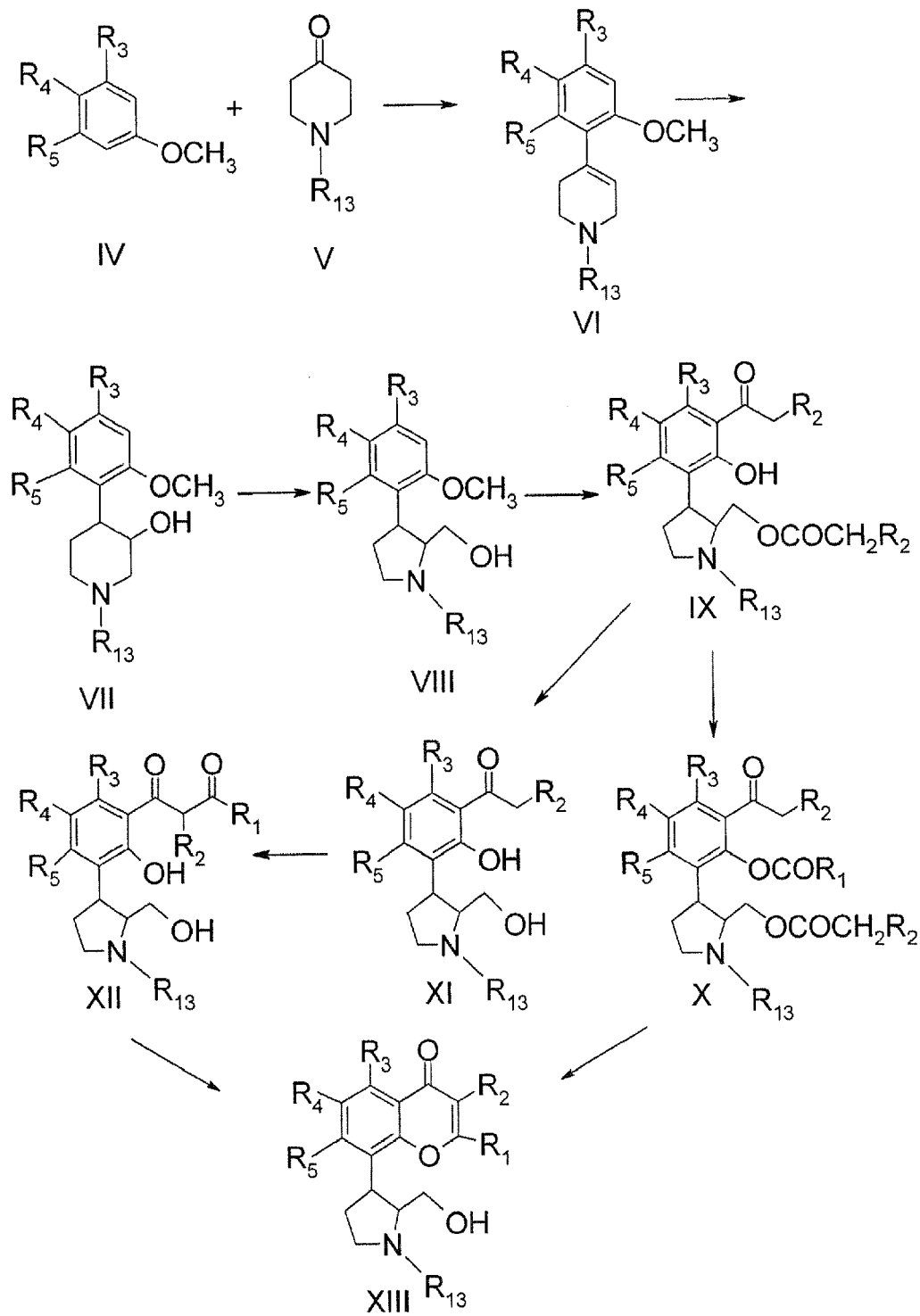

Scheme 2 (FIG. 2)

Alternatively, the preparation of compounds of general formula (Ia), (Ib), (Ic) or (Ig) (denoted as compounds of formula (XIII)) wherein Z is O, A is a 5-membered ring corresponding to general structures (i), (iii) or (iv) wherein $X_1$ is C, $X_2$ is $NR_{13}$, $R_6$ is alkyl and $R_7$ is hydrogen (wherein both $R_6$ and $R_7$ are substitutions on A as defined hereinabove) can be carried out in accordance with the steps shown in the scheme in FIG. 2.

In compounds of the formulae (VI) to (XIII), the group $R_{13}$ as depicted in Scheme 2 is preferably alkyl. As outlined in Scheme 2, the preparation steps up to compounds of formula (VII) starting from the compound of general formula (IV) are described in U.S. Pat. No. 4,900,727, which is incorporated herein by reference. In the conversion of the compound of formula (VII) to that of formula (VIII) in Scheme 2, the hydroxyl function on the piperidine ring may be converted to a good leaving group such as tosyl, mesyl, triflate or halide by treatment with appropriate reagents like p-toluenesulfonylchloride, methanesulfonylchloride, triflic anhydride or $PCl_5$ in the presence of an appropriate organic or inorganic base like triethylamine, pyridine, $K_2CO_3$ or $Na_2CO_3$, followed by ring contraction using a base such as sodium acetate in a solvent such as isopropanol. The ring contraction involved in this step may be effected before flavone formation as depicted in Scheme 2 or it may be done after building the flavone with desired substitutions. The compound of general formula (VIII) may be resolved by reacting it with a chiral auxiliary such as (+)-dibutyl tartaric acid, (+)-ketopinic acid, (+)-camphor-10-sulphonic acid or (+)-camphoric acid in the presence of a solvent such as methanol, isopropanol, diisopropyl ether, ethyl acetate or chloroform, crystallising out the required diastereomeric salt and subsequently treating with base such as $NaHCO_3$, $Na_2CO_3$ or $K_2CO_3$ to obtain the desired enantiomer of compound of formula (VIII). The compound of formula (VIII) may then be treated with an acylating agent such as a carboxylic acid, an acid chloride, an acid anhydride or any activated form of an acid, in the presence of a Lewis acid catalyst such as $BF_3$ $Et_2O$, $ZnCl_2$, $AlCl_3$ or $TiCl_4$ to obtain the corresponding acylated compound of formula (IX). Subsequently the compound of formula (IX) can be converted to the compound of formula (X) by treating it with a reagent like an acid chloride of the type $R_1COCl$, an anhydride of the type $(RICO)_2O$, an ester of the type $R_1COOCH_3$ or any like reagent wherein $R_1$ is as defined hereinabove. The said conversion can also be brought about by treating the compound of formula (IX) with an acid of the type $R_1COOH$ and phosphorus oxychloride in presence of an acid scavenger such as pyridine to obtain an acid chloride in situ under neutral conditions. Conversion of the compound of formula (IX) to the compound of formula (X) can also be brought about by a combination of $R_1COOH$ and polyphosphoric acid. The compound of the formula (IX) may be converted to that of the formula ($X_1$) by standard ester hydrolysis using bases like KOH or NaOH in aqueous ethanol or methanol. The resultant alcohol of formula ($X_1$) may be converted to a β-diketone of formula (XII) by treatment with an appropriate carboxylic acid ester such as $R_1COOMe$, $R_1COOEt$ etc. or with an acid chloride like $R_1COX$ wherein X is a halogen or with an activated ester such as an anhydride in the presence of a base such as NaH in a solvent such as DMF, THF or 1,4-dioxane. The β-diketone of formula (XII) may finally be converted into the required flavone of formula (XIII) by treatment with a base such as NaH followed by cyclization using a strong acid such as concentrated HCl and subsequent treatment with a mild base such as $Na_2CO_3$, $NaHCO_3$ or $K_2CO_3$. Alternatively, the intermediate of formula (X) may be converted into the flavone of formula (XIII) by treatment with a base such as NaH followed by cyclization using a strong acid like concentrated HCl followed by treatment with a mild base like $Na_2CO_3$, $NaHCO_3$ or $K_2CO_3$.

Figure 6:
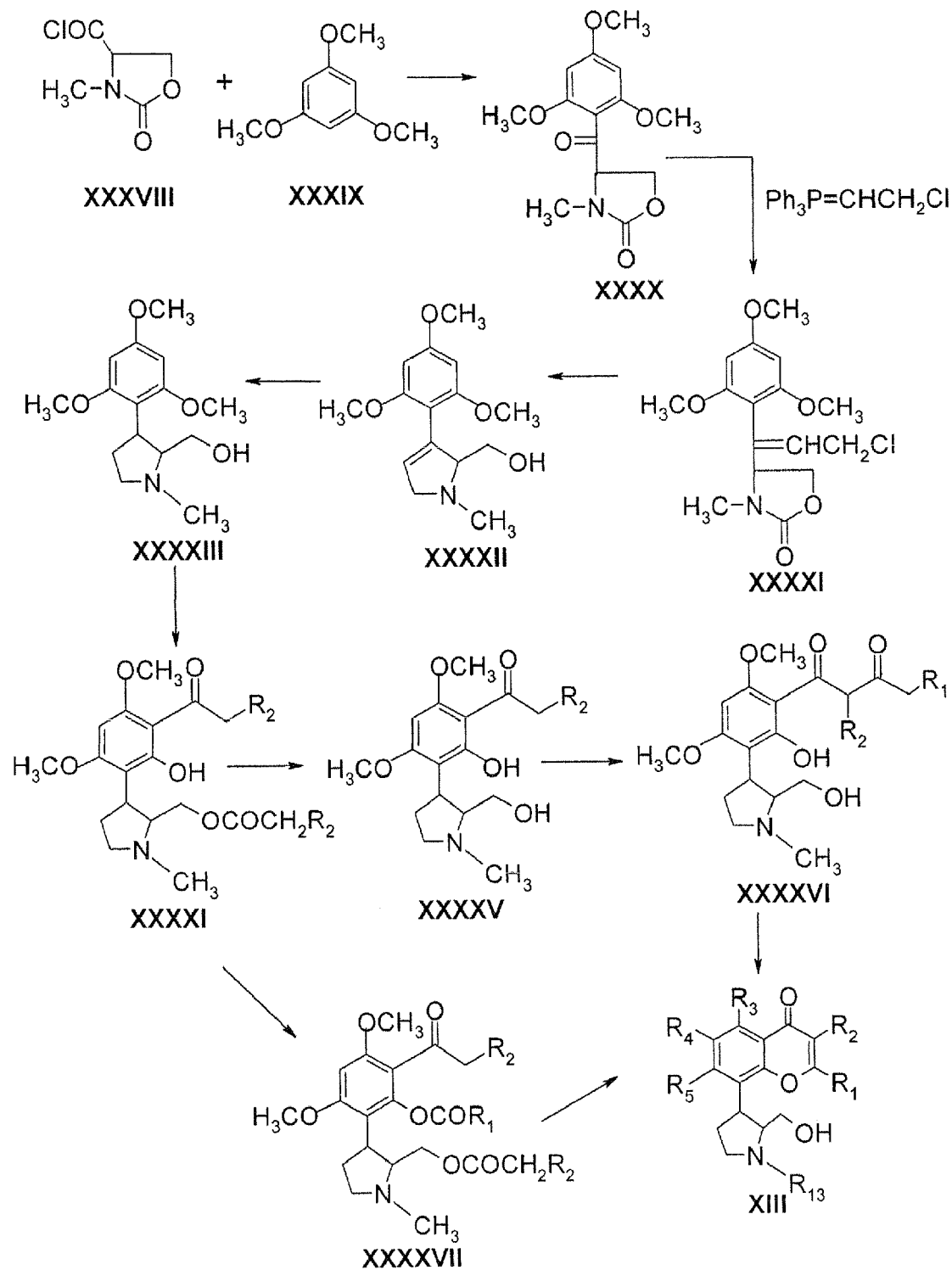

An alternative method for preparing the compound of formula (VIII), which is a key intermediate in the preparation of a compound of general formula (Ia), (Ib), (Ic) or (Ig), is represented in FIG. 6 (compound of formula (XXXXIII).

Figure 3:
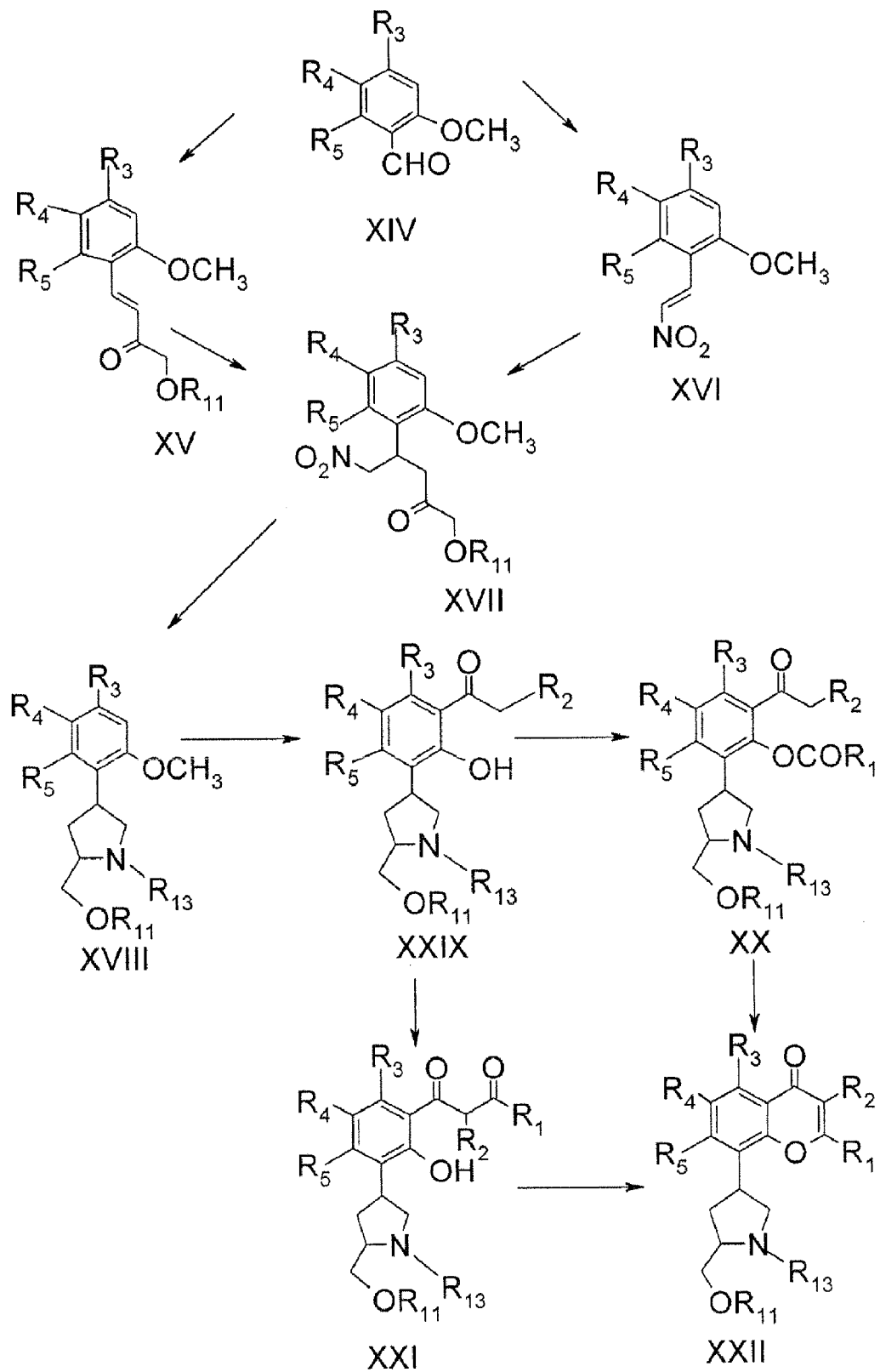

Scheme 3 (FIG. 3)

Scheme 3 outlines the preparation of the intermediate compound represented by formula (XVIII), which is subsequently converted to a compound of formula (XXII) by following similar process steps as described in Scheme 2 for the conversion of the compound of formula (VIII) to the compound of formula (XIII). The compound of formula (XXII) as prepared herein is a compound of general formula (Ia), (Ib), (Ic) or (Ig) above wherein Z is O, A is a 5-membered ring corresponding to general structure (i), (iii) or (iv) wherein $X_1$ is C and $X_2$ is $NR_{13}$ and the substitutions $R_6$ and $R_7$ on A are —$CH_2$—$OR_{11}$, and H, respectively.

As outlined in scheme 3, the compound of formula (XVIII) is prepared in three steps starting from an aldehyde of formula (XIV). The compound of formula (XIV) is first converted into the compound of formula (XVII) in two steps involving condensation of the compound of formula (XIV) with an appropriate ketone using a Knoevenagel reaction, followed by a Michael reaction of the resulting intermediate of formula (XV) with nitromethane in the presence of base to obtain the compound of formula (XVII). The Michael reaction in the presence of a chiral base such as proline leads to chiral compound of formula (XVII). Alternatively, the compound of formula (XVII) can be obtained by first converting the aldehyde (XIV) into the nitrostyrene derivative of formula (XVI) which in turn is reacted with an appropriate ketone by a Michael reaction, using base as described above.

The resulting compound of formula (XVII) is then subjected to a sequence of reactions involving selective reduction of the nitro group by known methods such as treatment with Tin/HCl or Iron/HCl followed by cyclization and subsequent reduction to yield the compound of formula (XVIII). Alternatively, reductive cyclization of the compound of formula (XVII) using a catalyst like Raney nickel directly gives the compound of formula (XVIII). This pivotal intermediate is then converted to the compound of formula (XXII) as described in scheme 3. Process steps from the compound of formula (XVIII) to the compound of formula (XXII) are as described for the conversion of the compound of formula (VIII) to the compound of formula (XIII) in scheme 2.

Figure 4:
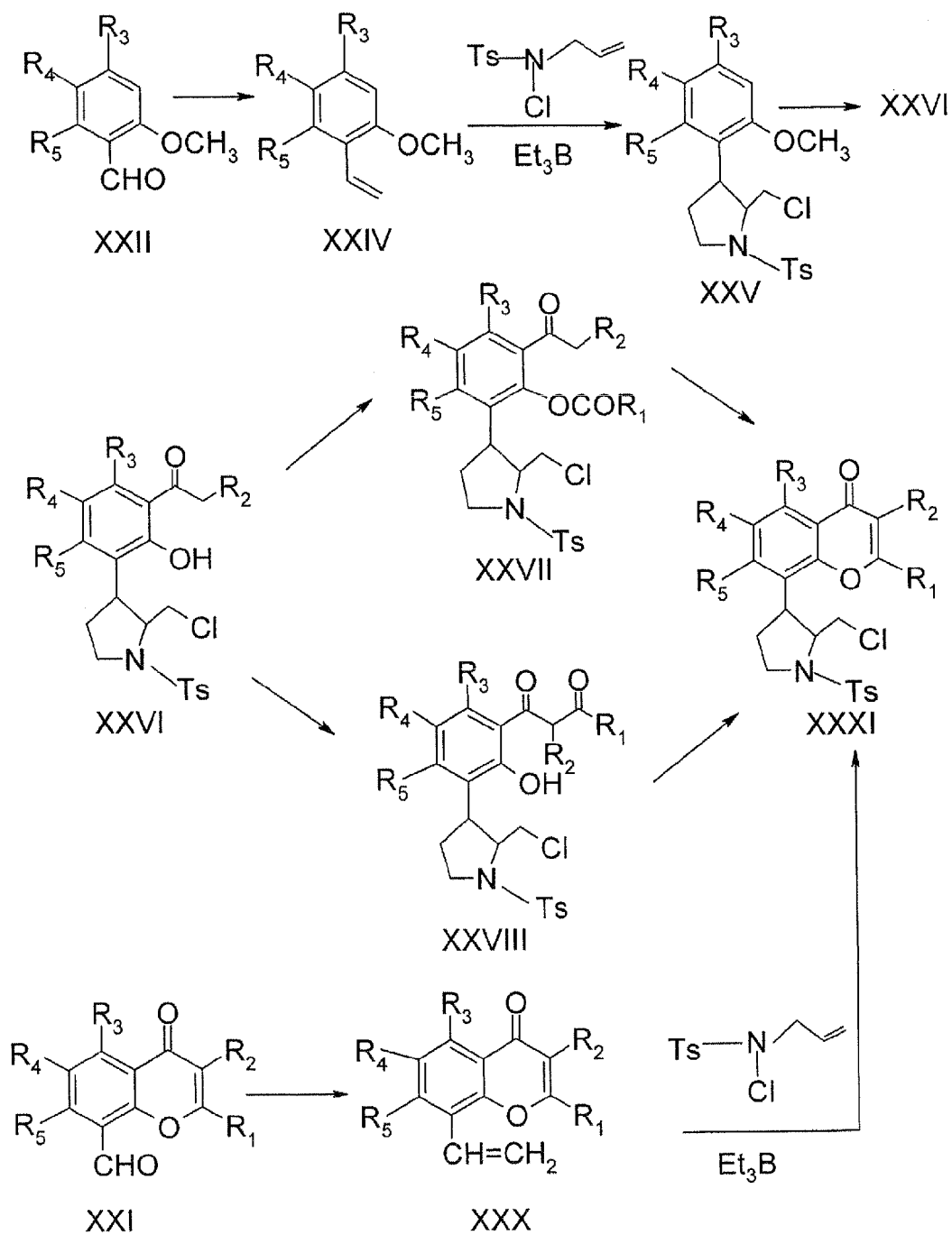

Scheme 4 (FIG. 4)

Another method of obtaining a compound of general formula (Ia), (Ib), (Ic) or (Ig) (denoted as formula XXXI), wherein Z is O, A is a 5-membered ring represented by general structure (i), (iii) or (iv) wherein $X_1$=C and $X_2$=$NR_{13}$, wherein $R_{13}$ represents p-toluenesulfonyl (Ts), $R_6$ is a haloalkyl group, with the halo atom preferably being Cl, and $R_7$ is H, is described in scheme 4.

As outlined in scheme 4, the compound of formula (XXXI) is prepared starting from the aldehyde of formula (XXIII). The compound of formula (XXIII) is converted using a Wittig reaction to the corresponding styrene compound of formula (XXIV) which in turn is converted into the compound of formula (XXV) by a [3+2]cycloaddition with N-allyl N-chlorotosylamide in the presence of alkylboranes such as triethyl borane ($Et_3B$) (Oshima et. al. Org. Lett., 2001, 3, 2709-2711). The compound of formula (XXV) is then converted into the compound of formula (XXXI) via the compounds of formulae (XXVI), (XXVII) and (XXVIII) as described in scheme 2. The use of an alternative intermediate of formula (XXIX) also leads to the compound of formula (XXXI) by following the above cycloaddition route.

Figure 5:
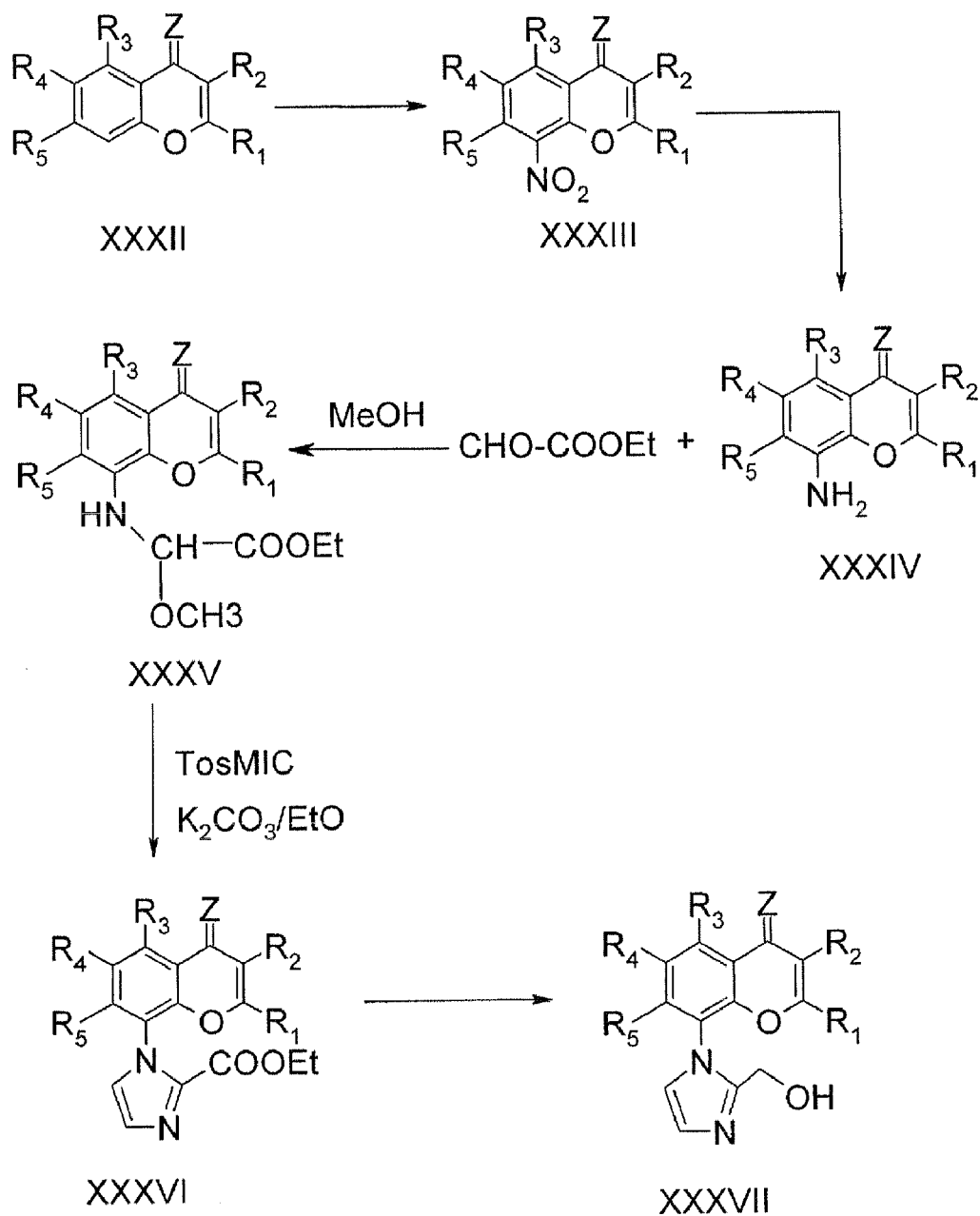

Scheme 5 (FIG. 5)

Preparation of the Preferred Compound of General Formula (Ia) or (Ic) (Denoted as the compound of formula (XXXVII), wherein A is a 5-membered ring corresponding to general structure (ii), wherein $X_1$=N, $X_2$=N, A is an unsaturated ring and the substitution $R_6$ on A is —$CH_2OH$, is depicted in Scheme 5.

As outlined in scheme 5, the compound of formula (XXXVI) is prepared starting from the compound of formula (XXXII). The compound of formula (XXXII) on nitration provides the compound of formula (XXXIII) which on reduction gives the corresponding amino compound of formula (XXXIV) (Larget et al, Bioorganic Med. Chem. Lett., 2000, 10, 835). Conversion of amino flavone of formula (XXXIV) to the compound of formula (XXXV) may be effected by treatment with ethyl glyoxylate in methanol. Further conversion of the intermediate of formula (XXXV) to that of formula (XXXVI) may be brought about by employing the method described in the literature (Tet. Lett., 2000, 41, 5453) for the transformation of α-anilino-α-alkoxyacetates to imidazoles using tosylmethylisocyanide (TosMIC) in presence of a base such as $Na_2CO_3$ or $K_2CO_3$ in a solvent such as ethanol or methanol. The compound of formula (XXXVI) may then be converted to the required final compound of the formula (XXXVII) by reduction using a reagent like lithium aluminium hydride.

Scheme 6 (FIG. 6)

As stated herein above in respect of scheme 2, the key intermediate of formula (VIII), which corresponds to the compound of formula (XXXXIII) in FIG. 6, may be prepared by the alternative process steps illustrated in scheme 6. The compound of formula (XXXXIII) may be prepared starting from the chiral compound of formula (XXXVIII), which in turn is prepared in accordance with the procedure described in Syn. Commun., 1993, 23(20), 2839-2844. The compound of formula (XXXVIII) on reacting with trimethoxybenzene (formula (XXXIX) under Friedel-Crafts conditions gives the resulting ketone of formula (XXXX), which on treatment with $Ph_3P$=$CHCH_2Cl$ using Wittig conditions leads to the compound of formula (XXXXI). Ring opening using a mild aqueous base followed by cyclization in the presence of a base such as sodium hydride leads to the compound of formula (XXXXII). Subsequent hydrogenation of the double bond in the 5-membered ring by a conventional reducing agent gives the corresponding compound of formula (XXXXIII) (corresponding to the compound of formula (VIII) in scheme 2), which may be further converted to the compound of formula (XIII) (corresponding to the compound of general formula (Ia), (Ib), (Ic) or (Ig) by following the same process steps as described in scheme 2 for the conversion of the compound of formula (VIII) to the compound of formula XIII.

Intermediates of this invention may also be prepared by a process disclosed in the prior art or by a modification of the procedure described in U.S. Pat. No. 4,900,727, which is incorporated as reference herein.

The compounds according to the general formula (Ia), (Ib), (Ic) or (Ig) can be used to inhibit the activity of various cyclin-dependent kinases and are helpful pharmaceutical compounds for the treatment of various diseases. In the context of the present invention, treatment includes the therapy as well as the prophylaxis of the respective diseases.

In one embodiment, the compounds of the present invention are for use in regulating cell proliferation. The compounds of the present invention are capable of inhibiting cell proliferation and are therefore useful in treating diseases which are due to an excessive or abnormal cell growth.

There are a wide variety of pathological conditions with excessive or abnormal cell proliferation against which the compounds of the invention can act to provide therapeutic benefits. Examples of such pathological conditions include:

a. various cancers and leukemias including (but not limited to) the following:

i. carcinoma, including that of bladder, breast, colon, kidney, liver, lung, ovary, pancreas, stomach, cervix, thyroid, prostate, and skin;

ii. hematopoietic tumors of lymphoid lineage, including acute lymphocytic leukemia, B-cell lymphoma, and Burkett's lymphoma;

iii. hematopoietic tumors of myeloid lineage, including acute and chronic myelogenous leukemias and promyelocytic leukemia;

iv. tumors of mesenchymal origin, including fibrosarcoma and rhabdomysarcoma; and v. other tumors including melanoma, seminoma, teratocarcinoma, osteosarcoma, neuroblastoma and glioma, b. chemotherapy- and/or radiation-therapy induced epithelial cytotoxicity side-effects such as alopecia;

c. dermatology (psoriasis);

d. bone diseases;

e. inflammation and arthritis;

f. fibroproliferative disorders such as those involving connective tissues, atherosclerosis and other smooth muscle proliferative disorders, as well as chronic inflammation;

g. cardiovascular abnormalities (restenosis, tumoral angiogenesis, atherosclerosis);

h. nephrology (glomerulonephritis);

i. parasitology (unicellular parasites such as *Plasmodium, Trypanosoma, Toxoplasma*, etc);

j. neurology (Alzheimer's disease, stroke);

k. viral infections (cytomegalovirus, human immunodeficiency virus, herpes); and l. mycotic infections.

In addition to proliferative disorders, the present compounds can be used in the treatment of differentiative disorders which result from, for example, de-differentiation of tissue, optionally accompanied by abortive reentry into mitosis. Such degenerative disorders include chronic neurodegenerative diseases of the nervous system, including Alzheimers's disease as suggested by the finding that CDK5 is involved in the phosphorylation of tau protein (J. Bio. Chem. 1995, 117, 741-749), Parkinson's disease, Huntington's chorea, amylotrophic lateral sclerosis and the like, as well as spinocerebellar degenerations. Other differentiative disorders include, for example, disorders associated with connective tissue, such as those that may occur due to de-differentiation of chondrocytes or osteocytes, as well as vascular disorders which involve de-differentiation of endothelial tissue and smooth muscle cells, gastric ulcers characterized by degenerative changes in glandular cells, and renal conditions marked by failure to differentiate, e.g. Wilm's tumors.

In addition to therapeutic applications (e.g., for both human and veterinary uses) it will be apparent that the compounds of the present invention can be used as a cell culture additive for controlling proliferative and/or differentiation states of cells in vitro and can also be used for ex vivo tissue generation as for example, to enhance the generation of prosthetic tissue devices for implantation such as described in U.S. Pat. No. 5,733,920 which is incorporated herein by reference.

Differential screening assays known in the art can be used to select for those compounds of the present invention with specificity for non-human CDK enzymes. Thus, compounds which act specifically on eukaryotic pathogens, e.g., antifungal or anti-parasitic agents, can be selected from the subject compounds of general formula (Ia), (Ib), (Ic) or (Ig). Such inhibitors are useful in patients where fungal infections are a particular problem such as in patients with leukemias and lymphomas, diabetes mellitus, AIDS, or in people who are receiving immunosuppressive therapy.

When selected for ant-mycotic uses the formulations of the inhibitors can be provided with those inhibitors which inhibit a cyclin-dependent kinase complex of the human pathogen with an $IC_{50}$ at least an order of magnitude less than an $IC_{50}$ for inhibition of a human cyclin-dependent kinase complex, though more preferably at least two or three orders of magnitude less.

In a similar manner, certain of the present compounds can be selected on the basis of inhibitory specificity for insect or plant CDK's relative to the mammalian enzyme in a differential screen. Such insect or plant CDK inhibitors of the present invention find use in insecticides and agricultural applications, respectively.

The present invention therefore also relates to the compounds of the formula (Ia), (Ib), (Ic) or (Ig) and/or their pharmaceutically acceptable salts and/or their prodrugs for use as pharmaceuticals (or medicaments), to the use of the compounds of the formula (Ia), (Ib), (Ic) or (Ig) and/or their physiologically tolerable salts and/or their prodrugs for the production of pharmaceuticals for the inhibition of cell proliferation or for the therapy or prophylaxis of the diseases mentioned above, for example for the production of pharmaceuticals for the therapy and prophylaxis of cancer, inflammation and arthritis, psoriasis, bone diseases, mycotic or viral infections, cardiovascular disorders, Alzheimers's disease, etc., and to methods of treatment aiming at such purposes including methods for said therapies and prophylaxes. The present invention furthermore relates to pharmaceutical compositions that contain an effective amount of at least one compound of the formula (Ia), (Ib), (Ic) or (Ig) and/or its physiologically tolerable salts and/or its prodrugs in addition to a customary pharmaceutically acceptable carrier, and to a process for the production of a pharmaceutical, which comprises bringing at least one compound of formula (Ia), (Ib), (Ic) or (Ig) into a suitable administration form using a pharmaceutically suitable and physiologically tolerable excipient and, if appropriate, further suitable active compounds, additives or auxiliaries. The pharmaceutical preparation comprises the compound of formula (Ia), (Ib), (Ic) or (Ig) in an amount adequate to inhibit proliferation of a eukaryotic cell, which may be a mammalian cell, a human pathogen, such as *Candida albicans, Aspergillus fumigatus, Rhizopus arrhizus, Mucor pusillus*, an insect cell or a plant cell.

The present invention also relates to a method for the preparation of a medicament for the treatment or prevention of disorders associated with excessive cell proliferation, characterized in that at least one compound of the general formula (Ia), (Ib), (Ic) or (Ig) is used as the pharmaceutically active substance.

The pharmaceuticals can be administered orally, for example in the form of pills, tablets, coated tablets, capsules, granules or elixirs. Administration, however, can also be carried out rectally, for example in the form of suppositories, or parentally, for example intravenously, intramuscularly or subcutaneously, in the form of injectable sterile solutions or suspensions, or topically, for example in the form of solutions or transdermal patches, or in other ways, for example in the form of aerosols or nasal sprays.

The pharmaceutical preparations according to the invention are prepared in a manner known per se and familiar to one skilled in the art. Pharmaceutically acceptable inert inorganic and/or organic carriers and/or additives can be used in addition to the compound (s) of the formula (Ia), (Ib), (Ic) or (Ig) and/or its (their) physiologically tolerable salts and/or its (their) prodrugs. For the production of pills, tablets, coated tablets and hard gelatin capsules it is possible to use, for example, lactose, corn starch or derivatives thereof, gum arabic, magnesia or glucose, etc. Carriers for soft gelatin capsules and suppositories are, for example, fats, wax, natural or hardened oils, etc. Suitable carriers for the production of solutions, for example injection solutions, or of emulsions or syrups are, for example, water, physiological sodium chloride solution or alcohols, for example, ethanol, propanol or glycerol, sugar solutions, such as glucose solutions or mannitol solutions, or a mixture of the various solvents which have been mentioned.

The pharmaceutical preparations normally contain about 1 to 99%, preferably about 5 to 70%, most preferably from about 10 to about 30% by weight of the compounds of the formula (Ia), (Ib), (Ic) or (Ig) and/or their physiologically tolerable salts and/or their prodrugs. The amount of the active ingredient of the formula (Ia), (Ib), (Ic) or (Ig) and/or its physiologically tolerable salts and/or its prodrugs in the pharmaceutical preparations normally is from about 5 to 500 mg. The dose of the compounds of this invention, which is to be administered, can cover a wide range. The dose to be administered daily is to be selected to suit the desired effect. About 20 to 1,000 mg are preferably administered daily per patient. If required, higher or lower daily doses can also be administered. Actual dosage levels of the active ingredients in the pharmaceutical compositions of this invention may be varied so as to obtain an amount of the active ingredient which is effective to achieve the desired therapeutic response for a particular patient, composition, and mode of administration without being toxic to the patient.

The selected dosage level will depend upon a variety of factors including the activity of the particular compound of the present invention employed, or the ester, salt or amide thereof, the route of administration, the time of administration, the rate of excretion of the particular compound being employed, the duration of the treatment, other drugs, compounds and/or materials used in combination with the particular compounds employed, the age, sex, weight, condition, general health and prior medical history of the patient being treated, and like factors well known in the medical arts.

In addition to the active ingredients of the formula (Ia), (Ib), (Ic) or (Ig) and/or their physiologically acceptable salts and/or prodrugs and to carrier substances, the pharmaceutical preparations can contain additives such as, for example, fillers, antioxidants, dispersants, emulsifiers, defoamers, flavor corrigants, preservatives, solubilizers or colorants. They can also contain two or more compounds of the formula (Ia), (Ib), (Ic) or (Ig) and/or their physiologically tolerable salts and/or their prodrugs. Furthermore, in addition to at least one compound of the formula (Ia), (Ib), (Ic) or (Ig) and/or its physiologically tolerable salts and/or its prodrugs, the pharmaceutical preparations can also contain one or more other therapeutically or prophylactically active ingredients.

The compounds of the present invention may be used as drugs in the treatment of proliferative disorders either alone or as part of combined therapies. For instance, the compounds of the present invention may be used in combination with known anti-cancer, cytostatic, and cytotoxic agents. If formulated as a fixed dose, such combination products employ the compounds of the present invention within the dosage range described above and the other pharmaceutically active agent within its approved dosage range. For example, the CDK inhibitor olomoucine has been found to act synergistically with known cytotoxic agents in inducing apoptosis (J. Cell Sci., 1995, 108, 2897). Compounds of general formula (Ia), (Ib), (Ic) or (Ig) may be used sequentially with known drugs such as anticancer or cytotoxic agents when a combination formulation is inappropriate.

It is understood that modifications that do not substantially affect the activity of the various embodiments of this invention are included within the invention disclosed herein. Accordingly, the following examples are intended to illustrate but not to limit the present invention.

Note:

1) Elemental analysis: The value in parenthesis stands for the theoretical value.

EXAMPLE 1

1-Methyl-4-(2,4,6-trimethoxy-phenyl)-1,2,3,6-tetrahydro-pyridine (Compound No. 1)

1-methyl-4-piperidone (340 g, 3×10$^3$ mmol) was added slowly, to a solution of 1,3,5-trimethoxy benzene (500 g, 2.976×10$^3$ mmol) in glacial acetic acid (600 mL), maintaining the temperature of the reaction mixture below 40° C. Concentrated HCl (450 mL) was added over 20 min. The temperature was raised to 85-90° C. and the reaction mixture was stirred for 3.5 h. It was allowed to cool to 40° C., poured over crushed ice (4 kg) and stirred for 20 min. The precipitated unreacted 1,3,5-trimethoxy benzene was filtered off. The filtrate was basified, at below 10° C., to pH 11-12 using a 50% aqueous NaOH solution. The off white solid (1) obtained was filtered, washed with water and dried.

Yield: 580 g (74%).

mp: 117-119° C.

IR cm$^{-1}$: 1600, 2800.

$^1$HNMR (CDCl$_3$): δ 6.15 (s, 2H), 5.55 (s, 1H), 3.75 (s, 6H), 3.85 (s, 3H), 3.1 (d, 2H), 2.55 (t, 2H), 2.4 (s, 3H), 2.35 (s, 1H), 2.0 (s, 1H).

MS: m/e 263 (M$^+$).

EXAMPLE 2

(+/−)-trans-1-Methyl-4-(2,4,6-trimethoxy-phenyl)-piperidin-3-ol (Compound No. 2)

Boron trifluoride etherate (300 mL, 2.37 mol) was added slowly with stirring, under an atmosphere of nitrogen, at 0° C., to a solution of compound (I) (300 g, 1.14×10$^3$ mmol) and NaBH$_4$ (75 gm, 1.97×10$^3$ mmol) in dry THF (2.25 L). The temperature of the reaction mixture was slowly raised to 55° C. and it was stirred for 1.5 h. It was cooled to 30° C. Ice cold water (100 mL) was slowly added followed by acidification with concentrated HCl (375 mL). The reaction mixture was stirred for 1 h at 50-55° C. It was cooled to 30° C. and basified using 50% aqueous NaOH solution to pH 11-12. Hydrogen peroxide (30%, 225 mL) was added over 0.5 h. The reaction mixture was stirred at 55-60° C. for 1.5 h. It was cooled to 30° C. and sufficient water added to dissolve the precipitated salts. The organic layer was separated and the aqueous portion extracted with EtOAc (2×1 L). The organic extracts were dried (anhy. Na$_2$SO$_4$) and concentrated. The crude viscous brown oil obtained was treated with 4N HCl (1.2 L) and extracted with EtOAc (2×500 mL). The aqueous portion was cooled, basified with 50% aqueous NaOH solution and extracted using EtOAc (2×1 L). The organic extract was dried (anhy. Na$_2$SO$_4$) and concentrated to give the product (2).

Yield: 210 g (65.6%).

mp: 89-91° C.

IR cm$^{-1}$: 3500.

$^1$HNMR (CDCl$_3$): δ 6.15 (s, 2H), 4.4 (m, 1H), 3.79 (s, 3H), 3.74 (s, 6H), 2.4 (s, 3H), 3.3 (m, 1H), 2.55 (t, 2H), 2.35 (s, 1H), 2.0 (s, 1H).

MS: m/e 281 (M$^+$), 263 (M-H$_2$O).

EXAMPLE 3

(+/−)-trans-Acetic acid 1-methyl-3-(2,4,6-trimethoxy-phenyl)-pyrrolidin-2-ylmethyl ester (Compound No. 3)

Distilled triethyl amine (344 mL, 2.49×10$^3$ mmol) was added slowly to a solution of compound (2) (350 g, 1.25×10$^3$ mmol) in dry CH$_2$Cl$_2$ (2.5 L). To the reaction mixture methanesulfonyl chloride (122 mL, 171.1 g, 1.49×10$^3$ mmol) was added with stirring, at 0° C., under an atmosphere of N$_2$ and over a period of 20 min. The reaction mixture was further stirred for 1 h at 0° C. It was poured over saturated aqueous NaHCO$_3$ solution (1.5 L). The organic layer was separated, washed with brine, dried (anhy. Na$_2$SO$_4$) and concentrated to obtained the O-mesylated derivative. It was dissolved in distilled isopropyl alcohol (1.5 L), anhydrous sodium acetate (408 g, 4.97 mmol) was added and the reaction mixture was refluxed for 1 h. It was cooled to room temperature. Sodium acetate was filtered off and washed with CHCl$_3$. The filtrate was concentrated to obtain the title compound (3), which was purified using a silica gel column and 60% EtOAc/petroleum ether 60-80° C. as eluant.

Yield: 241 g (60%).

$^1$HNMR (CDCl$_3$): δ 6.15, (s, 2H), 3.92 (m, 1H), 3.79 (s, 3H), 3.74 (s, 6H), 3.6 (dd, 1H), 3.45 (dd, 1H), 3.2 (m, 1H), 2.78 (m, 1H), 2.6 (m, 1H), 2.42 (s, 3H), 2.2 (s, 3H), 2.0 (m, 2H).

MS: m/e 323 (M$^+$).

EXAMPLE 4

(+/−)-trans-[1-Methyl-3-(2,4,6-trimethoxy-phenyl)-pyrrolidin-2-yl]-methanol (Compound No. 4)

A 10% aqueous NaOH solution (596 mL, 149 mmol) was added to a solution of the product (3) (241 g, 746 mmol) in methanol (596 mL). The reaction mixture was stirred at 50° C. for 45 min. It was concentrated to approximately half its volume and then poured into ice water (2 L). It was then extracted using ethyl acetate (2×1 L), washed with brine and dried (anhy. Na$_2$SO$_4$) to obtain the title compound (4) as a light yellow syrup.

Yield: 198 g (94%).

$^1$HNMR (CDCl$_3$): δ 6.15 (s, 2H), 3.92 (m, 1H), 3.79 (s, 3H), 3.74 (s, 6H), 3.6 (dd, 1H), 3.45 (dd, 1H), 3.2 (m, 1H), 2.78 (m, 1H), 2.6 (m, 1H), 2.42 (s, 3H), 2.0 (m, 2H).

MS: m/e 281 (M$^+$), 249 (M−31).

EXAMPLE 5

(−)-trans-[1-Methyl-3-(2,4,6-trimethoxy-phenyl)-pyrrolidin-2-yl]-methanol (Compound No. 5)

(+/−)-trans-[1-Methyl-3-(2,4,6-trimethoxy-phenyl)-pyrrolidin-2-yl]-methanol (Compound No. 4) (27.3 g, 97.1 mmol), was dissolved in methanol (100 mL) and heated to 70° C. To this hot solution was added (+)DBTA (36.51 g, 101.9 mmol) and the heating was continued for 10 min. It was concentrated to get a solid (63.81 g), which was crystallized using methanol (45 mL) and isopropanol (319 mL). Filtration and an isopropanol wash with subsequent drying afforded the crystalline tartarate salt (13.14 g), $[α]_D^{25}$=+55.34°(c=1.14, methanol). This product was then recrystallized using methanol (10 mL) and isopropanol (40 mL). It was isolated as described above, yield: 9.04 g, $[α]_D^{25}$=+49.67° (c=1.248, methanol). The free base was obtained from this product as follows.

The salt (9 g) was suspended in ethyl acetate (100 mL). To this suspension 5% aqueous NaHCO$_3$ solution (100 mL) was added and the mixture was stirred for 30 minutes. The organic portion was separated and the aqueous portion was further extracted using ethyl acetate (2×50 mL). The organic portions were combined and concentrated to obtain the title compound (5).

Yield: 3.6 g (91.51%).

$[α]_D^{25}$=−17.6° (c=1.1, methanol).

$^1$HNMR (CDCl$_3$): δ 6.15 (s, 2H), 3.92 (m, 1H), 3.79 (s, 3H), 3.74 (s, 6H), 3.6 (dd, 1H), 3.45 (dd, 1H), 3.2 (m, 1H), 2.78 (m, 1H), 2.6 (m, 1H), 2.42 (s, 3H), 2.0 (m, 2H).

MS: m/e 281 (M$^+$), 249 (M−31).

EXAMPLE 6

(−)-trans-Acetic acid 3-(3-acetyl-2-hydroxy-4,6-dimethoxy-phenyl)-1-methyl-pyrrolidin-2-yl methyl ester (Compound No. 6)

BF$_3$-etherate (32.5 mL, 250 mmol) was added dropwise, with stirring, at 0° C., under N$_2$ atmosphere to a solution of product (5) (14.4 g, 51 mmol) in acetic anhydride (26 mL, 250 mmol). The reaction mixture was stirred at room temperature for 2 h. It was poured over crushed ice (1 kg) and basified using a saturated aqueous Na$_2$CO$_3$ solution. It was extracted using EtOAc (3×200 mL). The organic extract was washed with brine, dried (anhy. Na$_2$SO$_4$) and concentrated to get title compound (6).

Yield: 11.5 g (64%).

$^1$HNMR (CDCl$_3$): δ 14.2 (s, 1H), 5.95 (s, 1H), 4.1 (d, 2H), 3.92-3.75 (m, 7H), 3.25 (m, 1H), 2.82 (m, 2H), 2.65 (s, 3H), 2.5 (s, 3H), 2.1 (m, 5H).

$[α]_D^{25}$=−7.02° (c=0.7, methanol).

EXAMPLE 7

(+/−)-trans-1-[2-Hydroxy-3-(2-hydroxymethyl-1-methyl-pyrrolidin-3-yl)-4,6-dimethoxy-phenyl]-ethanone (Compound No. 7)

To a solution of (−)-trans-Acetic acid 3-(3-acetyl-2-hydroxy-4,6-dimethoxy-phenyl)-1-methyl-pyrrolidin-2-yl methyl ester (11 g, 31 mmol), obtained from compound (4), as described in Example 6 in methanol (25 ml) was added with stirring, at room temperature, a 10% aqueous NaOH (25 mL, 62 mmol) solution. The temperature of the reaction mixture was raised to 50° C. for 45 min. It was cooled to room temperature, acidified using concentrated HCl and concentrated to remove methanol. It was basified using a saturated aqueous. Na$_2$CO$_3$ solution. The precipitated title compound (7) was filtered, washed with water and dried.

Yield: 8.5 g. (87%).

$^1$HNMR (CDCl$_3$): δ 5.9 (s, 1H), 3.98 (m, 1H), 3.9 (two singlets, 6H), 3.6 (dd, 1H), 3.38 (d, 1H), 3.15 (m, 1H), 2.8 (m, 1H), 2.6 (s, 3H), 2.58 (m, 1H), 2.4 (s, 3H), 2.0 (m, 2H).

MS: m/e 309 (M$^+$), 278 (M−31).

EXAMPLE 8

(+/−)-trans-2-(2-Chloro-phenyl)-8-(2-hydroxymethyl-1-methyl-pyrrolidin-3-yl)-5,7-dimethoxy-chromen-4-one. (Compound No. 8)

Sodium hydride (50%, 2.17 g, 45.3 mmol) was added in portions to a solution of compound (7) (2.8 g, 9 mmol) in dry DMF (30 mL) at 0° C., under nitrogen atmosphere and with stirring. After 10 min. methyl 2-chlorobenzoate (5.09 g, 29.9 mmol) was added. The reaction mixture was stirred at room temperature for 2 h. Methanol was added carefully at below 20° C. followed by, addition of concentrated HCl (25 mL) and passage of a strong stream of HCl gas for 2 h. The reaction mixture was poured over crushed ice (300 g) and made basic using a saturated aqueous Na$_2$CO$_3$ solution. The mixture was extracted using CHCl$_3$ (3×200 mL).

The organic extract was washed with water, dried (anhy. Na$_2$SO$_4$) and concentrated to obtain the title compound (8) which was purified using a silica gel column and a mixture of 2% methanol+1% liquor ammonia in CHCl$_3$ as eluant.

Yield: 2.5 g (64.6%).

mp: 95-97° C.

IR cm$^{-1}$: 3400, 1660.

$^1$HNMR (CDCl$_3$): δ 7.7 (dd, 1H), 7.55 (m, 1H), 7.45 (m, 2H), 6.45 (s, 1H), 6.55 (s, 1H), 4.17 (m, 1H), 3.95 (s, 3H), 4.05 (s, 3H), 3.65 (dd, 1H), 3.37 (dd, 1H), 3.15 (m, 1H), 2.77 (d, 1H), 2.5 (m, 1H), 2.3 (s, 3H), 2.05 (m, 2H).

MS: m/e 430 (M$^+$), 398 (M−31).

EXAMPLE 9

(+/−)-trans-2-(2-Chloro-phenyl)-5,7-dihydroxy-8-(2-hydroxymethyl-1-methyl-pyrrolidin-3-yl)-chromen-4- one. (Compound No. 9)

A mixture of compound (8) (0.25 g, 0.5 mmol) and dry pyridine hydrochloride (2.5 g, 21 mmol) was heated at 180° C. for 1.5 h. The reaction mixture was cooled to room temperature, treated with water (50 mL) and basified using an aq. saturated $Na_2CO_3$ solution. It was extracted using $CHCl_3$ (3×100 mL). The organic extract was washed with water, dried (anhy. $Na_2SO_4$) and concentrated. Traces of pyridine were removed using high vacuum. Purification was carried out using a silica gel column and a mixture of 5% methanol+1% liquor ammonia in $CHCl_3$ as eluant to obtain title compound (9).

Yield: 0.133 g (56%).
mp: 228-230° C.
$^1$HNMR ($CDCl_3$): δ 12.6 (s, 1H), 7.5 (m, 4H), 6.45 (s, 1H), 6.3 (s, 1H), 4.15 (m, 1H), 3.9 (m, 2H), 3.29 (m, 2H), 2.92 (m, 1H), 2.78 (s, 3H), 2.48 (m, 1H), 1.98 (m, 1H).
MS: m/e 402 (M+1), 384 (M−18), 370 (M−31).
IR $cm^{-1}$: 3350, 3180, 1680.
Analysis: $C_{21}H_{20}ClNO_5.2H_2O$, C, 59.45 (60.00); H, 5.17 (5.28); N, 3.68 (3.33); Cl, 8.84 (8.44).

EXAMPLE 10

(+)-trans-2-(2-Chloro-phenyl)-8-(2-hydroxymethyl-1-methyl-pyrrolidin-3-yl)-5,7-dimethoxy-chromen-4- one. (Compound No. 11)

Compound (5) was converted into (−)-trans-1-[2-Hydroxy-3-(2-hydroxymethyl-1-methyl-pyrrolidin-3-yl)-4,6-dimethoxyphenyl]-1-ethanone (compound (10) using the procedures described in examples 6 & 7. Compound (10) (0.75 g, 2.4 mmol), was reacted with methyl 2-chlorobenzoate (1.36 g, 7.9 mmol) in dry DMF (15 mL) in the presence of NaH (50%, 0.582 g, 12.9 mmol), using the procedure described in example 8 to get the title compound (11).

Yield: 0.67 g (64%).
mp: 95-97° C.
IR $cm^{-1}$: 3400, 1660.
$^1$HNMR ($CDCl_3$): δ 7.7 (dd, 1H), 7.55 (m, 1H), 7.45 (m, 2H), 6.45 (s, 1H), 6.55 (s, 1H), 4.17 (m, 1H), 3.95 (s, 3H), 4.05 (s, 3H), 3.65 (dd, 1H), 3.37 (dd, 1H), 3.15 (m, 1H), 2.77 (d, 1H), 2.5 (m, 1H), 2.3 (s, 3H), 2.05 (m, 2H).
MS: m/e 430 ($M^+$), 398 (M−31).
Analysis: $C_{23}H_{24}ClNO_5.2H_2O$, C, 59.67 (59.29); H, 5.37 (6.05); N, 3.24 (3.0); Cl, 7.56 (7.6).

EXAMPLE 11

(+)-trans-2-(2-Chloro-phenyl)-5,7-dihydroxy-8-(2-hydroxymethyl-1-methyl-pyrrolidin-3-yl)-chromen-4- one. (Compound No. 12)

Compound (11) (0.4 g, 0.9 mmol) subjected to demethylation using pyridine hydrochloride (4.1 g, 35.4 mmol) as described in example 9, afforded the title compound (12).
Yield: 0.2 g, (56%).
mp: 228-230° C.
$^1$HNMR ($CDCl_3$): δ 12.6 (s, 1H), 7.5 (m, 4H), 6.45 (s, 1H), 6.3 (s, 1H), 4.15 (m, 1H), 3.9 (m, 2H), 3.29 (m, 2H), 2.92 (m, 1H), 2.78 (s, 3H), 2.48 (m, 1H), 1.98 (m, 1H).
MS: m/e 402 (M+1), 384 (M−18), 370 (M−31).
IR $cm^{-1}$: 3350, 3180, 1680.
Analysis: $C_{21}H_{20}ClNO_5.2H_2O$, C, 59.45 (60.00); H, 5.17 (5.28); N, 3.68 (3.33); Cl, 8.84 (8.44).
$[\alpha]_D^{25}$=+12.12° (c=0.132, methanol: $CHCl_3$, 40:60).

EXAMPLE 12

(−)-trans-2-(2-Chloro-phenyl)-8-(2-hydroxymethyl-1-methyl-pyrrolidin-3-yl)-5,7-dimethoxy-chromen-4- one. (Compound No. 14)

(+)-trans-1-[2-Hydroxy-3-(2-hydroxymethyl-1-methyl-pyrrolidin-3-yl)-1-4,6-dimethoxyphenyl]-1-ethanone (compound 13), was prepared from (+)-trans-[1-Methyl-3-(2,4,6-trimethoxy-phenyl-pyrrolidin-2-yl]-methanol using the procedures described in examples 6 & 7. Compound 13, (0.7 g, 2.2 mmol) was reacted with methyl 2-chlorobenzoate (1.15 g, 6.75 mmol) in dry DMF (15 mL) in the presence of NaH (50%, 0.54 g, 11.25 mmol), using the procedure described in example 8 to afford the title compound (14).

Yield: 0.25 g (26%).
mp: 95-97° C.
IR $cm^{-1}$: 3400, 1660.
$^1$HNMR ($CDCl_3$): δ 7.7 (dd, 1H), 7.55 (m, 1H), 7.45 (m, 2H), 6.45 (s, 1H), 6.55 (s, 1H), 4.17 (m, 1H), 4.05 (s, 3H), 3.95 (s, 3H), 3.65 (dd, 1H), 3.37 (dd, 1H), 3.15 (m, 1H), 2.77 (d, 1H), 2.5 (m, 1H), 2.3 (s, 3H), 2.05 (m, 2H).
MS: m/e 430 ($M^+$), 398 (M−31).

EXAMPLE 13

(−)-trans-2-(2-Chloro-phenyl)-5,7-dihydroxy-8-(2-hydroxymethyl-1-methyl-pyrrolidin-3-yl)-chromen-4- one. (Compound No. 15)

Compound (14) (0.2 g, 0.46 mmol) subjected to demethylation using pyridine hydrochloride (2 g, 17.3 mmol), as described in example 9, afforded the title compound (15).
Yield: 0.1 g (56%).
mp: 228-230° C.
$^1$HNMR ($CDCl_3$): δ 12.6 (s, 1H), 7.5 (m, 4H), 6.45 (s, 1H), 6.3 (s, 1H), 4.15 (m, 1H), 3.9 (m, 2H), 3.29 (m, 2H), 2.92 (m, 1H), 2.78 (s, 3H), 2.48 (m, 1H), 1.98 (m, 1H).
MS: m/e 402 (M+1), 384 (M−18), 370 (M−31).
IR $cm^{-1}$: 3350, 3180, 1680.
Analysis: $C_{21}H_{20}ClNO_5.2H_2O$, C, 59.45 (60); H, 5.17 (5.28); N, 3.68 (3.33); Cl, 8.84 (8.44).
$[\alpha]_D^{25}$=−12.28° (c=0.114, methanol: $CHCl_3$, 40:60).

EXAMPLE 14

(+)-trans-2-(2-Bromo-phenyl)-8-(2-hydroxymethyl-1-methyl-pyrrolidin-3-yl)-5,7-dimethoxy-chromen-4- one. (Compound No. 16)

Compound (10) (0.7 g, 2.26 mmol) in dry DMF (10 mL) was reacted with methyl 2-bromobenzoate (1.6 g, 7.44 mmol) in the presence of NaH (50%, 0.54 g, 11.3 mmol) as detailed in example 8, to afford the title compound (16).
Yield: 0.4 g (37.3%).
$^1$HNMR ($CDCl_3$): δ 7.7 (d, 1H), 7.65 (t, 1H), 7.4 (m, 2H), 6.45 (s, 1H), 6.4 (s, 1H), 4.15 (m, 1H), 3.9 (two singlets, 6H), 3.65 (dd, 1H), 3.38 (d, 1H), 3.08 (m, 1H), 2.68 (d, 1H), 2.45 (m, 1H), 2.27 (s, 3H), 2.05 (m, 2H).
MS: m/e 474 (M$^+$), 442 (M–31).

EXAMPLE 15

(+)-trans-2-(2-Bromo-phenyl)-5,7-dihydroxy-8-(2-hydroxymethyl-1-methyl-pyrrolidin-3-yl)-chromen-4-one. (Compound No. 17)

Compound (16) (0.36 g, 0.76 mmol) subjected to demethylation using pyridine hydrochloride (3.6 g, 31.6 mmol) as described in example 9, afforded the title compound (17).
Yield: 0.182 g (58%).
mp: 235-237° C.
$^1$HNMR (CDCl$_3$): δ 12.75 (s, 1H), 7.86 (d, 1H), 7.74 (d, 1H), 7.56 (m, 2H), 6.44 (s, 1H), 6.12 (s, 1H), 3.78 (m, 1H), 3.6-3.12 (m, 3H), 2.9 (m, 1H), 2.85 (m, 1H), 2.4 (s, 3H), 2.15 (m, 1H), 1.8 (m, 1H).
IR cm$^{-1}$: 3450, 1660.
MS: m/e 447 (M$^+$), 428 (M–32).
Analysis: C$_{21}$H$_{20}$BrNO$_5$, C, 56.53 (56.52); H, 4.65 (4.52); N, 4.17 (3.14); Br, 17.75 (17.90).

EXAMPLE 16

(+)-trans-2-(4-Bromo-phenyl)-8-(2-hydroxymethyl-1-methyl-pyrrolidin-3-yl)-5,7-dimethoxychromen-4-one. (Compound No. 18)

Compound (10) (0.83 g, 2.6 mmol) in dry DMF (10 mL) was reacted with methyl 4-bromobenzoate (1.87 g, 8.70 mmol) in the presence of NaH (50%, 0.63 g, 13.18 mmol) as described in example 8, to afford the title compound (18).
Yield: 0.97 g (78%).
$^1$HNMR (CDCl$_3$): δ 7.9 (d, 2H), 7.6 (d, 2H), 6.65 (s, 1H), 6.45 (s, 1H), 4.35 (m, 1H), 4.05 (two singlets, 6H), 3.75 (dd, 1H), 3.35 (m, 2H), 2.75 (m, 2H), 2.45 (s, 3H), 2.15 (m, 2H).
MS: m/e 474 (M$^+$), 442 (M–32).

EXAMPLE 17

(+)-trans-2-(4-Bromo-phenyl)-5-hydroxy-8-(2-hydroxymethyl-1-methyl-pyrrolidin-3-yl)-7-methoxy-chromen-4-one. (Compound No. 19)

and (+)-trans-2-(4-Bromo-phenyl)-5,7-dihydroxy-8-(2-hydroxymethyl-1-methyl-pyrrolidin-3-yl)-chromen-4-one (Compound No. 20)
Compound (18) (0.61 g, 1.29 mmol) subjected to demethylation with pyridine hydrochloride (6.1 g, 52.81 mmol) as described in example 9, afforded the two title compounds (19) and (20) which were separated using column chromatography.
Compound 19:
Yield: 0.2 g (36%).
mp.: 163-165° C.
IR cm$^{-1}$: 3420, 2970, 1680.
$^1$HNMR (DMSO d$_6$): δ 13.1 (s, 1H), 8.1 (d, 2H), 7.8 (d, 2H), 7.1 (s, 1H), 6.65 (s, 1H), 3.99 (m, 4H), 3.55 (m, 2H), 3.3 (m, 1H), 2.75 (m, 1H), 2.45 (s, 3H), 2.05 (m, 2H).
MS: m/e 461 (M$^+$), 428 (M–32).

Analysis: C$_{22}$H$_{22}$BrNO$_5$H$_2$O, C, 54.95 (55.24); H, 4.66 (5.05); N, 3.39 (2.93); Br, 16.68 16.70.
Compound 20:
Yield: 0.21 g (38%).
mp: 193-195° C.
IR cm$^{-1}$: 3410, 1710.
$^1$HNMR (DMSO d$_6$): δ 12.85 (s, 1H), 8.09 (d, 2H), 7.8 (d, 2H), 6.95 (s, 1H), 6.15 (s, 1H), 4.0 (m, 1H), 3.5-3.25 (m, 2H), 3.2 (s, 1H), 2.95 (m, 2H), 2.5 (s, 3H), 2.25 (m, 1H), 1.97 (m, 1H).
MS: m/e 446 (M$^+$), 428 (M–18), 414 (M–32).
Analysis: C$_{21}$H$_{20}$BrNO$_5$H$_2$O, C, 54.00 (54.23); H, 4.59 (4.76); N, 3.10 (3.01); Br, 17.37 (17.17).

EXAMPLE 18

(+)-trans-2-(3-Chloro-phenyl)-8-(2-hydroxymethyl-1-methyl-pyrrolidin-3-yl)-5,7-dimethoxy-chromen-4-one (Compound No. 21)

Compound (10) (1 g, 3.24 mmol) in DMF (15 mL), reacted with methyl 3-chlorobenzoate (2.66 g, 15.6 mmol) in the presence of NaH (0.776 g, 16.16 mmol) as described in example 8, afforded the title compound (21).
Yield: 0.35 g (25%).
$^1$HNMR (CDCl$_3$): δ 8.08 (d, 1H), 7.9 (d, 1H), 7.45 (m, 2H), 6.65 (s, 1H), 6.45 (s, 1H), 4.4 (m, 1H), 4.0 (two doublets, 6H), 3.75 (dd, 1H), 3.35 (m, 2H), 2.75 (m, 2H), 2.45 (s, 3H), 2.1 (m, 2H).
MS: m/e 430 (M+1), 398 (M–32).

EXAMPLE 19

(+)-trans-2-(3-Chloro-phenyl)-5-hydroxy-8-(2-hydroxymethyl-1-methyl-pyrrolidin-3-yl)-7-methoxy-chromen-4-one. (Compound No. 22)

and (+)-trans-2-(3-Chloro-phenyl)-5,7-dihydroxy-8-(2-hydroxymethyl-1-methyl-pyrrolidin-3-yl)-chromen-4-one (Compound No. 23)
Compound (21) (0.25 g, 0.58 mmol) subjected to demethylation using pyridine hydrochloride (2.5 g, 21.64 mmol) as described in example 9, afforded the title compounds (22) and (23).
Compound (22):
Yield: 0.035 g (17%).
mp: 146-147° C.
IR cm$^{-1}$: 3300, 1650.
$^1$HNMR (DMSO d$_6$): δ 13.1 (s, 1H), 8.27 (s, 1H), 8.1 (d, 1H), 7.65 (m, 2H), 7.15 (s, 1H), 6.65 (s, 1H), 4.4 (bs, 1H), 3.95 (s, 3H), 3.6-3.3 (m, 2H), 3.12 (m, 1H), 2.9-2.6 (m, 2H), 2.45 (s, 3H), 2.05 (m, 2H).
MS: m/e 416 (M$^+$), 384 (M–32).
Analysis: C$_{22}$H$_{22}$ClNO$_5$.2H$_2$OC, 58.76 (58.47); H, 5.19 (5.70); N, 3.34 (3.1); Cl, 7.43 (7.84).
Compound (23):
Yield: 0.085 g (41%).
mp: 215-217° C.
IR cm$^{-1}$: 3400, 1660.
$^1$HNMR (DMSO d$_6$): δ 12.8 (s, 1H), 8.2 (s, 1H), 8.08 (d, 1H), 7.65 (m, 2H), 7.0 (m, 1H), 6.18 (s, 1H), 4.0 (m, 1H), 3.6-3.1 (m, 2H), 3.0 (m, 3H), 2.45 (s, 3H), 2.25 (m, 1H), 1.98 (m, 1H).

MS: m/e 402 (M+), 384 (M–18), 370 (M–32).
Analysis: $C_{21}H_{20}ClNO_5.\frac{1}{2}H_2O$, C, 61.18 (61.39); H, 5.03 (5.15); N, 3.46 (3.4); Cl, 8.97 (8.62).

EXAMPLE 20

(+)-trans-8-(2-hydroxymethyl-1-methyl-pyrrolidin-3-yl)-2-(2-iodo-phenyl)-5,7-dimethoxy-chromen-4-one. (Compound No. 24)

Compound (10) (0.45 g, 1.46 mmol) in dry DMF (10 mL) reacted with methyl 2-iodobenzoate (2.5 g, 9.54 mmol) in the presence of NaH (0.35 g, 50%, 7.29 mmol) as described in example 8, afforded the title compound (24).
Yield: 0.29 g (40%).
$^1$HNMR (CDCl$_3$): δ 7.98 (d, 1H), 7.5 (m, 2H), 7.3 (s, 1H), 6.45 (s, 1H), 6.35 (s, 1H), 4.15 (m, 1H), 4.0 (two singlets, 6H), 3.7 (dd, 1H), 3.55 (d, 1H), 3.25 (m, 1H), 3.05 (m, 1H), 2.57 (m, 1H), 2.4 (s, 3H), 2.15 (m, 2H).
MS: m/e 522 (M+1), 490 (M–32).

EXAMPLE 21

(+)-trans-5,7-Dihydroxy-8-(2-hydroxymethyl-1-methyl-pyrrolidin-3-yl)-2-(2-iodo-phenyl)-chromen-4-one (Compound No. 25)

Compound (24) (0.29 g, 0.588 mmol) subjected to demethylation using pyridine hydrochloride (3 g, 25.97 mmol) as described in example 9, afforded the title compound (25).
Yield: 0.145 g (50%).
mp: 233-235° C.
IR cm$^{-1}$: 3400, 1660.
$^1$HNMR (DMSO d$_6$): δ 12.8 (s, 1H), 8.2 (s, 1H), 8.08 (d, 1H), 7.65 (m, 2H), 7.0 (s, 1H), 6.18 (s, 1H), 4.0 (m, 1H), 3.6-3.1 (m, 2H), 3.0 (m, 3H), 2.45 (s, 3H), 2.25 (m, 1H), 1.98 (m, 1H).
MS: m/e 494 (M+), 368 (M–127).
Analysis: $C_{21}H_{20}INO_5.H_2OC$, 49.5 (49.33); H, 4.05 (4.33); N, 2.84 (2.73); I, 24.48 (24.81).
$[α]_D^{25}$=+1.92° (c=0.208, 1:1MeOH:CHCl$_3$).

EXAMPLE 22

(+)-trans-2-(2-Fluoro-phenyl)-8-(2-hydroxymethyl-1-methylpyrrolidin-3-yl)-5,7-dimethoxy-chromen-4-one. (Compound No. 26)

Compound (10) (0.8 g, 2.5 mmol) in dry DMF (10 mL) treated with methyl 2-fluorobenzoate (1.76 g, 11.42 mmol) in the presence of NaH (0.62 g, 50%, 12.9 mmol) as described in example 8, afforded the title compound (26).
Yield: 0.68 g (65%).
$^1$HNMR (CDCl$_3$): δ 7.98 (d, 1H), 7.5 (m, 2H), 7.3 (s, 1H), 6.45 (s, 1H), 6.35 (s, 1H), 4.15 (m, 1H), 4.0 (two singlets, 6H), 3.7 (dd, 1H), 3.55 (d, 1H), 3.25 (m, 1H), 3.05 (m, 1H), 2.57 (m, 1H), 2.4 (s, 3H), 2.15 (m, 2H).
MS: m/e 414 (M+1), 382 (M–32).

EXAMPLE 23

(+)-trans-2-(2-Fluoro-phenyl)-5,7-dihydroxy-8-(2-hydroxymethyl-1-methylpyrrolidin-3-yl)-chromen-4-one. (Compound No. 27)

Compound (26) (0.07 g, 0.169 mmol) subjected to demethylation with pyridine hydrochloride (1 g, 8.65 mmol) as described in example 9, afforded the title compound (27).
Yield: 0.017 g (26%).
mp: 206-208° C.
IR cm$^{-1}$: 3400, 1660.
$^1$HNMR (DMSO d$_6$): δ 12.8 (s, 1H), 8.08 (m, 1H), 7.65 (m, 1H), 7.4 (m, 2H), 6.68 (s, 1H), 6.18 (s, 1H), 4.2 (m, 1H), 3.85 (dd, 1H), 3.7 (m, 1H), 3.58 (m, 1H), 3.48 (m, 1H), 3.3 (m, 1H), 2.85 (s, 3H), 2.35 (m, 2H).
MS: m/e 386 (M+1).
Analysis: $C_{21}H_{20}FNO_5H_2O$, C, 63.09 (62.53); H, 5.5 (4.99); N, 3.4 (3.4)

EXAMPLE 24

(+)-trans-2-(3-Fluoro-phenyl)-5,7-dimethoxy-8-(2-hydroxymethyl-1-methyl-pyrrolidin-3-yl)-chromen-4-one. (Compound No. 28)

Compound (10) (0.83 g, 2.69 mmol) in dry DMF (10 mL) reacted with methyl 3-fluorobenzoate (1.82 g, 11.82 mmol) in the presence of NaH (0.64 g, 50%, 13.33 mmol) as described in example 8, afforded the title compound (28).
Yield: 0.73 g (68%).
$^1$HNMR (CDCl$_3$): δ 8.05 (t, 2H), 7.65 (dd, 1H), 7.45 (m, 1H), 7.12 (s, 1H), 6.6 (s, 1H), 4.35 (m, 1H), 3.95 (two doublets, 6H), 3.6-3.25 (m, 4H), 3.05 (m, 1H), 2.65 (m, 1H), 2.35 (s, 3H), 1.97 (m, 2H).
MS: m/e 414 (M+1), 382 (M–32).

EXAMPLE 25

(+)-trans-2-(3-Fluoro-phenyl)-5,7-dihydroxy-8-(2-hydroxymethyl-1-methyl-pyrrolidin-3-yl)-chromen-4-one (Compound No. 29)

Compound (28) (0.51 g, 1.23 mmol) demethylated using pyridine hydrochloride (5.1 g, 44.15 mmol) as described in example 9, gave the title compound (29).
Yield: 0.25 g (52.8%).
mp: 218-220° C.
IR cm$^{-1}$: 3390, 1660.
$^1$HNMR (DMSO d$_6$): δ 12.85 (s, 1H), 8.0 (m, 2H), 7.65 (m, 1H), 7.45 (m, 1H), 7.05 (s, 1H), 6.18 (s, 1H), 4.05 (m, 1H), 3.7-3.2 (m, 2H), 2.95 (m, 3H), 2.5 (s, 3H), 2.25 (m, 1H), 1.98 (m, 1H).
MS: m/e 386 (M+1), 368 (M–18), 354 (M–32).
Analysis: $C_{21}H_{20}FNO_5.\frac{1}{2}H_2O$, C, 63.25 (63.96); H, 5.09 (5.36); N, 3.57 (3.55).

EXAMPLE 26

(+)-trans-2-(2,6-Difluoro-phenyl)-8-(2-hydroxymethyl-1-methyl-pyrrolidin-3-yl)-5,7-dimethoxy-chromen-4-one (Compound No. 30)

Compound (10) (1.5 g, 4.85 mmol) in dry DMF (20 mL) was reacted with 2,6-difluoro-1-benzoyl chloride (0.8 mL, 1.13 g, 6.4 mmol) at 0-5° C., in the presence of NaH (1.02 g, 50%, 21.25 mmol) as described in example (8).
The reaction mixture was diluted with ice water and extracted using EtOAc (3×100 mL). The organic portion was washed with water, dried (anhy. Na$_2$SO$_4$) and concentrated. The semisolid residue thus obtained was treated with concentrated HCl (50 mL) and stirred at room temperature for 2 h. Further purification done as described in example 8, afforded the title compound (30).
Yield: 0.09 g (5%).

¹HNMR (CDCl₃): δ 7.5 (m, 1H), 7.1 (t, 2H), 6.42 (two singlets, 2H), 4.11 (m, 1H), 3.97 (two singlets, 6H), 3.66 (dd, 1H), 3.52 (d, 1H), 3.25 (m, 1H), 2.95 (m, 1H), 2.65 (m, 1H), 2.45 (s, 3H), 2.0 (m, 2H).
MS: m/e 432 (M+1), 400 (M−32).

EXAMPLE 27

(+)-trans-2-(2,6-Difluoro-phenyl)-5,7-dihydroxy-8-(2-hydroxymethyl-1-methyl-pyrrolidin-3-yl)-chromen-4- one. (Compound No. 31)

Compound (30) (0.09 g, 0.208 mmol) subjected to demethylation using pyridine hydrochloride (1 g, 8.66 mmol), as described in example 9, afforded the title compound (31).
Yield: 0.032 g (38%).
mp: 242-244° C.
IR cm⁻¹: 3300, 1660.
¹HNMR (DMSO d₆): δ 12.65 (s, 1H), 7.75 (m, 1H), 7.4 (t, 2H), 6.6 (s, 1H), 6.15 (s, 1H), 3.7 (m, 1H), 3.6-3.1 (m, 2H), 3.88 (m, 3H), 2.45 (s, 3H), 2.15 (m, 1H), 1.85 (m, 1H).
MS: m/e 404 (M+1), 386 (M−18), 372 (M−32).
Analysis: C₂₁H₁₉F₂NO₅H₂O, C, 60.43 (59.85); H, 4.96 (5.02); N, 3.96 (3.32).

EXAMPLE 28

(+/−)-trans-4-[8-(2-hydroxymethyl-1-methyl-pyrrolidin-3-yl)-5,7-dimethoxy-4-oxo-4H-chromen-2-yl]-benzonitrile. (Compound No. 32)

Compound (7) (1.5 g, 4.85 mmol) in dry DMF (15 mL) reacted with methyl 4-cyanobenzoate (2.57 g, 15.9 mmol) in the presence of NaH (1.2 g, 50%, 25 mmol), as described example 8, afforded the title compound (32).
Yield: 0.65 g (31.8%)
mp: 214-216° C.
IR cm⁻¹: 3400, 2210, 1640.
¹HNMR (CDCl₃): δ 8.15 (d, 2H), 7.78 (d, 2H), 6.75 (s, 1H), 6.48 (s, 1H), 4.45 (m, 1H), 4.02 (two singlets, 6H), 3.7 (dd, 1H), 3.3 (m, 3H), 2.78 (m, 1H), 2.6 (d, 1H), 2.42 (s, 3H), 2.08 (m, 2H),
MS: m/e 421 (M+1), 378 (M−42).
Analysis: C₂₄H₂₄ClN₂O₅.½H₂O, C, 67.05 (67.12); H, 5.78 (5.63); N, 6.1 (6.5).

EXAMPLE 29

(+/−)-trans-4-5-Hydroxy-8-(2-hydroxymethyl-1-methyl-pyrrolidin-3-yl)-7-methoxy-4-oxo-4H-chromen-2-yl]-benzonitrile (Compound No. 33)

and (+/−)-trans-4-[5,7-Dihydroxy-8-(2-hydroxymethyl-1-methylpyrrolidin-3-yl)-4-oxo-4H-chromen-2-yl]-benzonitrile (Compound No. 34)

Compound (32) (0.30 g, 0.71 mmol) was reacted with pyridine hydrochloride (3 g, 26.0 mmol) as described in example 9. This afforded the title compounds, (33) and (34).
Compound (33):
Yield: 0.033 g (10%)
mp: decomposition>250° C.
IR cm⁻¹: 3320, 2210, 1640.
¹HNMR (CDCl₃): δ 12.98 (s, 1H), 8.35 (d, 2H), 8.08 (d, 2H), 7.2 (s, 1H), 6.65 (s, 1H), 3.38 (m, 1H), 3.95 (s, 3H), 3.5-3.2 (m, 2H), 3.1 (m, 2H), 2.65 (m, 1H), 2.4 (s, 3H), 2.0 (m, 2H).
MS: m/e: 407 (M+1).
Analysis: C₂₃H₂₂N₂O₅.½H₂O, C, 63.96 (63.73); H, 5.46 (5.81); N, 5.63 (5.46).
Compound (34):
Yield: 0.1 g (36%).
mp: 273-275° C.
IR cm⁻¹: 3500, 2220, 1660.
¹HNMR (DMSO d₆): δ 12.8 (s, 1H), 8.26 (d, 2H), 8.08 (d, 2H), 7.1 (s, 1H), 6.15 (s, 1H), 4.05 (m, 1H), 3.7-3.4 (m, 2H), 2.95 (m, 3H), 2.55 (s, 3H), 2.25 (m, 1H), 2.0 (m, 1H).
MS: m/e 393 (M+1), 376 (M−18).
Analysis: C₂₂H₂₀N₂O₅.¼H₂O, C, 66.59 (66.57); H, 5.26 (5.2); N, 6.63 (7.05).

EXAMPLE 30

(+)-trans-4-[8-(2-hydroxymethyl-1-methyl-pyrrolidin-3-yl)-5,7-dimethoxy-4-oxo-4H-chrom-2-yl]-benzonitrile. (Compound No. 35)

Compound (10) (0.98 g, 3.17 mmol) in dry DMF (15 mL) reacted with methyl 4-cyanobenzoate (1.02 g, 6.34 mmol) in the presence of NaH (50%, 0.762 g, 15.86 mmol) as described in example 8, afforded the title compound (35).
Yield: 0.56 g (43%)
IR cm⁻¹: 3400, 2210, 1640.
¹HNMR (DMSO d₆): δ 8.28 (d, 2H), 8.05 (d, 2H), 6.98 (s, 1H), 6.7 (s, 1H), 4.3 (m, 1H), 4.0 (s, 3H), 3.95 (s, 3H), 3.55-3.4 (m, 2H), 3.25-3.15 (m, 2H), 2.65 (m, 1H), 2.4 (s, 3H), 2.0 (m, 2H).
MS: m/e 421 (M+1), 378 (M−42).

EXAMPLE 31

(+)-trans-4-[5-Hydroxy-8-(2-hydroxymethyl-1-methyl-pyrrolidin-3-yl)-7-methoxy-4-oxo-4H-chromen-2-yl]-benzonitrile (Compound No. 36)

and (+)-trans-4-[5,7-Dihydroxy-8-(2-hydroxymethyl-1-methylpyrrolidin-3-yl)-4-oxo-4H-chromen-2-yl]-benzonitrile (Compound No. 37)

Compound (35) (0.50 g, 1.19 mmol) reacted with pyridine hydrochloride (5 g, 43.29 mmol) as described in example 9, afforded the title compounds (36) and (37).
Compound (36):
Yield: 0.1 g (20%).
mp: 117-119° C.
IR cm⁻¹: 3420, 2250, 1660.
¹HNMR (DMSO d₆): δ 12.98 (s, 1H), 8.35 (d, 2H), 8.08 (d, 2H), 7.2 (s, 1H), 6.65 (s, 1H), 4.3 (m, 1H), 3.95 (s, 3H), 3.5-3.2 (m, 3H), 3.08 (m, 1H), 2.6 (m, 1H), 2.35 (s, 3H), 1.98 (m, 2H).
MS: m/e 407 (M+1), 375 (M−32).
Analysis: C₂₃H₂₂N₂O₅.½H₂O, C, 64.44 (64.39); H, 5.11 (5.6); N, 6.31 (6.53).
Compound (37):
Yield: 0.19 g (40%).
mp: 245-246° C.
IR cm⁻¹: 3400, 2240, 1660.
¹HNMR (DMSO d₆): δ 12.8 (s, 1H), 8.28 (d, 2H), 8.05 (d, 2H), 7.1 (s, 1H), 6.15 (s, 1H), 4.0 (m, 1H), 3.6-3.4 (m, 2H), 3.0 (m, 3H), 2.5 (s, 3H), 2.25 (m, 1H), 1.98 (m, 1H).
MS: m/e 393 (M+1), 376 (M−18).

Analysis: $C_{22}H_{20}N_2O_5 \cdot \frac{1}{2}H_2O$, C, 63.38 (63.0); H, 5.22 (5.52); N, 6.64 (6.67).

EXAMPLE 32

(+/−)-trans-8-(2-hydroxymethyl-1-methyl-pyrrolidin-3-yl)-5,7-dimethoxy-2-(4-trifluoromethyl-phenyl)-chromen-4-one. (Compound No. 38)

Compound (7) (1.5 g, 4.84 mmol) in dry DMF (15 mL) was reacted with methyl 4-trifluoromethylbenzoate (3.27 g, 16.02 mmol) in the presence of NaH (1.2 g, 50%, 25 mmol) as described in example 8, to obtain the title compound (38).
Yield: 0.7 g (31.8%).
mp: 114-115° C.
IR cm$^{-1}$: 3450, 1640.
$^1$HNMR (CDCl$_3$): δ 8.17 (d, 2H), 7.78 (d, 2H), 6.75 (s, 1H), 6.48 (s, 1H), 4.38 (m, 1H), 4.0 (two singlets, 6H), 3.7 (dd, 1H), 3.38 (d, 1H), 3.28 (t, 1H), 2.75 (q, 1H), 2.65 (d, 1H), 2.44 (s, 3H), 2.08 (m, 2H).
MS: m/e 464 (M+1), 421 (M−42).
Analysis: $C_{24}H_{24}F_3NO_5 \cdot H_2O$, C, 59.13 (59.8); H, 5.51 (5.44); N, 2.34 (2.9).

EXAMPLE 33

(+/−)-trans-5,7-Dihydroxy-8-(2-hydroxymethyl-1-methyl-pyrrolidin-3-yl)-2-(4-trifluoromethyl-phenyl)-chromen-4-one. (Compound No. 39)

Compound (38) (0.5 g, 1.08 mmol) was demethylated using pyridine hydrochloride (4.5 g, 38.96 mmol) as described in example 9, to obtain the title compound (39).
Yield: 0.28 g, (59%).
mp: 238° C.
IR cm$^{-1}$: 3350, 1660.
$^1$HNMR (DMSO d$_6$): δ 12.7 (s, 1H), 8.33 (d, 2H), 7.98 (d, 1H), 7.08 (s, 1H), 6.18 (s, 1H), 4.05 (m, 1H), 3.6-3.4 (m, 2H), 3.0 (m, 3H), 2.55 (s, 3H), 2.25 (m, 1H), 1.98 (m, 1H).0
MS: m/e 434 (M−1), 404 (M−31).
Analysis: $C_{22}H_{20}F_3NO_5$, C, 60.34 (60.69); H, 4.48 (4.63); N, 2.89 (3.42).

EXAMPLE 34

(+)-trans-8-(2-hydroxymethyl-1-methyl-pyrrolidin-3-yl)-5,7-dimethoxy-2-(4-trifluoromethyl-phenyl)-chromen-4-one. (Compound No. 40)

Compound (10) (0.8 g, 2.6 mmol) in dry DMF (15 mL) was reacted with methyl 4-trifluoromethylbenzoate (1.74 g, 8.53 mmol) in the presence of NaH (0.63 g, 50%, 13.13 mmol) as described in example 8, to obtain the title compound(40).
Yield: 1.0 g (87%).
mp: 114-115° C.
$^1$HNMR (CDCl$_3$): δ 8.15 (d, 2H), 7.78 (d, 2H), 6.75 (s, 1H), 6.48 (s, 1H), 4.48 (m, 1H), 4.0 (two singlets, 6H), 3.8 (d, 1H), 3.46 (m, 2H), 2.88 (m, 2H), 2.55 (s, 3H), 2.18 (m, 2H).
MS: m/e 464 (M+1), 432 (M−31).

EXAMPLE 35

(+)-trans-5,7-Dihydroxy-8-(2-hydroxymethyl-1-methyl-pyrrolidin-3-yl)-2-4-trifluoromethyl-phenyl)-chromen-4-one. (Compound No. 41)

Compound (40) (0.7 g, 1.51 mmol) was demethylated using pyridine hydrochloride (7 g, 60.60 mmol) as described in example 9, to obtain the title compound (41).

Yield: 0.28 g (42%).
mp: 235-237° C.
IR cm$^{-1}$: 3400, 1660.
$^1$HNMR (DMSO d$_6$): δ 12.82 (s, 1H), 8.35 (d, 2H), 7.95 (d, 2H), 7.08 (s, 1H), 6.17 (s, 1H), 4.05 (m, 1H), 3.56 (m, 2H), 2.98 (m, 3H), 2.5 (s, 3H), 2.25 (m, 1H), 1.98 (m, 1H).
MS: m/e 436 (M+1), 404 (M−32).
Analysis: $C_{22}H_{20}F_3NO_5 \cdot 2H_2O$, C, 55.79 (56.04); H, 4.53 (5.1); N, 2.91 (2.97).

EXAMPLE 36

(−)-trans-8-(2-hydroxymethyl-1-methyl-pyrrolidin-3-yl)-5,7-dimethoxy-2-(4-trifluoromethyl-phenyl)-chromen-4-one. (Compound No. 42)

Compound (13) (1 g, 3.24 mmol) in dry DMF (35 mL) was reacted with methyl 4-trifluoromethylbenzoate (2.1 g, 10.29 mmol) in the presence of NaH (0.776 g, 50%, 16.16 mmol) as described in example 8, to obtain the title compound (42).
Yield: 0.6 g (40%).
$^1$HNMR (CDCl$_3$): δ 8.15 (d, 2H), 7.78 (d, 2H), 6.72 (s, 1H), 6.45 (s, 1H), 4.42 (m, 1H), 4.05 (two singlets, 6H), 3.75 (dd, 1H), 3.35 (m, 2H), 2.78 (m, 2H), 2.45 (s, 3H), 2.1 (m, 2H).
MS: m/e 464 (M+1), 432 (M−31).

EXAMPLE 37

(−)-trans-5,7-Dihydroxy-8-(2-hydroxymethyl-1-methyl-pyrrolidin-3-yl-)-2-(4-trifluoromethyl-phenyl)-chromen-4-one. (Compound No. 43)

Compound (42) (0.5, 1.08 mmol) was demethylated using pyridine hydrochloride (5 g, 43.29 mmol) as described in example 9, to obtain the title compound (43).
Yield: 0.195 g (42%).
mp: 234-236° C.
IR cm$^{-1}$: 3380, 1660.
$^1$HNMR (DMSO d$_6$): δ 12.8 (s, 1H), 8.32 (d, 2H), 7.95 (d, 2H), 7.1 (s, 1H), 6.15 (s, 1H), 4.05 (m, 1H), 3.58 (m, 2H), 3.0 (m, 3H), 2.5 (s, 3H), 2.22 (s, 1H), 1.95 (s, 1H).
MS: m/e 436 (M+1), 404 (M−32).
Analysis: $C_{22}H_{20}F_3NO_5 \cdot \frac{1}{2}H_2O$, C, 57.08 (57.15); H, 4.51 (5.05); N, 3.0 (3.02).

EXAMPLE 38

(+)-trans-8-(2-hydroxymethyl-1-methyl-pyrrolidin-3-yl)-5,7-dimethoxy-2-phenyl-chromen-4-one (Compound No. 44)

Compound (10) (1 g, 3.23 mmol) in dry DMF (15 mL) was reacted with methyl benzoate (2.29 g, 16.84 mmol) in the presence of NaH (50%, 0.77 g, 16.04 mmol) as described in example (8) to obtain the title compound (44).
Yield: 0.49 g (38.3%).
$^1$HNMR (CDCl$_3$): δ 8.00 (m, 2H), 7.5 (m, 3H), 6.68 (s, 1H), 6.45 (s, 1H), 4.4 (m, 1H), 4.0 (two singlets, 6H), 3.72 (dd, 1H), 3.45 (d, 1H), 3.35 (m, 1H), 2.82 (m, 2H), 2.48 (s, 3H), 2.1 (m, 2H).
MS: m/e 395 (M$^+$).

EXAMPLE 39

(+)-trans-5,7-Dihydroxy-8-(2-hydroxymethyl-1-methyl-pyrrolidin-3-yl)-2-phenyl-chromen-4-one. (Compound No. 45)

Compound (44) (0.5 g, 1.27 mmol) was treated with dry pyridine hydrochloride (5 g, 43.29 mmol) as described in the example 9, to obtain the title compound (45).
Yield: 0.3 g (64%).
mp: 212-215° C.
IR cm$^{-1}$: 3420, 1660.
$^1$HNMR (DMSO d$_6$): δ 12.9 (s, 1H), 8.1 (d, 2H), 7.62 (m, 3H), 6.95 (s, 1H), 6.18 (s, 1H), 4.05 (m, 1H), 3.55 (m, 2H), 3.0 (m, 3H), 2.52 (s, 3H), 2.25 (m, 1H), 1.95 (m, 1H).
MS: m/e 368 (M+1), 363 (M−32).
Analysis: C$_{21}$H$_{21}$NO$_5$.½H$_2$O, C, 66.95 (67.0); H, 5.81 (5.89); N, 3.67 (3.72).

EXAMPLE 40

(+)-trans-8-(2-hydroxymethyl-1-methyl-pyrrolidin-3-yl)-5,7-dimethoxy-2-thiophen-2-yl-chromen-4-one. (Compound No. 46)

Compound (10) (0.95 g, 3.07 mmol) in dry DMF (15 mL) was treated with thiophene-2-carboxylic acid ethyl ester (2.25 g, 14.42 mmol) in the presence of NaH (0.741 g, 50%, 15.43 mmol) as described in example 8, to get the title compound (46).
Yield: 0.5 g (40%).
$^1$HNMR (CDCl$_3$): δ 7.88 (d, 1H), 7.55 (d, 1H), 7.18 (t, 1H), 6.55 (s, 1H), 6.45 (s, 1H), 4.38 (m, 1H), 4.0 (two singlets, 6H), 3.75 (dd, 1H), 3.45 (m, 2H), 2.92 (m, 2H), 2.58 (s, 3H), 2.2 (m, 2H).
MS: m/e 402 (M+1), 369 (M−31).

EXAMPLE 41

(+)-trans-5,7-Dihydroxy-8-(2-hydroxymethyl-1-methyl-pyrrolidin-3-yl)-2-thiophen-2-yl-chromen-4-one (Compound No. 47)

Compound (46) (0.29 g, 0.72 mmol) of was subjected to demethylation using pyridine hydrochloride (2.9 g, 25.11 mmol) as described in example 9 to obtain the title compound (47).
Yield: 0.149 g (55%).
mp: 218-220° C.
IR cm$^{-1}$: 3340, 1650.
$^1$HNMR (DMSO d$_6$): δ 12.9 (s, 1H), 8.08 (d, 1H), 8.0 (d, 1H), 7.32 (t, 1H), 6.85 (s, 1H), 6.2 (s, 1H), 3.95 (m, 1H), 3.58 (m, 2H), 2.52 (m, 3H), 2.65 (s, 3H), 2.25 (m, 1H), 2.15 (m, 1H).
MS: m/e 374 (M+1), 342 (M−31).
Analysis: C$_{19}$H$_{19}$NO$_5$S.1.5H$_2$O, C, 57.11 (56.96); H, 5.03 (5.5); N, 3.44 (3.49).

EXAMPLE 42

(+)-trans-4-[8-(2-hydroxymethyl-1-methyl-pyrrolidin-3-yl)-5,7-dimethoxy-4-oxo-4H-chromen-2-yl]-3-methyl-benzonitrile. (Compound No. 48)

Compound (10) (1.0 g, 3.24 mmol) in dry DMF (15 mL) was reacted with ethyl 2-methyl-4-cyanobenzoate (1.34 g, 7.09 mmol) in the presence of NaH (50%, 0.776 g, 16.16 mmol) as described in example 8, to get the title compound (48).
Yield: 0.8 g (57%).
$^1$HNMR (CDCl$_3$): δ 7.76 (d, 1H), 7.65 (bs, 2H), 6.48 (s, 1H), 6.35 (s, 1H), 4.2 (m, 1H), 4.0 (two singlets, 6H), 3.74 (d, 1H), 3.4 (d, 1H), 3.35 (m, 1H), 2.86 (d, 1H), 2.75 (m, 1H), 2.5 (two singlets, 6H), 2.08 (m, 2H).
MS: m/e 435 (M+1), 403 (M−32).

EXAMPLE 43

(+)-trans-4-[5,7-Dihydroxy-8-(2-hydroxymethyl-1-methyl-pyrrolidin-3-yl)-4-oxo-4H-chromen-2-yl]-3-methyl-benzonitrile. (Compound No. 49)

Compound (48) (0.6 g, 1.38 mmol) was demethylated using pyridine hydrochloride (6 g, 51.95 mmol) as described in example 9 to obtain the title compound (49).
Yield: 0.35 g (62%).
mp: 145-147° C.
IR cm$^{-1}$: 3400, 2250, 1670.
$^1$HNMR (DMSO d$_6$): δ 12.52 (s, 1H), 7.55 (m, 3H), 6.25 (two singlets, 2H), 4.05 (m, 1H), 3.7 (d, 2H), 3.34 (m, 1H), 3.2 (m, 2H), 3.05 (m, 1H), 2.65 (s, 3H), 2.55 (m, 1H), 2.48 (s, 3H), 2.32 (m, 1H), 2.02 (m, 1H).
MS: m/e 407 (M+1), 375 (M−32).
Analysis: C$_{23}$H$_{22}$N$_2$O$_5$.2H$_2$O, C, 62.35 (62.43); H, 5.06 (5.0); N, 6.1 (6.63).

EXAMPLE 44

(+/−)-trans-2-(2-Bromo-5-methoxy-phenyl)-8-(2-hydroxymethyl-1-methyl-1-pyrrolidin-3-yl)-5,7-dimethoxy-chromen-4-one (Compound No. 50)

Compound (7) (1.5 g, 4.85 mmol) in dry DMF (25 mL) was reacted with methyl 2-bromo-5-methoxybenzoate (3.11 g, 12.69 mmol) in the presence of NaH (50%, 1.16 g, 24.17 mmol) as described in example 8, to obtain the title compound (50).
Yield: 1.8 g (73.6%).
$^1$HNMR (CDCl$_3$): δ 7.55 (d, 1H), 7.12 (d, 1H), 6.9 (dd, 1H), 6.4 (two singlets, 2H), 4.15 (m, 1H), 4.0 (two singlets, 6H), 3.85 (s, 3H), 3.65 (dd, 1H), 3.4 (d, 1H), 3.15 (m, 1H), 2.75 (d, 1H), 2.5 (m, 1H), 2.34 (s, 3H), 2.05 (m, 2H).
MS: m/e 504 (M$^+$), 472 (M−31), 394 (M−111).

EXAMPLE 45

(+/−)-trans-2-(2-Bromo-5-methoxy-phenyl)-5,7-dihydroxy-8-(2-hydroxymethyl-1-methyl-pyrrolidin-3-yl)-chromen-4-one. (Compound No. 51)

and (+/−)-trans-2-(2-Bromo-5-hydroxy-phenyl)-5,7-dihydroxy-8-(2-hydroxymethyl-1-methyl-pyrrolidin-3-yl)-chromen-4-one (Compound No. 52)

Compound (50) (0.97 g, 1.92 mmol) was demethylated using pyridine hydrochloride (15 g, 129.87 mmol) as described in example 9 to obtain the title compounds (51) & (52) respectively.
Compound (51):
Yield: 0.2 g (21.8%).
mp: 233-235° C.

¹HNMR (DMSO d₆): δ 12.8 (s, 1H), 7.75 (d, 1H), 7.35 (d, 1H), 7.15 (dd, 1H), 6.5 (s, 1H), 6.15 (s, 1H), 3.85 (s, 4H), 3.65-3.2 (m, 2H), 2.95 (m, 3H), 2.5 (s, 3H), 2.22 (m, 1H), 1.85 (m, 1H).

MS: m/e 476 (M$^+$), 458 (M–18), 444 (M–32).

Compound (52):

Yield: 0.14 g (15.7%).

mp.: 256-258° C.

¹HNMR (DMSO d₆): δ 12.8 (s, 1H), 7.6 (d, 1H), 7.1 (d, 1H), 6.94 (dd, 1H), 6.4 (s, 1H), 6.15 (s, 1H), 3.8 (m, 1H), 3.65-3.2 (m, 2H), 3.0-2.8 (m, 3H), 2.5 (s, 3H), 2.2 (m, 1H), 1.85 (m, 1H).

MS: m/e 463 (M+1), 430 (M–32).

EXAMPLE 46

(+)-trans-2-(2-Bromo-5-methoxy-phenyl)-8-(2-hydroxymethyl-1-methyl-pyrrolidin-3-yl)-5,7-dimethoxy-chromen-4-one (Compound No. 53)

Compound (10) (1.9 g, 6.12 mmol) in dry DMF (25 mL) was reacted with methyl 2-bromo-5-methoxybenzoate (4.3 g, 17.55 mmol) in the presence of NaH (50%, 1.92 g, 40 mmol) as described in example 8, to obtain the title compound (53).

Yield: 2.0 g (66%).

¹HNMR (CDCl₃): δ 7.58 (d, 1H), 7.33 (d, 1H), 6.92 (dd, 1H), 6.38 (s, 1H), 6.48 (s, 1H), 4.15 (m, 1H), 4.0 (s, 3H), 3.98 (s, 3H), 3.85 (s, 3H), 3.62 (dd, 1H), 3.35 (bd, 1H), 3.1 (t, 1H), 2.70 (d, 1H), 2.5 (m, 1H), 2.28 (s, 3H), 1.9 (m, 2H).

MS: m/e 504 (M$^+$).

EXAMPLE 47

(+)-trans-2-(2-Bromo-5-methoxy-phenyl)-5,7-dihydroxy-8-(2-hydroxymethyl-1-methyl-pyrrolidin-3-yl)-chromen-4-one. (Compound No. 54)

and (+)-trans-2-(2-Bromo-5-hydroxy-phenyl)-8-(2-hydroxymethyl-1-methylpyrrolidin-3-yl)-5,7-dihydroxy-chromen-4-one. (Compound No. 55)

Compound (53) (1.7 g, 3.37 mmol) was demethylated using pyridine hydrochloride (24 g, 236 mmol) as described in example 9 to obtain the title compounds (54) & (55) respectively.

Compound (54):

Yield: 0.4 g (25%).

mp: 233-235° C.

¹HNMR (DMSO d₆): δ 12.8 (s, 1H), 7.8 (d, 1H), 7.35 (d, 1H), 7.1 (m, 1H), 6.4 (s, 1H), 6.2 (s, 1H), 3.8 (s, 3H), 3.8-3.2 (m, 3H), 2.85 (m, 3H), 2.5 (s, 3H), 2.2 (m, 1H), 1.85 (m, 1H).

MS: m/e 476 (M+1)

Compound (55):

Yield: 0.23 g (15%).

mp.: 256-258° C.

¹HNMR (DMSO d₆): δ 12.8 (s, 1H), 7.75 (d, 1H), 7.1 (d, 1H), 6.9 (m, 1H), 6.5 (s, 1H), 6.2 (s, 1H), 3.8 (s, 1H), 3.6-3.2 (m, 2H), 3.1 (m, 2H), 2.8 (m, 1H), 2.48 (s, 3H), 2.22 (m, 1H), 1.9 (m, 1H).

MS: m/e 460 (M–1).

EXAMPLE 48

(+/–)-trans-2-[(3,5-Bis-trifluoromethyl)-phenyl]-8-(2-hydroxymethyl-1-methylpyrrolidin-3-yl)-5,7-dimethoxy-chromen-4-one. (Compound No. 56)

Compound (7) (1.26 g, 3.59 mmol) in dry DMF (20 mL) was condensed with 3,5-bis-(trifluoromethyl)-1-benzoyl chloride (1 g, 3.62 mmol) in the presence of NaH (50%, 0.72 g, 15 mmol), as described in example 26 to obtain the title compound (56).

Yield: 0.85 g (44.5%).

¹HNMR (CDCl₃): δ 8.52 (s, 2H), 8.0 (s, 1H), 7.75 (s, 1H), 6.5 (s, 1H), 4.42 (m, 1H), 4.05 (two singlets, 6H), 3.75 (dd, 1H), 3.3 (m, 2H), 2.9-2.6 (m, 2H), 2.45 (s, 3H), 2.1 (m, 2H).

MS: m/e 532 (M+1).

EXAMPLE 49

(+/–)-trans-2-[(3,5-Bis-trifluoromethyl)-phenyl]-5,7-dihydroxy-8-(2-hydroxymethyl-1-methylpyrrolidin-3-yl)-chromen-4-one. (Compound No. 57)

Compound (56) (0.71 g, 1.34 mmol) was reacted with pyridine hydrochloride (7.1 g, 61.47 mmol) as described in example (9) to obtain the title compound (57).

Yield: 0.4 g (59%).

mp: 228-230° C.

IR cm$^{-1}$: 3400, 1650.

¹HNMR (DMSO d₆): δ 12.8 (s, 1H), 8.72 (s, 2H), 8.4 (s, 1H), 7.32 (s, 1H), 6.2 (s, 1H), 4.0 (m, 1H), 3.55 (m, 2H), 3.2-2.9 (m, 3H), 2.5 (s, 3H), 2.1 (m, 2H).

MS: m/e 504 (M+1), 486 (M–18).

Analysis: $C_{23}H_{19}F_6NO_5$, C, 54.1 (54.8); H, 4.13 (3.8); N, 2.82 (2.78).

EXAMPLE 50

(+)-trans-2-(2-Chloro-5-methyl-phenyl)-8-(2-hydroxymethyl-1-methylpyrrolidin-3-yl)-5,7-dimethoxy-chromen-4-one (Compound No. 58)

Compound (10) (1 g, 3.2 mmol) in dry DMF (30 mL) was reacted with methyl 2-chloro-5-methylbenzoate (3.97 g, 21.5 mmol) in the presence of NaH (50%, 0.776 g, 16.2 mmol) as described in example 8, to get the title compound (58).

Yield: 0.537 g (37.4%).

¹HNMR (CDCl₃): δ 7.58 (s, 1H), 7.4 (d, 1H), 7.2 (d, 2H), 6.55 (s, 1H), 6.45 (s, 1H), 4.2 (m, 1H), 4.0 (two singlets, 6H), 3.65 (dd, 1H), 3.4 (d, 1H), 3.18 (m, 1H), 2.75 (d, 1H), 2.55 (m, 1H), 2.4 (two singlets, 6H), 2.05 (m, 2H).

MS: m/e 444.5 (M$^+$)

EXAMPLE 51

(+)-trans-2-(2-Chloro-5-methyl-phenyl)-5,7-dihydroxy-8-(2-hydroxymethyl-1-methyl-pyrrolidin-3-yl)-chromen-4-one (Compound No. 59)

Compound (58), (0.48 g, 1.1 mmol) was reacted with pyridine hydrochloride (5 g, 43.3 mmol) as described in example (9) to obtain the title compound (59).

Yield: 0.31 g (68%).
mp: 206-208° C.
$^1$HNMR (CDCl$_3$): δ 12.59 (s, 1H), 7.35 (t, 2H), 7.18 (d, 1H), 6.35 (s, 1H), 6.2 (s, 1H), 4.05 (d, 1H), 3.72 (m, 2H), 3.15 (m, 2H), 2.9 (q, 1H), 2.6 (s, 3H), 2.35 (s, 4H), 1.9 (m, 1H).
IR cm$^{-1}$: 3200, 1735
MS: m/e 415 (M+1), 384 (M−31)

EXAMPLE 52

(+)-trans-2-(2-Bromo-5-nitro-phenyl)-8-(2-hydroxymethyl-1-methyl-pyrrolidin-3-yl)-5,7-dimethoxy-chromen-4-one (Compound No. 61)

2-Bromo-5-nitrobenzoic acid (2.85 g, 12.5 mmol) was added to a solution of compound (6) (2.2 g, 6.27 mmol) in dry pyridine (25 mL), with stirring, under N$_2$ atmosphere at 0° C. POCl$_3$ (5.2 mL, 8.73 g, 57.32 mmol) was added dropwise and the reaction mixture stirred for 1.5 h at 0-5° C. It was then poured over crushed ice, treated with saturated aqueous Na$_2$CO$_3$ solution and extracted with chloroform (3×200 mL). The organic extract was washed with brine, dried (anhy. Na$_2$SO$_4$) and concentrated. Traces of pyridine were removed under high vacuum to obtain (+)-trans-2-Bromo-5-nitro-benzoic acid 2-(2-acetoxymethyl-1-methyl-pyrrolidin-3-yl)-6-acetyl-3,5-dimethoxy-phenyl ester (compound No. 60) (3.62 g, 6.25 mmol) a viscous oil, which was converted to the title compound (61) in situ using NaH (50%, 1.5 g, 31.2 mmol) in dry 1,4-dioxane (50 mL) as described in Example 26.
Yield: 0.13 g (10%).
$^1$HNMR (CDCl$_3$): δ 8.5 (d, 1H), 8.22 (dd, 1H), 7.9 (d, 1H), 6.45 (two singlets, 2H), 4.18 (m, 1H), 4 (two singlets, 6H), 3.65 (dd, 1H), 3.35 (d, 1H), 3.15 (m, 1H), 2.72 (m, 1H), 2.5 (m, 1H), 2.32 (s, 3H), 2.02 (m, 2H).
MS: m/e 519 (M$^+$).

EXAMPLE 53

(+)-trans-2-(2-Bromo-5-nitro-phenyl)-8-(2-hydroxymethyl-1-methylpyrrolidin-3-yl)-5,7-dihydroxy-chromen-4-one. (Compound No. 62)

Compound (61) (0.12 g, 0.23 mmol) was demethylated using pyridine hydrochloride (1.2 g, 10.39 mmol) as described in example 9 to obtain the title compound (62).
Yield: 0.07 g (61%)
IR cm$^{-1}$: 3350, 1660.
$^1$HNMR (DMSO d$_6$): δ 12.4 (s, 1H), 8.45 (d, 1H), 8.2 (dd, 1H), 7.62 (d, 1H), 6.48 (s, 1H), 6.2 (s, 1H), 4.02 (m, 1H), 3.7 (m, 2H), 3.4-2.9 (m, 2H), 2.6 (s, 3H), 2.32 (s, 3H), 1.9 (m, 2H).
MS: m/e 491

EXAMPLE 54

(+)-trans-2-(2-Chloro-pyridin-3-yl)-8-(2-hydroxymethyl-1-methyl-pyrrolidin-3-yl)-5,7-dimethoxy-chromen-4-one. (Compound No. 64)

Compound (6) (4.2 g, 11.97 mmol) was reacted with 2-chloro-pyridine-3-carboxylic acid (3.78 g, 24 mmol) in presence of dry pyridine (25 mL) and POCl$_3$ (4.4 mL, 7.35 g, 47.88 mmol) using the conditions described in example 52. trans-2-Chloro-nicotinic acid 2-(2-acetoxymethyl-1-methyl-pyrrolidin-3-yl)-6-acetyl-3,5-dimethoxy-phenyl ester (63) obtained in situ was converted to the title compound (64) using NaH (50%, 2.44 g, 50.83 mmol) in 1,4-dioxane (50 mL) as described in Example 26.
Yield: 0.63 g (12%).
$^1$HNMR (CDCl$_3$): δ 8.52 (d, 1H), 8.25 (d, 1H), 7.42 (m, 1H), 6.45 (s, 1H), 6.12 (s, 1H), 6.18 (s, 1H), 4.05 (two singlets, 6H), 3.65 (d, 1H), 3.35 (d, 1H), 3.18 (t, 1H), 2.8-2.5 (m, 2H), 2.3 (s, 3H), 2.08 (m, 2H).
MS: m/e 431 (M+1), 399 (M−32).

EXAMPLE 55

(+)-trans-2-(2-Chloro-pyridin-3-yl)-5,7-dihydroxy-8-(2-hydroxymethyl-1-methyl-pyrrolidin-3-yl)-chromen-4-one. (Compound No. 65)

Compound (64) (0.58 g, 1.35 mmol) was demethylated using pyridine hydrochloride (5.8 g, 50.22 mmol) as described in example 9, to obtain the title compound (65).
Yield: 0.1 g (18%).
mp: 125-127° C.
IR cm$^{-1}$: 3380, 1660.
$^1$HNMR (CDCl$_3$+DMSO d$_6$): δ 12.5 (s, 1H), 8.5 (dd, 1H), 8.0 (d, 1H), 7.4 (dd, 1H), 6.45 (s, 1H), 6.28 (s, 1H), 4.1 (m, 1H), 3.7 (m, 2H), 3.25 (m, 3H), 2.65 (s, 3H), 2.35 (m, 1H), 2.0 (m, 1H).
MS: m/e 403 (M+1).
Analysis: C$_{20}$H$_{19}$ClN$_2$O$_5$.H$_2$OC, 57.29 (57.17); H, 5.1 (5.01); N, 6.36 (6.66); Cl, 8.94 (8.44).

EXAMPLE 56

(+/−)-trans-2-(2-Chloro-pyridin-3-yl)-8-(2-hydroxymethyl-1-methyl-pyrrolidin-3-yl)-5,7-dimethoxy-chromen-4-one. (Compound No. 66)

(+/−)-trans-Acetic acid 3-(3-acetyl-2-hydroxy-4,6-dimethoxy-phenyl)-1-methyl-pyrrolidin-2-ylmethyl ester (1.65 g, 4.7 mmol) was reacted with 2-chloro-pyridine-3-carboxylic acid (2.44 g, 15.49 mmol) in the presence of dry pyridine (25 mL) and POCl$_3$ (2.1 mL, 23.43 mmol) using the conditions described in example 52 to get trans-2-Chloro-nicotinic acid 2-(2-acetoxymethyl-1-methyl-pyrrolidin-3-yl) 6-acetyl-3,5-dimethoxy-phenyl ester. This was converted in situ to the title compound (66) using NaH (1.29 g, 26.86 mmol) in 1,4-dioxane (25 mL) as described in example 26.
Yield: 0.38 g (19%).
$^1$HNMR (CDCl$_3$): δ 8.55 (d, 1H), 8.22 (d, 1H), 7.45 (m, 1H), 6.7 (s, 1H), 6.48 (s, 1H), 4.25 (m, 1H), 4.02 (two singlets, 6H), 3.7 (dd, 1H), 3.4 (d, 1H), 3.24 (s, 1H), 2.9-2.6 (m, 2H), 2.45 (s, 3H), 2.15 (m, 2H).
MS: m/e 431 (M+1), 399 (M−32).

EXAMPLE 57

(+/−)-trans-2-(2-Chloro-pyridin-3-yl)-5,7-dihydroxy-8-(2-hydroxymethyl-1-methyl-pyrrolidin-3-yl)-chromen-4-one. (Compound No. 67)

Compound (66) (0.3 g, 0.69 mmol) was demethylated using pyridine hydrochloride (3 g, 25.97 mmol) as described in example 9 to obtain the title compound (67).
Yield: 0.072 g (25%).
$^1$HNMR (DMSO d$_6$): δ 12.7 (s, 1H), 8.68 (d, 1H), 8.25 (m, 1H), 7.65 (m, 1H), 6.65 (s, 1H), 6.15 (s, 1H), 3.95-3.2 (m, 3H), 3.0-2.7 (m, 3H), 2.5 (s, 3H), 2.2 (m, 1H), 1.85 (m, 1H).
MS: m/e 403 (M+1), 385 (M−18), 371 (M−32).

Analysis: $C_{20}H_{19}ClN_2O_5.H_2O$ C, 57.29 (57.17); H, 5.1 (5.01); N, 6.36 (6.66); Cl, 8.94 (8.44).

EXAMPLE 58

(+)-trans-8-(2-hydroxymethyl-1-methyl-pyrrolidin-3-yl)-5,7-dimethoxy-2-(4-nitro-phenyl)-chromen-4-one. (Compound No. 69)

Compound (6) (5.19 g, 14.79 mmol) was reacted with 4-nitrobenzoic acid (5.01 g, 30 mmol) in the presence of dry pyridine. (35 mL) and $POCl_3$ (5.5 mL, 23.43 mmol) using the conditions described in example 52 to get trans-4-nitro-benzoic acid 2-(2-acetoxymethyl-1-methyl-pyrrolid-in-3-yl)-6-acetyl-3,5-dimethoxy-phenyl ester (Compound No. 68). This was converted in situ to the title compound (69) using NaH (50%, 3.41 g, 71.04 mmol) in 1,4-dioxane (90 mL) as described in example 26.

Yield: 1.9 g (30%).
$^1$HNMR ($CDCl_3$+DMSO $d_6$): δ 8.3 (d, 2H), 8.18 (d, 2H), 6.7 (s, 1H), 6.4 (s, 1H), 4.32 (m, 1H), 3.98 (two singlets, 6H), 3.68 (dd, 1H), 3.3 (m, 2H), 2.85-2.5 (m, 2H), 2.45 (s, 3H), 2.08 (m, 2H).
MS: m/e 441 (M+1), 423 (M−18), 411 (M−31).

EXAMPLE 59

(+)-trans-5,7-Dihydroxy-8-(2-hydroxymethyl-1-methyl-pyrrolidin-3-yl)-2-(4-nitro-phenyl)-chromen-4-one. (Compound No. 70)

Compound (69) (1.9 g, 4.32 mmol) was demethylated using pyridine hydrochloride (19 g, 164.5 mmol) as described in example 9 to obtain the title compound (70).

Yield: 1.2 g (75%).
mp: 275-277° C.
IR cm$^{-1}$: 3500, 1660, 1540.
$^1$HNMR (DMSO $d_6$): δ 12.7 (s, 1H), 8.35 (s, 4H), 7.1 (s, 1H), 6.15 (s, 1H), 4.15 (m, 1H), 3.6 (m, 2H), 3.05 (m, 3H), 2.55 (s, 3H), 2.25 (m, 1H), 2.0 (m, 1H).
MS: m/e 413 (M+1), 381 (M−31), 365 (M−46).
Analysis: $C_{21}H_{20}N_2O_7$, C, 61.48 (61.16); H, 4.68 (4.89); N, 6.81 (6.79).

EXAMPLE 60

(+)-trans-2-(4-Amino-phenyl)-5,7-dihydroxy-8-(2-hydroxymethyl-1-methyl-pyrrolidin-3-yl)-chromen-4-one. (Compound No. 71)

Compound (70) (1 g, 2.43 mmol) was dissolved in methanol (20 mL) and subjected to hydrogenation at 35 psi using Pd—C (10%, 0.05 g) as a catalyst for 2 h. Pd—C was then filtered. The filtrate was concentrated and the solid product obtained was purified using a silica gel column and 5% methanol+1% liquor ammonia in $CHCl_3$ as eluant to obtain the title compound (71)

Yield: 0.72 g (77%).
mp: 172-174° C.
IR cm$^{-1}$: 3340, 1660.
$^1$HNMR (DMSO $d_6$): δ 13.2 (s, 1H), 7.8 (d, 2H), 6.7 (d, 2H), 6.6 (s, 1H), 6.1 (two singlets, 2H), 4.0 (m, 1H), 3.6-3.3 (m, 2H), 3.1-2.85 (m, 3H), 2.5 (s, 3H), 2.2 (m, 1H), 1.98 (m, 1H).
MS: m/e 383 (M+1), 365 (M−17), 351 (M−32).

Analysis: $C_{21}H_{22}N_2O_5.\frac{1}{2}H_2O$, C, 63.88 (64.4); H, 5.92 (5.92); N, 7.12 (7.15).

EXAMPLE 61

2-Bromo-5-nitrobenzoic acid (Compound No. 72)

2-bromobenzoic acid (10 g, 49.75 mmol) was added in portions with stirring to an ice cold nitrating mixture (98% $H_2SO_4$, 25 mL and 69% $HNO_3$, 12 mL maintaining the temperature of the mixture below 5° C. The reaction mixture was stirred for 1 h below 5° C. It was poured into ice water (200 mL). The white crystalline product (72) obtained was filtered, washed with water and dried.

Yield: 7.5 g (66%).
$^1$HNMR ($CDCl_3$): δ 8.68 (d, 1H), 8.15 (dd, 1H), 7.85 (d, 1H).
MS: m/e 246 (M$^+$).

EXAMPLE 62

5-Amino-2-bromo-benzoic acid methyl ester (Compound No. 73)

Glacial acetic acid (75 mL) was added dropwise with stirring, at 40-50° C. to a mixture of compound (72) (15 g, 57.62 mmol) and iron dust (15 g, 0.267 mol) in water (120 mL). The reaction mixture was stirred vigorously at room temperature for 1 h. It was poured into water (200 mL), basified using saturated aqueous $Na_2CO_3$ solution and extracted with EtOAc (3×250 mL). The organic extract was washed, dried (anhy. $Na_2SO_4$) and concentrated to obtain the title compound (73).

Yield: 12 g (90%).
$^1$HNMR ($CDCl_3$): δ 7.38 (d, 1H), 7.14 (d, 1H), 6.65 (m, 1H), 3.99 (s, 3H)
MS: m/e 231 (M$^+$), 199 (M−32), 150 (M−80).

EXAMPLE 63

2-Bromo-5-hydroxy-benzoic acid methyl ester (Compound No. 74)

Compound (73) (12 g, 52.1 mmol) was added to 10% aqueous sulfuric acid (110 mL) at 0° C. An aqueous solution (40 ml) of $NaNO_2$ (4.3 g, 62.32 mmol) was added dropwise, with stirring at 0-5° C. The reaction mixture was stirred for 10 min. and then it was added to an ice cold aqueous solution of copper sulfate (156 g, 1 L, 625 mmol) containing $Cu_2O$ (6.8 g, 47.55 mmol). The resultant mixture was stirred at 0° C. for 10 min. It was diluted with water and extracted using EtOAc (3×500 mL). The organic extract was washed with water dried (anhy. $Na_2SO_4$), concentrated and purified using a silica gel column and 2% EtOAc in petroleum ether (60-80° C.) as eluant to obtain the title compound (74).

Yield: 6.5 g (53%).
$^1$HNMR ($CDCl_3$): δ 7.5 (d, 1H), 7.35 (d, 1H), 6.85 (m, 1H), 5.35 (bs, —OH), 3.95 (s, 3H).
MS: m/e: 231 (M$^+$), 198 (M−32).

EXAMPLE 64

2-Bromo-5-methoxy-benzoic acid methyl ester (Compound No. 75)

Compound (74) (6.5 g, 28.1 mmol) was dissolved in dry 1,4-dioxane (50 mL) under dry $N_2$ atmosphere. To this solution NaH (50%, 3.37 g, 70.20 mmol) was added in portions at room temperature. The reaction mixture was stirred for 10 min at room temperature. Dimethyl sulfate (4 mL, 5.31 g, 40.48 mmol) was added and the reaction mixture was stirred at 50° C. for 1 h. It was poured into ice water, acidified using 6N HCl and extracted using EtOAc (3×100 mL). The organic extract was washed with water, dried (anhy. $Na_2SO_4$), concentrated and purified using a silica gel column and 5% EtOAc in pet ether (60-80° C.) as eluant to obtain the title compound (75).

Yield: 3.9 g (57%).
$^1$HNMR ($CDCl_3$): δ 7.55 (d, 1H), 7.32 (d, 1H), 6.9 (m 1H), 3.95 (s, 3H), 3.8 (s, 3H).
MS: m/e 246 (M+1), 215 (M−31).

EXAMPLE 65

2-Chloro-5-nitro-benzoic acid (Compound No. 76)

2-Chlorobenzoic acid (2 g, 12.7 mmol) was added with stirring at room temperature to a nitrating mixture (20 mL) prepared from 1:1 $HNO_3$ (70%) and $H_2SO_4$ (98%). It was stirred for 1 h and poured into ice water. The title compound (76) obtained was filtered and dried.

Yield: 2.0 g (95%).
$^1$HNMR ($CDCl_3$): δ 8.6 (s, 1H), 8.2 (d, 1H), 7.6 (d, 1H).
MS: m/e 200.9 (M−1).

EXAMPLE 66

2-Chloro-5-nitro-benzoic acid methyl ester (Compound No. 77)

2-Chloro-5-nitrobenzoic acid (76) (11 g, 54.5 mmol) was dissolved in methanol (100 mL). Concentrated $H_2SO_4$ (2 mL) was added slowly and the reaction mixture heated to reflux for 4 h. The mixture was concentrated and the residue was allowed to cool to room temperature. It was poured over crushed ice. The organic product was extracted using diethyl ether (2×200 mL). The organic extract was washed with water, 10% aqueous $NaHCO_3$, dried (anhy. $Na_2SO_4$) and concentrated to get the title compound (77).

Yield: 12 g (100%).
$^1$HNMR ($CDCl_3$): δ 8.6 (s, 1H), 8.2 (d, 1H), 7.6 (d, 1H), 3.9 (s, 3H).
MS: m/e 214.9 (M−1).

EXAMPLE 67

5-Amino-2-chloro-benzoic acid methyl ester (Compound No. 78)

Compound (77) (12 g, 55.6 mmol) was dissolved in a mixture of $CHCl_3$:MeOH (4:1) (50 mL) and subjected to hydrogenation using Pd—C as a catalyst (10%, 0.2 g) to furnish the title compound (78).

Yield: 10.1 g (95%).
$^1$HNMR ($CDCl_3$): δ 7.1 (d, 1H), 7.05 (d, 1H), 6.8 (dd, 1H), 3.8 (s, 3H).
MS: m/e 185.03 ($M^+$).

EXAMPLE 68

2-Chloro-5-fluoro-benzoic acid methyl ester (Compound No. 79)

A solution of $NaNO_2$ (3.69 g, 53.4 mmol in 50 mL water) was added dropwise to a stirred suspension of methyl 5-amino-2-chlorobenzoate (78) (9 g, 48.5 mmol) in HCl (10%, 90 mL), keeping the temperature between 0-5° C. The reaction mixture was stirred for ten minutes and a solution of fluoroboric acid (70%, excess) was added to the mixture. A precipitate of diazonium fluoroborate salt separated which was filtered, washed with water and dried. The pyrolysis of this salt was then carried out at 140° C. for 15-20 min. The residue was purified using a silica gel column and 10% $CHCl_3$ in petroleum ether (60-80° C.) as an eluent to furnish the title compound (79).

Yield: 2.8 g (30%).
$^1$HNMR ($CDCl_3$): δ 3.95 (s, 3H), 7.15 (m, 1H), 7.4 (m, 1H), 7.55 (dd, 1H).
MS: m/e 189.99 (M+1).

EXAMPLE 69

2-Chloro-5-hydroxy-benzoic acid methyl ester (Compound No. 80)

Compound (78) (9 g, 48.5 mmol) was subjected to diazotization using $NaNO_2$ (4.5 g 48.5 mmol) in water (50 mL) and $H_2SO_4$ (10%, 100 mL). Excess nitrous acid was neutralized with urea. The reaction mixture was poured into a suspension of $CuSO_4$. $5H_2O$ (144 g, 577 mmol) and $Cu_2O$ (5.22 g, 41.4 mmol) in water (900 mL) at 0° C. The reaction mixture was stirred for 15 min. at 0-5° C. and was then extracted using diethyl ether (200 mL×3). The organic extract was washed, dried (anhy. $Na_2SO_4$), concentrated and purified using a silica gel column and 10% EtOAc in petroleum ether (60-80° C.) as eluant to obtain the title compound (80).

Yield: 4 g (44%).
$^1$HNMR ($CDCl_3$): δ 3.9 (s, 3H), 6.9 (dd 1H), 7.25 (d, 1H), 7.3 (t, 1H).
MS: m/e 187.93 (M+1).

EXAMPLE 70

2-Chloro-5-methoxy-benzoic acid methyl ester (Compound No. 81)

As described in example 64, compound (80) (4 g, 21.4 mmol) was subjected to methylation using NaH (50%, 1 g), dry 1,4-dioxane (20 mL) as solvent and dimethyl sulfate (5.4 g, 42.8 mmol). Purification using a silica gel column and 20% EtOAc in petroleum ether (60-80° C.) as eluant afforded the title compound (81).

Yield: 4.1 g, (96%).
$^1$HNMR ($CDCl_3$): δ 3.7 (s, 3H), 3.9 (s, 3H), 6.9 (dd, 1H), 7.25 (d, 1H), 7.3 (t, 1H).

EXAMPLE 71

2-Chloro-5-dimethylamino-benzoic acid methyl ester (Compound No. 82)

Compound (76) (4 g, 19.8 mmol) from example 65 was subjected to hydrogenation (40 psi, Pd—C (10%, 50 mg) under methylating conditions using aqueous HCHO (40%, 8 mL) and HCOOH (100%, 8 mL) for 4 h.

The catalyst was filtered off and the filtrate concentrated to get the title compound (82).

Yield: 4 g (95%).
$^1$HNMR ($CDCl_3$): δ 3.0 (s, 6H), 3.9 (s, 3H), 6.9 (d, 1H), 7.3 (t, 1H), 7.35 (d, 1H).
MS: m/e 213 ($M^+$).

EXAMPLE 72

2-Chloro-4-nitro-benzoic acid methyl ester
(Compound No. 83)

2-Chloro-4-nitrobenzoic acid (50 g, 248 mmol) was subjected to methylation using methanol (500 mL) and $H_2SO_4$ (98%, 15 mL) according to the procedure described in the example 66 to obtain the title compound (83)

EXAMPLE 73

4-Amino-2-chloro-benzoic acid methyl ester
(Compound No. 84)

Compound (83) (50 g, 232 mmol) was subjected to reduction as described in example 67 to obtain the title compound (84).
Yield: 40 g (93%).
$^1$HNMR (CDCl$_3$): δ 3.7 (s, 3H), 6.5 (dd, 1H), 6.7 (s, 1H), 7.8 (d, 1H).
MS: m/e 186.06 (M$^+$).

EXAMPLE 74

2-Chloro-4-hydroxy-benzoic acid methyl ester
(Compound No. 85)

Compound (84) (7.9 g, 42.5 mmol) suspended in 10% aqueous $H_2SO_4$ (80 mL) was reacted with NaNO$_2$ (3.5 g, 52.1 mmol in 35 mL water) as described in example 69. It was treated with a solution of CuSO$_4$.5H$_2$O (128 g, 513 mmol) and Cu$_2$O (5.5 g, 38.4 mmol) in water (800 mL) as described in the same procedure to obtain the title compound (85).
Yield: 2.5 g (31%).
$^1$HNMR (CDCl$_3$): δ 3.9 (s, 3H), 6.75 (d, 1H), 6.95 (s, 1H), 7.89 (d, 1H).

EXAMPLE 75

2-Chloro-4-methoxy-benzoic acid methyl ester
(Compound No. 86)

To a solution of compound (85) (2.8 g, 15 mmol) in dry dioxane (50 mL) was added NaH (50%, 1.44 g, 30 mmol) and DMS (3.78 g, 30 mmol). It was stirred at 60-65° C. for 1 h. It was poured into ice water and extracted with EtOAc (100 mL×2)
The organic extract was washed with brine, dried (anhy. Na$_2$SO$_4$) and concentrated to obtain the title compound (86).
Yield: 2.5 g (83%)
NMR (CDCl$_3$): δ 7.85 (d, 1H), 6.95 (s, 1H), 6.75 (d, 1H), 3.9 (s, 3H), 3.85 (s, 3H).

EXAMPLE 76

2-Chloro-4-cyano-benzoic acid methyl ester
(Compound No. 87)

4-Amino-2-chloro-benzoic acid methyl ester (25 g, 72.7 mmol) was dissolved in 10% aqueous $H_2SO_4$ (150 mL) and the solution was cooled to 0° C. A solution of NaNO$_2$ (11.15 g, 16.88 mmol) in water (50 mL) was added dropwise maintaining the temperature between 0-5° C. The mixture was stirred for 10 min., excess nitrous acid was neutralized using a saturated aqueous NaHCO$_3$ solution. The resulting mixture was then added to a precooled (0-5° C.) suspension of CuCN (13.87 g, 155 mmol) and KCN (10.07 g, 155 mmol) in water (200 mL). It was stirred for 10 min., then allowed to attain room temperature. It was stirred for 0.5 h and finally heated on a steam bath for 0.5 h. Excess saturated FeCl$_3$ solution was then added to the reaction mixture.
It was extracted using EtOAc (200 mL×3). The organic extract was washed with water, dried (anhy.), concentrated and purified using a silica gel column and CHCl$_3$:petroleum ether (60-80° C.) (1:1) as eluant to obtain the title compound (87).
Yield: 12 g (84%).
$^1$HNMR (CDCl$_3$): δ 4.0 (s, 3H), 7.6 (d, 1H), 7.75 (s, 1H), 7.9 (d, 1H).
MS: m/e: 196.88 (M+1).

EXAMPLE 77

4-Bromo-2-chloro-benzoic acid methyl ester
(Compound No. 88)

Compound (84) (10 g, 54 mmol) was subjected to diazotisation, using HBr (48%, 16 mL, water 150 mL) and NaNO$_2$ (4.1 g, 59.4 mmol in 20 mL water). The diazonium salt formed was poured into a hot (70-80° C.) solution of CuBr (4.25 g, 29.6 mmol) in HBr (48%, 5 mL, water 100 mL). The reaction mixture was stirred at room temperature for 15 min. It was extracted using diethyl ether (3×100 mL), processed and purified as described in example 74 to obtain the title compound (88).
Yield: 8.0 g (59%).
$^1$HNMR (CDCl$_3$): δ 3.95 (s, 3H), 7.45 (d, 1H), 7.65 (s, 1H), 7.75 (d, 1H).
MS: m/e 249.8 (M−1).

EXAMPLE 78

2-Chloro-5-cyano-benzoic acid methyl ester
(Compound No. 89)

Compound (78) (10 g, 54 mmol) was diazotized using the procedure and quantities of reagents as described in example 76 to get the title compound (89)
Yield: 8.0 g (59%).
$^1$HNMR (CDCl$_3$): δ 3.95 (s, 3H), 7.35 (m, 1H), 7.7 (d, 1H), 7.95 (d, 1H).

EXAMPLE 79

(+/−)-trans-8-(2-hydroxymethyl-1-methyl-pyrrolidin-3-yl)-5,7-dimethoxy-2-(2-methoxy-phenyl)-chromen-4-one. (Compound No. 90)

Compound (7) (0.7 g, 2.2 mmol) in dry DMF (10 mL) was reacted with 2-Methoxy-benzoic acid methyl ester (1.13 g, 6.8 mmol) in the presence of NaH (50%, 0.272 g) as described in example 8, to obtain the title compound (90).
Yield: 0.4 g (41%).
$^1$HNMR (CDCl$_3$): δ 2.1 (m, 2H), 2.65 (s, 3H), 2.85 (m, 2H), 3.4 (m, 1H), 3.64 (d, 1H), 3.67 (d, 1H), 3.95 (two singlets, 9H), 4.25 (m, 1H), 5.95 (s, 1H), 6.45 (s, 1H), 7.0 (d, 1H), 7.1 (t, 1H), 7.45 (t, 1H), 8.0 (d, 1H).
MS: m/e 426.06 (M+1).

EXAMPLE 80

(+/−)-trans-5,7-Dihydroxy-8-(2-hydroxymethyl-1-methyl-pyrrolidin-3-yl)-2-(2-hydroxy-phenyl)-chromen-4-one. (Compound No. 91)

Compound (90) (0.4 g 0.9 mmol) was demethylated using pyridine hydrochloride (6 g, 52.0 mmol) as described in example 9 to obtain the title compound (91).
Yield: 0.1 g (29%).
mp: 212-213° C.
IR cm$^{-1}$: 3400, 1650.
MS: m/e 384.15 (M−1).
Analysis: C, 59.32 (58.87); H, 5.35 (5.88); N, 3.74 (3.26).

EXAMPLE 81

(+)-trans-3-Chloro-4-[8-(2-hydroxymethyl-1-methyl-pyrrolidin-3-yl)-5,7-dimethoxy-4-oxo-4H-chromen-2-yl]-benzonitrile. (Compound No. 92)

Compound (10) (0.7 g, 2.2 mmol) in dry DMF (15 mL) was reacted with methyl 2-chloro-4-cyanobenzoate (0.885 g, 4.5 mmol) in the presence of NaH (50%, 0.272 g) as described in example 8, to obtain the title compound (92).
Yield: 0.31 g (31%).
$^1$HNMR (CDCl$_3$): δ 2.1 (m, 2H), 2.65 (s, 3H), 2.85 (m, 2H), 3.4 (m, 1H), 3.64 (d 1H), 3.67 (d, 1H), 3.95 (two singlets, 6H), 4.25 (m, 1H), 6.45 (s, 1H), 7.05 (s, 1H), 7.25 (s, 1H), 7.4 (d 1H), 8.3 (d, 1H).
MS: m/e 455.12 (M+1).

EXAMPLE 82

(+)-trans-3-Chloro-4-[5,7-dihydroxy-8-(2-hydroxymethyl-1-methyl-pyrrolidin-3-yl)-4-oxo-4H-chromen-2-yl]benzonitrile (Compound No. 93)

Compound (92) (0.3 g, 0.6 mmol) was demethylated using pyridine hydrochloride (3 g, 26.0 mmol) as described in example 9 to obtain the title compound (93).
Yield: 0.12 g (46%).
mp: 237-239° C.
IR cm$^{-1}$: 3450, 2210, 1650
$^1$HNMR (DMSO d$_6$): δ 13.0 (s, 1H), 8.05 (d, 1H), 7.25 (m, 2H), 7.2 (s, 1H), 6.2 (s 1H), 4.04 (m, 1H), 2.65 (s, 3H), 2.1 (m, 2H).
MS: m/e 426.86 (M−1)
Analysis: C$_{22}$H$_{19}$ClN$_2$O$_5$.½H$_2$O, C, 60.47 (60.60); H, 5.07 (4.62); N, 7.36 (6.42); Cl, 8.88 (8.13)

EXAMPLE 83

(+)-trans-2-(4-Bromo-2-chloro-phenyl)-8-(2-hydroxymethyl-1-methyl-pyrrolidin-3-yl)-5,7-dimethoxy-chromen-4-one. (Compound No. 94)

Compound (10) (0.7 g, 2.2 mmol) in dry DMF (15 mL) was reacted with methyl 4-bromo-2-chlorobenzoate (88) (1.13 g, 4.5 mmol) in the presence of NaH (50%, 0.271 g, 11.3 mmol) as described in example 8, to obtain the title compound (94).
Yield: 0.3 g (27%).
$^1$HNMR (CDCl$_3$): δ 7.95 (d, 1H), 7.68 (d, 1H), 7.55 (d, 1H), 6.55 (s, 1H), 6.45 (s 1H), 4.15 (m, 1H), 4.05 (two singlets, 6H), 3.7 (m, 1H), 3.4 (t 1H), 3.25 (m, 1H), 2.7 (m, 2H), 2.4 (s, 3H), 2.1 (m, 2H).
MS: m/e 509.95 (M+1).

EXAMPLE 84

(+)-trans-2-(4-Bromo-2-chloro-phenyl)-5,7-dihydroxy-8-(2-hydroxymethyl-1-methyl-pyrrolidin-3-yl)-chromen-4-one (Compound No. 95)

Compound (94) (0.3 g, 0.59 mmol) was demethylated using pyridine hydrochloride (3 g, 26.0 mmol) as described in example 9 to obtain the title compound (95).
Yield: 0.1 g (35%).
mp: 155-156° C.
IR cm$^{-1}$: 3400, 1660.
$^1$HNMR (DMSO d$_6$): δ 12.7 (s, 1H), 8.32 (s, 1H), 8.02 (s, 1H), 7.8 (s, 1H), 6.55 (s, 1H), 6.12 (s, 1H), 3.8 (m, 1H), 3.5 (m, 3H), 2.3 (m, 2H), 2.5 (s, 3H), 2.2 (m, 1H), 1.9 (m, 1H).
MS: m/e 482.9 (M+1).
Analysis: C$_{21}$H$_{19}$BrClNO$_5$. 5H$_2$O: C, 50.81 (50.69); H, 4.27 (4.25); N, (2.98 (2.81); Halogens (Cl+Br), 23.97 (23.18).

EXAMPLE 85

(+/−)-trans-2-(2-Chloro-5-dimethylamino-phenyl-8-(2-hydroxymethyl-1-methyl-pyrrolidin-3-yl)-5,7-dimethoxy-chromen-4-one (Compound No. 96)

Compound (7) (0.8 g, 2.58 mmol) in dry DMF (15 mL) was reacted with ester (82) in the presence of NaH (50%, 0.31 g, 12.9 mmol) as described in example 8, to obtain the title compound (96).
Yield: 0.150 g (12%).
$^1$HNMR (CDCl$_3$): δ 7.68 (d, 1H), 6.75 (d, 1H), 6.66 (m, 1H), 6.4 (s, 1H), 6.0 (s, 1H), 3.7 (m, 2H), 3.0 (s, 6H), 2.9 (m, 2H), 2.65 (s, 3H), 2.2 (m, 2H).
MS: m/e 471.08 (M−1).

EXAMPLE 86

(+/−)-trans-2-(2-Chloro-5-dimethylamino-phenyl)-5,7-dihydroxy-8-(2-hydroxymethyl-1-methyl-pyrrolidin-3-yl)-chromen-4-one (Compound No. 97)

Compound (96) (0.25 g, 0.53 mmol) was demethylated using pyridine hydrochloride (2.5 g, 21.6 mmol) as described in example 9 to obtain the title compound (97).
Yield: 0.04 g, (17%).
MP: 208-210° C.
$^1$HNMR (DMSO d$_6$): δ 12.75 (s, 1H), 7.4 (d, 1H), 6.6 (d, 1H), 6.5 (d, 1H), 6.38 (s, 1H), 6.2 (s, 1H), 3.8 (m, 2H), 3.3 (m, 2H), 3.0 (m, 2H), 2.8 (d, 3H), 2.6 (s, 3H), 2.35 (m, 1H), 2.0 (m, 1H).
MS: m/e 431.42 (M+1).
Analysis: C$_{22}$H$_{23}$ClN$_2$O$_5$.3H$_2$O, C, 54.83 (54.49); H, 5.58 (6.02); N, 5.33 (5.77).

EXAMPLE 87

(+/−)-trans-2-(2-Chloro-4-methoxy-phenyl)-8-(2-hydroxymethyl-1-methyl-pyrrolidin-3-yl)-5,7-dimethoxy-chromen-4-one (Compound No. 98)

Compound (7) (1.0 g, 3.2 mmol) in dry DMF (25 mL) was reacted with methyl 2-chloro-4-methoxybenzoate (86) (1.29 g, 6.4 mmol) in the presence of NaH (50%, 0.388 g, 16 mmol) as described in example 8, to obtain the title compound (98).
Yield: 0.28 g (19%).

¹HNMR (CDCl₃): δ 7.7 (d, 1H), 7.02 (s, 1H), 6.9 (d, 1H), 6.55 (s, 1H), 6.45 (s, 1H), 4.2 (m, 1H), 4.05 (two singlets, 6H), 3.86 (s, 3H), 3.7 (dd, 1H), 3.45 (d, 1H), 3.2 (m, 1H), 2.8 (d, 1H), 2.7 (d, 1H), 2.4 (s, 3H), 2.1 (m, 2H).
MS: m/e 460.23 (M+1).

EXAMPLE 88

(+/−)-trans-2-(2-Chloro-4-hydroxy-phenyl)-5,7-dihydroxy-8-(2-hydroxymethyl-1-methylpyrrolidin-3-yl)-chromen-4-one. (Compound No. 99)

Compound (98) (0.25 g, 0.54 mmol) was demethylated using pyridine hydrochloride (4.0 g, 34.6 mmol) as described in example 9 to obtain the title compound (99).
Yield: 0.1 g (44%).
mp: >300° C.
IR cm⁻¹: 3400, 1660.
¹HNMR (DMSO d₆): δ 12.7 (s, 1H), 7.4 (d, 1H), 6.9 (s 1H), 6.8 (d, 1H), 6.35 (s, 1H), 6.25 (s, 1H), 4.1 (m, 1H), 3.8 (d, 1H), 3.6 (m, 1H), 3.4 (m, 2H), 3.2 (m, 1H), 2.7 (s, 3H), 2.2 (m, 2H).
MS: m/e 416.22 (M−1).

EXAMPLE 89

(+/−)-trans-2-(2-Chloro-5-fluoro-phenyl)-8-(2-hydroxymethyl-1-methyl-pyrrolidin-3-yl)-5,7-dimethoxy-chromen-4-one. (Compound No. 100)

Compound (7) (1.0 g, 3.2 mmol) in dry DMF (25 mL) was reacted with compound (79) (1.22 g, 6.4 mmol) in the presence of NaH (50%, 0.388 g, 16 mmol) as described in example 8, to obtain the title compound (100).
Yield: 0.9 g (63%).
¹HNMR (CDCl₃): δ 7.55 (m, 1H), 7.46 (m, 1H), 7.15 (m, 1H), 6.6 (s, 1H), 6.45 (s 1H), 4.25 (m, 1H), 4.05 (two singlets 6H), 3.7 (d, 1H), 3.4 (d, 1H), 3.3 (m, 1H), 2.8 (d, 1H), 2.6 (m, 1H), 2.5 (s, 3H), 2.1 (m, 2H).
MS: m/e 448.21 (M+1).

EXAMPLE 90

(+/−)-trans-2-(2-Chloro-5-fluoro-phenyl)-5,7-dihydroxy-8-(2-hydroxy-methyl-1-methyl-pyrrolidin-3-yl)-chromen-4-one. (Compound No. 101)

Compound (100) (0.8 g, 1.78 mmol) was demethylated using pyridine hydrochloride (8.0 g, 69.0 mmol) as described in example 9 to obtain the title compound (101).
Yield: 0.45 g (60%).
mp: 253-254° C.
IR cm⁻¹: 3450, 1665.
¹HNMR (DMSO d₆): δ 12.7 (s, 1H), 7.8 (m, 2H), 7.55 (m, 1H), 6.55 (s, 1H), 6.15 (s, 1H), 3.9 (m, 1H), 3.6 (m, 3H), 2.9 (m, 2H), 2.5 (s, 3H), 2.2 (m, 1H), 1.9 (m, 1H).
MS: m/e 420.31 (M+1).
Analysis: C₂₁H₁₉ClFNO₅, C, 60.2 (60.08); H, 4.53 (4.56); N, 3.86 (3.34); Cl, 8.17 (8.44).

EXAMPLE 91

(+/−)-trans-2-(2-Chloro-5-methoxy-phenyl)-8-(2-hydroxymethyl-1-methyl-pyrrolidin-3-yl)-5,7-dimethoxy-chromen-4-one (Compound No. 102)

Compound (7) (1.0 g, 3.2 mmol) in dry DMF (25 mL) was reacted with compound (81) (1.3 g, 6.4 mmol) in the presence of NaH (50%, 0.776 g, 16.0 mmol) as described in example 8, to obtain the title compound (102).
Yield: 0.8 g (54%).
¹HNMR (CDCl₃): δ 7.4 (d, 1H), 7.18 (s, 1H), 6.95 (m, 1H), 6.46 (s, 1H), 6.42 (s, 1H), 4.2 (m, 1H), 4.05 (two singlets, 6H), 3.85 (s, 3H), 3.6 (d, 1H), 3.45 (d, 1H), 3.2 (m, 1H), 3.0 (s, 1H), 2.8 (d, 1H), 2.6 (m, 3H), 2.1 (m, 2H).
MS: m/e 460.36 (M+1).

EXAMPLE 92

(+/−)-trans-2-(2-Chloro-5-hydroxy-phenyl)-5,7-dihydroxy-8-(2-hydroxymethyl-1-methyl-pyrrolidin-3-yl)-chromen-4-one. (Compound No. 103)

and (+/−)-trans-2-(2-Chloro-5-methoxy-phenyl)-5,7-dihydroxy-8-(2-hydroxymethyl-1-methyl-pyrrolidin-3-yl)-chromen-4-one. (Compound No. 104)

Compound (102) (0.75 g, 1.63 mmol) was demethylated using pyridine hydrochloride (8.0 g, 69.0 mmol) as described in example 9 to obtain the title compounds (103) and (104).
Compound (103)
Yield: 0.05 g (7%)
mp: 220-221° C.
IR cm⁻¹: 3450, 1655.
¹HNMR (CDCl₃): δ 12.6 (s, 1H), 7.4 (d, 1H), 7.1 (d, 1H), 7.0 (m, 1H), 6.45 (s, 1H), 6.3 (s, 1H), 4.2 (m, 1H), 3.85 (s, 3H), 3.4 (m, 1H), 3.3 (m, 1H), 3.2 (m, 1H), 2.7 (s, 3H), 2.65 (m, 1H), 2.4 (m, 1H), 2.1 (m, 1H).
MS: m/e 430.19 (M−1).
Analysis: C₂₂H₂₂ClNO₆.2H₂O, C, 56.6 (56.47); H, 4.76 (5.60); N, 2.45 (2.99).
Compound (104):
Yield: 0.3 g (44%).
mp: 266-267° C.
IR cm⁻¹: 3500, 1660.
¹HNMR (DMSO d₆): δ 12.7 (s, 1H), 7.47 (d, 1H), 7.12 (s, 1H), 7.0 (m, 1H), 6.45 (s, 1H), 6.25 (s, 1H), 3.35 (m, 1H), 3.5 (m, 3H), 3.0 (m, 2H), 2.5 (s, 3H), 2.2 (m, 1H), 1.9 (m, 1H).
MS: m/e 416 (M−1).
Analysis: C₂₁H₂₀ClNO₆.½H₂O, C, 59.48 (59.09); H, 4.88 (4.95); N, 3.53 (3.28); Cl, 8.0 (8.3).

EXAMPLE 93

(+/−)-trans-1-[2-Hydroxy-3-(3-hydroxy-1-methyl-piperidin-4-yl)-4,6-dimethoxy-phenyl]-ethanone (Compound No. 105)

Compound (2) (15 g, 53.4 mmol) was reacted with acetic anhydride (27.2 g, 269 mmol) in the presence of BF₃ Et₂O (37.9 g, 267 mmol) at room temperature overnight.
The reaction mixture was poured onto crushed ice, made basic using sat. Na₂CO₃ solution. It was extracted using CHCl₃ (200 mL×3). The organic extract was washed with water, dried (anhy.), and concentrated. The solid obtained was treated with 5% aqueous NaOH (85 mL) at 55-60° C. for 1 h. It was treated with, ice water (100 mL), acetic acid (pH 5), then made basic using aqueous Na₂CO₃ until the precipitation of the product was complete.
Filtration afforded the title compound (105) which was washed with water and dried.
Yield: 9 g (54.5%).

¹HNMR (CDCl₃): δ 5.98 (s, 1H), 4.45 (m, 1H), 3.90 (d, 6H), 3.25 (dd, 1H), 3.1 (t, 1H), 2.95 (d, 1H), 2.6 (s, 3H), 2.35 (s, 3H), 2.1 (t, 1H), 1.95 (t, 1H), 1.58 (m, 2H).
MS: m/e 310 (M+1).

EXAMPLE 94

(+/−)-trans-2-(2-Chloro-phenyl)-8-(3-hydroxy-1-methyl-piperidin-4-yl)-5,7-dimethoxy-chromen-4-one. (Compound No. 106)

Compound (105) (9 g, 29 mmol) in dry DMF (50 mL) was reacted methyl 2-chlorobenzoate (16.5 g, 96.7 mmol) in the presence of NaH (50%, 6.99 g, 145.6 mmol) as described in example 8, to obtain the title compound (106).
Yield: 7.5 g (60%)
1HNMR (CDCl₃): δ 7.65 (d, 1H), 7.55-7.4 (m, 3H), 6.4 (d, 2H), 4.55 (m, 1H), 3.95 (s, 6H), 3.45 (t, 1H), 3.35-3.2 (m, 2H), 2.95 (d, 1H), 2.4 (s, 3H), 2.0 (m, 1H), 1.6 (d, 2H).
MS: m/e 429.05 (M−1).

EXAMPLE 95

(+/−)-trans-8-(2-Azidomethyl-1-methyl-pyrrolidin-3-yl)-2-(2-chloro-phenyl)-5,7-dimethoxy-chromen-4-one. (Compound No. 107)

Et₃N (0.705 g, 7 mmol) was added to a solution of compound (106) (1.5 g, 3.5 mmol) in dry CH₂Cl₂ (25 mL) with stirring at (0-5° C.), followed by a drop wise addition of methane sulfonyl chloride (0.479 g, 4.1 mmol). The reaction mixture was, then stirred for 30 min. in an ice-bath, poured into ice water, extracted with EtOAc (2×100 mL), washed with, brine, then a saturated aqueous NaHCO₃ solution, dried (anhy. Na₂SO₄) and concentrated to obtain a syrup. It was dissolved in DMF (25 mL) treated with NaN₃ (0.57 g, 8.7 mmol) and stirred for 2 h at 60-70° C. The reaction mixture was poured onto crushed ice, extracted using CHCl₃ (100 mL×3). The organic extract was washed with water, dried (anhy. Na₂SO₄) and concentrated to obtain the title compound (107) which was subjected to purification by column chromatography using silica gel and EtOAc:pet ether (1:1) as eluant.
Yield: 0.6 g (37%).
IR cm⁻¹: 2160, 1640.
¹HNMR (CDCl₃): δ 7.6 (d, 1H), 7.36-7.5 (m, 3H), 6.46 (d, 2H), 4.05 (hump, 1H), 4.05 (d, 6H), 3.45 (two doublets, 1H), 3.3-3.1 (hump, 2H), 2.7 (m, 1H), 2.43 (m, 1H), 2.35 (s, 3H), 2.2 (m, 1H), 2.0 (m, 1H).
MS: m/e 455.09 (M−1).

EXAMPLE 96

(+/−)-trans-8-(2-Aminomethyl-1-methyl-pyrrolidin-3-yl)-2-(2-chloro-phenyl)-5,7-dimethoxy-chromen-4-one. (Compound No. 108)

Compound (107) (0.6 g, 1.6 mmol) and Ph₃P (0.414 g, 1.58 mmol) were dissolved in THF (10 mL) containing water (0.1 mL). The resultant solution was stirred for 12 h. It was concentrated and the residue obtained was subjected to flash column chromatography using silica gel and 5% IPA+1% liquor ammonia in CHCl₃ as eluant to obtain the title compound (108).
Yield: 0.45 g (81%)

¹H NMR (CDCl₃): δ 7.6-7.45 (m, 4H), 6.45 (s, 2H), 4.0 (d, 6H), 3.95 (m, 1H), 3.08 (t, 1H), 2.75 (dd, 1H), 2.58 (d, 1H), 2.5 (m, 1H), 2.35 (m, 1H), 2.25 (s, 3H), 2.0 (m, 2H).
MS: m/e 429.03 (M−1).

EXAMPLE 97

(+/−)-trans-8-(2-Aminomethyl-1-methyl-pyrrolidin-3-yl)-2-(2-chloro-phenyl)-5,7-dihydroxy-chromen-4-one. (Compound No. 109)

Compound (108) (0.45 g, 1.0 mmol) was demethylated using pyridine hydrochloride (5.0 g, 43.0 mmol) as described in example 9 to obtain the title compound (109).
Yield: 0.25 g (62%)
mp: 218-219° C.
IR cm⁻¹: 3450, 1660
¹HNMR (DMSO d₆): δ 12.7 (s, 1H), 7.7-7.5 (m, 4H), 6.2 (s, 1H), 5.8 (s, 1H), 3.55 (m, 1H), 2.85-2.65 (m, 3H), 2.38 (m, 1H), 2.2 (s, 3H), 2.05 (m, 1H), 1.9 (m, 2H).
MS: m/e 400.95 (M−1).
Analysis: C₂₁H₂₁ClN₂O₄, C, 62.52 (62.92); H, 5.28 (5.28); N, 7.24 (6.99); Cl, 8.51 (8.84).

EXAMPLE 98

(+/−)-trans-{3-[2-(2-Chloro-phenyl)-5,7-dimethoxy-4-oxo-4H-chromen-8-yl]-1-methyl-pyrrolidin-2-yl}-acetonitrile. (Compound No. 110)

Et₃N (0.352 g, 3.5 mmol) was added to a solution of compound (106) (1.0 g, 2.3 mmol) in dry CH₂Cl₂ (20 mL) with stirring at (0-5° C.), followed by a drop wise addition of methane sulfonyl chloride (0.319 g, 2.8 mmol). The reaction mixture was then stirred for 30 min, at (0-5° C.), diluted with CHCl₃ (100 mL), washed with, water, saturated aqueous NaHCO₃ solution, dried (anhy. Na₂SO₄) and concentrated. The residue was dissolved in isopropanol (20 mL) and treated with KCN (0.925 g, 14.2 mmol). The reaction mixture was then stirred at 80° C. for 1 h. Aqueous FeCl₃ was added to destroy excess KCN. It was basified with aqueous Na₂CO₃, extracted with EtOAc (100 mL×3), washed with water, dried (anhy. Na₂SO₄), and concentrated. The crude obtained was purified using a silica gel column and 30% EtOAc+1% liq. ammonia in CHCl₃ as an eluent to obtain the title compound (110).
Yield: 0.5 g (49.5%)
¹HNMR (CDCl3): δ 7.6 (d, 1H), 7.55-7.35 (m, 3H), 6.45 (d, 2H), 4.05 (d, 6H), 3.9 (m, 1H), 3.1 (t, 1H), 2.78 (m, 1H), 2.4 (m, 2H), 2.35 (s, 3H), 2.18 (m, 1H), 2.0 (m, 1H), 1.8 (m, 1H).
MS: m/e 437.9 (M−1).

EXAMPLE 99

(+/−)-trans-{3-[2-(2-Chloro-phenyl)-5,7-dihydroxy-4-oxo-4H-chromen-8-yl]-1-methyl-pyrrolidin-2-yl}-acetonitrile. (Compound No. 111)

Compound (110) (0.45 g, 1.0 mmol) was demethylated using pyridine hydrochloride (4.5 g, 39.0 mmol) as described in example 9 to obtain the title compound (111).
Yield: 0.35 g (85%)
mp: 107-108° C.
IR cm⁻¹: 3400, 2300, 1650

¹HNMR (DMSO d₆): δ 12.7 (s, 1H), 7.75 (d, 1H), 7.6-7.4 (m, 3H), 6.5 (s, 1H), 6.3 (s, 1H), 4.15 (d, 1H), 3.55 (t, 1H), 3.35 (t, 1H), 2.8-2.4 (m, 4H), 2.6 (s, 3H), 2.0 (m, 1H)

MS: m/e 411 (M+1)

Analysis: $C_{22}H_{21}ClN_2O_4$, C, 64.22 (64.00); H, 4.74 (5.13); N, 6.54 (6.79); Cl, 8.93 (8.59).

EXAMPLE 100

(+/−)-trans-2-(2-Chloro-phenyl)-8-(2-imidazol-1-ylmethyl-1-methyl-pyrrolidin-3-yl)-5,7-dimethoxy-chromen-4-one. (Compound No. 112)

Compound (106), (0.7 g, 1.6 mmol) in CHCl₃ (20 mL) was treated with triethyl-amine (0.3 g, 2.8 mmol) and subsequently with methane sulfonyl chloride (0.28 g 2.4 mmol) as described in example 98. The sulfonyl ester obtained was reacted with imidazole (0.44 g, 6.5 mmol) to get the title compound (112).

Yield: 0.35 g (46%)

¹HNMR (CDCl₃): δ 7.54-7.3 (m, 5H), 6.77 (s, 1H), 6.67 (s, 1H), 6.4 (d, 2H), 4.0 (two singlets, 6H), 3.9 (m, 1H), 3.8 (m, 1H), 3.1 (m, 2H), 2.4 (m, 1H), 2.25 (s, 3H), 2.1 (m, 1H), 1.9 (m, 2H).

MS: m/e 480.04 (M+1).

EXAMPLE 101

(+/−)-trans-2-(2-Chloro-phenyl)-5,7-dihydroxy-8-(2-imidazol-1-ylmethyl-1-methyl-pyrrolidin-3-yl)-chromen-4-one. (Compound No. 113)

A mixture of compound (112) (0.3 g, 0.625 mmol) and pyridine hydrochloride (3.0 g, 26.0 mmol) was heated as described in example 9 to get the title compound (113).

Yield: 0.15 g (53%)

mp: 249-250° C.

IR cm⁻¹: 3500, 1670

¹HNMR (DMSO d₆): δ 12.7 (s, 1H), 7.67 (s, 1H), 7.6-7.4 (m, 4H), 6.97 (s, 1H), 6.87 (s, 1H), 6.45-6.3 (d, 2H), 4.25 (m, 1H), 4.05 (m, 1H), 3.88 (m, 1H), 3.45 (m, 1H), 2.95 (m, 2H), 2.5 (s, 3H), 2.28 (m, 1H), 2.0 (m, 1H).

MS: m/e 451.96

Analysis: $C_{24}H_{22}ClN_3O_4$, C, 63.97 (63.79); H, 5.10 (4.91); N, 8.96 (9.30); Cl, 7.99 (7.85).

EXAMPLE 102

(+/−)-trans-2-[2-Chloro-phenyl-8-(2-mercaptomethyl-1-methyl-pyrrolidin-3-yl)]-5,7-dimethoxy-chromen-4-one. (Compound No. 114).

Compound (106) (1.0 g, 2.3 mmol) in CHCl₃ (20 mL) was treated with triethylamine (0.3 g, 2.8 mmol) and subsequently with methane sulfonyl chloride (0.319 g, 2.8 mmol) as described in example 98. The sulfonyl ester obtained was reacted with thiourea (0.7 g, 9.2 mmol) to get the title compound (114).

Yield: 0.6 g, (58.5%)

¹HNMR (CDCl₃): δ 7.6-7.4 (m, 4H), 6.4 (d, 2H), 4.6-4.3 (m, 4H), 4.0 (two singlets 6H), 3.3 (m, 1H), 3.1 (m, 1H), 2.8-2.6 (m, 2H), 2.3 (s, 3H), 2.0 (m, 2H).

MS: m/e 444 (M−1).

EXAMPLE 103

(+/−)-trans-2-(2-Chloro-phenyl)-5,7-dihydroxy-8-(2-mercaptomethyl-1-methyl-pyrrolidin-3-yl)-chromen-4-one. (Compound No. 115)

Compound (114) (0.6 g, 1.3 mmol) was demethylated using pyridine hydrochloride (6.0 g, 52.0 mmol) as described in example 9 to obtain the title compound (115).

Yield: 0.15 g (28%)

mp: 205-206° C.

IR cm⁻¹: 3400, 1650.

¹HNMR (CDCl₃): δ 12.7 (s, 1H), 7.6 (m, 1H), 7.5 (m, 2H), 7.35 (m, 1H), 6.6 (s, 1H), 6.5 (s, 1H), 4.2 (m, 2H), 3.7 (t, 1H), 3.6 (t, 1H), 3.4 (d, 1H), 3.3 (m, 1H), 3.1 (m, 1H), 2.9 (m, 1H), 2.5 (s, 3H), 2.3 (m, 2H).

MS: m/e 418.05 (M+1)

Analysis: $C_{21}H_{20}ClN_2O_4S \cdot \frac{1}{2}H_2O$, C, 59.43 (59.08); H, 5.58 (4.95); N, 3.7 (3.28).

EXAMPLE 104

1-Benzyl-1-methyl-4-oxo-piperidinium bromide (Compound No. 116)

To a solution of 1-methyl-4-piperidinone (15 g, 132.6 mmol) in dry acetone (100 mL) was added 1-bromomethyl-benzene (24.9 g, 145 mmol) dropwise. It was stirred for 3 h. The title compound (116) separated which was filtered, washed with dry acetone and dried.

Yield: 35 g (93%)

EXAMPLE 105

1-(4-Methoxyphenyl)-4-piperidone (Compound No. 117)

Anhy. $K_2CO_3$ was added to a solution of 4-methoxyaniline (1.0 g, 8.1 mmol) in ethanol (10 mL) followed by a dropwise addition of a solution of compound (116) (2.77 g, 9.8 mmol) in water (3.0 mL). The reaction mixture was heated at 100° C. for 1 h. It was allowed to cool to room temperature, poured into ice water (100 mL) and extracted using EtOAc (50 mL×3). The organic extract was washed with water, dried (anhy.) and concentrated to get the title compound (117).

Yield: 1.58 g (79%)

¹HNMR (CDCl₃): δ 6.95 (d, 2H), 6.85 (d, 2H), 3.8 (s, 3H), 3.45 (t, 4H), 2.6 (t, 4H).

MS: m/e 205 (M⁺).

EXAMPLE 106

1-(4-Methoxy-phenyl)-4-(2,4,6-trimethoxy-phenyl)-1,2,3,6-tetrahydro-pyridine (Compound No. 118)

Compound (117) (19.0 g, 92 mmol) was added to a solution of 1,3,5-trimethoxy benzene (21.8 g, 130 mmol) in glacial acetic acid (50 mL) at room temperature. HCl gas was bubbled through the reaction mixture for 1 h, slowly raising the temperature up to 90° C. Acetic acid was removed under reduced pressure and the semisolid residue was poured over crushed ice (300 g). The resulting solution was made basic using an aqueous 50% NaOH solution. The precipitated solid was filtered, washed with water and dried. The solid was added slowly to boiling methanol, stirred for fifteen minutes and filtered to remove traces of trimethoxy benzene and the filtrate was concentrated to get the title compound (118)

Yield: 30 g (91%)

¹HNMR: (DMSO d₆): δ 6.97 (d, 2H), 6.87 (d, 2H), 6.15 (s, 2H), 5.6 (s, 1H), 3.85 (s, 3H), 3.80 (s, 9H), 3.4 (t, 2H), 2.45 (bs, 2H).

MS: m/e 355 (M−1).

EXAMPLE 107

1-(4-Methoxy-phenyl)-4-(2,4,6-trimethoxy-phenyl)-piperidin-3-ol.

(Compound No. 119)

Compound (118) (15 g, 42 mmol) was subjected to hydroboration using NaBH₄ (2.7 g, 71.4 mmol) and BF₃ Et₂O (12.6 g, 88.8 mmol) in THF (50 mL). Excess diborane was destroyed by the addition of water. Concentrated HCl (15 mL) was added and the reaction mixture was stirred at 50-55° C. for 1 h. It was cooled to room temp. The resulting mixture, was made basic (pH 12-14) using an aqueous 50% NaOH solution. 30% H₂O₂ (9 mL) was added and the reaction mixture was stirred at 50-55° C. for 1 h. The reaction mixture was processed as described in example 2 to obtain the title compound (119).

Yield: 9.5 g (60.2%)

¹HNMR (CDCl₃): δ 7.0 (d, 2H), 6.9 (d, 2H), 6.2 (s, 2H), 4.5 (m, 1H), 3.85 (3s, 9H), 3.8 (s, 3H), 3.65 (d, 1H), 3.2 (m, 1H), 2.7 (m, 1H), 2.6 (m 2H), 1.6 (m, 2H).

MS: m/e 374 (M+1).

EXAMPLE 108

(+/−)-trans-Acetic acid 4-(3-acetyl-2-hydroxy-4,6-dimethoxy-phenyl)-1-(4-methoxy-phenyl)-piperidin-3-yl ester (Compound No. 120)

Compound (119) (0.5 g, 1.3 mmol) was subjected to acylation using BF₃ Et₂O (0.82 mL, 0.95 g, 6.7 mmol) and acetic anhydride (0.68 g, 6.7 mmol) according to the procedure described in the example 6 to obtain the title compound (120).

Yield: 0.15 g (25%).

¹HNMR (CDCl₃): δ 7.1 (d, 2H), 6.9 (d, 2H), 5.95 (s, 1H), 5.8 (m, 1H), 3.95 (two singlets, 6H), 3.8 (m, 2H), 3.0-2.8 (m, 2H), 2.7 (s, 3H), 1.75 (m, 2H), 1.9 (s, 3H).

MS: m/e 443 (M−1).

EXAMPLE 109

(+/−)-trans-1-{2-Hydroxy-3-[3-hydroxy-1-(4-methoxy-phenyl)-piperidin-4-yl]-4,6-dimethoxy-phenyl}-ethanone. (Compound No. 121)

Compound (120) (0.25 g, 0.5 mmol) was subjected to hydrolysis for 30 minutes using aqueous NaOH (2.5%, 2.0 mL) as given in example 7, to obtain the title compound (121).

Yield: 0.2 g (88%).

¹HNMR (CDCl₃): δ 6.95 (d, 2H), 6.8 (d, 2H), 6.0 (1H), 4.5 (m, 1H), 3.95 (two singlets, 6H), 3.85 (m, 1H), 3.8 (s, 3H), 3.55 (d, 1H), 3.2 (m, 1H), 2.7 (m, 1H), 2.65 (s, 3H), 2.55 (m, 1H), 1.7 (m, 2H).

MS: m/e 401 (M−1).

EXAMPLE 110

(+/−)-trans-2-(2-Chloro-phenyl)-8-[3-hydroxy(4-methoxy-phenyl)-piperidin-4-yl-5,7-dimethoxy-chromen-4-one (Compound No. 122)

Compound (121) (2.0 g, 5.0 mmol) in dry DMF (25 mL) was reacted with methyl 2-chlorobenzoate (2.55 g, 15 mmol) in the presence of NaH (50%, 1.19 g, 25 mmol) as described in example 8, to obtain the title compound (122).

Yield: 1.8 g (69%).

¹HNMR (CDCl₃): δ 7.8 (m, 4H), 7.6 (d, 1H), 7.45 (m, 1H), 6.9 (m, 1H), 6.8 (d, 1H), 6.46 (s 1H), 6.4 (s, 1H), 4.6 (m, 1H), 4.0 (s, 6H), 3.85 (m, 1H), 3.75 (s, 3H), 3.55 (m, 1H), 3.4 (m, 1H), 2.75 (m, 1H), 2.55 (m, 1H), 1.75 (m, 2H).

MS: m/e 521 (M−1).

EXAMPLE 111

(+/−)-trans-Acetic acid 3-[2-(2-chloro-phenyl)-5,7-dimethoxy-4-oxo-4H-chromen-8-yl]-1-(4-methoxy-phenyl)-pyrrolidin-2-ylmethyl ester (Compound No. 123)

Compound (122) (1.7 g, 3.2 mmol) was subjected to ring contraction as described in example 3 using methane sulfonyl chloride (0.448 g, 0.3 mL, 3.9 mmol), Et₃N (0.66 g, 0.95 mL, 6.5 mmol) and anhy. sodium acetate (1.06 g, 13 mmol) to furnish the title compound (123).

Yield: 1.2 g (66%).

1HNMR (CDCl₃): δ 7.5 (d, 1H), 7.4 (d, 1H), 7.3 (t, 1H), 7.1 (t, 1H), 6.8 (d, 2H), 6.65 (d, 2H), 6.55 (s, 1H), 6.35 (s, 1H), 4.35 (m, 1H), 4.28 (m, 1H), 4.2 (m, 1H), 4.12 (s, 3H), 3.95 (m, 1H), 3.78 (s, 3H), 3.7 (s, 3H), 3.5 (m, 1H), 3.35 (m, 1H), 2.25 (m, 2H), 1.75 (s, 3H).

EXAMPLE 112

(+/−)-trans-2-(2-Chloro-phenyl)-8-[2-hydroxymethyl-1-(4-methoxy-phenyl)-pyrrolidin-3-yl]-5,7-dimethoxy-chromen-4-one (Compound No. 124)

Compound (123) (1.1 g, 1.94 mmol) was hydrolyzed for 1 h using 2% methanolic NaOH (10 mL) at 50° C., to get the title compound (124).

The workup process is as described in example 4.

Yield: 0.7 g (69%).

¹HNMR (CDCl₃): δ 7.6 (m, 1H), 7.4 (d, 1H), 7.3 (m, 1H), 7.05 (m, 1H), 6.8 (d, 2H), 6.65 (m, 2H), 6.6 (s, 1H), 6.4 (s, 1H), 4.4 (m, 1H), 4.0 (s, 6H), 4.15 (m, 1H), 3.85 (m, 1H), 3.75 (s, 3H), 3.65 (m, 1H), 3.5 (m, 1H), 3.4 (t, 1H), 2.4-2.1 (m, 2H).

MS: m/e 522.53 (M+1).

EXAMPLE 113

(+/−)-trans-2-(2-Chloro-phenyl)-5,7-dihydroxy-8-[2-hydroxymethyl-1-(4-methoxy-phenyl)-pyrrolidin-3-yl]-chromen-4-one (Compound No. 125)

Compound (124) (0.7 g, 1.3 mmol) was demethylated using pyridine hydrocloride (10.5 g, 9.0 mmol) as described in example 9 to obtain the title compound (125).

Yield: 0.03 g (5%).

mp: 212-213° C.

¹HNMR (CDCl₃): δ 7.6 (m, 1H), 7.45-7.25 (m, 3H), 6.77 (d, 2H), 6.7 (d, 2H), 6.42 (s, 1H), 6.35 (s, 1H), 4.6 (m, 1H), 3.65 (d, 1H), 3.45 (d, 1H), 3.2 (m, 1H), 2.6-2.3 (m, 2H), 1.65 (d, 1H), 0.8 (m, 1H).
MS: m/e 480.17 (M+1).

EXAMPLE 114

(+/−)-trans-Acetic acid 4-[2-(2-chloro-phenyl)-5,7-dimethoxy-4-oxo-4H-chromen-8-yl]-1-methyl-piperidin-3-yl ester (Compound No. 126)

To a solution of compound (106) (3.35 g, 7.79 mmol) in dry CHCl₃ (25 mL) was added acetic anhydride (1.76 g, 17.43 mmol) at room temperature with stirring, followed by the addition of dimethylamino pyridine (0.033 g 1% w/w). The mixture was stirred for 0.5 h. It was poured into ice water (50 mL), basified using a saturated aqueous Na₂CO₃ solution and extracted using CHCl₃ (100 mL×3). The organic extract was washed with water, dried (anhy. Na₂SO₄) and concentrated. The oil obtained was purified using a silica gel column and 0.1% MeOH+1% ammonia in CHCl₃ as eluant to get the title compound (126).
Yield: 3.33 g (89.7%)
¹HNMR (CDCl₃): δ 7.68 (dd, 1H), 7.6 (dd, 1H), 7.42 (t, 2H), 6.5 (s, 1H), 6.38 (s, 1H), 5.5 (m, 1H), 4.0 (s, 6H), 3.5 (m, 1H), 3.22 (d, 1H), 2.95 (m, 1H), 2.55 (m, 1H), 2.4 (s, 3H), 2.08 (m, 2H), 1.7 (s, 3H).
MS: m/e 472 (M+1), 412 (M−60).

EXAMPLE 115

(+/−)-trans-Acetic acid 4-[2-(2-chloro-phenyl)-5,7-dimethoxy-4-oxo-4H-chromen-8-yl]-1-cyano-piperidin-3-yl ester (Compound No. 127)

To compound (126) (2.9 g, 0.615 mmol) in dry CHCl₃ (40 mL) at 0° C. was added cyanogen bromide (2.1 g, 19.8 mmol). The reaction mixture was stirred at room temperature for 8 h. It was poured into water (100 mL) and extracted with CHCl₃ (100 mL×3). The organic extract was washed with water, dried (anhy. Na₂SO₄) and concentrated. The solid residue obtained was purified using a silica gel column and 2% IPA+1% liquor ammonia in CHCl₃ as eluant to obtain the title compound (127).
Yield: 2.218 g (75%)
IR cm⁻¹: 3400, 2220, 1740, 1640
¹HNMR (CDCl₃): δ 7.52 (m, 4H), 6.45 (two doublets, 2H), 5.68 (m, 1H), 4.02 (s, 7H), 3.6 (m, 3H), 3.1 (t, 1H), 2.9 (t, 1H), 2.58 (m, 1H), 1.7 (s, 3H).
MS: m/e 483.3 (M+1), 423 (M−60).

EXAMPLE 116

(+/−)-trans-2-(2-Chloro-phenyl)-8-(3-hydroxy-piperidin-4-yl)-5,7-dimethoxy-chromen-4-one (Compound No. 128)

Compound (127) (2 g, 4.14 mmol) was stirred with H₃PO₄ (6N, 50 mL) at 100° C. for 1.5 h. The solution was cooled to room temperature and poured onto ice (~100 g). It was made basic using a saturated aqueous Na₂CO₃ solution and extracted with EtOAc (3×150 mL). The organic extract was washed with water, dried (anhy.), and concentrated. The crude obtained was purified using a silica gel column and 10% methanol+1% ammonia in CHCl₃ as eluant to furnish the title compound (128).
Yield: 0.87 g (50.5%)
¹HNMR (CDCl₃+DMSO d₆): δ 7.5 (dd, 1H), 7.25 (m, 3H), 6.28 (two singlets, 2H), 4.15 (s, 1H), 3.8 (two singlets, 6H), 3.2 (m, 3H), 2.9 (m, 1H), 2.35 (m, 2H), 2.05 (m, 1H).
MS: m/e 416 (M+1), 397 (M−18), 380 (M−36).

EXAMPLE 117

(+/−)-trans-2-(2-Chloro-phenyl)-8-(3-hydroxy-1-propyl-piperidin-4-yl) 5,7-dimethoxy-chromen-4-one. (Compound No. 129)

A mixture of compound (128) (0.871 g, 2.09 mmol), n-propyl bromide (0.335 g, 2.72 mmol) and anhydrous K₂CO₃ (1.15 g, 8.33 mmol) in dry DMF (20 mL) was stirred at room temperature for 2 h. The reaction mixture was treated with water and extracted with EtOAc (2×100 mL). The organic extract was washed with water, dried (anhy. Na₂SO₄) and concentrated. The crude obtained was purified on a silica gel column using a mixture of 1% MeOH+1% ammonia in CHCl₃ as eluant to get the title compound (129).
Yield: 0.53 g (57.4%)
¹HNMR (CDCl₃): δ 7.62 (d, 1H), 7.45 (m, 3H), 6.42 (two doublets 2H), 4.65 (m, 1H), 3.98 (two singlets, 6H), 3.35 (m, 2H), 3.05 (s, 1H), 2.5 (s, 3H), 2.1 (m, 3H), 1.62 (d, 2H), 0.92 (t, 3H).
MS: m/e 458.4 (M+1), 440 (M−18), 428 (M−29).

EXAMPLE 118

(+/−)-trans-Acetic acid 3-[2-(2-chloro-phenyl)-5,7-dimethoxy-4-oxo-4H-chromen-8-yl]-1-propyl-pyrrolidin-2-ylmethyl ester (Compound No. 131)

Methane sulfonyl chloride (0.178 g, 1.55 mmol) was added to a mixture of compound (129) (0.55 g, 1.2 mmol) and triethylamine (1 mL) in CHCl₃ (10 mL), with stirring, at 0° C. The reaction mixture was stirred for 1 h. It was poured carefully into a cold saturated aqueous solution of Na₂CO₃. The organic layer was separated and the aqueous layer was extracted using CHCl₃ (2×50 mL). The combined organic extracts were washed with water, dried (anhy. Na₂SO₄) and concentrated to obtain compound (+/−)-trans-Methanesulfonic acid 4-[2-(2-chloro-phenyl)-5,7-dimethoxy-4-oxo-4H-chromen-8-yl]-1-propyl-piperidin-3-yl ester (130). It was dissolved in dry IPA at 80-90° C. and anhy. NaOAc (0.49 g, 5.98 mmol) was added. It was stirred for 2.5 h at 80-90° C. The mixture was allowed to attain room temperature and poured into ice water (100 mL). It was basified using a sat. aq. Na₂CO₃ solution. It was extracted using EtOAc (2×100 mL). The organic extract was washed with water, dried (anhy. Na₂SO₄) and concentrated. The oily residue was purified using a silica gel column and 1% IPA+1% ammonia in CHCl₃ as eluant to obtain the title compound (131).
Yield: 0.2 g (33.8%)
¹HNMR (CDCl₃): δ 7.5 (m, 4H), 6.45 (s, 2H), 4.02 (two singlets, 8H), 3.1 (m, 2H), 2.25 (m, 4H), 1.65 (m, 7H), 0.9 (t, 3H).
MS: m/e 500.4 (M+1), 440.0 (M−60).

EXAMPLE 119

(+/−)-trans-2-(2-Chloro-phenyl)-8-(2-hydroxymethyl-1-propyl-pyrrolidin-3-yl)-5,7-dimethoxy-chromen-4-one. (Compound No. 132)

Compound (131) (0.2 g, 0.04 mmol) was subjected to hydrolysis using a 1% methanolic NaOH solution (10 mL) according to the procedure in example 4 to get the title compound (132).

Yield: 0.17 g (92.8%)

$^1$HNMR (CDCl$_3$): δ 7.7 (dd, 1H), 7.48 (m, 3H), 6.48 (two singlets, 2H), 4.2 (m, 1H), 4.0 (two singlets, 6H), 3.66 (dd, 1H), 3.4 (m, 2H), 3.1 (bs, 1H), 2.8 (m, 1H), 2.62 (m, 1H), 2.15 (m, 3H), 1.6 (m, 2H), 0.9 (t, 3H).

MS: m/e 458.4 (M+1), 426.4 (M−32).

EXAMPLE 120

(+/−)-trans-2-(2-Chloro-phenyl)-5,7-dihydroxy-8-(2-hydroxymethyl-1-propyl-pyrrolidin-3-yl)-chromen-4-one. (Compound No. 133)

Following the procedure in example 9, compound (132) (0.155 g, 0.33 mmol) was demethylated using pyridine hydrochloride (2.0 g, 17.3 mmol) to obtain the title compound (133).

Yield: 0.046 g (31.6%)

mp: 94-96° C.

IR cm$^{-1}$: 3000, 1650

$^1$HNMR (CDCl$_3$): δ 7.61 (dd, 1H), 7.45 (m, 3H), 6.45 (s, 3H), 6.3 (s, 1H), 4.15 (m, 1H), 3.85 (m, 2H), 3.4 (m, 2H), 2.9 (m, 3H), 2.45 (m, 1H), 2.08 (m, 1H), 1.68 (m, 2H), 0.95 (t, 3H).

MS: m/e 430.5 (M+1), 412.4 (M−18).

EXAMPLE 121

(+)-trans-2-(2-Chloro-3-fluoro-phenyl)-8-(2-hydroxymethyl-1-methyl-pyrrolidin-3-yl)-5,7-dimethoxy-chromen-4-one (Compound No. 134)

Compound (6) (0.9 g, 2.9 mmol) in dry DMF (10 mL) was reacted with methyl 2-Chloro-3-fluorobenzoate (0.656 g, 3.48 mmol) in the presence of 50% NaH (0.696 g, 14.5 mmol) as detailed in example 8, to obtain the title compound (134).

Yield: 29%.

$^1$HNMR (CDCl$_3$): δ 7.58 (d, 1H), 7.35 (m, 2H), 6.55 (s, 1H), 6.45 (s, 1H), 4.2 (m, 1H), 4.08 (s, 3H), 3.98 (s, 3H), 3.68 (dd, 1H), 3.4 (m, 1H), 3.2 (bt, 1H), 2.75 (bd, 1H), 2.6 (m, 1H), 2.35 (s, 3H), 2.05 (m, 2H).

MS: m/e 448 (M+1), 416 (M−32).

EXAMPLE 122

(+)-trans-2-(2-Chloro-3-fluoro-phenyl)-5,7-dihydroxy-8-(2-hydroxymethyl-1-methyl-pyrrolidin-3-yl)-chromen-4-one (Compound No. 135)

Compound (134) (0.31 g, 0.74 mmol) was subjected to demethylation using pyridine hydrochloride. (3.1 g, 26.84 mmol) as described in example 9, to obtain the title compound (135).

Yield: 41.8% mp: 221-223° C.

IR cm$^{-1}$: 3400, 1650, 1200

$^1$HNMR (DMSO d$_6$): δ 12.3 (s, 1H, exchangeable), 7.18 (m, 3H), 6.18 (s, 1H), 5.98 (s, 1H), 3.8 (m, 1H), 3.5 (m, 2H), 2.96 (m, 2H), 2.75 (m, 1H), 2.42 (s, 3H), 2.1 (m, 1H), 1.7 (m, 1H).

MS: m/e 420 (M+1), 387 (M−32).

Analysis: C$_{21}$H$_{19}$FNO$_5$, C, 58.77 (58.87); H, 4.61 (4.67); N, 3.27 (3.27), Cl, 7.86 (7.8).

EXAMPLE 123

(+)-trans-2-(2-Bromo-3-fluoro-phenyl)-8-(2-hydroxymethyl-1-methyl-pyrrolidin-3-yl)-5,7-dimethoxy-chromen-4-one (Compound No. 136)

Compound (6) (1.1 g, 3.6 mmol) in dry DMF (10 mL) was reacted with methyl 2-bromo-3-fluorobenzoate (2 g, 8.58 mmol) in the presence of 50% NaH (0.854 g, 17.79 mmol) as detailed in example 8, to obtain the title compound (136).

Yield: 28.5%.

$^1$HNMR (CDCl$_3$): δ 7.75 (m, 1H), 7.4 (m, 2H), 6.46 (s, 1H), 6.42 (s, 1H), 4.15 (m, 1H), 4.02 (s, 3H), 3.98 (s, 3H), 3.65 (m, 1H), 3.35 (m, 1H), 3.1 (m, 1H), 2.7 (m, 1H), 2.45 (m, 1H), 2.28 (s, 3H), 2.02 (m, 2H).

MS: m/e 491.8 (M+1), 462 (M−32).

EXAMPLE 124

(+)-trans-2-(2-Bromo-3-fluoro-phenyl)-5,7-dihydroxy-8-(2-hydroxymethyl-1-methylpyrrolidin-3-yl)-chromen-4-one (Compound No. 137)

Compound (136) (0.45 g, 0.914 mmol) was subjected to demethylation using pyridine hydrochloride (4.5 g, 38.96 mmol) as described in example 9, to obtain the title compound (137).

Yield: 49.5%.

mp: 237-239° C.

IR cm$^{-1}$: 3400, 1650

$^1$HNMR (CDCl$_3$+TFA d): δ 12.5 (s, 1H, exchangeable), 7.6 (m, 1H), 7.4 (m, 2H), 6.85 (s, 1H), 6.65 (s, 1H), 4.06 (m, 5H), 3.5 (m, 1H), 3.1 (s, 3H), 2.5 (m, 1H), 2.4 (m, 1H).

MS: m/e 465 (M+1), 433 (M−31).

Analysis: C$_{21}$H$_{19}$BrFNO$_5$, C, 53.47 (53.29); H, 3.53 (4.2); N, 2.51 (2.95), Br, 16.45 (16.88)

EXAMPLE 125

(+)-trans-2-(2-Bromo-5-fluoro-phenyl)-8-(2-hydroxymethyl-1-methyl-pyrrolidin-3-yl)-5,7-dimethoxy-chromen-4-one (Compound No. 138)

Compound (6) (6 g, 19.42 mmol) in dry DMF (60 mL) was reacted with methyl 2-bromo-5-fluorobenzoate (6.7 g, 28.75 mmol) in the presence of 50% NaH (3.88 g, 80.8 mmol) as detailed in example 8, to obtain the title compound (138).

Yield: 47.1%.

$^1$HNMR (CDCl$_3$): δ 7.68 (m, 1H), 7.45 (m, 1H), 7.1 (m, 1H), 6.48 (s, 1H), 6.4 (s, 1H), 4.15 (m, 1H), 4.02 (s, 3H), 3.92 (s, 3H), 3.64 (m, 1H), 3.35 (d, 1H), 3.1 (m, 1H), 2.65 (m, 1H), 2.45 (m, 1H), 2.3 (s, 3H), 2.0 (m, 2H).

MS: m/e 493 (M+1), 461 (M−32)

EXAMPLE 126

(+)-trans-2-(2-Bromo-5-fluoro-phenyl)-5,7-dihydroxy-8-(2-hydroxymethyl-1-methyl-pyrrolidin-3-yl)-chromen-4-one (Compound No. 139)

Compound (138) (3.9 g, 7.92 mmol) was subjected to demethylation using pyridine hydrochloride (39 g, 337.6 mmol) as described in example 9, to obtain the title compound (139).

Yield: 48.9%
mp: 145-147° C.
IR cm$^{-1}$: 3450, 640
1HNMR (CDCl$_3$+TFA d): δ 12.4 (s, 1H, exchangeable), 7.55 (m, 1H), 7.28 (m, 1H), 7.0 (m, 1H), 6.31 (s, 1H), 6.28 (s, 1H), 3.98 (m, 1H), 3.68 (m, 2H), 3.5 (m, 2H), 3.15 (m, 1H), 2.8 (s, 3H), 2.3 (m, 1H), 2.08 (m, 1H).
MS: m/e 465 (M+1).
Analysis: Methanesulfonate salt C$_{22}$H$_{23}$BrFSO$_8$.H$_2$O, C, 46.08 (45.68); H, 4.61 (4.35); N, 2.63 (2.42); Br, 14.73 (13.81); S, 4.99 (5.54).

EXAMPLE 127

(+)-trans-2-(2-Chloro-5-iodo-phenyl)-8-(2-hydroxymethyl-1-methyl-pyrrolidin-3-yl)-5,7-dimethoxy-chromen-4-one (Compound No. 140)

Compound (6) (0.6 g, 1.94 mmol) in dry DMF (10 mL) was reacted with methyl 2-Chloro-5-iodobenzoate (1.269, 4.24 mmol) in the presence of 50% NaH (0.466 g, 9.7 mmol) as detailed in example 8, to obtain the title compound (140).
Yield: 27.8%.
$^1$HNMR (CDCl$_3$): δ 8.08 (d, 1H), 7.75 (m, 2H), 6.58 (s, 1H), 6.42 (s, 1H), 4.2 (m, 1H), 4.02 (s, 3H), 3.98 (s, 3H), 3.7 (m, 1H), 3.38 (m, 1H), 3.2 (m, 1H), 2.7 (m, 1H), 2.55 (m, 1H), 2.32 (s, 3H), 2.05 (m, 1H).
MS: m/e 556 (M+1), 524 (M–32)

EXAMPLE 128

(+)-trans-2-(2-Chloro-5-iodo-phenyl)-5,7-dihydroxy-8-(2-hydroxymethyl-1-methyl-pyrrolidin-3-yl)-chromen-4-one (Compound No. 141)

Compound (140) (0.1 g, 0.18 mmol) was subjected to demethylation using pyridine hydrochloride (1 g, 8.65 mmol) as described in example 9, to obtain the title compound (141).
Yield: 52.6%
IR cm$^{-1}$: 3450, 640
$^1$HNMR (CDCl$_3$): δ 12.4 (s, 1H, exchangeable), 7.9 (s, 1H), 7.8 (d, 1H), 7.1 (d, 1H), 6.2 (s, 1H), 6.1 (s, 1H), 3.98 (m, 1H), 3.8 (m, 2H), 3.1 (m, 2H), 2.7 (m, 1H), 2.5 (s, 3H), 2.2 (m, 1H), 1.9 (m, 1H).
MS: m/e 528 (M+1).

EXAMPLE 129

(+)-trans-2-(2-Bromo-5-chloro-phenyl)-8-(2-hydroxymethyl-1-methyl-pyrrolidin-3-yl)-5,7-dimethoxy-chromen-4-one (Compound No. 142)

Compound (6) (1 g, 3.23 mmol) in dry DMF (10 mL) was reacted with methyl 2-Bromo-5-chlorobenzoate (1.59 g, 6.25 mmol) in the presence of 50% NaH (0.768 g, 16 mmol) as detailed in example 8, to obtain the title compound (142).
Yield: 8%
$^1$HNMR (CDCl$_3$): δ 7.7 (m, 1H), 7.4 (m, 1H), 6.96 (d, 1H), 6.48 (s, 2H), 4.2 (m, 1H), 3.98 (s, 3H), 3.95 (s, 3H), 3.7 (m, 1H), 3.4 (m, 1H), 3.2 (m, 1H), 2.75 (m, 1H), 2.35 (s, 3H), 2.02 (m, 2H).
MS: m/e 510 (M+1), 478 (M–32).

EXAMPLE 130

(+)-trans-2-(2-Bromo-5-chloro-phenyl)-5,7-dihydroxy-8-(2-hydroxymethyl-1-methyl-pyrrolidin-3-yl)-chromen-4-one (Compound No. 143)

Compound (142) (0.11 g, 0.216 mmol) was subjected to demethylation using pyridine hydrochloride (1.1 g, 9.9 mmol) as described in example 9, to obtain the title compound (143).
Yield: 48%
mp: 233-235° C.
IR cm$^{-1}$: 3400, 1640
$^1$HNMR (CDCl$_3$ DMSO d$_6$): δ 12.4 (s, 1H, exchangeable), 7.48 (d, 1H), 7.3 (s, 1H), 7.12 (d, 1H), 6.12 (s, 1H), 5.98 (s, 1H), 3.85 (m, 1H), 3.5 (m, 2H), 2.98 (m, 1H), 2.75 (m, 1H), 2.45 (s, 3H), 2.31 (m, 1H), 2.15 (m, 1H), 1.7 (m, 1H).
MS: m/e 481 (M+1), 449 (M–31).
Analysis: C$_{21}$H$_{19}$BrClNO$_5$, C, 51.27 (51.53); H, 4.26 (4.11); N, 3.07 (2.86).

EXAMPLE 131

(+/–)-trans-3-[2-(2-Chloro-phenyl)-5,7-dimethoxy-4-oxo-4H-chromen-8-yl]-1-methyl-pyrrolidine-2-carbaldehyde (Compound No. 144)

Dimethyl sulfoxide (1.8 ml, 25.3 mmol) in methylene chloride (20 ml) was added to a stirred solution of oxalyl chloride (840 .mu.l, 9.84 mmol) in dry methylene chloride (120 ml) drop wise at –50° C. The reaction mixture was stirred for half an hour. Compound (8) (2.0 g, 4.65 mmol) in methylene chloride (20 ml) was added dropwise to the reaction mixture. The resulting mixture was further stirred for one and half hour. Triethyl amine was then added dropwise at –50° C. Reaction mixture was then warmed to room temperature and basified with NaHCO$_3$ solution (10 ml). Reaction mixture was extracted with methylene chloride, organic layer was washed with water, brine and dried (anhydrous Na$_2$SO$_4$) to afford the title compound (144)
Yield: 0.950 g (47.7%)
$^1$HNMR (CDCl$_3$): δ 7.4-7.6 (m, 4H), 6.5 (s, 1H), 6.4 (s, 1H), 4.2 (m, 1H), 3.95 (s, 3H), 3.85 (s, 3H), 3.18 (m, 1H), 3.1 (m, 1H), 2.45 (m, 1H), 2.3 (s, 3H), 2.05 (m, 2H)
MS: m/e (M+1) 428, (M–30) 398.

EXAMPLE 132

(+/–)-trans-3-[2-(2-Chloro-phenyl)-5,7-dimethoxy-4-oxo-4H-chromen-8-yl]-1-methyl-1-oxy-pyrrolidine-2-carboxylic acid (Compound No. 145)

55% m-chloro perbenzoic acid (2.193 g, 0.7 mmol) in tetrahydrofuran (20 ml) was added dropwise to precooled (0° C.) solution of compound (144) (1 g, 2.33 mmol) in THF (50 ml). Reaction mixture was brought to room temperature in 2 hours and concentrated to obtain a solid. Saturated NaHCO$_3$ solution was added to the solid, stirred for 5 min, filtered, washed with water and dried in vacuum to afford the title compound (145)
Yield: 0.7 g (65.3%)
$^1$HNMR (CDCl$_3$+DMSO d$_6$): δ 7.32 (dd, 1H), 7.05-7.17 (m, 3H), 6.15 (s, 1H), 6.05 (s, 1H), 4.2 (m, 1H), 3.9 (d, 1H), 3.65 (s, 3H), 3.6 (s, 3H), 3.3 (m, 2H), 3.05 (br s, 3H), 2.2 (m, 2H).

EXAMPLE 133

(+/−)-trans-3-[2-(2-Chloro-phenyl)-5,7-dimethoxy-4-oxo-4H-chromen-8-yl]-1-methyl-pyrrolidine-2-carboxylic acid (Compound No. 146)

10% Pd/C (30 mg) was added to a solution of compound (145) (400 mg, 0.869 mmol) in 50 ml methanol. The reaction mixture was hydrogenated at 10 psi for 2 h.

Reaction mass was then filtered (celite) and purified using HP-20 column and water and methanol in the ratio 75:25 as an eluant to obtain the title compound (146)
Yield: 0.230 g (59.6%)
mp: 165-167° C.
$^1$HNMR (D$_2$O): δ 7.75 (dd, 1H), 7.4-7.6 (m, 3H), 6.25 (s, 1H), 6.5 (s, 1H), 4.12 (m, 1H), 3.82 (s, 3H), 3.9 (s, 3H), 3.52 (m, 2H), 3.15 (m, 1H), 2.78 (s, 3H), 2.1 (m, 1H)
MS: m/e 444 (M+1), 410 (M−35)

EXAMPLE 134

(+/−)-trans-3-[2-(2-Chloro-phenyl)-5,7-dihydroxy-4-oxo-4H-chromen-8-yl]-1-methyl-pyrrolidine-2-carboxylic acid (Compound No. 147)

Compound (146) (0.25 g, 0.563 mmol) was treated with pyridine hydrochloride (2.5 g) at 180° C. Reaction mixture was further heated at 180° C. for 2 h. 1 ml water was added after completion of the reaction and reaction mixture was purified on HP-20 column using as eluant water, followed by methanol and water in the ratio 70:30 to obtain the title compound (147)
Yield: 0.102 g (43.6%)
mp: 295-297° C.
$^1$HNMR (CDCl3+DMSO d$_6$+TFA d): δ 7.52 (dd, 1H), 7.0-7.4 (m, 3H), 6.05 (s, 1H), 6.1 (s, 1H), 4.1 (m, 1H), 3.9 (m, 1H), 3.46 (m, 1H), 3.1 (m, 1H), 2.65 (s, 3H), 2.05 (m, 2H)
MS: m/e 416 (M+1), 382 (M−35).
Analysis: C$_{21}$H$_{18}$ClNO$_6$.½H$_2$OC, 59.22 (59.37); H, 4.20 (4.50); N, 2.85 (3.29); Cl, 8.14 (8.34)

EXAMPLE 135

(+/−)-trans-2-(2-Chloro-phenyl)-5,7-dihydroxy-8-(2-hydroxymethyl-1-methyl-1-oxy-pyrrolidin-3-yl)chromen-4-one (Compound No. 148)

Compound (147) (0.1 g, 0.249 mmol) in methylene chloride was added to m-chloroperbenzoic acid (0.078 g, 0.250 mmol). Methanol (30 ml) was added to dissolve the reaction mixture and it was stirred for 30 min. It was concentrated to obtain a solid mixture, basified with saturated NaHCO$_3$ solution and stirred further for 5 mins. Mixture was then filtered, washed with water and dried in vacuum to obtain the title compound (148)
Yield: 0.035 g (33.4%)
$^1$HNMR (CDCl$_3$+TFA d+DMSO d$_6$): δ 7.4-7.55 (m, 4H), 6.4 (s, 1H), 6.47 (s, 1H), 4.2 (m, 2H), 3.96 (m, 2H, 1H), 3.65 (s, 3H), 3.58 (m, 1H), 2.21 (m, 1H), 2.52 (m, 1H).
MS: m/e (M+1) 416

EXAMPLE 136

2-Bromo-4-nitro-aniline (Compound No. 149)

N-Bromosuccinimide (26 gm, 146 mmol) was added to a stirred solution of 4-nitro aniline (20 gm, 145 mmol) in 75 ml dry DMF in portions under stirring at temperature 25-30° C. Reaction mixture was stirred for 30 min. It was poured over crushed ice slowly under vigorous stirring, filtered and dried, to afford the title compound (149)
Yield: 30 gm (95%)
$^1$HNMR (CDCl$_3$): δ 8.4 (s, 1H), 8.1 (d, 1H), 6.75 (d, 1H), 4.85 (bs, 2H).
MS: m/e 218 (M+1).

EXAMPLE 137

2-Bromo-4-nitro-benzonitrile (Compound No. 150)

Compound (149) (20 g, 92.2 mmol) was dissolved in 10% aqueous H$_2$SO$_4$ (100 mL) and the solution was cooled to 0° C. A solution of NaNO$_2$ (7.64 g, 110 mmol) in water (20 mL) was added dropwise maintaining the temperature between 0-5° C. The mixture was stirred for 10 min., excess nitrous acid was neutralized using a saturated aqueous NaHCO$_3$ solution. The resulting mixture was then added to a precooled (0-5° C.) suspension of CuCN (9.46 g, 105 mmol and NaCN (5.20 g, 106 mmol) in water (200 mL). It was stirred for 10 min., then allowed to attain room temperature. It was stirred for 0.5 h and finally heated on a steam bath for 0.5 h. Excess saturated FeCl$_3$ solution was then added to the reaction mixture. It was extracted using EtOAc (200 mL×3). The organic extract was washed with water, dried (anhy. Na$_2$SO$_4$), concentrated and purified using a silica gel column and CHCl$_3$: petroleum ether (60-80° C.) (1:1) as eluant to obtain the title compound (150).
Yield: 3.6 gm (17%)
$^1$HNMR (CDCl$_3$): δ 8.58 (s, 1H), 8.3 (d, 1H), 7.9 (d, 1H).
MS: m/e 228 (M+1).
IR cm$^{-1}$: 3100, 2233, 1600, 1350.

EXAMPLE 138

2-Bromo-4-nitro-benzoic acid (Compound No. 151)

2-Bromo-4-nitro-benzonitrile (0.5 gm, 2.34 mmol) was hydrolysed using H$_2$SO$_4$ (2.2 ml) in 2.7 ml water at 80° C. for 8 hrs. After completion of reaction solution was poured over crushed ice, basified with sodium carbonate and extracted with ethyl acetate. Aqueous layer was separated, acidified with 1:1 HCl and extracted with ethyl acetate. Combined organic layer was then concentrated to obtained compound (151).
Yield: 300 mg (55.0%)
mp: 164-166° C.
$^1$HNMR (DMSO d$_6$): δ 8.4 (s, 1H), 8.1 (d, 1H), 7.85 (d, 1H), 5.95 (s, 1H).
MS: m/e EI 248 (M+1).
IR cm$^{-1}$: 3100, 1700, 1534, 1350.

EXAMPLE 139

(+)-trans-2-(2-Bromo-4-nitro-phenyl)-8-(2-hydroxymethyl-1-methylpyr-rolidin-3-yl)-5,7-dimethoxy-chromen-4-one (Compound No. 153)

2 Bromo-4-nitrobenzoic acid (3.70 gm, 15 mmol) was reacted with compound (6) (2.12 g, 6 mmol) in dry pyridine (25 mL) using POCl$_3$ (7 gm, 45.8 mmol) as described in Example 52 to obtain (+)-trans-2-Bromo-4 nitro-benzoic acid 2-(2-acetoxymethyl-1-methyl-pyrrolidin-3-yl)-6-acetyl-3,5-dimethoxy-phenyl ester (compound no. 152) (3.4 gm, 5.9 mmol) a viscous oil, which was converted to the title compound (53) in situ using NaH (50%, 2.8 g, 50 mmol) in dry 1,4-dioxane (100 mL) as described in Example 26.

Yield: 11%

IR cm$^{-1}$: 3400, 1660, 1525, 1350

1HNMR (CDCl$_3$): δ 8.6 (s, 1H), 8.32 (d, 1H), 7.95 (d, 1H), 6.6 (s, 1H), 6.44 (s, 1H), 4.2 (m, 1H), 4.02 (s, 3H), 3.98 (s, 3H), 3.65 (dd, 1H), 3.2 (m, 1H), 2.75 (d, 1H), 2.6 (d, 1H), 2.45 (s, 3H), 2.1 (m, 2H).

MS: m/e 521 (M+1), 489 (M−32).

EXAMPLE 140

(+)-trans-2-(2-Bromo-4-nitro-phenyl)-5,7-dihydroxy-8-(2-hydroxymethyl-1-methyl-pyrrolidin-3-yl)-chromen-4-one (Compound No. 154)

Compound (153) (0.3 g, 0.6 mmol) was demethylated using pyridine hydrochloride (3 g, 26 mmol) as described in example 9 to obtain the title compound (54).

Yield: 54% mp: 186° C.

IR cm$^{-1}$: 3400, 1650, 1525, 1350

$^1$HNMR (CDCl$_3$+DMSO d$_6$): δ 12.2 (s, 1H, exchangeable), 8.5 (s, 1H, 8.25 (d, 1H), 7.75 (d, 1H), 6.35 (s, 1H), 6.15 (s, 1H), 3.95 (m, 1H), 3.65 (m, 1H), 3.25 (m, 2H), 3.1 (m, 2H), 2.6 (s, 3H), 2.25 (m, 1H), 2.02 (m, 1H).

MS: m/e 493 (M+1),

EXAMPLE 141

(+)-trans-2-(4-Amino-2-bromo-phenyl)-8-(2-hydroxymethyl-1-methylpyrrolidin-3-yl)-5,7-dimethoxy-chromen-4-one (Compound No. 155)

Compound (153) (300 mg, 0.6 mmol) was treated with iron dust (300 mg) in water (1.2 mL) and glacial acetic acid (1.2 mL) as described in Example 62 to obtain the title compound (155)

Yield: 88%

$^1$HNMR (CDCl$_3$): δ 7.45 (d, 1H), 6.95 (s, 1H), 6.7 (d, 1H), 6.48 (s, 1H), 6.24 (s, 1H), 4.15 (m, 1H), 4.05 (s, 3H), 3.95 (s, 3H), 3.6 (dd, 1H), 3.5 (m, 1H), 3.15 (m, 1H), 2.64 (m, 1H), 2.58 (m, 1H), 2.35 (s, 3H), 2.01 (m, 2H).

MS: m/e 491 (M+1), 459 (M−32).

EXAMPLE 142

(+)-trans-2-(4-Amino-2-bromo-phenyl)-5,7-dihydroxy-8-(2-hydroxymethyl-1-methyl-pyrrolidin-3-yl)-chromen-4-one (Compound No. 156)

Compound (155) (150 mg, 0.3 mmol) was demethylated using pyridine hydrochloride (1.5 g, 13 mmol) as described in example 9 to obtain the title compound (156).

Yield: 70 mg (50%)

mp: 208° C.

IR cm$^{-1}$: 3400, 1650, 1575, 1380

$^1$HNMR (CDCl$_3$+DMSO d$_6$): δ 12.28 (s, 1H, exchangeable), 6.85 (d, 1H), 6.5 (s, 1H), 6.2 (d, 1H), 5.8 (s, 1H), 5.65 (s, 1H), 3.54 (m, 1H), 3.2 (d, 2H), 2.64 (m, 3H), 2.15 (s, 3H), 1.8 (m, 1H), 1.4 (m, 1H).

MS: m/e 462 (M+1).

EXAMPLE 143

2-Bromo-4-methoxy-benzoic acid (Compound No. 157)

2-Bromo-4-nitro benzoic acid (3 gm, 12.2 mmol) was reacted with sodium methoxide (6 gm, 111 mmol) in dry DMSO (250 ml) at 80° C.

After completion of reaction mixture was poured over crushed ice, acidified with 1:1 HCl and extracted with ethyl acetate.

Organic layer was then concentrated to obtain the title compound (157).

Yield: 81%

$^1$HNMR (DMSO d$_6$): δ 13.2 (s, 1H), 8.2 (d, 1H), 8.02 (d, 1H), 7.85 (d, 1H), 3.$\overline{85}$ (s, 3H).

MS: m/e 232 (M+1).

EXAMPLE 144

(+)-trans-2-(2-Bromo-4-methoxy-phenyl)-8-(2-hydroxymethyl-1-methyl-pyrrolidin-3-yl)-5,7-dimethoxy-chromen-4-one (Compound No. 159)

Compound (157) (2.8 gm, 12.1 mmol) was reacted with compound (6) (2.2 gm, 6.3 mmol) in dry pyridine (25 mL) using POCl$_3$ (7 gm, 45.8 mmol) as described in Example 52 to obtain (+)-trans-2-Bromo-4-methoxy benzoic acid 2-(2-acetoxymethyl-1-methyl-pyrrolidin-3-yl)-6-acetyl-3,5-dimethoxy-phenyl ester (compound no. 158) (3.2 gm, 5.7 mmol) a viscous oil, which was converted to the title compound (159) in situ using NaH (50%, 2.8 gm, 50 mmol) in dry 1,4-dioxane (100 mL) as described in Example 26.

Yield: 19%

$^1$HNMR (CDCl$_3$): δ 7.6 (d, 1H), 7.2 (s, 1H), 7.02 (d, 1H), 6.8 (s, 1H), 6.45 (s, 1H), 4.2 (m, 1H), 4.08 (s, 3H), 4.01 (s, 3H), 3.8 (s, 3H), 3.65 (m, 1H), 3.4 (m, 1H), 3.5 (m, 1H), 2.8 (m, 1H), 2.6 (m, 1H), 2.45 (s, 3H), 2.12 (m, 2H)

MS: m/e 504 (M+1), 473 (M−32).

EXAMPLE 145

(+)-trans-2-(2-Bromo-4-methoxy-phenyl)-5,7-dihydroxy-8-(2-hydroxymethyl-1-methyl-pyrrolidin-3-yl)-chromen-4-one (Compound No. 160)

Compound (159) (155 mg, 0.3 mmol) was demethylated using pyridine hydrochloride (1.6 g, 13.9 mmol) as described in example 9 to obtain the title compound (160).

Yield: 70 mg (49%)

$^1$HNMR (CDCl$_3$+DMSO d$_6$): δ 12.6 (s, 1H exchange), 7.4 (d, 1H), 7.1 (s, 1H), 6.8 (d, 1H), 6.25 (s, 1H), 6.15 (s, 1H), 4.01 (m, 1H), 3.75 (s, 3H), 3.25 (m, 2H), 3.05 (m, 3H), 2.65 (s, 3H), 2.2 (m, 1H), 1.98 (m, 1H).

EXAMPLE 146

(+)-trans-2-(2-Bromo-4-hydroxy-phenyl)-5,7-dihydroxy-8-(2-hydroxymethyl-1-methyl-pyrrolidin-3-yl)-chromen-4-one (Compound No. 161)

Compound (160) (150 mg, 0.25 mmol) was demethylated using pyridine hydrochloride (1.5 gm, 13 mmol) as described in example 9 to obtain the title compound (161)

Yield: 42%

¹HNMR (CDCl₃+DMSO d₆): δ 12.85 (s, 1H exchange), 7.4 (d, 1H), 7.1 (s, 1H), 6.85 (d, 1H), 6.32 (s, 1H), 6.25 (s, 1H), 4.1 (m, 1H), 3.62 (m, 1H), 3.45 (m, 2H), 3.15 (m, 1H), 2.95 (m, 1H), 2.7 (s, 3H), 2.45 (m, 1H) 2.2 (m, 1H).

MS: m/e 462 (M+1).

EXAMPLE 147

(+)-trans-Acetic acid 8-(2-acetoxymethyl-1-methyl-pyrrolidin-3-yl)-5-hydroxy-2-(4-nitro-phenyl)-4-oxo-4H-chromen-7-yl ester (Compound No. 162)

To a solution of compound (70) (50 mg, 0.12 mmol) in dichloromethane (10 mL) were added acetic anhydride (30 mg, 0.3 mmol) and dimethylaminopyridine (3 mg). The mixture was stirred for 45 min. at room temperature.

Reaction mixture was then adsorbed on 0.5 gm silica, concentrated and was purified using silica gel chromatography using 2% MeOH in chloroform+1% liquor ammonia as eluant to obtain the title compound (162).

Yield: 20 mg (33%)

¹HNMR (CDCl₃): δ 12.5 (s, 1H exchange), 8.4 (d, 2H), 8.05 (d, 2H), 6.75 (s, 1H), 6.32 (s, 1H), 4.55 (m, 1H), 4.2 (m, 2H), 3.4 (m, 2H), 2.9 (m, 1H), 2.7 (s, 3H), 2.45 (m, 2H), 2.15 (s, 3H), 2.05 (s, 3H).

MS: m/e 494.93 (M−1), 454.5 (M−42)

EXAMPLE 148

(+)-trans-2-(2,4-Dichloro-5-fluoro-phenyl)-8-(2-hydroxymethyl-1-methyl-pyrrolidin-3-yl)-5,7-dimethoxy-chromen-4-one (Compound No. 163)

Compound (6) (0.8 g, 2.58 mmol) in dry DMF (10 mL) was reacted with NaH (0.62 g, 12.5 mmol) at 0° C. for 10 min. It was then reacted with 2,4-Dichloro-5-fluoro-benzoyl chloride (0.887 g, 3.9 mmol) as detailed in example 8, to obtain the title compound (163).

Yield: 0.54 gm (40%)

¹HNMR (CDCl₃): δ 7.75 (d, 1H), 7.6 (d, 1H), 6.6 (s, 1H), 6.45 (s, 1H), 4.2 (m, 1H), 4.0 (d, 6H), 3.7 (m, 1H), 3.35 (d, 1H), 3.2 (m, 1H), 2.65 (m, 2H), 2.35 (s, 3H), 2.1 (m, 2H),

MS: m/e 481.91 (M+1)

EXAMPLE 149

(+)-trans-2-(2,4-Dichloro-5-fluoro-phenyl-5,7-dihydroxy-8-(2-hydroxymethyl-1-methyl-pyrrolidin-3-yl)-chromen-4-one (Compound No. 164)

Compound (163) (0.53 g, 1.1 mmol) was subjected to demethylation using pyridine hydrochloride (5.5 g, 47.6 mmol) as described in example 9, to obtain the title compound (164).

Yield: 0.29 (55%)

¹HNMR (CDCl₃+DMSO d₆): δ 7.4 (m, 2H), 6.3 (s, 1H), 6.05 (s, 1H), 3.9 (d, 1H), 3.6 (m, 2H), 3.0 (m, 2H), 2.8 (q, 1H), 2.5 (s, 3H), 2.45 (s, 1H), 2.25 (m, 1H).

MS: m/e 454 (M+1)

TABLE OF EXAMPLES

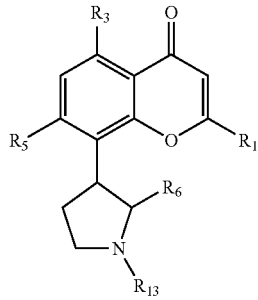

| Compound no. | R₁ | R₃ | R₅ | R₆ | R₁₃ |
|---|---|---|---|---|---|
| (±) 8 | 2-Chloro-phenyl | OCH3 | OCH3 | CH2OH | CH3 |
| (±) 9 | 2-Chloro-phenyl | OH | OH | CH2OH | CH3 |
| (+) 11 | 2-Chloro-phenyl | OCH3 | OCH3 | CH2OH | CH3 |
| (+) 12 | 2-Chloro-phenyl | OH | OH | CH2OH | CH3 |
| (−) 14 | 2-Chloro-phenyl | OCH3 | OCH3 | CH2OH | CH3 |
| (−) 15 | 2-Chloro-phenyl | OH | OH | CH2OH | CH3 |
| (+) 16 | 2-Bromo-phenyl | OCH3 | OCH3 | CH2OH | CH3 |
| (+) 17 | 2-Bromo-phenyl | OH | OH | CH2OH | CH3 |
| (+) 18 | 4-Bromo-phenyl | OCH3 | OCH3 | CH2OH | CH3 |
| (+) 19 | 4-Bromo-phenyl | OH | OCH3 | CH2OH | CH3 |
| (+) 20 | 4-Bromo-phenyl | OH | OH | CH2OH | CH3 |
| (+) 21 | 3-Chloro-phenyl | OCH3 | OCH3 | CH2OH | CH3 |
| (+) 22 | 3-Chloro-phenyl | OH | OCH3 | CH2OH | CH3 |
| (+) 23 | 3-Chloro-phenyl | OH | OH | CH2OH | CH3 |
| (+) 24 | 2-iodo-phenyl | OCH3 | OCH3 | CH2OH | CH3 |
| (+) 25 | 2-iodo-phenyl | OH | OH | CH2OH | CH3 |
| (+) 26 | 2-Fluoro-phenyl | OCH3 | OCH3 | CH2OH | CH3 |
| (+) 27 | 2-Fluoro-phenyl | OH | OH | CH2OH | CH3 |
| (+) 28 | 3-Fluoro-phenyl | OCH3 | OCH3 | CH2OH | CH3 |
| (+) 29 | 3-Fluoro-phenyl | OH | OH | CH2OH | CH3 |

-continued

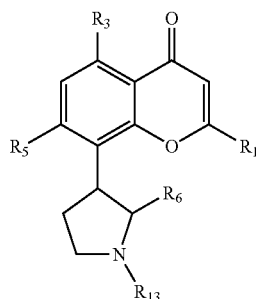

| Compound no. | R$_1$ | R$_3$ | R$_5$ | R$_6$ | R$_{13}$ |
|---|---|---|---|---|---|
| (+) 30 | 2,6-Difluoro-phenyl | OCH3 | OCH3 | CH2OH | CH3 |
| (+) 31 | 2,6-Difluoro-phenyl | OH | OH | CH2OH | CH3 |
| (±) 32 | 4-cyano-phenyl | OCH3 | OCH3 | CH2OH | CH3 |
| (±) 33 | 4-cyano-phenyl | OH | OCH3 | CH2OH | CH3 |
| (±) 34 | 4-cyano-phenyl | OH | OH | CH2OH | CH3 |
| (+) 35 | 4-cyano-phenyl | OCH3 | OCH3 | CH2OH | CH3 |
| (+) 36 | 4-cyano-phenyl | OH | OCH3 | CH2OH | CH3 |
| (+) 37 | 4-cyano-phenyl | OH | OH | CH2OH | CH3 |
| (±) 38 | 4-trifluoromethyl-phenyl | OCH3 | OCH3 | CH2OH | CH3 |
| (±) 39 | 4-trifluoromethyl-phenyl | OH | OH | CH2OH | CH3 |
| (+) 40 | 4-trifluoromethyl-phenyl | OCH3 | OCH3 | CH2OH | CH3 |
| (+) 41 | 4-trifluoromethyl-phenyl | OH | OH | CH2OH | CH3 |
| (−) 42 | 4-trifluoromethyl-phenyl | OCH3 | OCH3 | CH2OH | CH3 |
| (−) 43 | 4-trifluoromethyl-phenyl | OH | OH | CH2OH | CH3 |
| (+) 44 | 2-phenyl | OCH3 | OCH3 | CH2OH | CH3 |
| (+) 45 | 2-phenyl | OH | OH | CH2OH | CH3 |
| (+) 46 | 2-thiophen-2-yl | OCH3 | OCH3 | CH2OH | CH3 |
| (+) 47 | 2-thiophen-2-yl | OH | OH | CH2OH | CH3 |
| (+) 48 | 2-methyl-4-cyano-phenyl | OCH3 | OCH3 | CH2OH | CH3 |
| (+) 49 | 2-methyl-4-cyano-phenyl | OH | OH | CH2OH | CH3 |
| (±) 50 | 2-Bromo-5-methoxy-phenyl | OCH3 | OCH3 | CH2OH | CH3 |
| (±) 51 | 2-Bromo-5-methoxy-phenyl | OH | OH | CH2OH | CH3 |
| (±) 52 | 2-Bromo-5-hydroxy-phenyl | OH | OH | CH2OH | CH3 |
| (+) 53 | 2-Bromo-5-methoxy-phenyl | OCH3 | OCH3 | CH2OH | CH3 |
| (+) 54 | 2-Bromo-5-methoxy-phenyl | OH | OH | CH2OH | CH3 |
| (+) 55 | 2-Bromo-5-hydroxy-phenyl | OH | OH | CH2OH | CH3 |
| (±) 56 | 3,5-Bis-trifluoromethyl-phenyl | OCH3 | OCH3 | CH2OH | CH3 |
| (±) 57 | 3,5-Bis-trifluoromethyl-phenyl | OH | OH | CH2OH | CH3 |
| (+) 58 | 2-Chloro-5-methyl-phenyl | OCH3 | OCH3 | CH2OH | CH3 |
| (+) 59 | 2-Chloro-5-methyl-phenyl | OH | OH | CH2OH | CH3 |
| (+) 61 | 2-Bromo-5-nitro-phenyl | OCH3 | OCH3 | CH2OH | CH3 |
| (+) 62 | 2-Bromo-5-nitro-phenyl | OH | OH | CH2OH | CH3 |
| (+) 64 | 2-Chloro-pyridin-3-yl | OCH3 | OCH3 | CH2OH | CH3 |

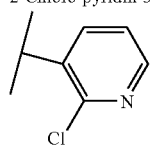

| (+) 65 | 2-Chloro-pyridin-3-yl | OH | OH | CH2OH | CH3 |
| (±) 66 | 2-Chloro-pyridin-3-yl | OCH3 | OCH3 | CH2OH | CH3 |
| (±) 67 | 2-Chloro-pyridin-3-yl | OH | OH | CH2OH | CH3 |
| (+) 69 | 4-nitro-phenyl | OCH3 | OCH3 | CH2OH | CH3 |
| (+) 70 | 4-nitro-phenyl | OH | OH | CH2OH | CH3 |
| (+) 71 | 4-Amino-phenyl | OH | OH | CH2OH | CH3 |
| (±) 90 | 2-methoxy-phenyl | OCH3 | OCH3 | CH2OH | CH3 |
| (±) 91 | 2-hydroxy-phenyl | OH | OH | CH2OH | CH3 |
| (+) 92 | 2 Chloro-4-cyano phenyl | OCH3 | OCH3 | CH2OH | CH3 |
| (+) 93 | 2 Chloro-4-cyano phenyl | OH | OH | CH2OH | CH3 |

-continued

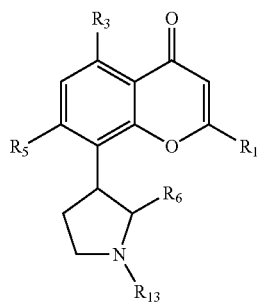

| Compound no. | R₁ | R₃ | R₅ | R₆ | R₁₃ |
|---|---|---|---|---|---|
| (+) 94 | 4-Bromo-2-chloro-phenyl | OCH3 | OCH3 | CH2OH | CH3 |
| (+) 95 | 4-Bromo-2-chloro-phenyl | OH | OH | CH2OH | CH3 |
| (±) 96 | 2-Chloro-5-dimethylamino-phenyl | OCH3 | OCH3 | CH2OH | CH3 |
| (±) 97 | 2-Chloro-5-methylamino-phenyl | OH | OH | CH2OH | CH3 |
| (±) 98 | 2-Chloro-4-methoxy-phenyl | OCH3 | OCH3 | CH2OH | CH3 |
| (±) 99 | 2-Chloro-4-hydroxy-phenyl | OH | OH | CH2OH | CH3 |
| (±) 100 | 2-Chloro-5-fluoro-phenyl | OCH3 | OCH3 | CH2OH | CH3 |
| (±) 101 | 2-Chloro-5-fluoro-phenyl | OH | OH | CH2OH | CH3 |
| (±) 102 | 2-Chloro-5-methoxy-phenyl | OCH3 | OCH3 | CH2OH | CH3 |
| (±) 103 | 2-Chloro-5-hydroxy-phenyl | OH | OH | CH2OH | CH3 |
| (±) 104 | 2-Chloro-5-methoxy-phenyl | OH | OH | CH2OH | CH3 |
| (±) 107 | 2-Chloro-phenyl | OCH3 | OCH3 | Azidomethyl | CH3 |
| (±) 108 | 2-Chloro-phenyl | OCH3 | OCH3 | Aminomethyl | CH3 |
| (±) 109 | 2-Chloro-phenyl | OH | OH | Aminomethyl | CH3 |
| (±) 110 | 2-Chloro-phenyl | OCH3 | OCH3 | CH2CN | CH3 |
| (±) 111 | 2-Chloro-phenyl | OH | OH | CH2CN | CH3 |
| (±) 112 | 2-Chloro-phenyl | OCH3 | OCH3 | 2-imidazol-1-ylmethyl | CH3 |
| (±) 113 | 2-Chloro-phenyl | OH | OH | 2-imidazol-1-ylmethyl | CH3 |
| (±) 114 | 2-Chloro-phenyl | OCH3 | OCH3 | 2-mercapto-methyl | CH3 |
| (±) 115 | 2-Chloro-phenyl | OH | OH | 2-mercapto-methyl | CH3 |
| (±) 124 | 2-Chloro-phenyl | OCH3 | OCH3 | CH2OH | 4-methoxy-phenyl |
| (±) 125 | 2-Chloro-phenyl | OH | OH | CH2OH | 4-methoxy-phenyl |
| (±) 131 | 2-Chloro-phenyl | OCH3 | OCH3 | CH₂OC(O)CH₃ | propyl |
| (±) 132 | 2-Chloro-phenyl | OCH3 | OCH3 | CH2OH | propyl |
| (±) 133 | 2-Chloro-phenyl | OH | OH | CH2OH | propyl |
| (+) 134 | 2-Chloro-3-fluoro-phenyl | OCH3 | OCH3 | CH2OH | CH3 |
| (+) 135 | 2-Chloro-3-fluoro-phenyl | OH | OH | CH2OH | CH3 |
| (+) 136 | 2-Bromo-3-fluoro-phenyl | OCH3 | OCH3 | CH2OH | CH3 |
| (+) 137 | 2-Bromo-3-fluoro-phenyl | OH | OH | CH2OH | CH3 |
| (+) 138 | 2-Bromo-5-fluoro-phenyl | OCH3 | OCH3 | CH2OH | CH3 |
| (+) 139 | 2-Bromo-5-fluoro-phenyl | OH | OH | CH2OH | CH3 |
| (+) 140 | 2-Chloro-5-iodo-phenyl | OCH3 | OCH3 | CH2OH | CH3 |
| (+) 141 | 2-Chloro-5-iodo-phenyl | OH | OH | CH2OH | CH3 |
| (+) 142 | 2-Bromo-5-chloro-phenyl | OCH3 | OCH3 | CH2OH | CH3 |
| (+) 143 | 2-Bromo-5-chloro-phenyl | OH | OH | CH2OH | CH3 |
| (±) 148 | 2-Chloro-phenyl | OH | OH | CH2OH | methyl and oxide |
| (+) 153 | 2-Bromo-4-nitro-phenyl | OCH3 | OCH3 | CH2OH | CH3 |
| (+) 154 | 2-Bromo-4-nitro-phenyl | OH | OH | CH2OH | CH3 |
| (+) 155 | 4-Amino-2-bromo-phenyl | OCH3 | OCH3 | CH2OH | CH3 |
| (+) 156 | 4-Amino-2-bromo-phenyl | OH | OH | CH2OH | CH3 |

-continued

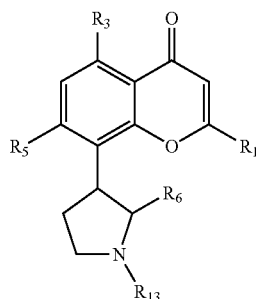

| Compound no. | $R_1$ | $R_3$ | $R_5$ | $R_6$ | $R_{13}$ |
|---|---|---|---|---|---|
| (+) 159 | 2-Bromo-4-methoxy-phenyl | OCH3 | OCH3 | CH2OH | CH3 |
| (+) 160 | 2-Bromo-4-methoxy-phenyl | OH | OH | CH2OH | CH3 |
| (+) 161 | 2-Bromo-4-hydroxy-phenyl | OH | OH | CH2OH | CH3 |
| (+) 163 | 2,4-Dichloro-5-fluoro-phenyl | OCH3 | OCH3 | CH2OH | CH3 |
| (+) 164 | 2,4-Dichloro-5-fluoro-phenyl | OH | OH | CH2OH | CH3 |

The efficacy of the present compounds in inhibiting the activity of cyclin-dependent kinases can be determined by a number of pharmacological assays well known in the art, such as described below or, for example, in Losiewics, M. D., et al. Biochem. Biophys. Res. Commun., 1994, 201, 589. The kinases, cyclins, and substrates used in the in vitro kinase assay can be proteins isolated from mammalian cells, or alternatively, they can be proteins produced recombinantly. The exemplified pharmacological assays which follow hereinbelow have been carried out with the compounds of the present invention and their salts.

CDK4/Cyclin D1 Kinase Assay and CDK2/Cyclin E Kinase Assay

The assays measure phosphorylation of retinoblastoma protein (Rb) by CDK4 or CDK2 upon activation by cyclin D1 or cyclin E, respectively, through the transfer of $(\gamma^{32}P)$-phosphate from $\gamma^{32}P$-ATP in a 96-well filter plate assay.

Materials:

CDK4 or CDK2 was coexpressed with cyclin D1 or cyclin E, respectively, by a baculovirus expression system in insect cells. For this, $1 \times 10^7$ Sf9 cells were coinfected with baculoviruses containing human CDK-4 or 2 and cyclin D1 or E genes and after 72 hours cells were lysed in 500 μL of a lysis buffer (50 mM HEPES (pH 7.5), 10 mM $MgCl_2$, 1 mM DTT, 5 μg/ml of aprotinin, 5 μg/ml of leupeptin, 0.1 mM NaF, 0.2 mM phenylmethylsulphonyl fluoride (PMSF), and sodium orthovanadate). Centrifuged lysate was purified on a GST-sepharose column. Purity of the proteins was checked by SDS-PAGE followed by western blots using specific antibodies (Santacruz Biotec, USA) to CDK4 or CDK2.

GST-retinoblastoma (Rb) (aa 776-928) fusion protein is expressed in the bacteria E. coli and purified by GSH-Sepharose affinity chromatography. The GST-Rb bound to these beads served as the substrate in the assay.

Readout

Quantitation was by scintillation detection of $(^{32}P)$-GST-Rb in 96-well filter plates using Top Count scintillation 96-well counter (Packard, USA).

Procedure:

The CDK 4 or CDK 2 enzyme assay was run in 96-well format using Millipore Multiscreen filtration plates. All assay steps took place in a single filter plate (Unifilter plates, Packard, USA). The filtration wells were pre-wet with kinase buffer (100 μl/well) and the solution was then removed by the application of vacuum, with the filter plate on a vacuum manifold and the vacuum on. 50 μl of GST-Rb bound to GSH-Sepharose beads in kinase buffer (0.5 μg GST-Rb/50 μl) was added to each well and vacuum was applied to removed the buffer. A further 25 μl of a reaction mix containing ATP (cold+hot) and phosphatase inhibitors diluted in kinase buffer were added to each well, followed by the addition of test compound (4×final concentration in kinase buffer) or kinase buffer (control) in an additional 25 μl volume. Finally 50 μl (100 ng) of human CDK4/D1 or CDK-2/E enzyme in kinase buffer was added to each well to initiate the reaction. The reaction was incubated for 30 min at 30° C. After the reaction was complete, vacuum was applied and the plate was washed with the wash buffer (TNEN buffer) three times. The filter plate was air-dried and placed in a Multiscreen adapter plate. To each well, 30 μl Packard Microscint-O cocktail was added and the plate was covered with a Top-Seal A film. The plate was counted in a Packard Top Count Scintillation Counter for 10 min. Flavopiridol was used as a standard inhibitor in all the experiments.

The concentration of compound at which 50% of phosphokinase activity of CDK4-cyclin D1 and CDK2-cyclin E was inhibited ($IC_{50}$) was calculated for representative compounds described in the Examples. The results are indicated in Table 1.

TABLE 1

| | | $IC_{50}$ (μM) | | |
|---|---|---|---|---|
| No. | Compound No. | CDK4-Cyclin D1 | CDK2-Cyclin E | Ratio of $IC_{50}$ CDK2/E:CDK/D1 |
| 1 | 31 | 0.28 | 8.75 | 31.2 |
| 2 | 54 | 0.08 | 6.00 | 75.0 |
| 3 | Flavopiridol | 0.04 | 0.18 | 4.5 |

The results indicate that the compounds of the present invention have significant inhibitory effects against CDK4/cyclin D1 and CDK2/cyclin E with greater selectivity towards CDK4-D1.

In Vitro Cell Proliferation and Cytotoxicity Assays:

Exponentially growing cultures of ten human cancerous cell lines (HL-60 Promyelocytic Leukemia, PC-3 Prostate, H-460 Lung, MDA-MB-231 Breast, MCF-7 Breast, HeLa Cervix, Colo-205 Colon, H9 Lymphoma (T Cells), U-937 Histiocytic Lymphoma (monocytes) and CaCO-2 Colon) obtained from NCCS, Pune, India were used. The in vitro cell proliferation (NCI, USA protocol) and cytotoxicity assays were carried out using standard procedures viz. $^3$H-Thymidine uptake and MTS assay, respectively (For $^3$H-Thymidine uptake: Cell Biology, A Laboratory Handbook, 1998, Vol 1 Ed Julio E. Celis, and For MTS assay: Promega Protocol, USA, 2000). In the $^3$H-Thymidine uptake assay, cells were harvested after 72 hours onto GF/B unifilter plates (Packard, USA) using a Packard Filtermate Universal harvester and the plates were counted on a Packard TopCount 96-well liquid scintillation counter. The concentration of compound at which 50% of proliferative activity was inhibited ($IC_{50}$) and the degree of toxicity of compound were calculated for representative compounds described in the Examples. The results are indicated in Table 2 below.

TABLE 2

| | | $IC_{50}$ (μM) | | | | |
|---|---|---|---|---|---|---|
| No. | Compound No. | HeLa Cervix | MCF-7 Breast | PC-3 Prostate | MDAMB-231 Breast | H460 Lung | U-937 Histiocytic lymphoma (monocytes) |
| 1 | 12 | 0.1-0.5 ++ | 0.5-1 NT | 0.5-1 ++ | 0.5-1 NT | 5.0-10 NT | 0.1-1 + |
| 2 | 17 | 0.1-1 + | 0.5-1 + | 1.0-10 NT | 0.1 NT | >10 NT | 0.1-1 + |
| 3 | Flavopiridol | 0.1-0.5 +++ | 0.5 + | 0.05-0.1 ++ | 0.1 ++ | 0.05 + | 0.1 ++ |

NA: not active >10 μM
NT: not toxic ≦30%
+: 30-50% toxic
++: 50-70% toxic
+++: above 70% toxic

The invention claimed is:

1. A method of inhibiting the activity of cyclin-dependent kinases selected from the group consisting of cyclin dependent kinase 2 (CDK2) and cyclin dependent kinase 4 (CDK4), which comprises administering to a mammal, an effective amount of a compound of the formula (Ig), or a stereoisomer, optical isomer, a pharmaceutically acceptable salt, or a pharmaceutically acceptable solvate thereof;

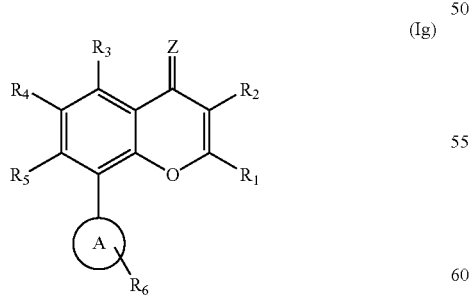

(Ig)

wherein $R_1$ is phenyl, which is unsubstituted or substituted by 1, 2, or 3 identical or different substituents selected from: halogen, $C_1$-$C_4$-alkyl, $C_1$-$C_4$-alkoxy, nitro, $NR_9R_{10}$, $SR_{11}$, trifluoromethyl, hydroxyl, cyano, carboxy, $C_1$-$C_4$-alkoxycarbonyl and —$C_1$-$C_4$-alkylenehydroxyl, or is a heterocycle, which is a saturated, partially unsaturated or aromatic ring containing 5 or 6 ring atoms of which 1, 2 or 3 are identical or different heteroatoms selected from: nitrogen, oxygen, sulfur, and phosphorus, and where the heterocycle is unsubstituted or substituted by 1, 2, or 3 identical or different substituents selected from: halogen, $C_1$-$C_4$-alkyl, $C_1$-$C_4$-alkoxy, nitro, $NR_9R_{10}$, $SR_{11}$, trifluoromethyl, hydroxyl, cyano, carboxy, $C_1$-$C_4$-alkoxycarbonyl and $C_1$-$C_4$-alkylenehydroxyl;

$R_2$ is hydrogen, $C_1$-$C_6$-alkyl and phenyl, which is unsubstituted or substituted by 1, 2 or 3 identical or different substituents selected from: halogen, $C_1$-$C_4$-alkyl, $C_1$-$C_4$alkoxy, nitro, $NR_9R_{10}$, $SR_{11}$, trifluoromethyl, hydroxyl, cyano, carboxy, $C_1$-$C_4$-alkoxycarbonyl and —$C_1$-$C_4$-alkylenehydroxyl; $OR_{11}$, halogen, cyano, nitro, $NR_9R_{10}$ or $SR_{11}$;

$R_3$, $R_4$ and $R_5$ are each independently selected from: hydrogen, $C_1$-$C_4$-alkyl, $C_1$-$C_4$-alkoxyl, halogen, $OR_{11}$, $C_1$-$C_4$-alkylcarbonyloxy, $NR_9R_{10}$, $SO_2NR_9R_{10}$, carboxyl, cyano and nitro;

Z is O or S;

A is a 5-membered saturated ring represented by any one of the general structures (i) to (v);

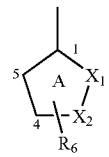

(i)

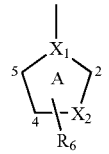

(ii)

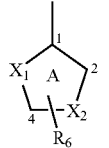

(iii)

-continued

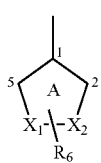
(iv)

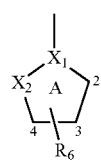
(v)

wherein $X_1$ and $X_2$ independently represent a carbon atom and a nitrogen atom provided that at least one of $X_1$ and $X_2$ is a nitrogen atom and wherein the nitrogen atom is at least monosubstituted by $R_{13}$, wherein $R_{13}$ is selected from: hydrogen, unsubstituted $C_1$-$C_6$-alkyl, or $C_1$-$C_6$-alkyl substituted by halogen, hydroxyl, or carboxyl, $C_2$-$C_6$-alkenyl, hydroxyl, $C_1$-$C_6$-alkoxy, $C_1$-$C_4$alkylcarbonyl, toluenesulfonyl, $SO_2R_{10}$, —CO$(CH_2)_mR_4$; cyano, phenyl, which is unsubstituted or substituted by 1, 2, or 3 identical or different substituents selected from: halogen, $C_1$-$C_4$-alkyl, $C_1$-$C_4$-alkoxy, nitro, $NR_9R_{10}$, $SR_{11}$, trifluoromethyl, hydroxyl, cyano, carboxy, $C_1$-$C_4$-alkoxycarbonyl and -$C_1$-$C_4$-alkylene-hydroxyl;

$R_6$ is $C_1$-$C_4$-alkyl, —$C_1$-$C_4$alkanoyl, hydroxyl, $C_1$-$C_4$alkoxy, —$C_1$-$C_4$-alkoxycarbonyl, —$C_1$-$C_4$-alkyleneOR$_{11}$, —$C_1$-$C_4$-alkylenehalo, —$C_1$-$C_4$-alkyleneNR$_9R_{10}$, —$C_1$-$C_4$-alkyleneC(O)OR$_9$, phenoxy, —NR$_9R_{10}$, SR$_{12}$, S(O)$_nR_{12}$ or —C(S)R$_{12}$;

$R_9$ and $R_{10}$ are each independently selected from: hydrogen, $C_1$-$C_4$-alkyl, $C_1$-$C_4$-alkanoyl, $C_1$-$C_4$-alkoxycarbonyl, $C_1$-$C_4$-alkylcarbonyl, carboxamide and sulfonamide;

$R_{11}$ is hydrogen, $C_1$-$C_4$-alkyl, $C_1$-$C_4$-alkanoyl, or $C_1$-$C_4$-alkoxycarbonyl;

$R_{12}$ is hydrogen, halogen, $C_1$-$C_4$-alkyl, —NR$_9R_{10}$, halogen, —SH, or —S—$C_1$-$C_4$-alkyl;

$R_{14}$ is hydrogen, $C_1$-$C_4$-alkyl, hydroxyl, NR$_9R_{10}$, halogen, SH, or —S—$C_1$-$C_4$-alkyl;

m is an integer of 0 to 6; and n is an integer of 1 or 2.

2. The method of claim 1, wherein in the compounds of formula (Ig), $R_6$ is —$C_1$-$C_4$-alkylene-OR$_{11}$.

3. The method of claim 1, wherein in the compounds of formula (Ig);

$R_1$ is phenyl, which is unsubstituted or substituted by 1, 2, or 3 identical or different substituents selected from: halogen, $C_1$-$C_4$-alkyl, $C_1$-$C_4$-alkoxy, nitro, NR$_9R_{10}$, SR$_{11}$, trifluoromethyl, hydroxyl, cyano, carboxy, $C_1$-$C_4$alkoxycarbonyl and —$C_1$-$C_4$-alkylenehydroxyl, or is a heterocycle, which is a saturated, partially unsaturated or aromatic ring containing 6 ring atoms of which 1, 2 or 3 are identical or different heteroatoms selected from: nitrogen, oxygen and sulfur, and where the heterocycle is unsubstituted or substituted by 1, 2, or 3 identical or different substituents selected from: halogen, $C_1$-$C_4$-alkyl, $C_1$-$C_4$-alkoxy, nitro, NR$_9R_{10}$, SR$_{11}$, trifluoromethyl, hydroxyl, cyano, carboxy, $C_1$-$C_4$-alkoxycarbonyl and $C_1$-$C_4$-alkylenehydroxyl;

$R_2$ and $R_4$ are hydrogen;

$R_3$ and $R_5$ are each independently selected from: hydroxyl, $C_1$-$C_4$-alkoxyl and $C_1$-$C_4$-alkylcarbonyloxy;

Z is O;

A is a saturated 5-membered ring represented by the following formula (i);

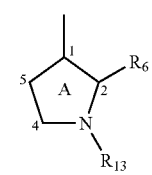
(i)

$R_6$ is —$C_1$-$C_4$-alkylene-OR$_{11}$;

$R_9$ and $R_{10}$ are each independently selected from: hydrogen, $C_1$-$C_4$-alkyl, $C_1$-$C_4$-alkanoyl, $C_1$-$C_4$-alkoxycarbonyl, $C_1$-$C_4$-alkylcarbonyl, carboxamide and sulfonamide;

$R_{11}$ is hydrogen, $C_1$-$C_4$-alkyl, $C_1$-$C_4$-alkanoyl, or $C_1$-$C_4$-alkoxycarbonyl; and $R_{13}$ is hydrogen or $C_1$-$C_4$-alkyl.

4. The method of claim 1, wherein in the compounds of formula (Ig);

$R_1$ is phenyl, which is unsubstituted or substituted by 1, 2, or 3 identical or different substituents selected from: halogen, $C_1$-$C_4$-alkyl, $C_1$-$C_4$-alkoxy, nitro, trifluoromethyl, hydroxyl, cyano, carboxy, $C_1$-$C_4$-alkoxycarbonyl and —$C_1$-$C_4$-alkylenehydroxyl, or is a heterocycle, which is a saturated, partially unsaturated or aromatic ring containing 6 ring atoms of which 1, 2 or 3 are identical or different heteroatoms selected from: nitrogen, oxygen and sulfur, and where the heterocycle is unsubstituted or substituted by 1, 2, or 3 identical or different substituents selected from: halogen, $C_1$-$C_4$-alkyl, $C_1$-$C_4$-alkoxy, nitro, NR$_9R_{10}$, SR$_{11}$, trifluoromethyl, hydroxyl, cyano, carboxy, $C_1$-$C_4$-alkoxycarbonyl and —$C_1$-$C_4$-alkylenehydroxyl;

$R_2$ and $R_4$ are hydrogen;

$R_3$ and $R_5$ are each independently selected from: hydroxyl, $C_1$-$C_4$-alkoxyl and $C_1$-$C_4$-alkylcarbonyloxy;

Z is O;

A is a 5-membered saturated ring represented by any one of the general structures (i) to (v);

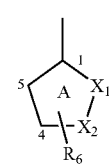
(i)

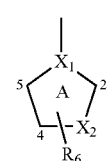
(ii)

-continued

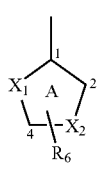
(iii)

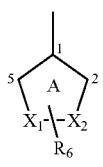
(iv)

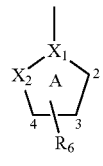
(v)

wherein $X_1$ and $X_2$ independently represent a carbon atom and a nitrogen atom, provided that at least one of $X_1$ and $X_2$ is a nitrogen atom and wherein the nitrogen atom is at least monosubstituted by $R_{13}$, wherein $R_{13}$ is selected from: hydrogen, unsubstituted $C_1$-$C_6$-alkyl, or $C_1$-$C_6$-alkyl substituted by halogen, hydroxyl, or carboxyl, $C_2$-$C_6$-alkenyl, hydroxyl, $C_1$-$C_6$-alkoxy, $C_1$-$C_4$-alkylcarbonyl, toluenesulfonyl, $SO_2R_{10}$, —$CO(CH_2)_mR_{14}$ and phenyl, which is unsubstituted or substituted by 1, 2, or 3 identical or different substituents selected from: halogen, $C_1$-$C_4$-alkyl, $C_1$-$C_4$-alkoxy, nitro, $NR_9R_{10}$, $SR_{11}$, trifluoromethyl, hydroxyl, cyano, carboxy, $C_1$-$C_4$-alkoxycarbonyl and —$C_1$-$C_4$-alkylenehydroxyl;

$R_6$ is $C_1$-$C_4$-alkyl, —$C_1$-$C_4$-alkanoyl, hydroxyl, $C_1$-$C_4$-alkoxy, —$C_1$-$C_4$-alkoxycarbonyl, —$C_1$-$C_4$-alkyleneOR$_{11}$, —$C_1$-$C_4$-alkylenehalo, —$C_1$-$C_4$-alkyleneNR$_9$R$_{10}$, —$C_1$-$C_4$-alkyleneC(O)OR$_9$, phenoxy, —$NR_9R_{10}$, $SR_{12}$, $S(O)_nR_{12}$ or —$C(S)R_{12}$;

$R_9$ and $R_{10}$ are each independently selected from: hydrogen, $C_1$-$C_4$-alkyl, $C_1$-$C_4$-alkanoyl, $C_1$-$C_4$-alkoxycarbonyl, $C_1$-$C_4$-alkylcarbonyl, carboxamide and sulfonamide;

$R_{11}$ is hydrogen, $C_1$-$C_4$-alkyl, $C_1$-$C_4$-alkanoyl, or $C_1$-$C_4$-alkoxycarbonyl;

$R_{12}$ is hydrogen, halogen, $C_1$-$C_4$-alkyl, —$NR_9R_{10}$, or $OR_9$;

$R_{14}$ is hydrogen, $C_1$-$C_4$-alkyl, hydroxyl, —$NR_9R_{10}$, halogen, —SH, or —S—$C_1$-$C_4$-alkyl;

m is an integer of 0 to 6; and n is an integer of 1 or 2.

5. The method of claim 1, wherein the compound of formula (Ig) is selected from the group consisting of:

(+/−)-trans-2-(2-Chloro-phenyl)-8-(2-hydroxymethyl-1-methyl-pyrrolidin-3-yl)-5,7-dimethoxy-chromen-4-one;

(+)-trans-2-(2-Chloro-phenyl)-8-(2-hydroxymethyl-1-methyl-pyrrolidin-3-yl)-5,7-dimethoxy-chromen-4-one;

(+)-trans-2-(2-Chloro-phenyl)-5,7-dihydroxy-8-(2-hydroxymethyl-1-methyl-pyrrolidin-3-yl)-chromen-4-one;

(−)-trans-2-(2-Chloro-phenyl)-8-(2-hydroxymethyl-1-methyl-pyrrolidin-3-yl)-5,7-dimethoxy-chromen-4-one;

(−)-trans-2-(2-Chloro-phenyl)-5,7-dihydroxy-8-(2-hydroxymethyl-1-methyl-pyrrolidin-3-yl)-chromen-4-one;

(+)-trans-2-(2-Bromo-phenyl)-8-(2-hydroxymethy-1-methyl-pyrrolidin-3-yl)-5,7-dimethoxy-chromen-4-one;

(+)-trans-2-(2-Bromo-phenyl)-5,7-dihydroxy-8-(2-hydroxymethyl-1-methyl-pyrrolidin-3-yl)-chromen-4-one;

(+)-trans-2-(4-Bromo-phenyl)-8-(2-hydroxymethyl-1-methyl-pyrrolidin-3-yl)-5,7-dimethoxy-chromen-4-one;

(+)-trans-2-(4-Bromo-phenyl)-5-hydroxy-8-(2-hydroxymethyl-1-methyl-pyrrolidin-3-yl)-7-methoxy-chromen-4-one;

(+)-trans-2-(4-Bromo-phenyl)-5,7-dihydroxy-8-(2-hydroxymethyl-1-methyl-pyrrolidin-3-yl)-chromen-4-one;

(+)-trans-2-(3-Chloro-phenyl)-8-(2-hydroxymethyl-1-methyl-pyrrolidin-3-yl)-5,7-dimethoxy-chromen-4-one;

(+)-trans-2-(3-Chloro-phenyl)-5-hydroxy-8-(2-hydroxymethyl-1-methyl-pyrrolidin-3-yl)-7-methoxy-chromen-4-one;

(+)-trans-2-(3-Chloro-phenyl)-5,7-dihydroxy-8-(2-hydroxymethyl-1-methyl-pyrrolidin-3-yl)-chromen-4-one;

(+)-trans-8-(2-1-1ydroxymethyl-1-methyl-pyrrolidin-3-yl)-2-(2-iodophenyl)-5,7-dimethoxy-chromen-4-one;

(+)-trans-5,7-Dihydroxy-8-(2-hydroxymethyl-1-methyl-pyrrolidin-3-yl)-2-(2-iodophenyl)-chromen-4-one;

(+)-trans-2-(2-Fluoro-phenyl)-8-(2-hydroxymethyl-1-methyl-pyrrolidin-3-yl)-5,7-dimethoxy-chromen-4-one;

(+)-trans-2-(2-Fluoro-phenyl)-5,7-dihydroxy-8-(2-hydroxymethyl-1-methyl-pyrrolidin-3-yl)-chromen-4-one;

(+)-trans-2-(3-Fluoro-phenyl)-5,7-dihydroxy-8-(2-hydroxymethyl-1-methyl-pyrrolidin-3-yl)-chromen-4-one;

(+)-trans-2-(3-Fluoro-phenyl)-8-(2-hydroxymethyl-1-methyl-pyrrolidin-3-yl)-5,7-dimethoxy-chromen-4-one;

(+)-trans-2-(2,6-Difluoro-phenyl)-8-(2-hydroxymethyl-1-methyl-pyrrolidin-3-yl)-5,7-dimethoxy-chromen-4-one;

(+)-trans-2-(2,6-Difluoro-phenyl)-5,7-dihydroxy-8-(2-hydroxymethyl-1-methyl-pyrrolidin-3-yl)-chromen-4-one;

(+/−)-trans-4-[8-(2-Hydroxymethyl-1-methyl-pyrrolidin-3-yl)-5,7-dimethoxy-4-oxo-4H-chromen-2-yl]-benzonitrile;

(+/−)-trans-4-[5,7-Dihydroxy-8-(2-hydroxymethyl-1-methyl-pyrrolidin-3-yl)-4-oxo-4H-chromen-2-yl]-benzonitrile;

(+)-trans-4-[8-(2-Hydroxymethyl-1-methyl-pyrrolidin-3-yl)-5,7-dimethoxy-4-oxo-4H-chromen-2-yl]-benzonitrile;

(+)-trans-4-[5,7-Dihydroxy-8-(2-hydroxymethyl-1-methyl-pyrrolidin-3-yl)-4-oxo-4H-chromen-2-yl]-benzonitrile;

(+/−)-trans-8-(2-Hydroxymethyl-1-methyl-pyrrolidin-3-yl)-5,7-dimethoxy-2-(4-trifluoromethyl-phenyl)-chromen-4-one;

(+/−)-trans-5,7-Dihydroxy-8-(2-hydroxymethyl-1-methyl-pyrrolidin-3-yl)-2-(4-trifluoromethyl-phenyl)-chromen-4-one;

(+)-trans-8-(2-Hydroxymethyl-1-methyl-pyrrolidin-3-yl)-5,7-dimethoxy-2-(4-trifluoromethy-phenyl)-chromen-4-one;

(+)-trans-5,7-Dihydroxy-8-(2-hydroxymethyl-1-methyl-pyrrolidin-3-yl)-2-(4-trifluoromethy-phenyl)-chromen-4-one;
(−)-trans-8-(2-Hydroxymethyl-1-methyl-pyrrolidin-3-yl)-5,7-dimethoxy-2-(4-trifluoromethy-phenyl)-chromen-4-one;
(−)-trans-5,7-Dihydroxy-8-(2-hydroxymethyl-1-methyl-pyrrolidin-3-yl)-2-(4-trifluoromethy-phenyl)-chromen-4-one;
(+)-trans-8-(2-Hydroxymethyl-1-methyl-pyrrolidin-3-yl)-5,7-dimethoxy-2-phenyl-chromen-4-one;
(+)-trans-5,7-Dihydroxy-8-(2-hydroxymethyl-1-methyl-pyrrolidin-3-yl)-2-phenyl-chromen-4-one;
(+)-trans-8-(2-Hydroxymethyl-1-methyl-pyrrolidin-3-yl)-5,7-dimethoxy-2-thiophen-2-yl-chromen-4-one;
(+)-trans-5,7-Dihydroxy-8-(2-hydroxymethyl-1-methyl-pyrrolidin-3-yl)-2-thiophen-2-yl-chromen-4-one;
(+)-trans-4-[5,7-Dihydroxy-8-(2-Hydroxymethyl-1-methyl-pyrrolidin-3-yl)-4-oxo-4H-chromen-2-yl]-3-methyl-benzonitrile;
(+)-trans-4-[8-(2-hydroxymethyl-1-methyl-pyrrolidin-3-yl)-5,7-dimethoxy-4-oxo-4H-chromen-2-yl]-3-methyl-benzonitrile;
(+/−)-trans-2-(2-Bromo-5-methoxy-phenyl)-8-(2-hydroxymethyl-1-methyl-pyrrolidin-3-yl)-5,7-dimethoxy-chromen-4-one;
(+/−)-trans-2-(2-Bromo-5-methoxy-phenyl)-5,7-dihydroxy-8-(2-hydroxymethyl-1-methyl-pyrrolidin-3-yl)-chromen-4-one;
(+)-trans-2-(2-Bromo-5-methoxy-phenyl)-8-(2-hydroxymethyl-1-methyl-pyrrolidin-3-yl)-5,7-dimethoxy-chromen-4-one;
(+)-trans-2-(2-Bromo-5-methoxy-phenyl)-5,7-dihydroxy-8-(2-hydroxymethyl-1-methyl-pyrrolidin-3-yl)-chromen-4-one;
(+/−)-trans-2-(2-bromo-5-hydroxy-phenyl)-5,7-dihydroxy-8-(2-hydroxymethyl-1-methyl-pyrrolidin-3-yl)-chromen-4-one;
(+)-trans-2-(2-bromo-5-methoxy-phenyl)-8-(2-hydroxymethyl-1-methyl-pyrrolidin-3-yl)-5,7-chromen-4-one;
(+/−)-trans-2-[(3,5-Bis-trifluoromethyl)-phenyl]-8-(2-hydroxymethyl-1-methyl-pyrrolidin-3-yl)-5,7-dimethoxy-chromen-4-one;
(+/−)-trans-2-[(3,5-Bis-trifluoromethyl)-phenyl]-5,7-dihydroxy-8-(2-hydroxymethyl-1-methyl-pyrrolidin-3-yl)-chromen-4-one;
(+)-trans-2-(2-Chloro-5-methyl-phenyl)-8-(2-hydroxymethyl-1-methyl-pyrrolidin-3-yl)-5,7-dimethoxy-chromen-4-one;
(+)-trans-2-(2-Chloro-5-methyl-phenyl)-5,7-dihydroxy-8-(2-hydroxymethyl-1-methyl-pyrrolidin-3-yl)-chromen-4-one;
(+)-trans-2-(2-Bromo-5-nitro-phenyl)-8-(2-hydroxymethyl-1-methyl-pyrrolidin-3-yl)-5,7-dimethoxy-chromen-4-one;
(+/−)-trans-2-(2-Bromo-5-nitro-phenyl)-8-(2-hydroxymethyl-1-methyl-pyrrolidin-3-yl)-5,7-dimethoxy-chromen-4-one;
(+/−)-trans-2-(2-Chloro-pyridin-3-yl)-8-(2-hydroxymethyl-1-methyl-pyrrolidin-3-yl)-5,7-dimethoxy-chromen-4-one;
(+/−)-trans-2-(2-Chloro-pyridin-3-yl)-5,7-dihydroxy-8-(2-hydroxymethyl-1-methyl-pyrrolidin-3-yl)chromen-4-one;
(+/−)-trans-2-(2-Bromo-5-nitrophenyl)-8-(2-hydroxymethyl-1-methyl-pyrrolidin-3-yl)-5,7-dihydroxy-chromen-4-one;
(+)-trans-2-(2-Chloro-pyridin-3-yl)-5,7-dihydroxy-8-(2-hydroxymethyl-1-methyl-pyrrolidin-3-yl)-chromen-4-one;
(+/−)-trans-8-(2-Hydroxymethyl-1-methyl-pyrrolidin-3-yl)-5,7-dimethoxy-2-(4-nitrophenyl)-4H-chromen-4-one;
(+/−)-trans-5,7-Dihydroxy-8-(2-hydroxymethyl-1-methyl-pyrrolidin-3-yl)-2-(4-nitrophenyl)-chromen-4-one;
(+/−)-trans-2-(4-Aminophenyl)-5,7-dihydroxy-8-(2-hydroxymethyl-1-methyl-pyrrolidin-3-yl)-chromen-4-one;
(+/−)-trans-8-(2-Hydroxymethyl-1-methyl-pyrrolidin-3-yl)-5,7-dimethoxy-2-(2-methoxy-phenyl)-chromen-4-one;
(+/−)-trans-5,7-Dihydroxy-8-(2-hydroxymethyl-1-methyl-pyrrolidin-3-yl)-2-(2-hydroxy-phenyl)-chromen-4-one;
(+)-trans-3-Chloro-4-[8-(2-hydroxymethyl-1-methyl-pyrrolidin-3-yl)-5,7-dimethoxy-4-oxo-4H-chromen-2-yl]benzonitrile;
(+)-trans-3-Chloro-4-[5,7-dihydroxy-8-(2-hydroxymethyl-1-methyl-pyrrolidin-3-yl)-4-oxo-4H-chromen-2-yl]benzonitrile;
(+)-trans-2-(4-Bromo-2-chloro-phenyl)-8-(2-hydroxymethyl-1-methyl-pyrrolidin-3-yl)-5,7-dimethoxy-chromen-4-one;
(+)-trans-2-(4-Bromo-2-chloro-phenyl)-5,7-dihydroxy-8-(2-hydroxymethyl-1-methyl-pyrrolidin-3-yl)-chromen-4-one;
(+/−)-trans-2-(2-Chloro-4-dimethylamino-phenyl)-8-(2-hydroxymethyl-1-methyl-pyrrolidin-3-yl)-5,7-dimethoxy-chromen-4-one;
(+/−)-trans-2-(2-Chloro-4-methylamino-phenyl)-5,7-dihydroxy-8-(2-hydroxymethyl-1-methyl-pyrrolidin-3-yl)-chromen-4-one;
(+/−)-trans-2-(2-Chloro-4-methoxy-phenyl)-8-(2-hydroxymethyl-1-methyl-pyrrolidin-3-yl)-5,7-dimethoxy-chromen-4-one;
(+/−)-trans-2-(2-Chloro-4-hydroxy-phenyl)-5,7-dihydroxy-8-(2-hydroxymethyl-1-methyl-pyrrolidin-3-yl)-chromen-4-one;
(+/−)-trans-2-(2-Chloro-5-fluoro-phenyl)-8-(2-hydroxymethyl-1-methyl-pyrrolidin-3-yl)-5,7-dimethoxy-chromen-4-one;
(+/−)-trans-2-(2-Chloro-5-fluoro-phenyl)-5,7-dihydroxy-8-(2-hydroxymethyl-1-methyl-pyrrolidin-3-yl)-chromen-4-one;
(+/−)-trans-2-(2-Chloro-5-methoxy-phenyl)-8-(2-hydroxymethyl-1-methyl-pyrrolidin-3-yl)-5,7-dimethoxy-chromen-4-one;
(+/−)-trans-2-(2-Chloro-5-hydroxy-phenyl)-5,7-dihydroxy-8-(2-hydroxymethyl-1-methyl-pyrrolidin-3-yl)-chromen-4-one;
(+/−)-trans-2-(2-Chloro-5-methoxy-phenyl)-5,7-dihydroxy-8-(2-hydroxymethyl-1-methyl-pyrrolidin-3-yl)-chromen-4-one;
(+/−)-trans-8-(2-Azidomethyl-1-methyl-pyrrolidin-3-yl)-2-(2-chloro-phenyl)-5,7-dimethoxy-chromen-4-one;
(+/−)-trans-8-(2-Aminomethyl-1-methyl-pyrrolidin-3-yl)-2-(2-chloro-phenyl)-5,7-dimethoxy-chromen-4-one;
(+/−)-trans-8-(2-Aminomethyl-1-methyl-pyrrolidin-3-yl)-2-(2-chloro-phenyl)-5,7-dihydroxy-chromen-4-one;
(+/−)-trans-{3-[2-(2-Chloro-phenyl)-5,7-dimethoxy-4-oxo-4H-chromen-8-yl]-1-methyl-pyrrolidin-2-yl}-acetonitrile;

(+/−)-trans-{3-[2-(2-Chloro-phenyl)-5,7-dihydroxy-4-oxo-4H-chromen-8-yl]-1-methyl-pyrrolidin-2-yl}-acetonitrile;
(+/−)-trans-2-[2-Chloro-phenyl-8-(2-mercaptomethyl-1-methyl-pyrrolidin-3-yl)]-5,7-dimethoxy-chromen-4-one;
(+/−)-trans-2-(2-Chloro-phenyl)-5,7-dihydroxy-8-(2-mercaptomethyl-1-methyl-pyrrolidin-3-yl)-chromen-4-one;
(+/−)-trans-Acetic acid 3-[2-(2-chloro-phenyl)-5,7-dimethoxy-4-oxo-4H-chromen-8-yl]-1-(4-methoxy-phenyl)-pyrrolidin-2-ylmethyl ester;
(+/−)-trans-2-(2-Chloro-phenyl)-8-[2-hydroxymethyl-1-(4-methoxy-phenyl)-pyrrolidin-3-yl]-5,7-dimethoxy-chromen-4-one;
(+/−)-trans-2-(2-Chloro-phenyl)-5,7-dihydroxy-8-[2-hydroxymethyl-1-(4-methoxy-phenyl)-pyrrolidin-3-yl]-chromen-4-one;
(+/−)-trans-Acetic acid 3-[2-(2-chloro-phenyl)-5,7-dimethoxy-4-oxo-4H-chromen-8-yl]-1-propyl-pyrrolidin-2-ylmethyl ester;
(+/−)-trans-2-(2-Chloro-phenyl)-8-[2-hydroxyrnethyl-1-propyl-pyrrolidin-3-yl]-5,7-dimethoxy-chromen-4-one;
(+/−)-trans-2-(2-Chloro-phenyl)-5,7-dihydroxy-8-(2-hydroxymethyl-1-propyl-pyrrolidin-3-yl)-chromen-4-one;
(+/−)-trans-2-(2-Chloro-4-nitro-phenyl)-5,7-dihydroxy-8-(2-hydroxymethyl-1-methylpyrrolidin-3-yl)-chromen-4-one;
(+/−)-trans-2-(2-Bromo-4-nitro-phenyl)-5,7-dihydroxy-8-(2-hydroxymethyl-1-methylpyrrolidin-3-yl)-chromen-4-one;
(+/−)-trans-3-Chloro-4-[5,7-dihydroxy-8-(2-hydroxymethyl-1-methyl-pyrrolidin-3-yl)-4-oxo-4H-chromen-2-yl]-benzoic acid;
(+/−)-trans-3-Bromo-4-[5,7-dihydroxy-8-(2-hydroxymethyl-1-methyl-pyrrolidin-3-yl)-4-oxo-4H-chromen-2-yl]-benzoic acid;
(+/−)-trans-2-(2-Chloro-4-fluoro-phenyl)-5,7-dihydroxy-8-(2-hydroxymethyl-1-methyl-pyrrolidin-3-yl)-chromen-4-one;
(+/−)-trans-2-(4-Amino-2-chloro-phenyl)-5,7-dihydroxy-8-(2-hydroxymethyl-1-methyl-pyrrolidin-3-yl)-chromen-4-one;
(+/−)-trans-2-(2-Bromo-5-fluoro-phenyl)-5,7-dihydroxy-8-(2-hydroxymethyl-1-methyl-pyrrolidin-3-yl)-chromen-4-one;
(+/−)-trans-2-(4-Amino-2-bromo-phenyl)-5,7-dihydroxy-8-(2-hydroxymethyl-1-methyl-pyrrolidin-3-yl)-chromen-4-one;
(+/−)-trans-4-Chloro-3-[5,7-dihydroxy-8-(2-hydroxymethyl-1-methyl-pyrrolidin-3-yl)-4-oxo-4H-chromen-2-yl]-benzoic acid;
(+/−)-trans-4-Bromo-3-[5,7-dihydroxy-8-(2-hydroxymethyl-1-methyl-pyrrolidin-3-yl)-4-oxo-4H-chromen-2-yl]-benzoic acid;
(+/−)-trans-4-Bromo-3-[5,7-dihydroxy-8-(2-hydroxymethyl-1-methyl-pyrrolidin-3-yl)-4-oxo-4H-chromen-2-yl]-N-hydroxy-benzamide;
(+/−)-trans-4-Chloro-3-[5,7-dihydroxy-8-(2-hydroxymethyl-1-methyl-pyrrolidin-3-yl)-4-oxo-4H-chromen-2-yl]-N-hydroxy-benzamide;
(+/−)-trans-3-Chloro-4-[5,7-dihydroxy-8-(2-hydroxymethyl-1-methyl-pyrrolidin-3-yl)-4-oxo-4H-chromen-2-yl]-N-hydroxy-benzamide;
(+/−)-trans-3-Bromo-4-[5,7-dihydroxy-8-(2-hydroxymethyl-1-methyl-pyrrolidin-3-yl)-4-oxo-4H-chromen-2-yl]-N-hydroxy-benzamide;
(+/−)-trans-2-(2,4-Difluoro-phenyl)-5,7-dihydroxy-8-(2-hydroxymethyl-1-methyl-pyrrolidin-3-yl)-chromen-4-one;
(+)-trans-2-(2-Chloro-3-fluoro-phenyl)-8-(2-hydroxymethyl-1-methyl-pyrrolidin-3-yl)-5,7-dimethoxy-chromen-4-one;
(+)-trans-2-(2-Chloro-3-fluoro-phenyl)-5,7-dihydroxy-8-(2-hydroxymethyl-1-methyl-pyrrolidin-3-yl)-chromen-4-one;
(+)-trans-2-(2-Bromo-3-fluoro-phenyl)-8-(2-hydroxymethyl-1-methyl-pyrrolidin-3-yl)-5,7-dimethoxy-chromen-4-one;
(+)-trans-2-(2-Bromo-3-fluoro-phenyl)-5,7-dihydroxy-8-(2-hydroxymethyl-1-methyl-pyrrolidin-3-yl)-chromen-4-one;
(+)-trans-2-(2-Bromo-5-fluoro-phenyl)-8-(2-hydroxymethyl-1-methyl-pyrrolidin-3-yl)-5,7-dimethoxy-chromen-4-one;
(+)-trans-2-(2-Bromo-5-fluoro-phenyl)-5,7-dihydroxy-8-(2-hydroxymethyl-1-methyl-pyrrolidin-3-yl)-chromen-4-one;
(+)-trans-2-(2-Chloro-5-iodo-phenyl)-8-(2-hydroxymethyl-1-methyl-pyrrolidin-3-yl)-5,7-dimethoxy-chromen-4-one;
(+)-trans-2-(2-Chloro-5-iodo-phenyl)-5,7-dihydroxy-8-(2-hydroxymethyl-1-methyl-pyrrolidin-3-yl)-chromen-4-one;
(+)-trans-2-(2-Bromo-5-chloro-phenyl)-8-(2-hydroxymethyl-1-methyl-pyrrolidin-3-yl)-5,7-dimethoxy-chromen-4-one;
(+)-trans-2-(2-Bromo-5-chloro-phenyl)-5,7-dihydroxy-8-(2-hydroxymethyl-1-methyl-pyrrolidin-3-yl)-chromen-4-one;
(+/−)-trans-2-(2-Chloro-phenyl)-5,7-dihydroxy-8-(2-hydroxmethyl-1-methyl-1-oxy-pyrrolidin-3-yl)-chromen-4-one;
(+)-trans-2-(2-Bromo-4-nitro-phenyl)-8-(2-hydroxyrnethyl-1-methylpyrrolidin-3-yl)-5,7-dimethoxy-chromen-4-one;
(+)-trans- 2-(2-Bromo-4-nitro-phenyl)-5,7-dihydroxy-8-(2-hydroxymethyl-1-methyl-pyrrolidin-3-yl)-chromen-4-one;
(+)-trans-2-(4-Amino-2-bromo-phenyl)-8-(2-hydroxymethyl-1-methyl-pyrrolidin-3-yl)-5,7-dimethoxy-chromen-4-one;
(+)-trans-2-(4-Amino-2-bromo-phenyl)-5,7-dihydroxy-8-(2-hydroxymethyl-1-methyl-pyrrolidin-3-yl)-chromen-4-one;
(+)-trans-2-(2-Bromo-4-methoxy-phenyl)-8-(2-hydroxymethyl-1-methyl-pyrrolidin-3-yl)-5,7-dimethoxy-chromen-4-one;
(+)-trans-2-(2-Bromo-4-methoxy-phenyl)-5,7-dihydroxy-8-(2-hydroxymethyl-1-methyl-pyrrolidin-3-yl)-chromen-4-one;
(+)-trans-2-(2-Bromo-4-hydroxy-phenyl)-5,7-dihydroxy-8-(2-hydroxymethyl-1-methyl-pyrrolidin-3-yl)-chromen-4-one;
(+)-trans-Acetic acid 8-(2-acetoxymethyl-1-methyl-pyrrolidin-3-yl)-5-hydroxy-2-(4-nitro-phenyl)-4-oxo-4H-chromen-7-yl ester;
(+)-trans-2-(2,4-Dichloro-5-fluoro-phenyl)-8-(2-hydroxymethyl-1-methyl-pyrrolidin-3-yl)-5,7-dimethoxy-chromen-4-one; and
(+)-trans-2-(2,4-Dichloro-5-fluoro-phenyl)-5,7-dihydroxy-8-(2-hydroxymethyl-1-methyl-pyrrolidin-3-yl)-chromen-4-one.

* * * * *